United States Patent
Hasslacher et al.

(10) Patent No.: US 12,071,468 B2
(45) Date of Patent: Aug. 27, 2024

(54) PURIFICATION OF FACTOR VIII SUBSPECIES

(71) Applicant: TAKEDA PHARMACEUTICAL COMPANY LIMITED, Osaka (JP)

(72) Inventors: Meinhard Hasslacher, Vienna (AT); Martin Feichtinger, Vienna (AT); Philipp M. Bärnthaler, Vienna (AT); Christa Mayer, Wolfsthal (AT); Birgit Reipert, Deutsch-Wagram (AT); Mantas Malisauskas, Vienna (AT); Julia Anzengruber, Vienna (AT)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 135 days.

(21) Appl. No.: 17/688,588

(22) Filed: Mar. 7, 2022

(65) Prior Publication Data

US 2022/0275058 A1    Sep. 1, 2022

Related U.S. Application Data

(62) Division of application No. 16/015,452, filed on Jun. 22, 2018, now Pat. No. 11,299,533.

(30) Foreign Application Priority Data

Jun. 23, 2017 (EP) ..................... 17177749

(51) Int. Cl.
| | | |
|---|---|---|
| C07K 14/755 | (2006.01) | |
| A61K 38/00 | (2006.01) | |
| B01D 15/32 | (2006.01) | |
| B01D 15/34 | (2006.01) | |
| B01D 15/36 | (2006.01) | |
| C07K 1/16 | (2006.01) | |
| C07K 1/18 | (2006.01) | |
| C07K 1/36 | (2006.01) | |

(52) U.S. Cl.
CPC .......... *C07K 14/755* (2013.01); *B01D 15/327* (2013.01); *B01D 15/34* (2013.01); *B01D 15/363* (2013.01); *C07K 1/16* (2013.01); *C07K 1/18* (2013.01); *C07K 1/36* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,250,008 A | 2/1981 | Mattock | |
| 4,465,574 A | 8/1984 | Mattock | |
| 5,659,017 A | 8/1997 | Bhattacharya | |
| 8,058,411 B2 | 11/2011 | Mundt et al. | |
| 8,329,871 B2 | 12/2012 | Borgvall et al. | |
| 8,354,505 B2 | 1/2013 | Debart et al. | |
| 2013/0040888 A1 | 2/2013 | Peschke | |
| 2013/0281671 A1 | 10/2013 | Peters et al. | |
| 2013/0345403 A1 | 12/2013 | Rischel | |
| 2016/0340410 A1* | 11/2016 | Winge | C07K 14/755 |

FOREIGN PATENT DOCUMENTS

| | | |
|---|---|---|
| CN | 102066417 A | 5/2011 |
| EP | 0062456 A3 | 1/1985 |
| EP | 0399321 | 11/1990 |
| EP | 1294864 | 3/2006 |
| JP | 2013515776 | 5/2013 |
| JP | 2017509593 | 4/2017 |
| RU | 2324495 C1 | 5/2008 |
| RU | 2417096 C2 | 4/2011 |
| RU | 2493163 C2 | 9/2013 |
| WO | 199615140 | 5/1996 |
| WO | 2008060063 A1 | 5/2008 |
| WO | 2009007451 A1 | 1/2009 |
| WO | 2009088713 | 7/2009 |
| WO | 2009156430 | 12/2009 |
| WO | 2001094383 | 12/2011 |
| WO | 2012006623 | 1/2012 |
| WO | 2012079979 A1 | 6/2012 |
| WO | 2012167271 | 12/2012 |
| WO | 2012170289 A1 | 12/2012 |
| WO | 2012179289 | 12/2012 |
| WO | 2016025615 | 2/2016 |

OTHER PUBLICATIONS

Office Action dated May 20, 2022 in connection with Russian Application No. 2020102459.
Search Report dated May 18, 2022 in connection with Russian Application No. 2020102459.
Sova V.V., M.I. Kusajkin,—Vladivostok: Publishing by Far Eastern University, 2006 (p. 10) Vydelenie i ochistka belkov. Metodicheskoe posobie po kursu «Himiya i biohimiya belkov i fermentov».
Ibragimov A.N., et al. Kazan: Kazan Federal University, 2013 (pp. 9-14, 21-25) Hromatograficheskie metody ochistki belkov. Uchebnometodicheskoe posobie.
Office Action issued Oct. 14, 2022 in connection with Russian patent application No. 2020102459.
Sazykin Yu.O. Biotechnologia: textbook for university students / Yu.O. Sazykin, S.N. Orekhov, I. and Sakaleva; edited by A.V. Katlinsky.—3d edition,—M.: Publishing Center "Academia", 2008.—256 p., OSBN 978-5-7695-5506-0 (p. 19).
N.A. Orlova, "Blood Clotting Factor VIII: From Evolution to Therapy", Acta Naturae, 2013, vol. 5, 2 (17), pp. 19-39.
First Office Action issued Feb. 17, 2023 in connection with Chinese patent application No. 201880054300.4.
Notice of Allowance issued Mar. 3, 2023 in connection with Japanese patent application No. 2022-21215.

(Continued)

*Primary Examiner* — Sudhakar Katakam
*Assistant Examiner* — Zachary J Miknis
(74) *Attorney, Agent, or Firm* — Troutman Pepper Hamilton Sanders LLP

(57) ABSTRACT

The present invention relates to a method for purifying a Factor VIII (FVIII) subspecies from a composition comprising FVIII, said method comprising an anion exchange chromatography step, a size exclusion chromatography step, and a concentration step. The invention also relates to a composition comprising a purified FVIII subspecies.

16 Claims, 67 Drawing Sheets

(56) References Cited

OTHER PUBLICATIONS

Mono Q anion exchange chromataography column https://www.cytivalifesciences.com/en/us/shop/chromatography/prepacked-columns/ion-exchange/mono-q-anion-exchange-chromatography-column-p-00608.

Ahmadian et al., "Molecular design and downstream processing of turoctocog alfa {NovoEight), a B-domain truncated factor VIII molecule" Blood Coagulation & Fibrinolysis, vol. 27, No. 5, Jul. 1, 2016, pp. 568-575, XP055415097.

Anonymous. "Ion exchange columns and media Selection Guide" GE Healthcare. (Year: 2000).

Anzengruber et al., (2017), "How full-length FVIII Benefits from its Heterogeneity—Insights into the Role of the B Domain." Res Pract Thromb Haemost, 1{Suppl. 1): p. 377 {Meeting abstract).

Anzengruber et al., (2018), "Comparative analysis of marketed factor VIII products: recombinant products are not alike is-a-vis soluble protein aggregates and subvisible particles." J. Thromb Haemost, 16(6): pp. 1176-1181.

Demasi et al., "Enhances Proteolytic Processing of Recombinant Human Coagulation Factor VIII B-Domain Variants 5 by Recombinant Furins" Molecular Biotechnology, Humana Press, Inc. US, vol. 58, No. 6, Apr. 28, 2016, pp. 404-414, XP035952846.

Extended European Search Report issued Jan. 9, 2018 in connection with EPO No. 17177749.

Garger et al., "BAY 81-8973, a full-length recombinant factor VIII: manufacturing processes and product characteristics" Haemophilia, vol. 23, No. 2, Dec. 19, 2016, pp. e67-e78, XP055415090.

Himmelspach et al., (2000), "Recombinant human factor X: high yield expression and the role of furin in proteolytic maturation in vivo and in vitro." Thromb Res, 97(2): pp. 51-67.

Keating & Dhillon, (2012), "Octocog alfa {Advate®): a guide to its use in hemophilia A." BioDrugs, 26(4): pp. 269-273.

Khan H "The Role of Ion Exhange Chromatography in Purification and Characterization of Molecules" Ion Exchange Technologies, Chapter 14. Ed. Kilislioglu A. IntechOpen (Year: 2012).

Malisauskas et al., (2017), "Different N-glycosylation of Factor VIII: Similarities and Differences of Plasma Derived and Recombinant Factor VIII Products." Res Pract Thromb Haemost, 1 {Suppl. 1 ): p. 93. {Meeting Abstract).

Mazurkiewicz-Pisarek et al. "The factor VII I protein and its function" Acta Biochimica Polonica 63: 11-16. (Year: 2016).

Preininger et al., (1999), "Strategies for recombinant Furin employment in a biotechnological process: complete target protein precursor cleavage." Cytotechnology, 30(1-3): pp. 1-15.

Ratnoff et al. "Antihemophilic Factor (Factor VIII)" Annals Intern. Med. 88:403-409. (Year: 1978).

Shapiro et al., "Anti-hemophilic factor {recombinant), plasma/albumin-free method {octocog-alpha; ADVATE) in the management of hemophilia A" Vascular Health and Risk Management, 2007, vol. 3, No. 5, pp. 555-565.

Siner et al., (2016), "Circumventing furin enhances factor VIII biological activity and ameliorates bleeding phenotypes n hemophilia models." JCI Insight, 1(16): p. e89371.

Steinnicke et al., (2013), "A novel B-domain O-glycoPEGylated FVIII {NB-GP) demonstrates full efficacy and prolonged effect in hemophilic mice models." Blood, 121(11): pp. 2108-2116.

Thim et al., "Purification and characterization of a new recombinant factor VIII {N8)" Haemophilia, Blackwell Science, Oxford, GB, vol. 16, No. 2, Mar. 1, 2010, pp. 349-359, XP002583862.

Office Action issued Sep. 17, 2021 in connection with Russian Application No. 2020102459.

Sang-Hwan Oh et al., Synthesis of recombinant blood coagulation factor VIII (FVIII) heavy and light chains and reconstitution of active form of FVIII, Experimental and Molecular Medicine, (1999), vol. 31, No. 2, pp. 95-100.

Office Action dated Feb. 14, 2022 in connection with JP Application No. 2019-570797.

* cited by examiner

FIG. 52 E

```
721 DSYEDISAYLLSKNNATEPRSFSQNSRHPSTRQKFNATTIPENDIEKTDPWFAHRTPMP
        725      730      735      740      745      750      755      760      765      770      775      780
```

```
781 KIQNVSSSDLMLLRQSPTPHGLSLSDLQEAKYETESDDPSPGAIDSNNSLSEMTHFRPQ
        785      790      795      800      805      810      815      820      825      830      835      840
```

```
841 LHHSGDMVFTPESGLQRLNEKLGTTAATELKKLDFKVSSTSNNLISTIPSDNLAAGTDN
        845      850      855      860      865      870      875      880      885      890      895      900
```

A

B

Invitrogen
4-12% Bis-Tris
MES Buffer

| Lane | Sample | Dilution | |
|---|---|---|---|
| 1 | Precision Plus Unstained (1:5 mit SB) | | |
| 2 | SB | | |
| 3 | Advate #AD002-02 (1:50) = 16µg/ml 153,8 U/ml | | |
| 4 | SB | | |
| 5 | SOS_240517_DV_1 (0,293 mg/ml) | 1: | 9,8 |
| 6 | SOS_240517_DV_2 (0,256 mg/ml) | 1: | 8,5 |
| 7 | SOS_240517_DV_3 (0,256 mg/ml) | 1: | 8,5 |
| 8 | SOS_240517_DV_4 (0,256 mg/ml) | 1: | 8,5 |
| 9 | SOS_240517_DV_5 (0,256 mg/ml) | 1: | 8,5 |
| 10 | ADV_240517_DV_1 (0,631 mg/ml) | 1: | 21 |
| 11 | ADV_240517_DV_2 (0,594 mg/ml) | 1: | 19,8 |
| 12 | ADV_240517_DV_3 (0,594 mg/ml) | 1: | 19,8 |
| 13 | ADV_240517_DV_4 (0,594 mg/ml) | 1: | 19,8 |
| 14 | ADV_240517_DV_5 (0,594 mg/ml) | 1: | 19,8 |
| 15 | BUF_240517_DV_1 | unv | |
| 16 | BUF_240517_DV_2 | unv | |
| 17 | BUF_240517_DV_3 | unv | |
| 18 | BUF_240517_DV_4 | unv | |
| 19 | BUF_240517_DV_5 | unv | |
| 20 | SB | | |

| Lane | Sample | Dilution | |
|---|---|---|---|
| 1 | Precision Plus Dual Color | | |
| 2 | SB | | |
| 3 | Advate #AD002-02 (1:50) = 16 µg/ml 153,8 U/ml | | |
| 4 | SB | | |
| 5 | SOS_240517_DV_1 (0,293 mg/ml) | 1: | 9,8 |
| 6 | SOS_240517_DV_2 (0,256 mg/ml) | 1: | 8,5 |
| 7 | SOS_240517_DV_3 (0,256 mg/ml) | 1: | 8,5 |
| 8 | SOS_240517_DV_4 (0,256 mg/ml) | 1: | 8,5 |
| 9 | SOS_240517_DV_5 (0,256 mg/ml) | 1: | 8,5 |
| 10 | ADV_240517_DV_1 (0,631 mg/ml) | 1: | 21 |
| 11 | ADV_240517_DV_2 (0,594 mg/ml) | 1: | 19,8 |
| 12 | ADV_240517_DV_3 (0,594 mg/ml) | 1: | 19,8 |
| 13 | ADV_240517_DV_4 (0,594 mg/ml) | 1: | 19,8 |
| 14 | ADV_240517_DV_5 (0,594 mg/ml) | 1: | 19,8 |
| 15 | BUF_240517_DV_1 | unv | |
| 16 | BUF_240517_DV_2 | unv | |
| 17 | BUF_240517_DV_3 | unv | |
| 18 | BUF_240517_DV_4 | unv | |
| 19 | BUF_240517_DV_5 | unv | |
| 20 | SB | | |

PURIFICATION OF FACTOR VIII SUBSPECIES

CROSS-REFERENCE TO RELATED APPLICATIONS

This application is a divisional application of U.S. application Ser. No. 16/015,452, filed Jun. 22, 2018, now U.S. Pat. No. 11,299,533, issued Apr. 12, 2022, which claims priority from European Patent Application No. EP 17177749.3, filed Jun. 23, 2017, each of which are hereby incorporated by reference in their entirety.

FIELD OF THE INVENTION

The present invention relates to a method for purifying a Factor VIII (FVIII) subspecies from a composition comprising FVIII, said method comprising an anion exchange chromatography step, a size exclusion chromatography step, and a concentration step. The invention also relates to a composition comprising a purified FVIII subspecies.

BACKGROUND

Haemostasis is a process which encompasses all reactions to stop blood loss after an injury or tissue damage has occurred. It involves three major steps:
1. Vasoconstriction, which means the narrowing of the affected blood vessel by contraction of surrounding muscle fibres to reduce blood flow and thereby decrease the acute blood loss.
2. Formation of a platelet plug for the temporary sealing of the damaged vessel wall, which takes place within the first minute after injury and is mainly due to contact with the underlying collagen of connective tissue mediated by von Willebrand factor (Clemetson, 2012).
3. Coagulation, which is the activation of blood coagulation factors and finally the activation of thrombin, the formation of fibrin and thereby thrombus stabilisation. Activation occurs in a cascade like, amplifying manner and thereby enhances the activity of each downstream following coagulation factor.

Blood coagulation factors are mainly serine proteases with few exceptions. These are FVIII and FV, which act as cofactors and exhibit no enzymatic function. Blood coagulation factors are generally termed with a capitalized F followed by roman numerals, e.g. FVII. When blood coagulation factors become activated they are often additionally denoted with a lowercased "a" in order to indicate their conversion from an inactive zymogen to an active serine protease, e.g. FVIIa. The coagulation cascade itself can be divided into two different pathways that meet in the fundamental step of thrombin activation.

The tissue factor pathway is also known as extrinsic pathway and starts with the exposure of tissue factor, a 47 kDa transmembrane protein located on the surface of subendothelial tissue cells. Upon tissue injury factor FVII forms a complex with tissue factor and is thereby activated. This complex also referred to as extrinsic tenase complex in turn activates the factors FIX to FIXa and FX to FXa, respectively. The second pathway is called contact activation pathway or intrinsic pathway and plays only a minor role in thrombus formation. The contact activation pathway involves initially the factors FXII, FXI and FIX. Active factor FIXa forms the so called intrinsic tenase complex with its active cofactor FVIIIa, calcium ions and phospholipids. The tenase complex is capable of activating factor FX to FXa (for an overview see FIG. 1).

Factor FXa, either activated by the tissue factor pathway or by the contact activation pathway, activates FV to FVa. Both factors, FXa and FVa together with calcium ions as cofactor act on prothrombin to form thrombin. Both the tissue factor pathway and the contact activation pathway meet at this point. Only small amounts of thrombin are formed in this initial phase, by far not capable of converting enough fibrinogen to fibrin to form a stable fibrin clot. But thrombin is part of a feed forward loop, catalysing its own formation. Thrombin activates FV, FXI and releases FVIII from vWF circulating as an inactive complex in the blood stream. FVIII is thereby activated to FVIIIa. As mentioned earlier, FXIa activates FIX which forms the intrinsic tenase complex together with FVIIIa and calcium ions. The tenase complex activates large amounts of FX, which leads to the production of even more thrombin. Thrombin is needed for the key purpose of coagulation, the conversion of fibrinogen to fibrin in the premature blood clot in order to stabilise and strengthen it. Furthermore thrombin activates FXIII to FXIIIa, whose responsibility is the crosslinking of fibrin within the clot.

Blood Coagulation Factor VIII is one of the largest blood clotting factors. The native single chain FVIII normally contains 2332 amino acids and its molecular weight is roughly 300 kDa (ExPASy, 2016). As shown in FIG. 2A, FVIII is composed of six domains, which are designated as A1-A2-B-A3-C1-C2.

The native blood coagulation FVIII is synthesised as one single polypeptide chain in hepatocytes, kidney cells, endothelial cells and lymphatic tissue. Under the influence of intracellular furin protease, FVIII is cleaved into two chains, one heavy chain and one light chain. There are different positions available throughout the single chain FVIII, where furin protease can attach and cleave. This results in a certain number of heterogeneous active FVIII subspecies, each comprising one heavy and one light chain. The heavy and light chain length varies according to the extent of B-domain truncation. The B-domain free light chain consists of the domains A3-C1-C2, whereas the extended light chain still contains a fraction of the B-domain. The molecular weights of light chain variants are 80 kDa for the standard light chain and 120 kDa for the extended light chain, respectively. The FVIII heavy chain can appear as full-length variant (180 kDa) where a major fraction of B-domain is still attached, as well as truncated variants (150 kDa and 110 kDa) with decreasing amounts of B-domain and the B-domain depleted heavy chain (90 kDa), completely free of B-domain. Domains A1 and A2 are part of each of the described heavy chain variants.

After secretion, FVIII circulates in the blood stream as an inactive form non-covalently bound to vWF, a large multimeric glycoprotein. The vWF binding site is a highly acidic area (shown as uncoloured space between domain designations in FIG. 2A) located near the N-terminus of the 80 kDa light chain (OBrien and Tuddenham, 1997). FVIII is released from vWF after removal of this acidic area by thrombin. Two additional acidic areas are located between the domains A1 and A2 and between A2 and B, respectively. Thrombin also causes cleavage of these acidic areas, thereby separating the domains A1, A2 and B. The active form of FVIII is then formed as a heterotrimeric molecule comprising the domains A1, A2 and the light chain A3-C1-C2- the B-domain is not part of the active FVIII molecule. The active FVIII molecule is inactivated by cleavage of the A2 domain by active protein C. Inactivated FVIII is rapidly cleared from the blood stream.

Each A domain contains approximately 330 amino acids and forms two highly conserved 3-barrels. Heavy chain and light chain are connected via a divalent metal ion bound to the domains A1 and A3. The domain A2 contains a specific FIXa binding site. The binding site for inactive FX is located in domain A1. The active FVIIIa can thus act as a mediator between FIXa and FX. FVIIIa itself has no enzymatic activity. The B-domain is the largest of all FVIII domains. It is highly glycosylated and at least partly removed during intracellular processing by furin protease. It seems to play a role in intracellular transport, targeting and secretion of FVIII. While the A- and C-domains form globular structures, the B-domain remains mostly unfolded as a linear structure. It also seems to play a major role in the prevention of intracellular aggregate formation due to its highly polar glycosylation and interaction with chaperones (Pipe et al., 1998). There are two C-domains in FVIII, each comprising approximately 150-160 amino acids. They are both located at the C-terminus of FVIII single chain. Parts of the C2-domain form a hydrophobic area which acts as phospholipid binding site and is important for the formation of the tenase complex during blood coagulation (Mazurkiewicz-Pisarek et al., 2016). The C1-domain seems to influence the binding strength to vWF (Liu et al., 2000).

Overall, human factor VIII (FVIII) is a plasma glycoprotein that plays an essential role in the blood coagulation cascade by serving as a cofactor for factor IXa in the conversion of factor X to factor Xa (Toole et al., 1984, Vehar et al., 1984). FVIII is primarily produced by liver sinusoidal cells (Do et al., 1999) as a large single chain protein (2332 amino acids) comprising the domain structure $NH_2$-A1-a1-A2-a2-B-a3-A3-C1-C2-COOH. Variable intra- and extracellular processing of the B domain result in a mixture of heterodimeric molecular species circulating in plasma. Thus FVIII contains a constant sized light chain (LC) (a3-A3-C1-C2) and a heavy chain (HC), minimally composed of the A1-a1-A2-a2 domains but variable in size due to the presence of some or all of the adjacent B domain (Jankowski et al, 2007) (FIG. 2B). HC and LC are associated via a non-covalent linkage which requires a divalent metal ion (Kaufman et al., 1988, Fay et al., 2006). FVIII is circulating in complex with von Willebrand factor (vWF) (Krishnaswamy et al., 2015, Pipe et al., 2016). Thrombin converts FVIII into its active form (FVIIIa) by specific cleavages in both the HC and LC (Lenting et al., 1998). During this proteolytic process the B domain is completely removed (Myles et al., 2002).

The FVIII B domain does not have amino acid homology to other known proteins, is heavily glycosylated, and is dispensable for procoagulant activity (Fay et al., 2006, Toole et al., 1986). However, it has been shown to have functional influences throughout the life cycle of FVIII as reviewed in detail by S. W. Pipe (Pipe et al., 2009). The B domain may play a major role in intracellular processing and trafficking of FVIII by interacting with chaperones to assist correct protein folding (Pipe et al., 1998) and with cargo-specific sorting receptors, mainly via carbohydrate moieties, to increase secretion efficiency (Pipe et al., 2005, Zhang et al., 2005). Further, it possibly prevents premature proteolysis (Khrenov et al., 2006) and decreases the affinity of inactive FVIII for activated platelets (Li et al., 1997), thus preserving circulating FVIII. The B domain has little effect on the overall FVIII secondary structure in solution (Grushin et al., 2014). Three dimensional structures solely available of BDD-rFVIII (Shen et al., 2008, Ngo et al., 2008) indicate difficulty in crystallizing the B domain. Recently a stabilizing function of the B domain under non-activating conditions was proposed, as it was shown to be tightly associated with the core of the FVIII molecule under low $Ca^{2+}$ concentrations (Bonazza et al., 2015).

A bleeding disorder is defined as any malfunction in the process of clot formation after injury, trauma or surgery. Any component of the blood coagulation cascade, i.e. blood clotting factors or associated processes such as temporary platelet plug formation can be affected. All bleeding disorders have in common that clot formation is not or only partly accomplished, which leads to spontaneous and/or extended bleeding events. These diseases can either be inherited or acquired, e.g. by the use of medicine or by other diseases. A few examples of bleeding disorders are given below.

1. The von Willebrand disease is caused by a deficiency of the von Willebrand factor. As a result platelet adhesion, which is mediated by vWF, does not properly work.
2. Haemophilia A occurs due to blood clotting factor VIII deficiency. Temporary platelet adhesion and the initiation phase of coagulation are functional but large scale thrombin formation in the propagation phase of coagulation cannot proceed.
3. Haemophilia B is a factor IX deficiency, resulting in similar symptoms as in haemophilia A. The intrinsic tenase complex fails to form and thereby factor FX remains mainly inactive, resulting in inefficient thrombin activation and insufficient fibrin generation.

Haemophilia A is an inherited bleeding disorder caused by coagulation FVIII deficiency. The affected F8A gene is located on the X chromosome. Therefore it is a sex-linked, recessive disease that mainly affects the male germ line. The most common cause is a large inversion with translocation of exons 1-22 as a consequence of homologous recombination (Mazurkiewicz-Pisarek et al., 2016). Other reasons for the outbreak of haemophilia A are point mutations and less commonly observed small deletions, insertions and inversions. As a consequence FVIII protein is either not expressed at all or protein expression leads to non-functional proteins. In case of an injury, primary haemostasis which means the adhesion of platelets to underlying connective tissue mediated by vWF functions properly. The absence of functional FVIII is first causing problems during the propagation phase of blood coagulation cascade. The intrinsic tenase complex, comprising FIXa, FVIIIa, calcium ions and phospholipids cannot form and therefore is not able to activate factor FX to FXa, which is its main responsibility. The consequence is a lack of active thrombin, required for fibrinogen cleavage. The water insoluble fibrin molecule, which would strengthen the blood clot is not formed and so the blood clot is very unstable and prone to disruption. Overall, a defect or deficiency in FVIII results in hemophilia A, the most common of the severe bleeding disorders (Mannucci et al., 2004).

Haemophilia A is divided into three forms of severity, classified by the amount of functional factor FVIII present in the blood. The amount of functional FVIII is defined by its activity, which can be determined by a two stage coagulation assay or more preferably by a chromogenic assay. The basic principle of the chromogenic assay is described below. Patients with 5-40 IU/dL factor VIII activity, which corresponds to 5-40% of FVIII activity in non-haemophilia A patients are generally considered as mild type haemophilia A patients. There are almost no spontaneous bleeding events but haemorrhage after surgery is very common. The moderate type of haemophilia A is defined by a FVIII activity of 1-5 IU/dL (1-5% of normal). Spontaneous bleedings occur infrequent, joint bleedings occur sometimes but not all moderate type patients are affected. Severe type haemophilia A patients exhibit less than 1 IU/dL of functional FVIII (<1% of normal). These patients suffer from spontaneous muscle haemorrhage during physical activity and intra-articular bleedings. Recurring joint bleeding can lead to inflammation and in further consequence to arthropathy and functional impairment (Valentino, 2010).

To prevent patients with haemophilia A from progression of the disease and associated consequences, which would threaten their health and reduce their life quality it is necessary to provide access to effective therapy. Some examples of commonly used as well as new and in the developmental stage situated drugs are given in the following.

The administration of the deficient blood coagulation factor, e.g. FVIII is called replacement or substitution therapy. It is used for prophylaxis and as on demand therapy in case of acute bleeding. Prophylaxis should start as early as possible in order to prevent disease related joint destruction. There are two different groups of replacement drugs. Plasma derived FVIII is separated from large plasma pools, subsequently lyophilised and thereby concentrated. However there is at least a theoretical risk of infectious agents such as viruses or prions arising from these medications. Recombinant FVIII is considered to be much safer as it is derived from and produced in mammalian cell lines and has not been in contact with human plasma. Regardless of the source of anti-haemophilic factor FVIII the main drawbacks, which are rather short half-lifes and the development of antibodies directed against these drugs, remain. The typical half-life of FVIII in the blood is approximately 8-12 hours, which makes very frequent administrations of 2-3 times per week necessary. Another disadvantage is the development of antibodies that rapidly initiate immune response and thereby degradation of those substitutes.

New approaches aim at the increase of half-life. The addition of polyethylene glycol polymers to FVIII or the fusion of FVIII to proteins with longer half-lifes such as human albumin or the Fc region of IgG led to an increased half-life but the improvement is on average only 1.5 times higher compared with the native factor FVIII (Peyvandi et al., 2016).

As mentioned above, recombinant protein technology led to the development and production of recombinant FVIII (rFVIII) products for the treatment of hemophilia A by protein replacement therapy. These products mainly distinguish each other by the presence or absence of the B domain, referred as full-length (FL-)rFVIII and B domain-deleted (BDD-)rFVIII, respectively (Jankowski et al., 2007, D'Amici et al., 2010, Thim et al., 2010, Peters et al., 2013, Kannicht et al., 2013).

FVIII being a protein therapeutic is exposed to same risks as other protein based therapeutics in particular the propensity to aggregate during manufacturing, shelf-storage and handling in the clinic (Joubert et al., 2011, Roberts et al., 2014). It has been demonstrated for protein therapeutics in the clinical setting, that the presence of aggregates can induce unwanted immune responses in patients that may affect efficacy of the therapies (Moussa et al., 2016, Hermeling et al., 2003, van Beers et al., 2010, Barnard et al., 2013, Robbins et al., 1987a, Robbins et al., 1987b, Maislos et al., 1986, Ahmadi et al., 2015, Joubert et al., 2012).

Non-replacement therapy follows different strategies. The following two approaches try to improve haemostasis rather than replace the missing clotting factors. Monoclonal antibodies targeted against tissue factor pathway inhibitor (TFPI) reduce the inhibitory effect of TFPI and thereby maintain the tissue factor pathway in an active state. The second strategy circumvents the absence of FVIII by application of bispecific antibodies capable of binding both FIXa and FX and thereby mimicking the cofactor role of FVIIIa. An artificial tenase complex composed of FIXa—bispecific antibody—FX can form and activate factor FX to FXa. A completely different approach is gene therapy. Since it aims at the persistent reduction of severity it is rather curative than prophylactic. Viral vectors are used for delivery and integration of functional F8 genes to hepatocytes—the site of FVIII production—in order to replace the non-functional F8 gene and enable expression of functional blood coagulation FVIII.

The recombinant FVIII product ADVATE is one of the most extensively studied and most commonly used replacement drugs for haemophilia A therapy, with a low incidence of side effects and adverse events (according to the FDA Approval 2003). Thus, it is considered to be a safe as well as efficient medication.

To further investigate the similarity of recombinant anti-haemophilic FVIII, which is produced in mammalian cell culture, to plasma-derived human FVIII in terms of composition, and to characterise the properties as well as the behaviour of all major subspecies, it is necessary to produce an adequate amount of each FVIII subspecies in sufficient purity. One or more of these purified FVIII subspecies, or a mixture thereof, could also be used in therapy.

Thus, the present invention provides a purification strategy based on chromatographic steps. Preferably, the purification strategy is capable of the following:

1. Yielding a sufficient amount of each FVIII subspecies.
2. Yielding a sufficient FVIII subspecies protein concentration in the final formulation.
3. Yielding a final formulation wherein the amount of other FVIII subspecies, which are considered as impurities, is sufficiently low, e.g. in order to be able to produce reliable results in subsequent immunological research. The final product should be sterile and free of biological contaminants.
4. The final FVIII subspecies fractions are provided in a defined matrix, e.g. a matrix at defined pH containing buffer components including salts as well as a surfactant.
5. Furthermore the process steps evaluated as useful in the present invention are easily upgradable to a preparative scale in order to ensure the production of a sufficient amount of product.

This invention relates to the early developmental phases in form of feasibility experiments on small scale chromatography columns, as well as to the upscale process to preparative scale and the final production scheme for each FVIII subspecies.

DESCRIPTION OF THE INVENTION

The present invention meets the above-described needs and solves the above-mentioned problems in the art by providing the embodiments described below.

In particular, in an effort to develop a method for purifying a Factor VIII subspecies from a composition comprising Factor VIII, the inventors found that employing two chromatography steps, namely an anion exchange chromatography step and a size exclusion chromatography step, followed by a concentration step, which can be another anion exchange chromatography step, yielded a composition comprising said Factor VIII subspecies in high purity and high concentration. Surprisingly, the inventors additionally found that furin protease treatment of the Factor VIII comprising composition as well as performing the first anion exchange chromatography step by linear gradient elution with an extended length of the gradient further improved separation of the Factor VIII subspecies during chromatography, and thus yielded a composition comprising said Factor VIII subspecies at even higher purity and concentration.

In further experiments, the inventors characterized purified Factor VIII subspecies obtained according to the present invention. Surprisingly, the inventors found that all purified rFVIII species and a mixture thereof showed increased activity compared to the unpurified starting material. Additionally, the inventors found that a Factor VIII subspecies containing 70% of the B-domain showed a significantly lower propensity to aggregate and a higher propensity to form oligomers than a Factor VIII subspecies lacking the entire B-domain. Thus, the purified Factor VIII subspecies obtained according to the method of the present invention can potentially be formulated in a pharmaceutically active composition (i.e., a medicament) with improved properties. The pharmaceutically active composition could contain a single purified FVIII subspecies. Alternatively, two or more of the purified FVIII subspecies could be mixed, e.g. in the same ratio of FVIII subspecies that is found in pdFVIII, or in rFVIII products that are currently used to treat patients. Such pharmaceutically active composition could be used to treat patients with bleedings disorders such as hemophilia A.

In additional experiments, the inventors surprisingly found that furin treatment of recombinant FVIII increases the activity of FVIII, even in the absence of subspecies purification.

Overall, the present invention provides improved means for purifying a Factor VIII subspecies from a composition comprising Factor VIII by providing the preferred embodiments listed as items 1 to 86 below:

1. A method for purifying a Factor VIII (FVIII) subspecies from a composition comprising FVIII, said method comprising the steps of:
   (1) subjecting the composition comprising FVIII to anion exchange chromatography, and collecting the eluate comprising said FVIII subspecies;
   (2) subjecting the eluate of step (1) comprising said FVIII subspecies to size exclusion chromatography, and collecting the eluate comprising said FVIII subspecies; and
   (3) concentrating the eluate of step (2) comprising said FVIII subspecies.
2. The method according to item 1, wherein the concentration step (3) is a step of subjecting the eluate of step (2) comprising said FVIII subspecies to anion exchange chromatography, and collecting the eluate comprising said FVIII subspecies.
3. The method according to item 1 or 2, wherein FVIII is recombinant FVIII (rFVIII) and the FVIII subspecies is a recombinant FVIII (rFVIII) subspecies.
4. The method according to any one of items 1 to 3, wherein the FVIII subspecies is a FVIII heavy chain that is associated with a FVIII light chain.
5. The method according to any one of items 1 to 4, wherein the FVIII subspecies is the FVIII 180 kDa heavy chain that is associated with a FVIII light chain.
6. The method according to any one of items 1 to 4, wherein the FVIII subspecies is the FVIII 150 kDa heavy chain that is associated with a FVIII light chain.
7. The method according to any one of items 1 to 4, wherein the FVIII subspecies is the FVIII 110 kDa heavy chain that is associated with a FVIII light chain.
8. The method according to any one of items 1 to 4, wherein the FVIII subspecies is the FVIII 90 kDa heavy chain that is associated with a FVIII light chain.
9. The method according to any one of items 1 to 8, wherein in step (1) a high resolution Q-resin with a bead size of less than 20 µm is used for anion exchange chromatography.
10. The method according to item 9, wherein the high resolution Q-resin with a bead size of less than 20 µm is a MonoQ resin.
11. The method according to any one of items 1 to 10, wherein in step (2) a size exclusion chromatography resin with a resolution range of 10000 Da to 60000 Da is used for size exclusion chromatography.
12. The method according to item 11, wherein the size exclusion chromatography resin with a resolution range of 10000 Da to 60000 Da is a Superdex 200 µg resin.
13. The method according to any one of items 2 to 12, wherein in step (3) a SourceQ resin is used for anion exchange chromatography.
14. The method according to any one of items 1 to 13, wherein the method additionally comprises the following step (0) prior to step (1):
   (0) subjecting the FVIII comprised in the composition to furin protease treatment.
15. The method according to item 14, wherein the furin protease treatment is performed using furin at a final concentration of more than 100 IU/mL.
16. The method according to item 14 or 15, wherein the method additionally comprises the following step (0') following step (0):
   (0') filtering the composition comprising FVIII through a filter with a pore size of about 0.2 µm.
17. The method according to any one of items 14 to 16, wherein the FVIII light chain is the FVIII 80 kDa light chain.
18. The method according to any one of items 1 to 17, wherein elution in step (1) is performed by linear gradient elution.
19. The method according to item 18, wherein in step (1) the gradient of the linear gradient elution has a length of at least about 16 column volumes.
20. The method according to item 18, wherein in step (1) the gradient of the linear gradient elution has a length of at least about 24 column volumes.
21. The method according to item 18, wherein in step (1) the gradient of the linear gradient elution has a length of at least about 32 column volumes.
22. The method according to any one of items 1 to 21, wherein in step (1) elution is performed using a buffer that comprises ethylene glycol.
23. The method according to item 22, wherein in step (1) elution is performed using a buffer that comprises ethylene glycol at a concentration of about 10% (v/v).
24. The method according to any one of items 1 to 23, wherein step (2) is replaced by the step of:
   (2) subjecting the eluate of step (1) comprising said FVIII subspecies to hydrophobic interaction chromatography.
25. The method according to item 24, wherein the method additionally comprises the following step (1') prior to step (2):
   (1') subjecting the FVIII subspecies comprised in the eluate of step (1) to furin protease treatment.

26. The method according to item 25, wherein the furin protease treatment is performed using furin at a final concentration of more than 100 IU/mL.
27. The method according to item 25 or 26, wherein the method additionally comprises the following step (1") following step (1'):
    (1") filtering the eluate comprising said FVIII subspecies through a filter with a pore size of about 0.2 μm.
28. The method according to any one of items 25 to 27, wherein the FVIII light chain is the FVIII 80 kDa light chain.
29. The method according to any one of items 24 to 28, wherein the hydrophobic interaction chromatography is negative mode chromatography.
30. The method according to any one of items 24 to 29, wherein the FVIII subspecies is the FVIII 150 kDa heavy chain that is associated with a FVIII light chain.
31. The method according to any one of items 24 to 29, wherein the FVIII subspecies is the FVIII 180 kDa heavy chain that is associated with a FVIII light chain.
32. The method according to any one of items 2 to 31, wherein elution in step (3) is performed by step gradient elution.
33. The method according to any one of items 1 to 4, 9, 10, 13 to 23 or 32, wherein the FVIII subspecies is the FVIII 90 kDa heavy chain, wherein step (2) of the method is omitted, and wherein in step (3) the eluate of step (1) comprising said FVIII subspecies replaces the eluate of step (2) comprising said FVIII subspecies.
34. A composition comprising a purified FVIII subspecies obtainable according to any one of items 1 to 33.
35. The composition comprising a purified FVIII subspecies according to item 34, wherein the weight ratio of the purified FVIII subspecies in the composition to all other FVIII subspecies in the composition is at least 9.
36. The composition comprising a purified FVIII subspecies according to item 34, wherein the weight ratio of the purified FVIII subspecies in the composition to all other FVIII subspecies in the composition is at least 8.
37. The composition comprising a purified FVIII subspecies according to any one of items 34 to 36, wherein the concentration of the purified FVIII subspecies is at least 0.1 mg/mL.
38. The composition comprising a purified FVIII subspecies according to any one of items 34 to 36, wherein the concentration of the purified FVIII subspecies is at least 0.3 mg/mL.
39. A composition comprising a purified Factor VIII (FVIII) subspecies.
40. The composition according to item 39, wherein FVIII is recombinant FVIII (rFVIII) and the FVIII subspecies is a recombinant FVIII (rFVIII) subspecies.
41. The composition according to item 39 or 40, wherein the FVIII subspecies is the FVIII 180 kDa heavy chain that is associated with a FVIII light chain, the FVIII 150 kDa heavy chain that is associated with a FVIII light chain, the FVIII 110 kDa heavy chain that is associated with a FVIII light chain, or the FVIII 90 kDa heavy chain that is associated with a FVIII light chain.
42. The composition according to any one of items 39 to 41, wherein the weight ratio of the purified FVIII subspecies in the composition to all other FVIII subspecies in the composition is at least 9, or at least 8.
43. The composition according to any one of items 39 to 42, wherein the concentration of the purified FVIII subspecies is at least 0.1 mg/mL, or at least 0.3 mg/mL.
44. The composition according to any one of items 34 to 43 for use as a medicament.
45. The composition according to any one of items 34 to 44 for use in the treatment of a bleeding disorder.
46. The composition according to any one of items 34 to 45 for use in the treatment of hemophilia A.
47. A method for purifying a protein or a subunit of a protein from a composition comprising several proteins or several subunits of a protein, said method comprising the steps of:
    (1) subjecting the composition comprising the protein or subunit of a protein to anion exchange chromatography, and collecting the eluate comprising said protein or subunit of a protein;
    (2) subjecting the eluate of step (1) comprising said protein or subunit of a protein to size exclusion chromatography, and collecting the eluate comprising said protein or subunit of a protein; and
    (3) concentrating the eluate of step (2) comprising said protein or subunit of a protein.
48. The method according to item 47, wherein the concentration step (3) is a step of subjecting the eluate of step (2) comprising said protein or subunit of a protein to anion exchange chromatography, and collecting the eluate comprising said protein or subunit of a protein.
49. The method according to item 47 or 48, wherein the protein or subunit of a protein is a recombinant protein or a recombinant subunit of a protein.
50. The method according to any one of items 47 to 49, wherein in step (1) a high resolution Q-resin with a bead size of less than 20 μm is used for anion exchange chromatography.
51. The method according to item 50, wherein the high resolution Q-resin with a bead size of less than 20 μm is a MonoQ resin.
52. The method according to any one of items 47 to 51, wherein in step (2) a size exclusion chromatography resin with a resolution range of 10000 Da to 60000 Da is used for size exclusion chromatography.
53. The method according to item 52, wherein the size exclusion chromatography resin with a resolution range of 10000 Da to 60000 Da is a Superdex 200 μg resin.
54. The method according to any one of items 48 to 53, wherein in step (3) SourceQ resin is used for anion exchange chromatography.
55. The method according to any one of items 47 to 54, wherein the method additionally comprises the following step (0) prior to step (1):
    (0) subjecting the protein or subunit of a protein comprised in the composition to furin protease treatment.
56. The method according to item 55, wherein the furin protease treatment is performed using furin at a final concentration of more than 100 IU/mL.
57. The method according to item 55 or 56, wherein the method additionally comprises the following step (0') following step (0):
    (0') filtering the composition comprising the protein or subunit of a protein through a filter with a pore size of about 0.2 μm.
58. The method according to any one of items 47 to 57, wherein elution in step (1) is performed by linear gradient elution.
59. The method according to item 58, wherein in step (1) the gradient of the linear gradient elution has a length of at least about 16 column volumes.

60. The method according to item 58, wherein in step (1) the gradient of the linear gradient elution has a length of at least about 24 column volumes.
61. The method according to item 58, wherein in step (1) the gradient of the linear gradient elution has a length of at least about 32 column volumes.
62. The method according to any one of items 47 to 61, wherein in step (1) elution is performed using a buffer that comprises ethylene glycol.
63. The method according to item 62, wherein in step (1) elution is performed using a buffer that comprises ethylene glycol at a concentration of about 10% (v/v).
64. The method according to any one of item 47 to 63, wherein step (2) is replaced by the step of:
   (2) subjecting the eluate of step (1) comprising said protein or subunit of a protein to hydrophobic interaction chromatography.
65. The method according to item 64, wherein the method additionally comprises the following step (1') prior to step (2):
   (1') subjecting the protein or subunit of a protein comprised in the eluate of step (1) to furin protease treatment.
66. The method according to item 65, wherein the furin protease treatment is performed using furin at a final concentration of more than 100 IU/mL.
67. The method according to item 65 or 66, wherein the method additionally comprises the following step (1") following step (1'):
   (1") filtering the eluate comprising said protein or subunit of a protein through a filter with a pore size of about 0.2 µm.
68. The method according to any one of items 64 to 67, wherein the hydrophobic interaction chromatography is negative mode chromatography.
69. The method according to any one of items 47 to 68, wherein elution in step (3) is performed by step gradient elution.
70. The method according to any one of items 47 to 51, 54 to 63 or 69, wherein step (2) of the method is omitted, and wherein in step (3) the eluate of step (1) comprising said protein or subunit of a protein replaces the eluate of step (2) comprising said protein or subunit of a protein.
71. A composition comprising a purified protein or subunit of a protein obtainable according to any one of items 47 to 71.
72. The composition comprising a purified protein or subunit of a protein according to item 71, wherein the weight ratio of the purified protein or subunit of a protein in the composition to all other proteins or subunits of a protein in the composition is at least 9.
73. The composition comprising a purified protein or subunit of a protein according to item 71, wherein the weight ratio of the purified protein or subunit of a protein in the composition to all other proteins or subunits of a protein in the composition is at least 8.
74. The composition comprising a purified protein or subunit of a protein according to any one of items 71 to 73, wherein the concentration of the purified protein or subunit of a protein is at least 0.1 mg/m L.
75. The composition comprising a purified protein or subunit of a protein according to any one of items 71 to 73, wherein the concentration of the purified protein or subunit of a protein is at least 0.3 mg/m L.
76. The composition according to any one of items 71 to 75 for use as a medicament.
77. A method of subjecting Factor VIII (FVIII) to furin protease treatment.
78. The method according to item 77, wherein FVIII is recombinant FVIII (rFVIII).
79. The method according to item 77 or 78, wherein the FVIII comprises single chain FVIII.
80. The method according to any one of items 77 to 79, wherein the furin protease treatment is performed using furin at a final concentration of more than 100 IU/mL.
81. The method according to any one of items 77 to 80, wherein the method additionally comprises a step of separating the furin protease from the FVIII.
82. The method according to any one of items 77 to 81, wherein the method is for increasing the activity of FVIII.
83. A composition comprising FVIII, wherein the FVIII is obtainable according to any one of items 77 to 82.
84. The composition comprising FVIII according to item 83 for use as a medicament.
85. The composition comprising FVIII according to item 83 or 84 for use in the treatment of a bleeding disorder.
86. The composition comprising FVIII according to any one of items 83 to 85 for use in the treatment of hemophilia A.

Figure 6:
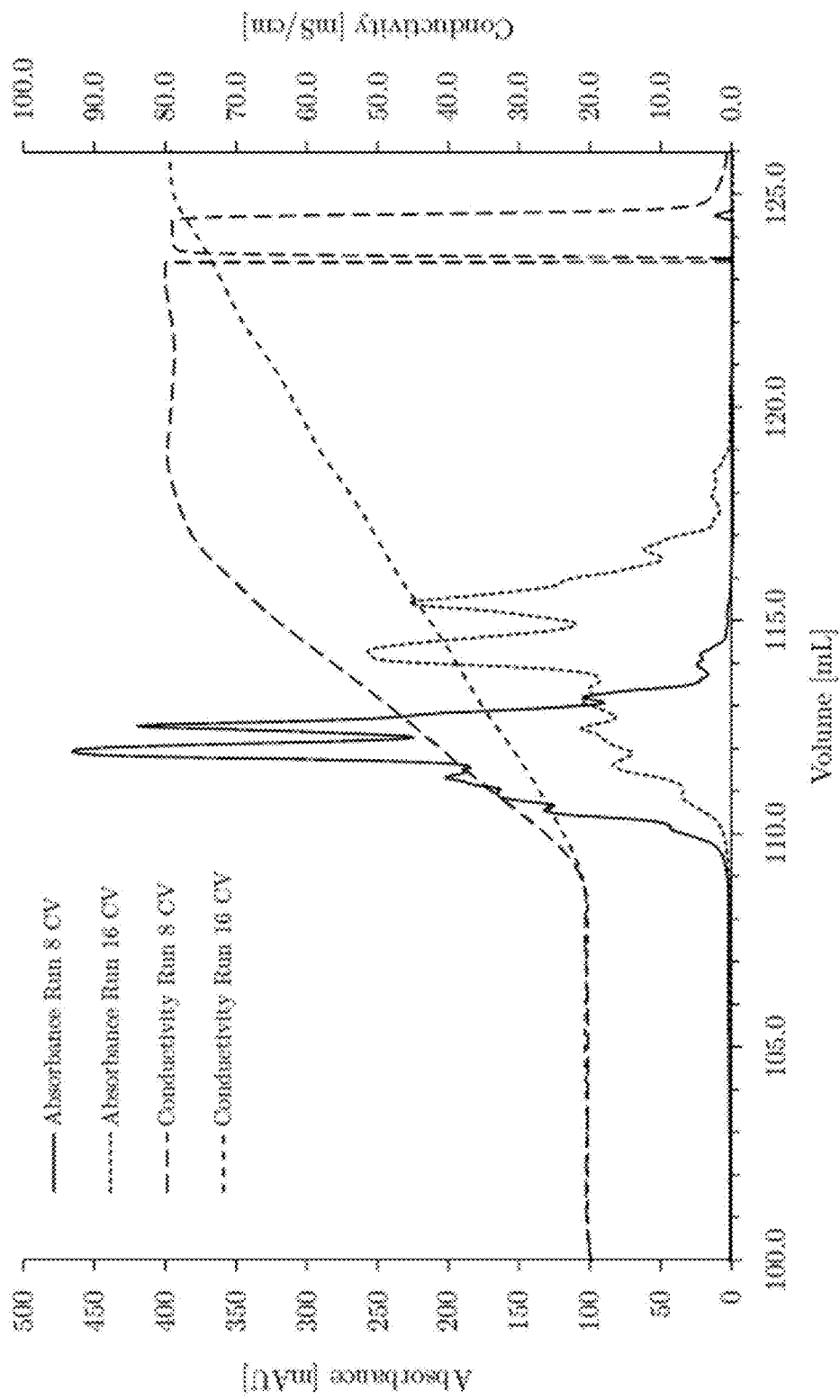

FIG. 6: Overlay of FVIII molecular subspecies separation on AIEX Mono 10Q resin separated with standard buffers QA1 and QB1 at pH 6.7. (1) Gradient: 135.0-750.0 mM sodium chloride in eight column volumes, Broken line: Conductivity, Solid line: Absorbance at 280 nm. (2) Gradient: 135.0-750.0 mM sodium chloride in 16 column volumes, Dashed line: Conductivity, Dotted line: Absorbance at 280 nm. Column dimensions: 0.5 cm inner diameter×5.0 cm bed height, 0.98 mL column volume.

Figure 7:
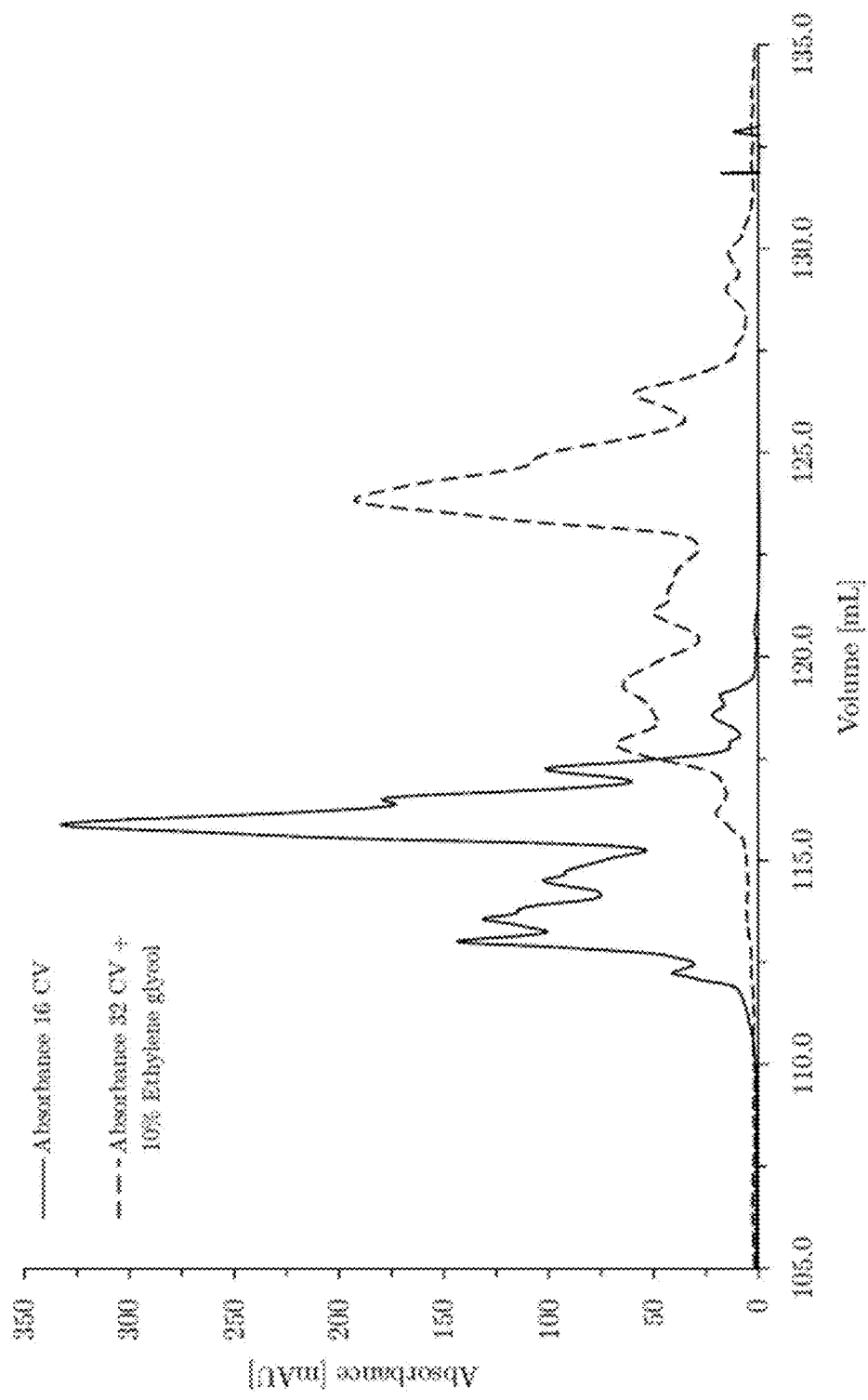

FIG. 7: Overlay of FVIII molecular subspecies separation on AIEX Mono 10Q resin at pH 6.7. Solid line) Gradient: 135.0-750.0 mM sodium chloride in 16 column volumes with standard buffers QA1 and QB1, Broken line) Gradient: 135.0-750.0 mM sodium chloride in 32 column volumes with 10% ethylene glycol containing QA1 and QB1 buffers. Column dimensions: 0.5 cm inner diameter×5.0 cm bed height, 0.98 mL column volume.

Figure 8:
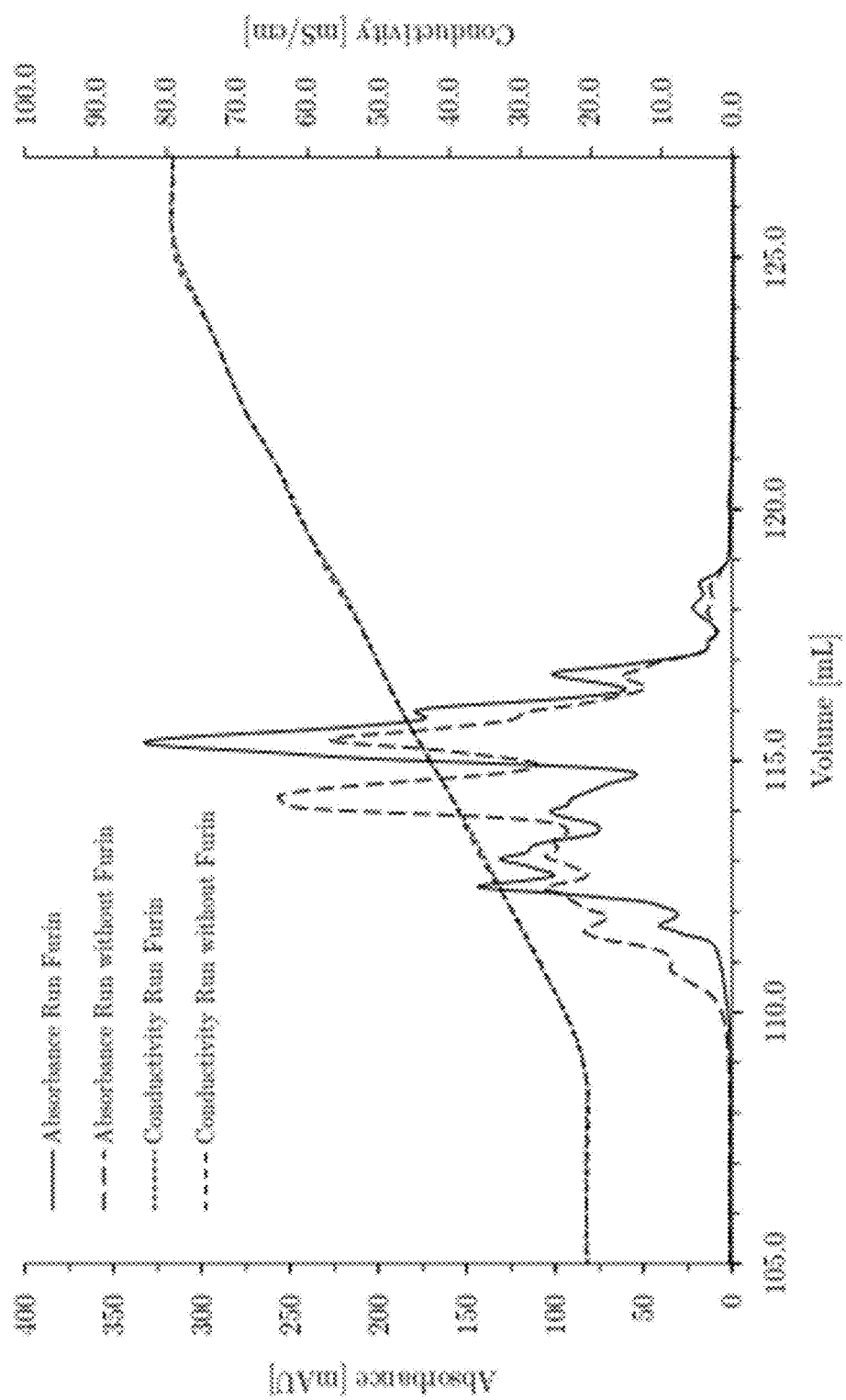

FIG. 8: Overlay of separation of furin treated and non-furin treated FVIII molecular subspecies on AIEX Mono 10Q resin separated with standard buffers QA1 and QB1 at pH 6.7. Gradient: 135.0-750.0 mM sodium chloride in 16 column volumes. (1) Sample without furin treatment: Dashed line) Conductivity, Broken line) Absorbance at 280 nm, (2) Furin treated sample: Dotted line) Conductivity, Solid line) Absorbance at 280 nm. Column dimensions: 0.5 cm inner diameter×5.0 cm bed height, 0.98 mL column volume.

Figure 9:
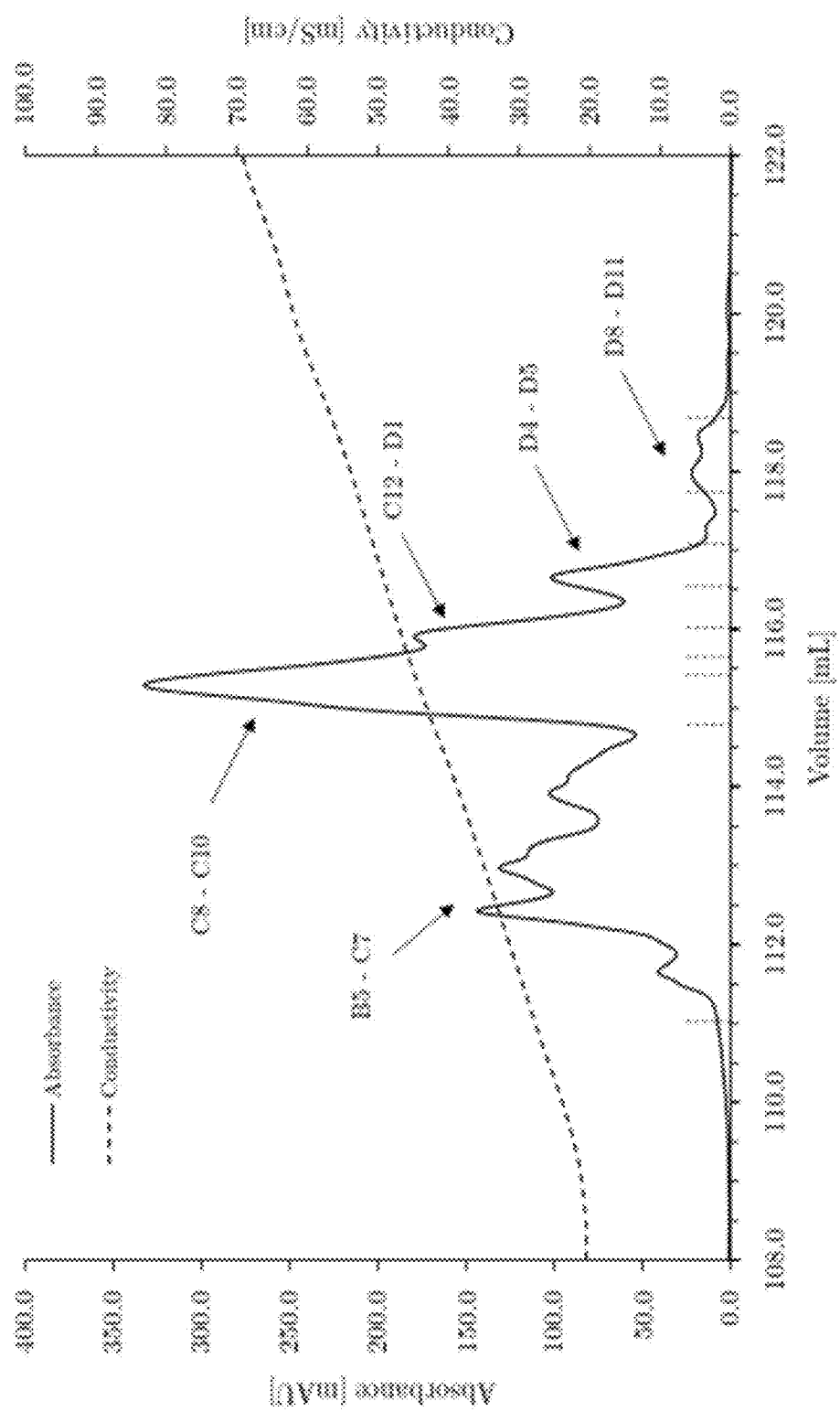

FIG. 9: Chromatogram of the elution phase of furin treated FVIII molecular subspecies on AIEX Mono 10Q resin separated with standard buffers QA1 and QB1 at pH 6.7. Gradient: 135.0-750.0 mM sodium chloride in 16 column volumes. Column dimensions: 0.5 cm inner diameter× 5.0 cm bed height, 0.98 mL column volume.

Figure 10:
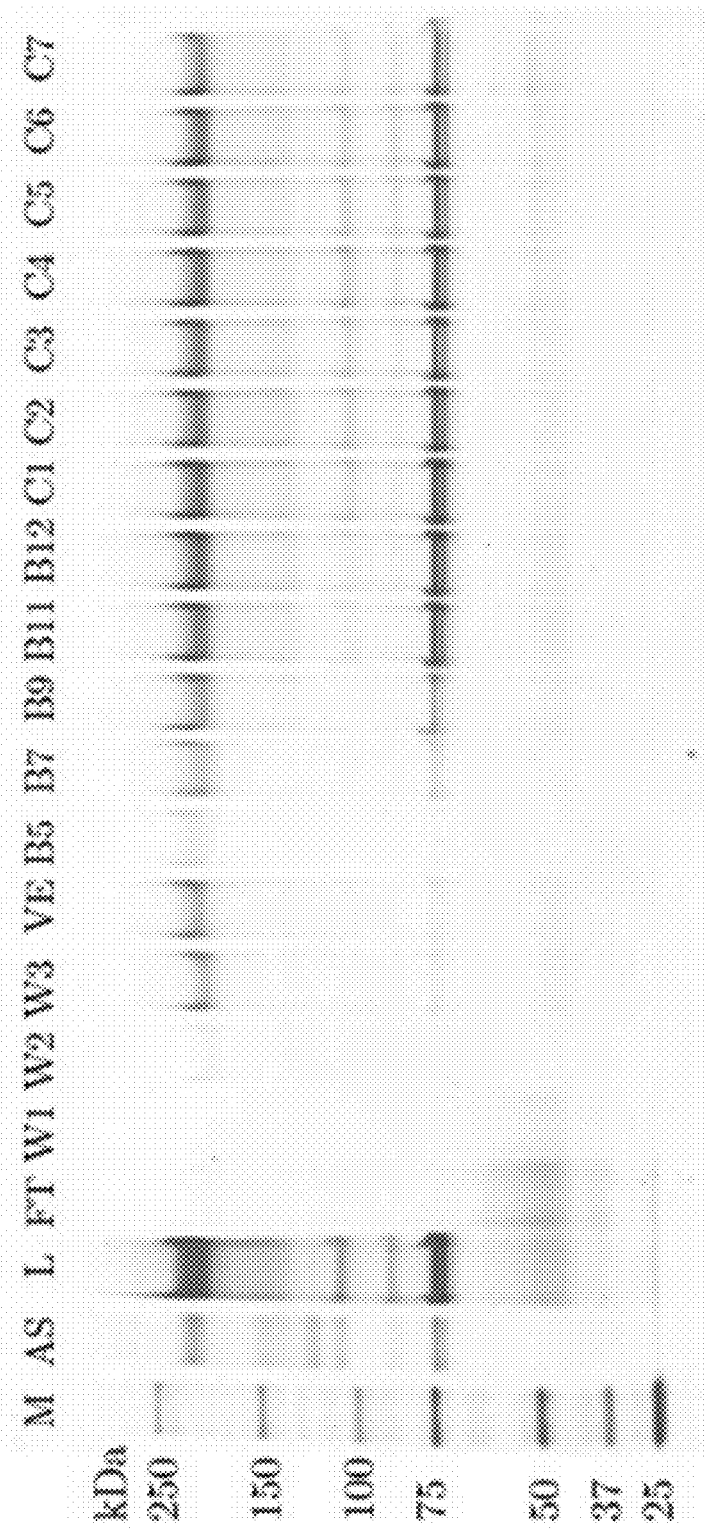

FIG. 10: SDS page gel electrophoresis of the separation of furin treated FVIII molecular subspecies on AIEX Mono 10Q resin separated with standard buffers QA1 and QB1 at pH 6.7. Gradient: 135.0-750.0 mM sodium chloride in 16 column volumes. M) Molecular weight marker, AS) Standard of the commercially available FVIII drug substance, showing all relevant heavy- and light chain species, L) Load, FT) Flow through, W1) Washing phase 1, W2) Washing phase 2, W3) Washing phase 3, VE) Pre-eluate, Fractions B5-C7.

Figure 11:
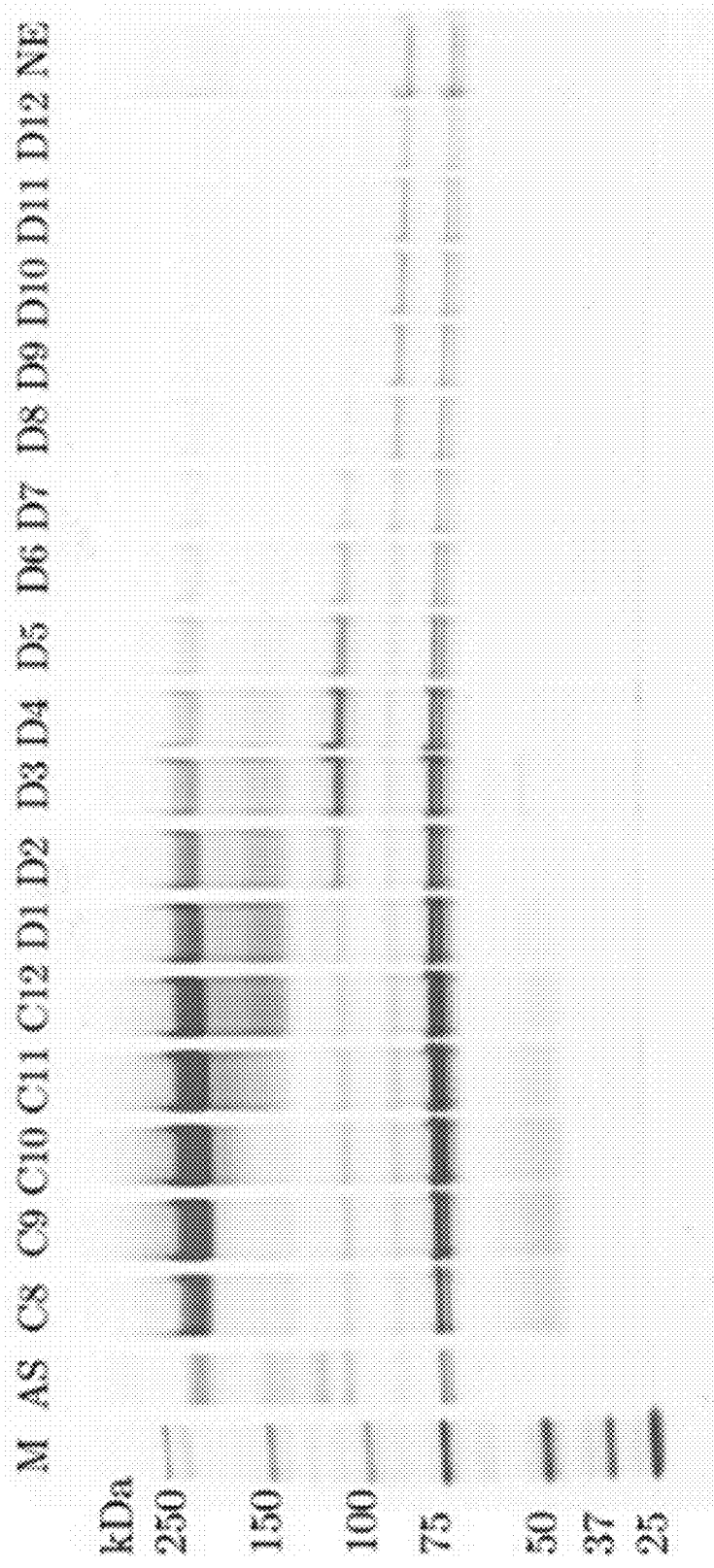

FIG. 11: SDS page gel electrophoresis of the separation of furin treated FVIII molecular subspecies on AIEX Mono 10Q resin separated with standard buffers QA1 and QB1 at pH 6.7. Gradient: 135.0-750.0 mM sodium chloride in 16 column volumes. M) Molecular weight marker, AS) Standard of the commercially available FVIII drug substance, showing all relevant heavy- and light chain species, Fractions C8-D12, NE) Posteluate.

Figure 12:
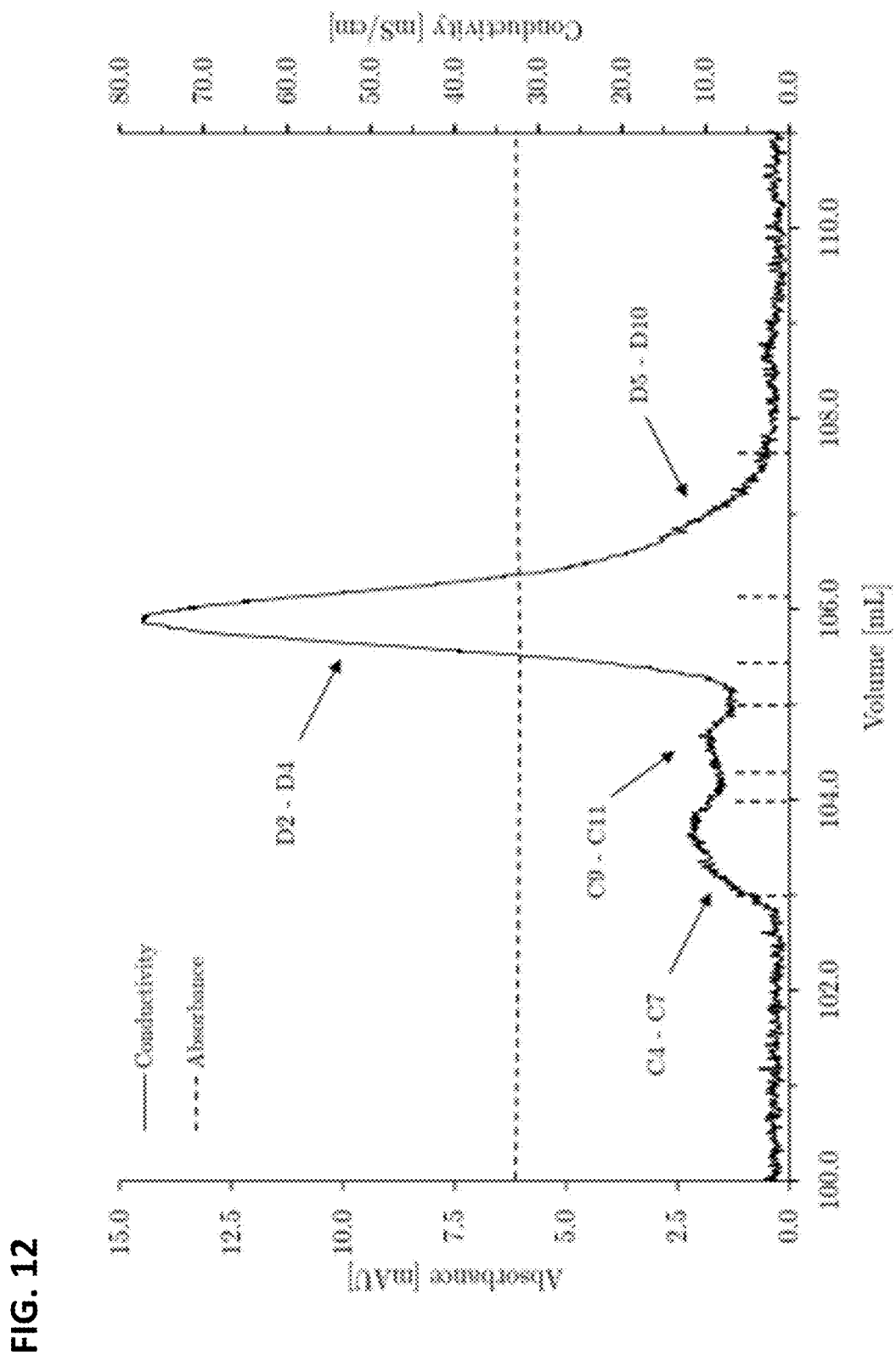

FIG. 12: Size exclusion chromatography polishing of the 110 kDa truncated heavy chain fragment on Superdex 200 Increase separated with approximately 300 mM sodium chloride buffer at pH 6.7. Column dimensions: 1.0 cm inner diameter×30.0 cm bed height, 23.56 mL column volume.

Figure 13:
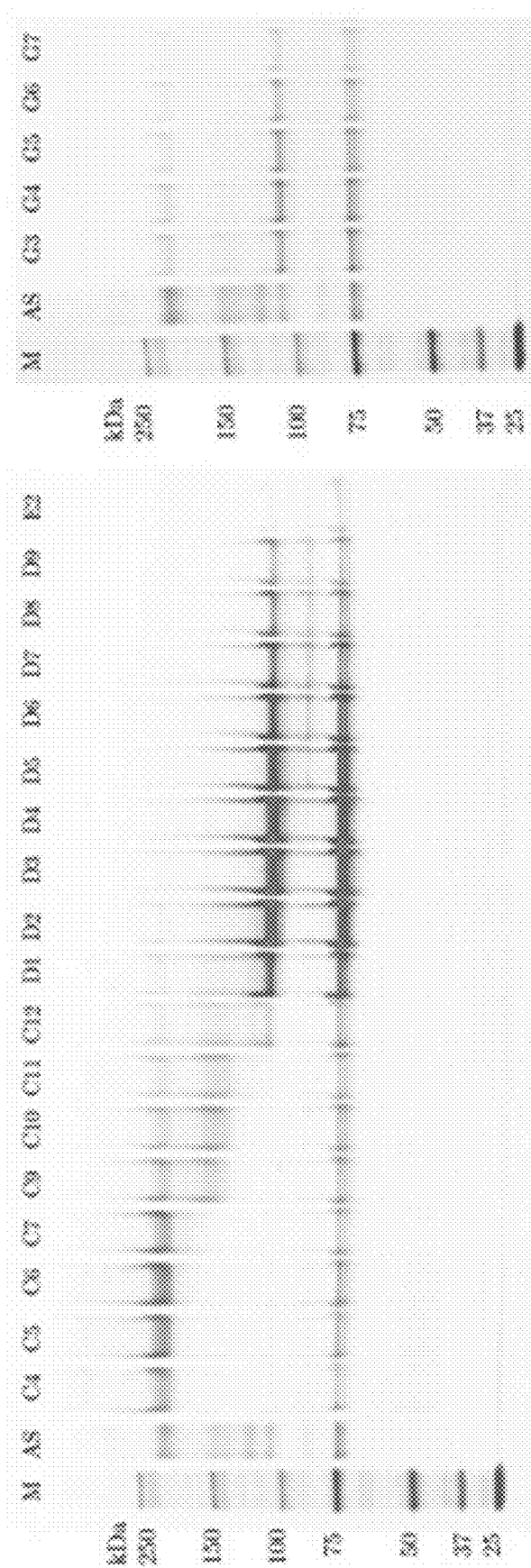

FIG. 13: SDS page gel electrophoresis of the SEC step for purification of the 110 kDa truncated heavy chain fragment and the respective starting material (fractions G4, G5 and G6) derived from MonoQ anion exchange chromatography. M) Molecular weight marker, AS) Standard of the commercially available FVIII drug substance, showing all relevant heavy- and light chain species, Fractions C4-E2.

Figure 14:
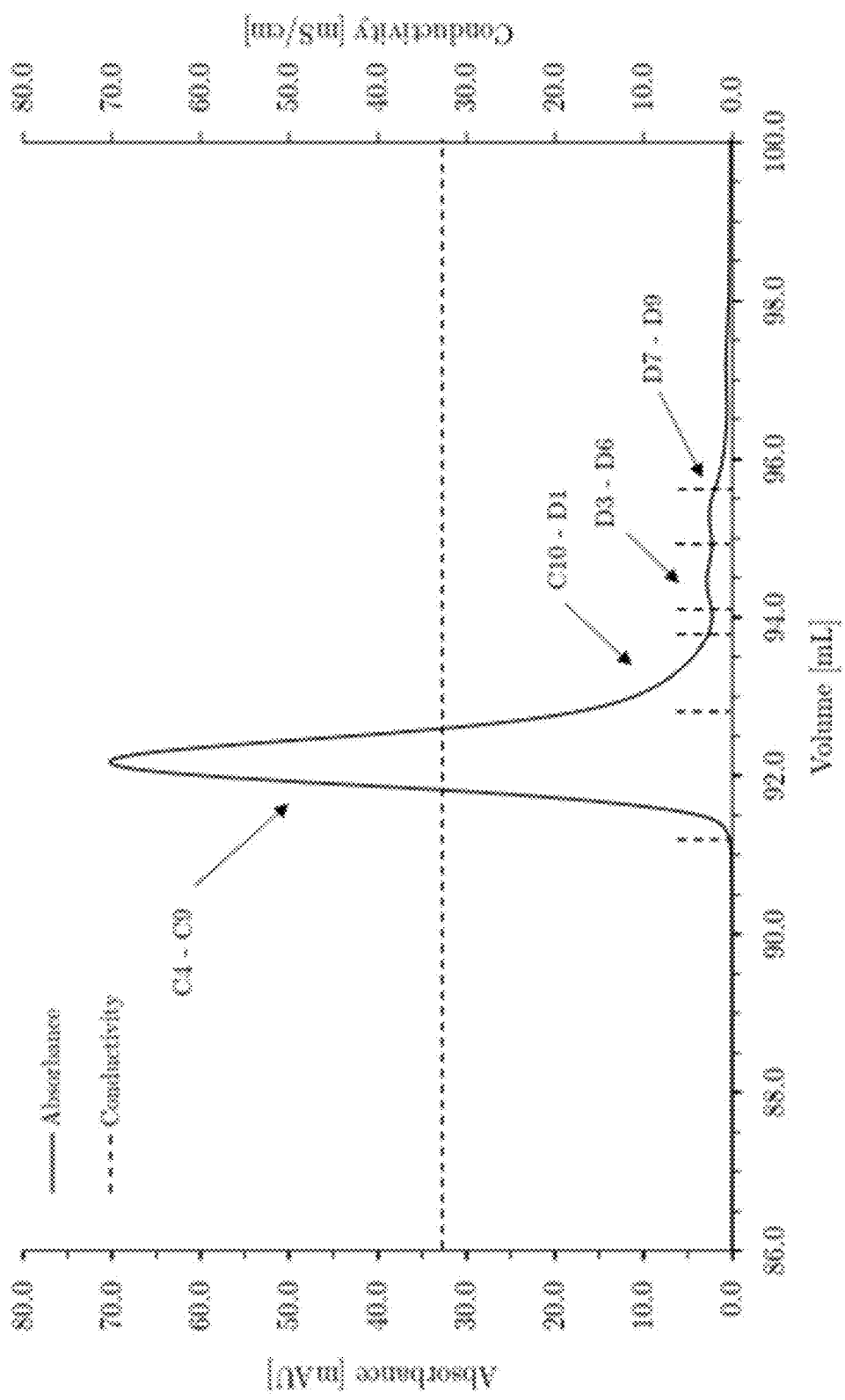

FIG. 14: Size exclusion chromatography polishing of the 180 kDa full length heavy chain on Superdex 200 Increase separated with approximately 300 mM sodium chloride buffer at pH 6.7. Column dimensions: 1.0 cm inner diameter×30.0 cm bed height, 23.56 mL column volume.

Figure 15:
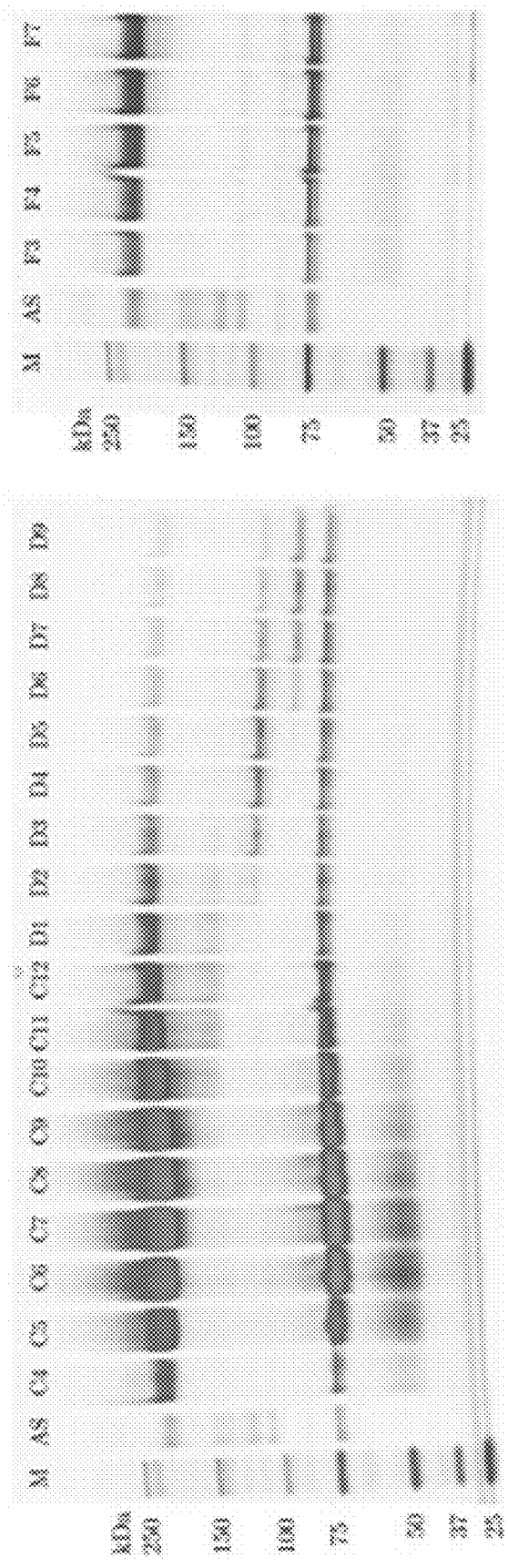

FIG. 15: SDS page gel electrophoresis of the SEC step for purification of the 180 kDa full length heavy chain fragment and the respective starting material (fractions F4, F5 and F6) derived from MonoQ anion exchange chromatography. M) Molecular weight marker, AS) Standard of the commercially available FVIII drug substance, showing all relevant heavy- and light chain species, Fractions C4-D9.

Figure 16:
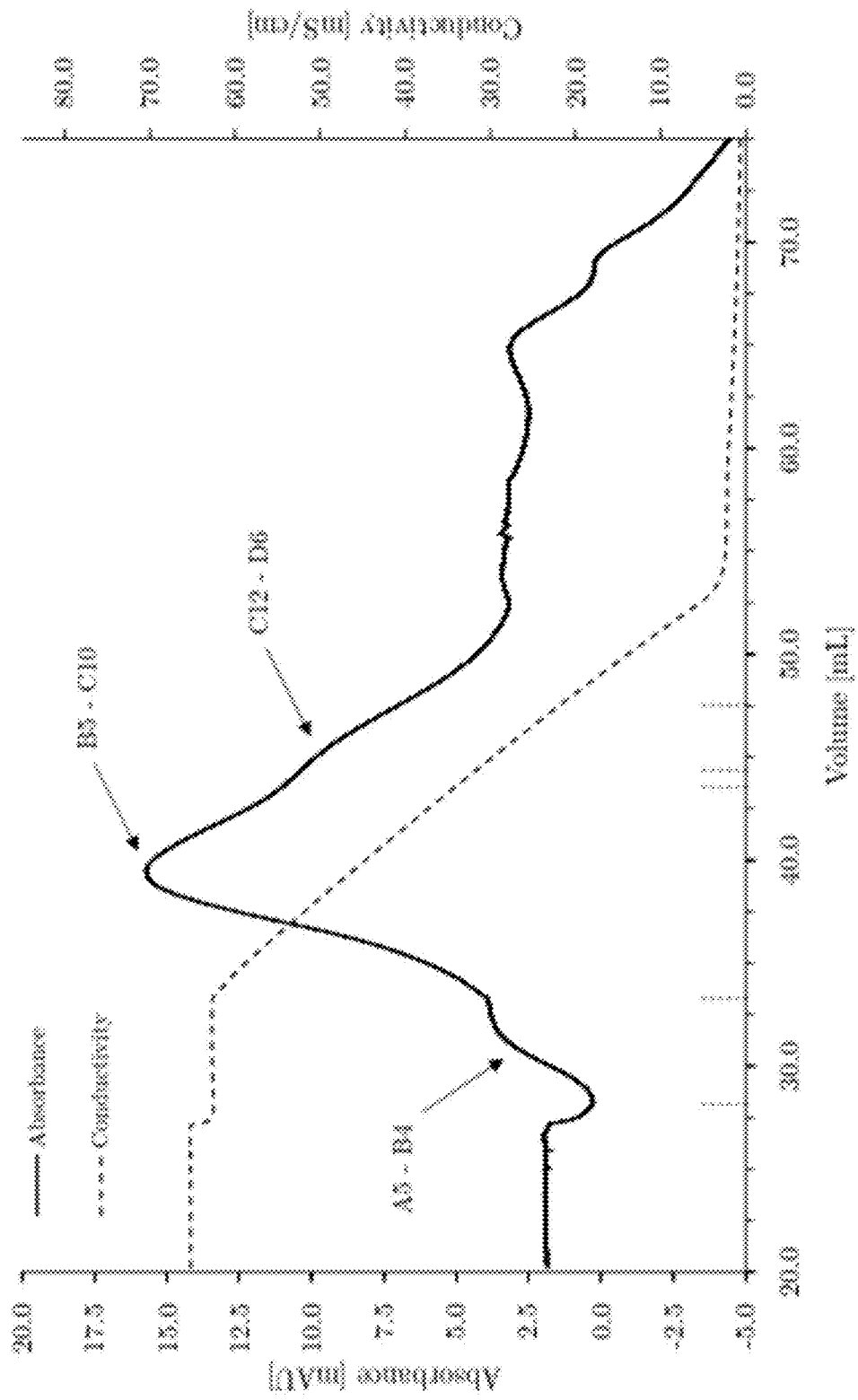

FIG. 16: Chromatogram of the two-dimensional elution phase of FVIII molecular subspecies separated on phenyl sepharose high performance. 1. Gradient: 680.0-0.0 mM sodium chloride in 20 column volumes, 2. Gradient: 0-50% ethylene glycol in 16 column volumes. Column dimensions: 0.5 cm inner diameter×5.0 cm bed height, 0.98 mL column volume.

Figure 17:
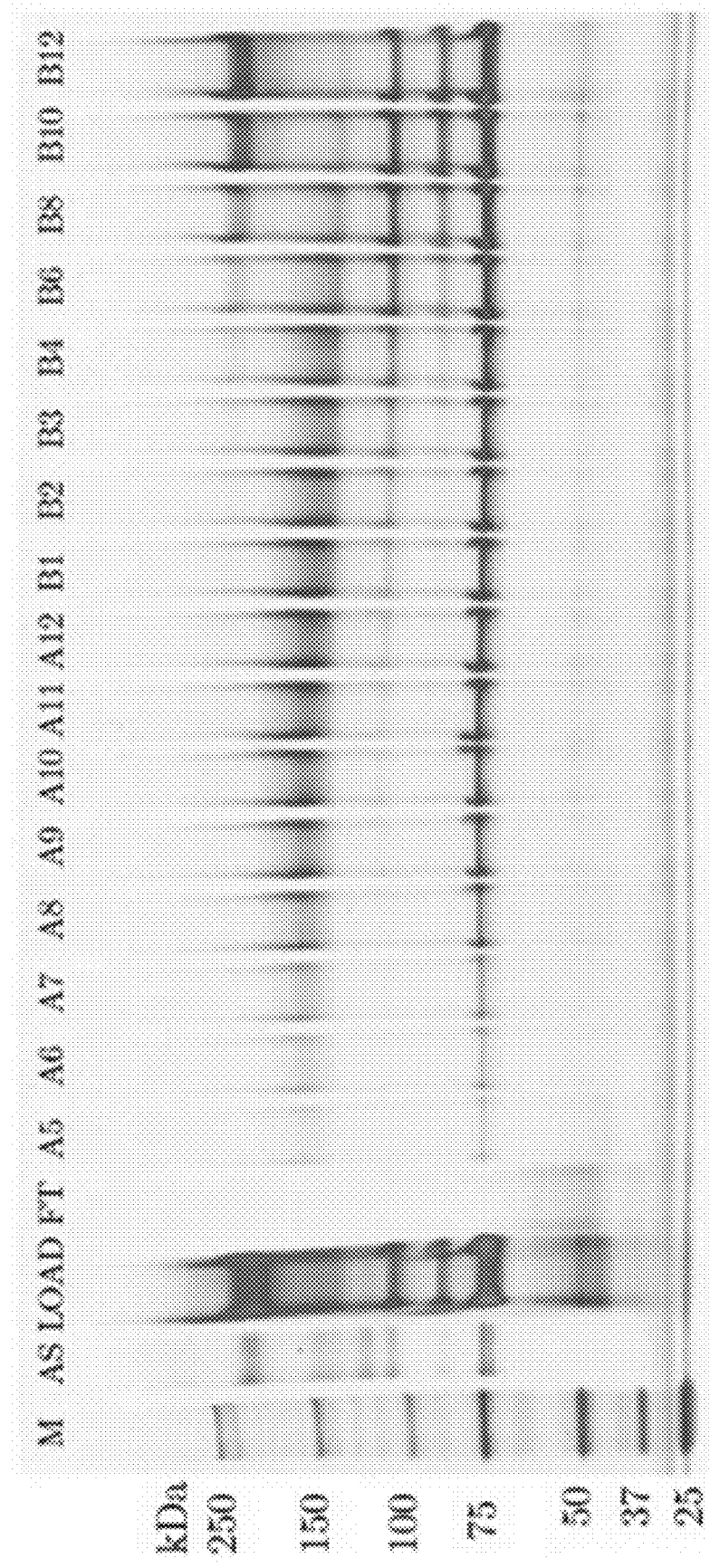

FIG. 17: SDS page gel electrophoresis of the two-dimensional HIC step for purification of FVIII molecular subspecies from the furin treated starting material B14390000-30. M) Molecular weight marker, AS) Standard of the commercially available FVIII drug substance, showing all relevant heavy- and light chain species, FT) Flow Through, Fractions A5-B12. Figure continued in FIG. 18.

Figure 18:
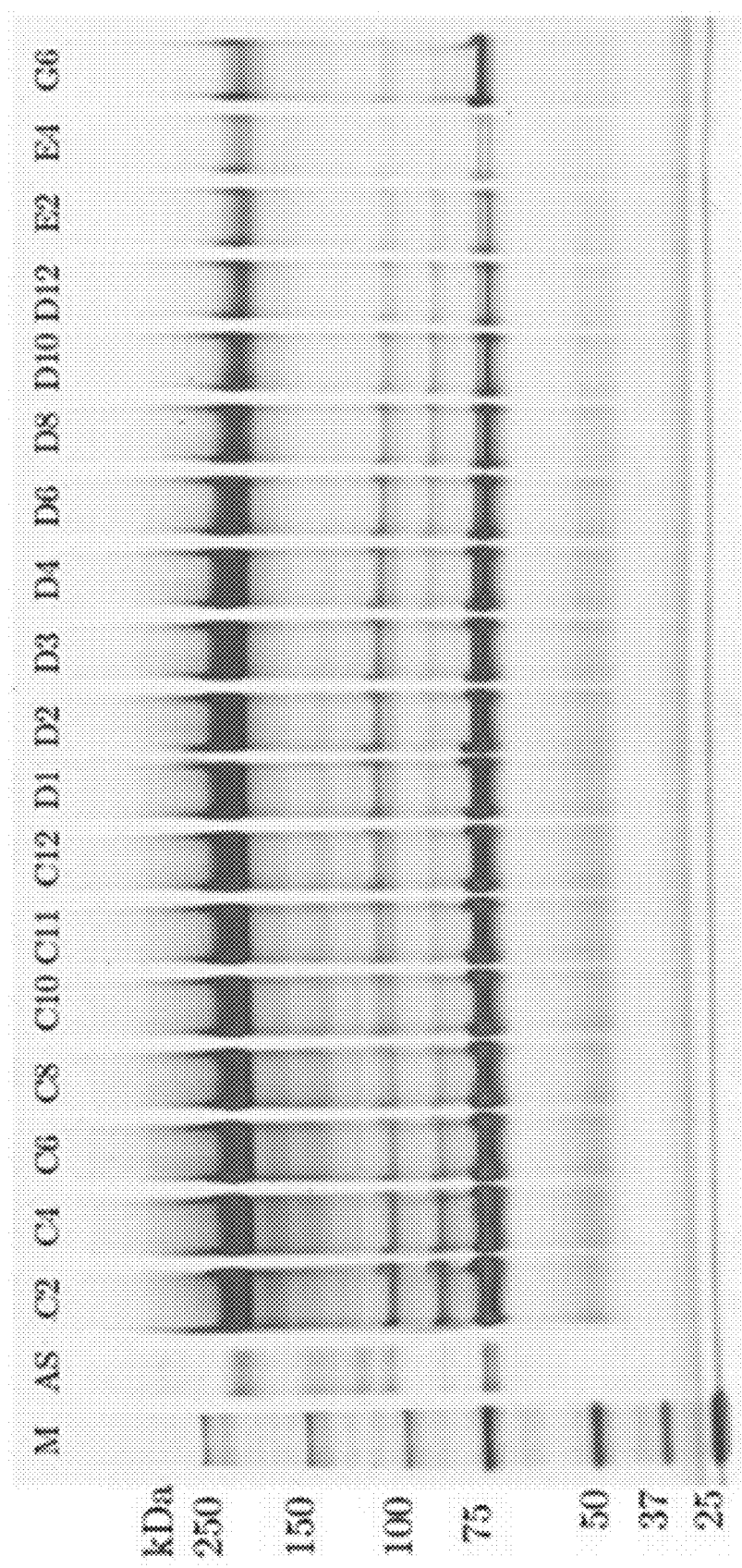

FIG. 18: SDS page gel electrophoresis of the two-dimensional HIC step for purification of FVIII molecular subspecies from the furin treated starting material B14390000-10. M) Molecular weight marker, AS) Standard of the commercially available FVIII drug substance, showing all relevant heavy- and light chain species, Fractions C2-G6.

Figure 19:
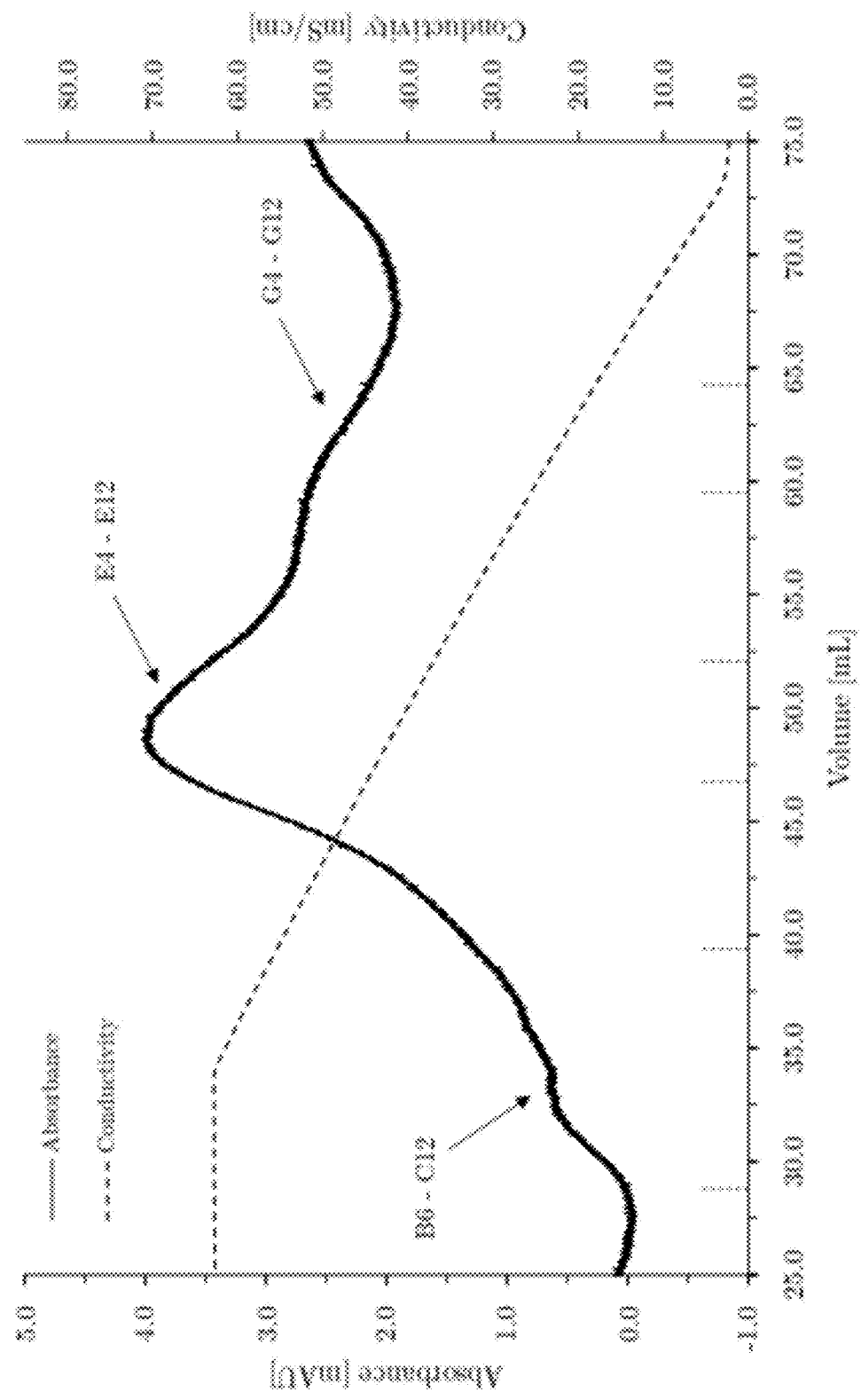

FIG. 19: Chromatogram of the one-dimensional elution phase of FVIII molecular subspecies separated on phenyl sepharose high performance. Gradient: 680.0-0.0 mM sodium chloride in 40 column volumes. Column dimensions: 0.5 cm inner diameter×5.0 cm bed height, 0.98 mL column volume.

Figure 20:
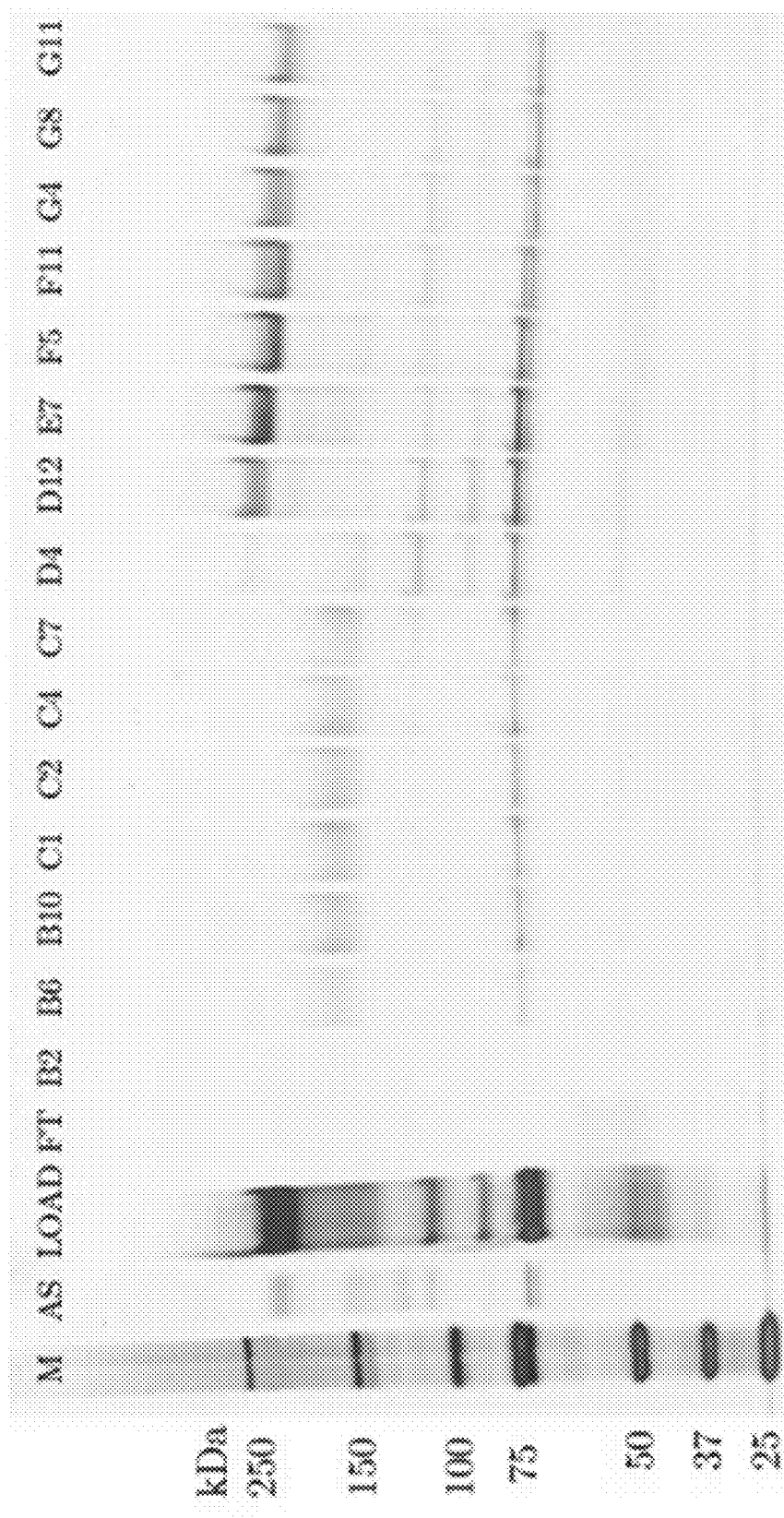

FIG. 20: SDS page gel electrophoresis of the one-dimensional HIC step for purification of the 150 kDa truncated heavy chain fragment from the furin treated starting material B14390000-10. M) Molecular weight marker, AS) Standard of the commercially available FVIII drug substance, showing all relevant heavy- and light chain species, FT) Flow Through, Fractions B2-G11.

Figure 21:
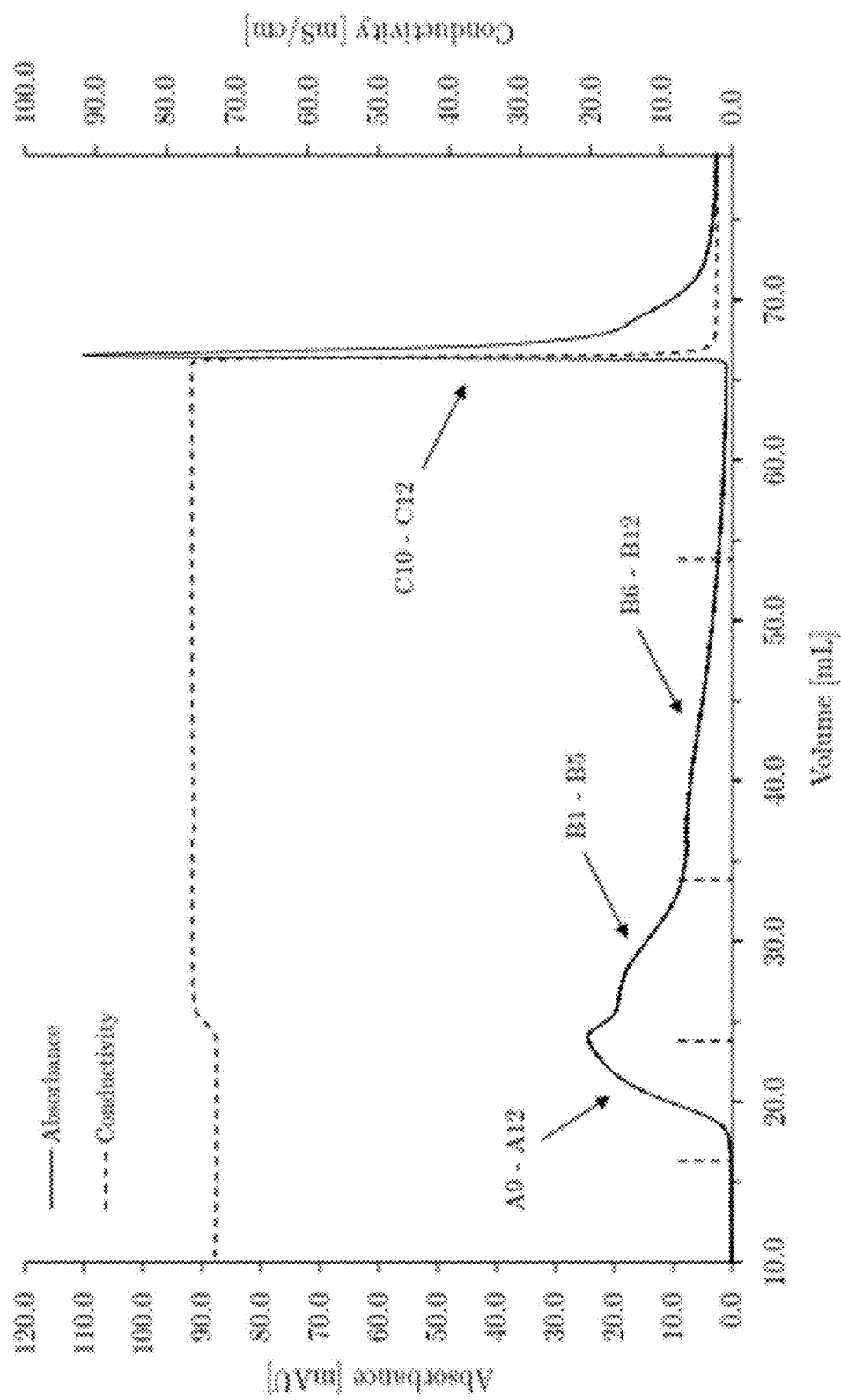

FIG. 21: Chromatogram of the negative mode washing and elution phase of FVIII molecular subspecies separated on phenyl sepharose high performance. Washing phase: 860 mM sodium chloride for 30 column volumes, Step elution: 0 mM sodium chloride for 10 column volumes. Column dimensions: 0.5 cm inner diameter×5.0 cm bed height, 0.98 mL column volume.

Figure 22:
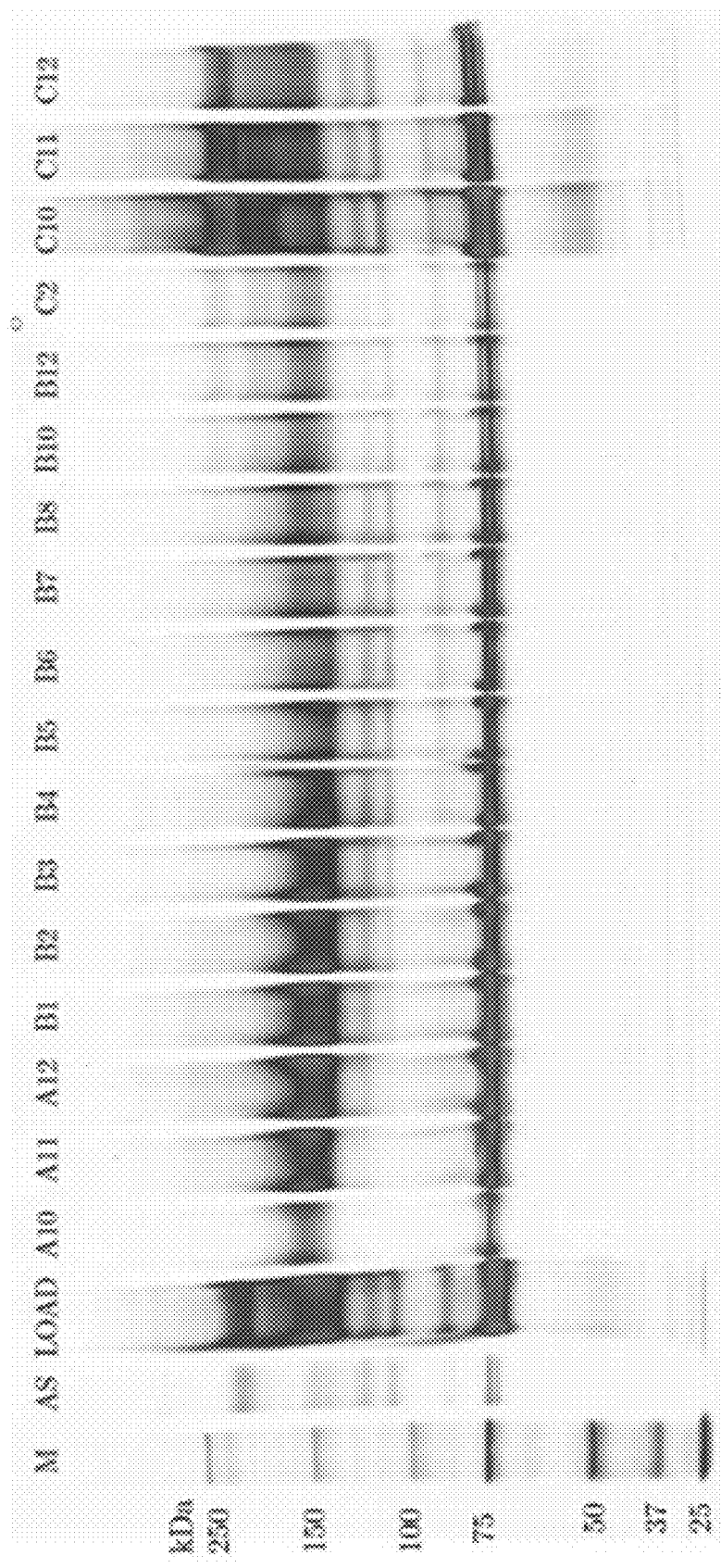

FIG. 22: SDS page gel electrophoresis of the negative mode HIC step for purification of the 150 kDa truncated heavy chain fragment. M) Molecular weight marker, AS) Standard of the commercially available FVIII drug substance, showing all relevant heavy- and light chain species, Fractions A10-C12.

Figure 23:
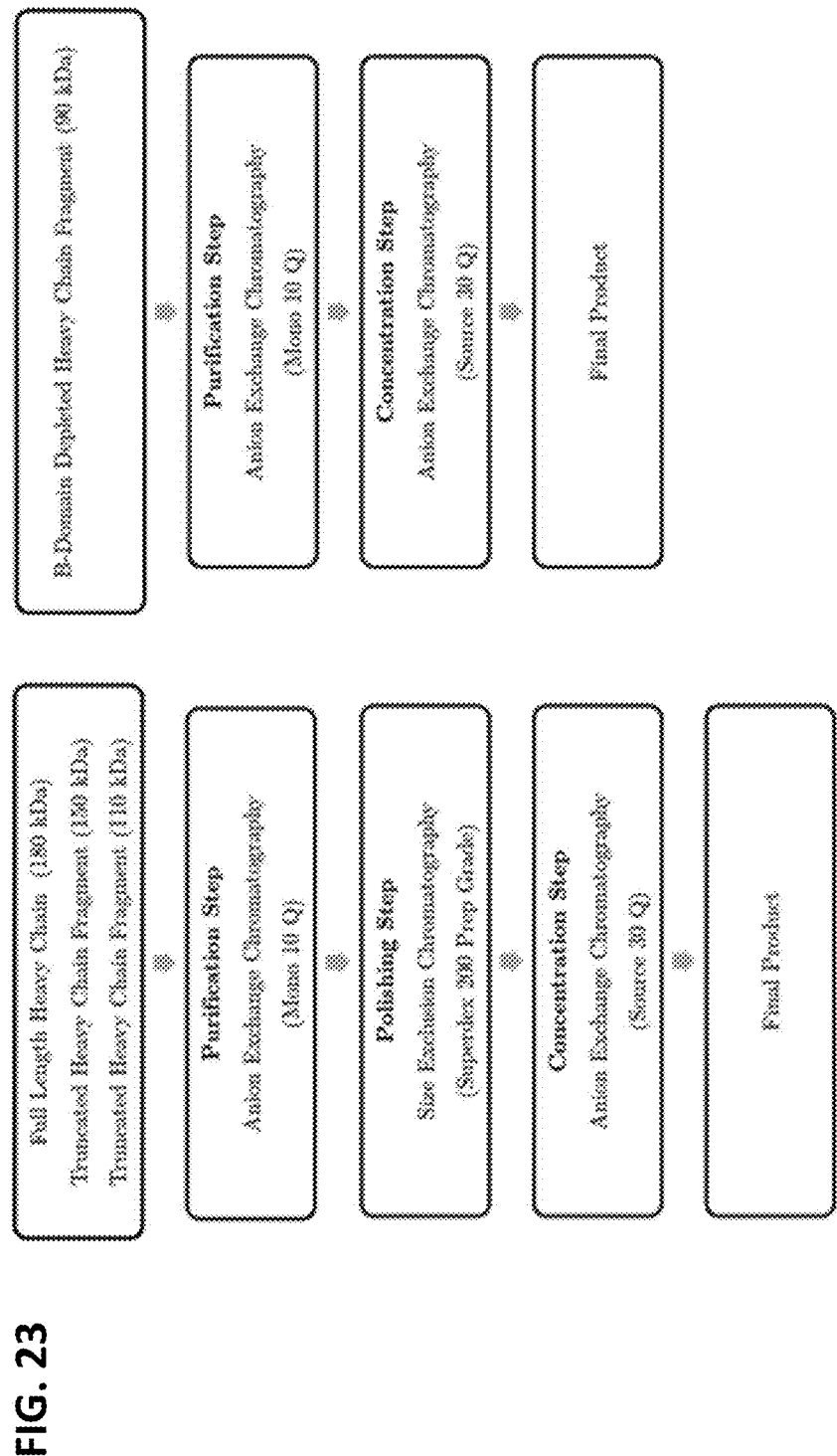

FIG. 23: Flow diagram of preparative purification process of FVIII molecular subspecies. The purification strategy for the subspecies with 180 kDa, 150 kDa and 110 kDa molecular weight includes two purification steps by AIEX (MonoQ) and SEC (Superdex 200) and finally a concentration step by AIEX (SourceQ). The B-domain depleted heavy chain fragment does not require further purification by size exclusion chromatography and is therefore applied to the MonoQ AIEX and afterwards concentrated on the SourceQ AIEX.

Figure 24:
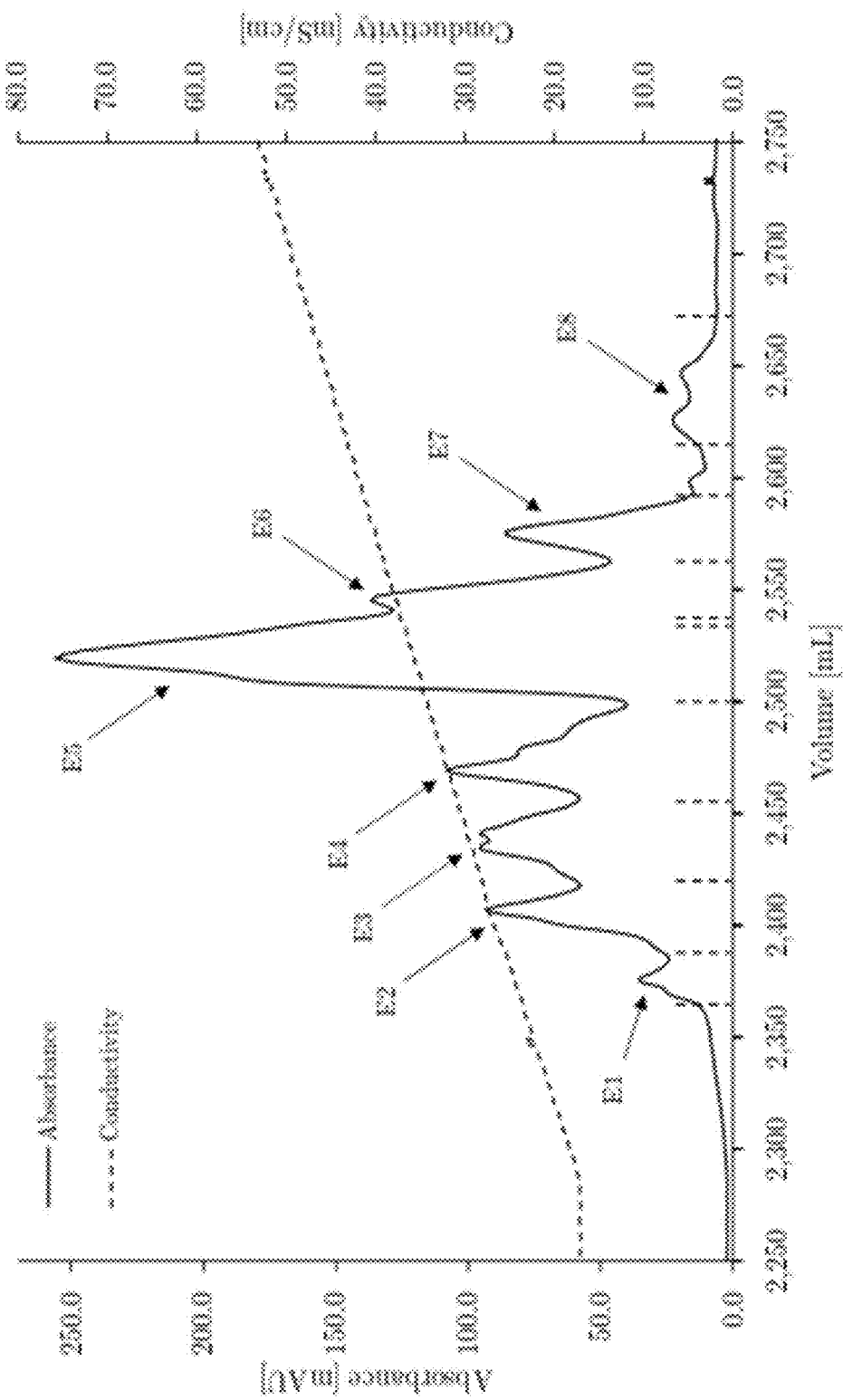

FIG. 24: Chromatogram of the preparative scale anion exchange chromatography elution phase of FVIII molecular subspecies separated on MonoQ resin. Gradient elution: 135-750 mM sodium chloride in 32 column volumes. Column dimensions: 1.6 cm inner diameter×10.0 cm bed height, 20.160 mL column volume. Fraction size: E1: 22.6 mL, E2: 31.5 mL, E3: 34.6 mL, E4: 43.7 mL, E5: 28.9 mL, E6: 22.9 mL, E7: 26.1 mL, E8: 53.1 mL.

Figure 25:
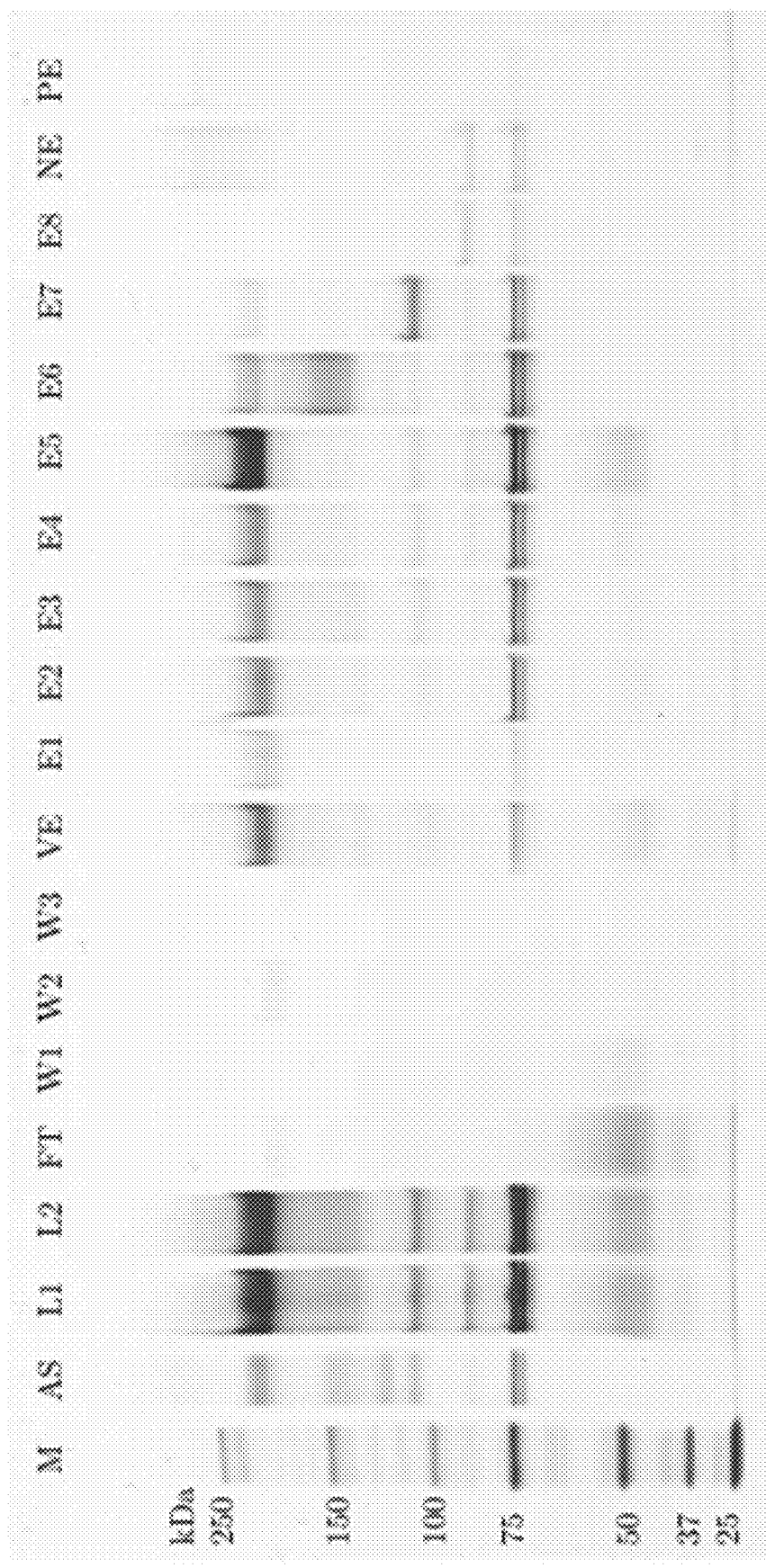

FIG. 25: SDS page gel electrophoresis of the preparative anion exchange chromatography step for purification of FVIII molecular subspecies. M) Molecular weight marker, AS) Standard of the commercially available FVIII drug substance, showing all relevant heavy- and light chain species, L1) Load prior to filtration, L2) Load after filtration, FT) Flow Through, W1) Washing step 1, W2) Washing step 2, W3) Washing step 3, VB) Pre eluate, E1-E8) Eluate Pool 1-8, NE) Posteluate 1, PE) Posteluate 2.

Figure 26:
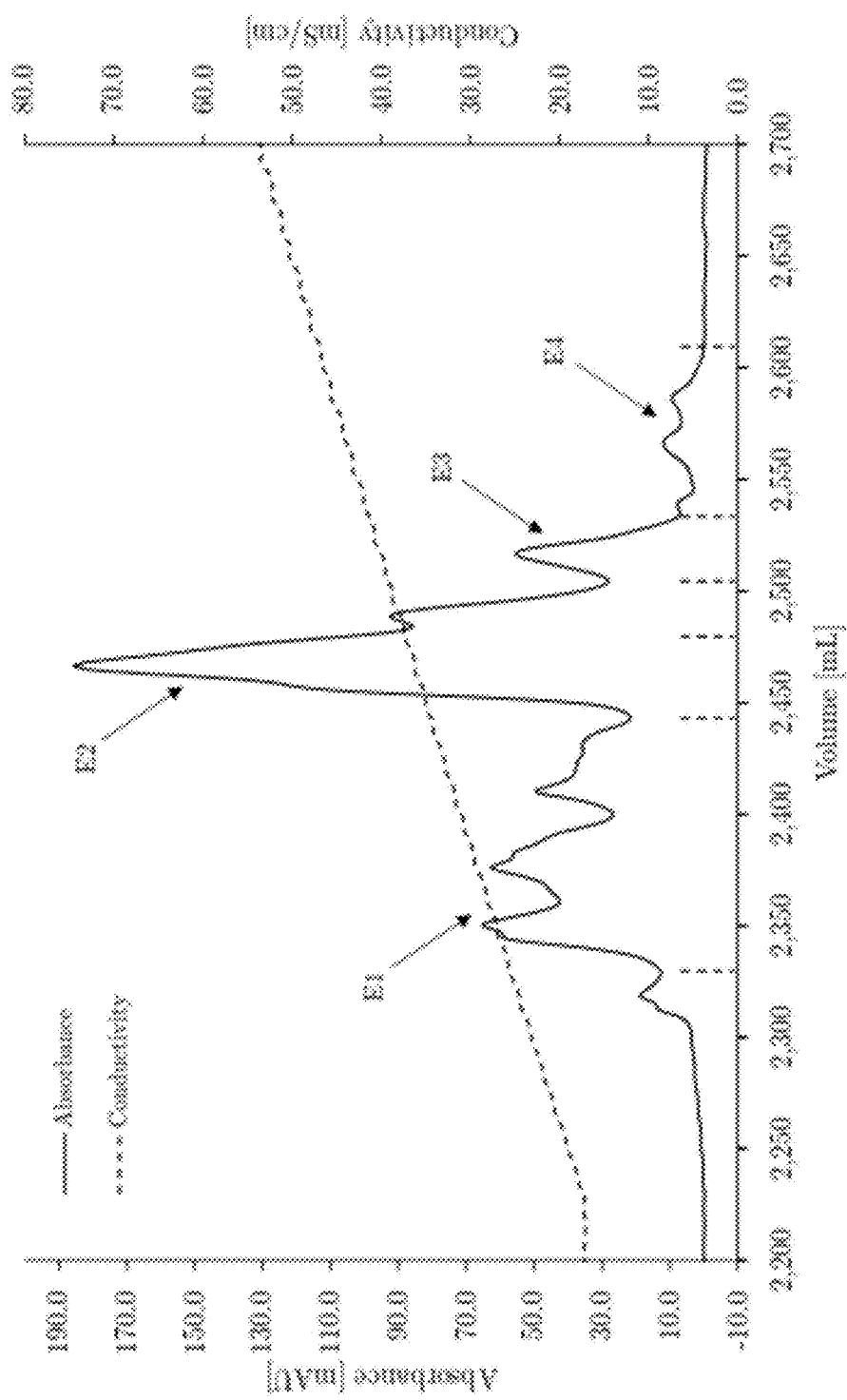

FIG. 26: Chromatogram of the preparative scale anion exchange chromatography elution phase of FVIII molecular subspecies separated on MonoQ resin. Gradient elution: 135-750 mM sodium chloride in 32 column volumes. Column dimensions: 1.6 cm inner diameter×10.0 cm bed height, 20.160 mL column volume. Fraction size: E1: 114.9 mL, E2: 24.0 mL, E3: 22.8 mL, E4: 83.6 mL.

Figure 27:
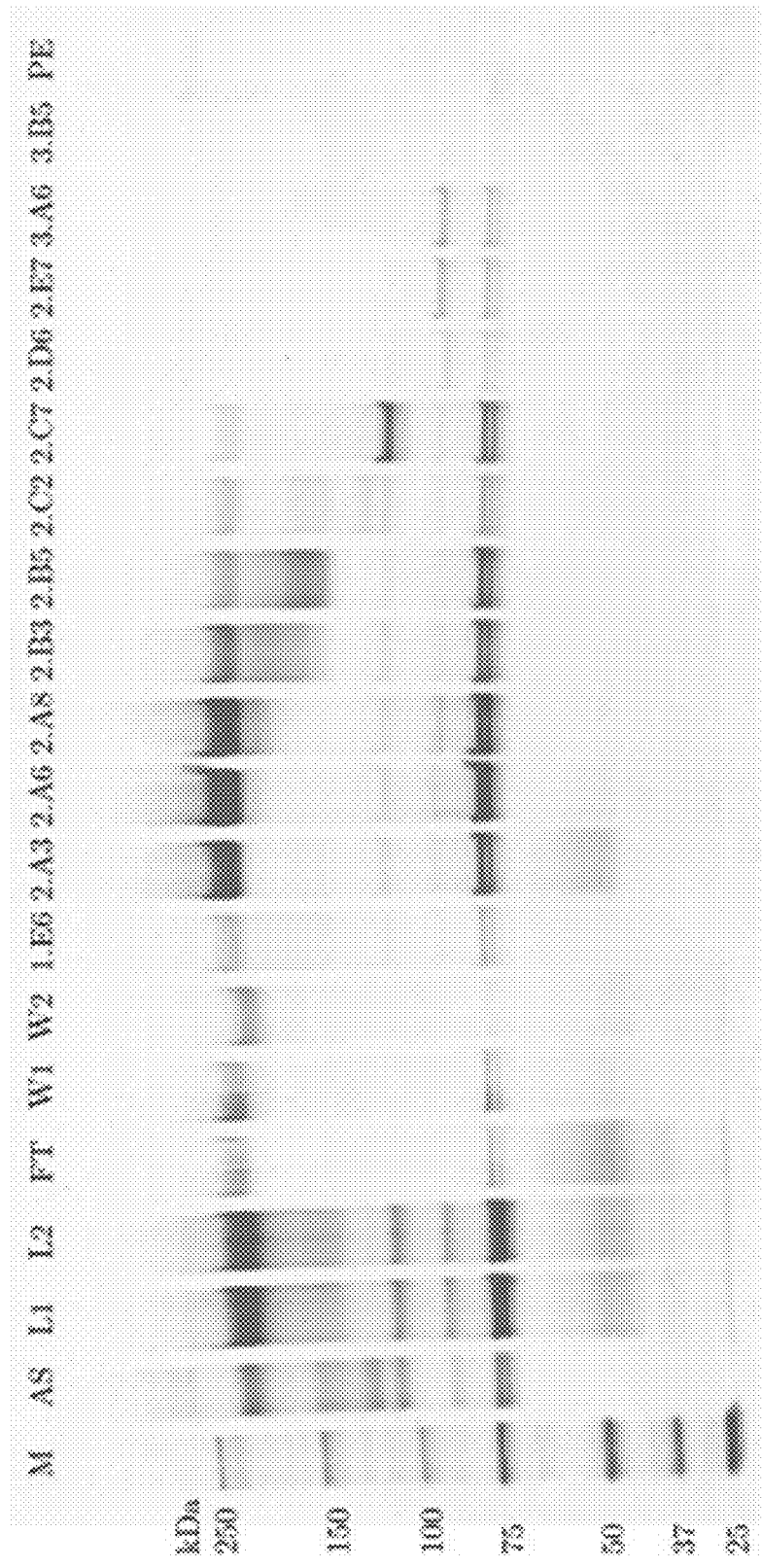

FIG. 27: SDS page gel electrophoresis of the preparative scale anion exchange chromatography step for purification of FVIII molecular subspecies. M) Molecular weight marker, AS) Standard of the commercially available FVIII drug substance, showing all relevant heavy- and light chain species, L1) Load prior to filtration, L2) Load after filtration, FT) Flow Through, W1) Washing step 1, W2) Washing step 2, Fractions 1.E6-3.B5, PE) Posteluate.

Figure 28:
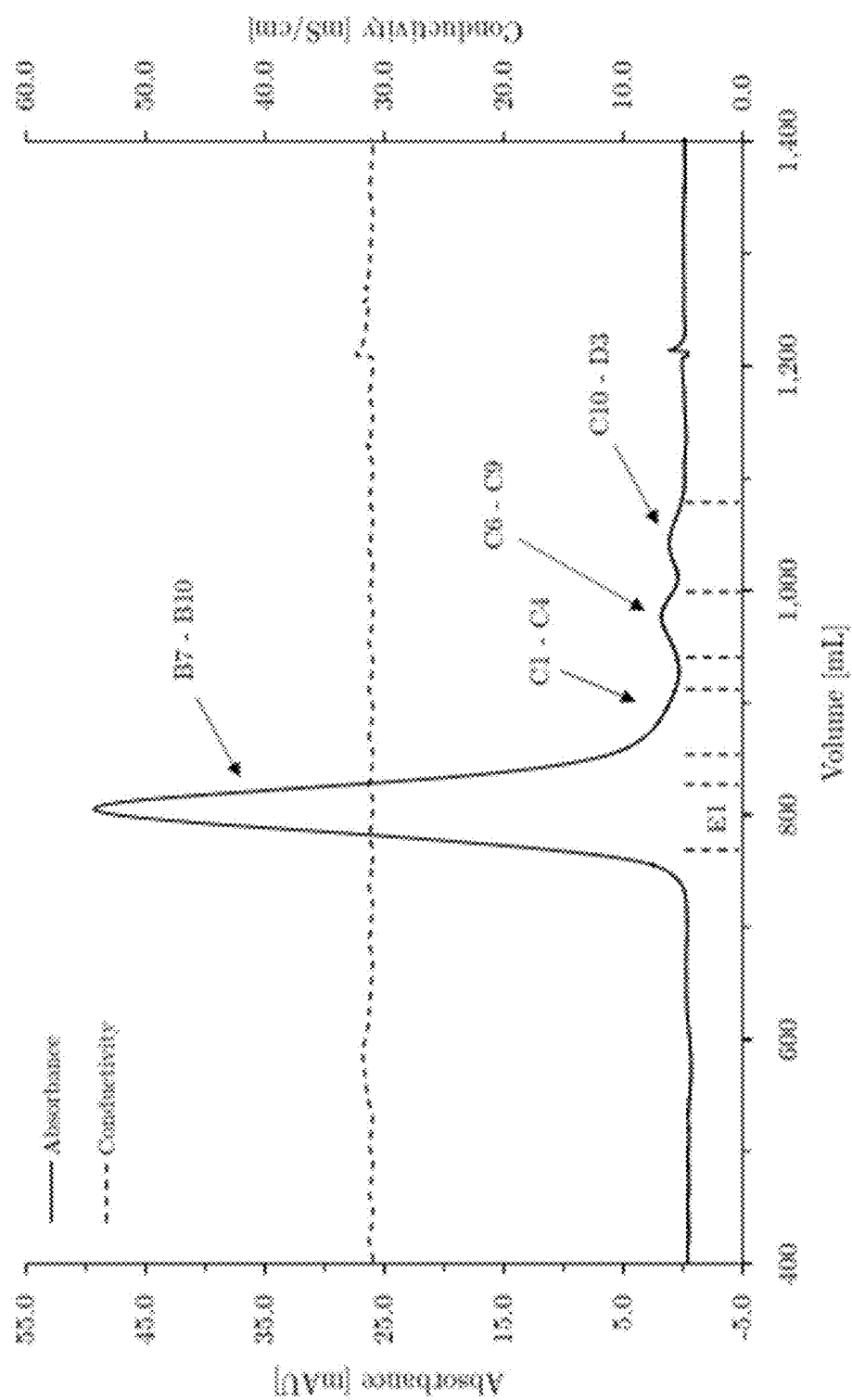

FIG. 28: Chromatogram of the preparative scale size exclusion chromatography for the purification of the 180 kDa full length heavy chain. Column dimensions: 5.0 cm inner diameter×94.4 cm bed height, 1853.54 mL column volume. Fraction size E1: 70.0 mL.

Figure 29:
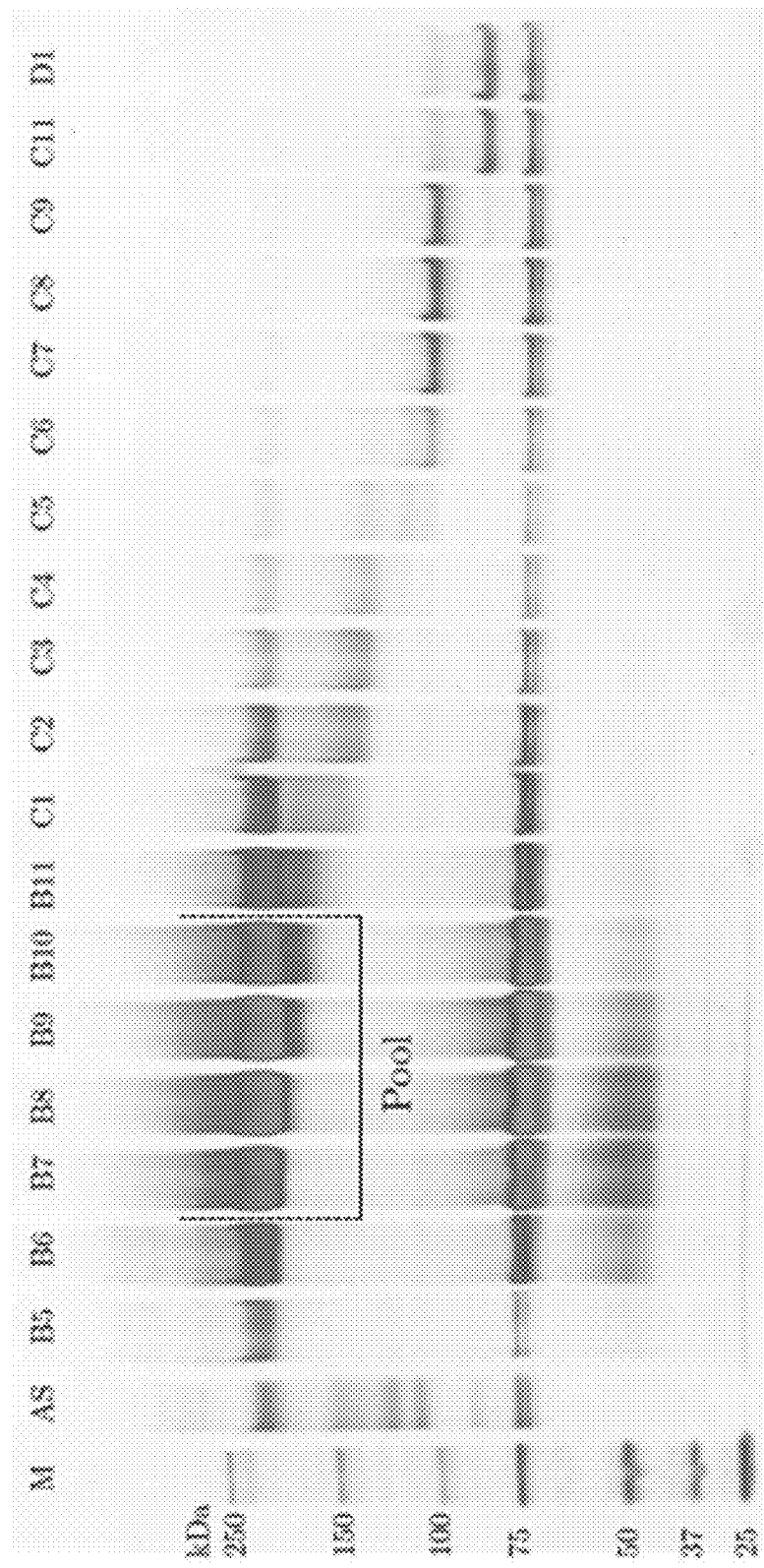

FIG. 29: SDS page gel electrophoresis of the preparative scale size exclusion chromatography step for the purification of the 180 kDa full length heavy chain derived from preparative MonoQ anion exchange chromatography. M) Molecular weight marker, AS) Standard of the commercially available FVIII drug substance, showing all relevant heavy- and light chain species, Fractions B5-D1.

Figure 30:
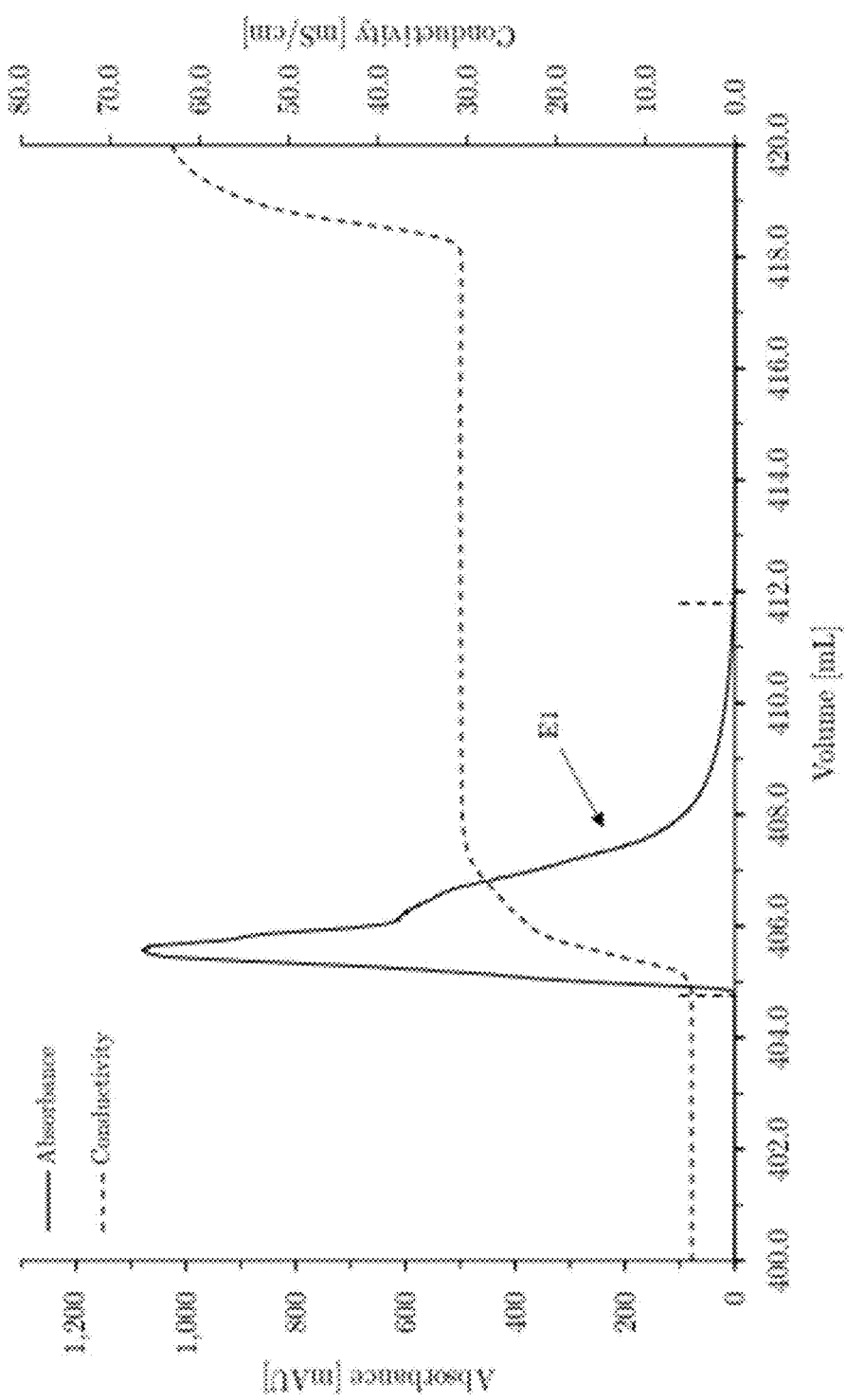

FIG. 30: Chromatogram of the preparative scale anion exchange chromatography elution phase of the 180 kDa full length heavy chain concentrated on SourceQ resin. Step elution: 300 mM sodium chloride. Column dimensions: 1.0 cm inner diameter×3.9 cm bed height, 3.06 mL column volume. Fraction size E1: 6.98 mL.

Figure 31:
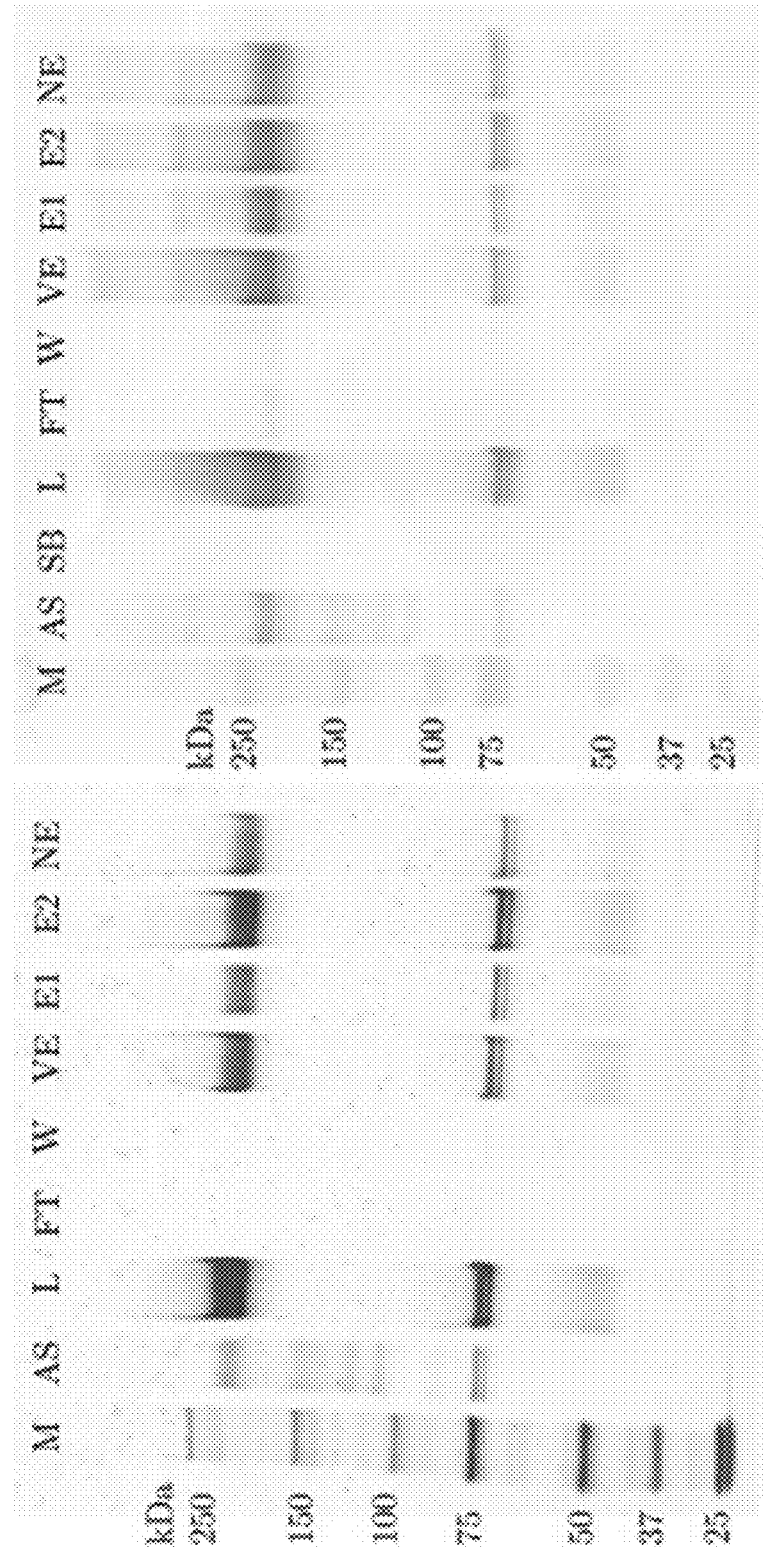

FIG. 31: SDS page gel electrophoresis of the SourceQ AIEX step for concentration of the 180 kDa full length heavy chain derived from preparative scale size exclusion chromatography, silver stained (left) and FVIII western blot (right). M) Molecular weight marker, AS) Standard of the commercially available FVIII drug substance, showing all relevant heavy- and light chain species, L) Load, SB) Sample buffer, FT) Flow through, W) Washing phase, VE) Pre-eluate, E1) Eluate pool in 1:198 dilution (silver stain) and 1:264 dilution (FVIII western blot), E2) Eluate pool in 1:66 dilution (silver stain) and 1:88 dilution (FVIII western blot), NE) Posteluate.

Figure 32:
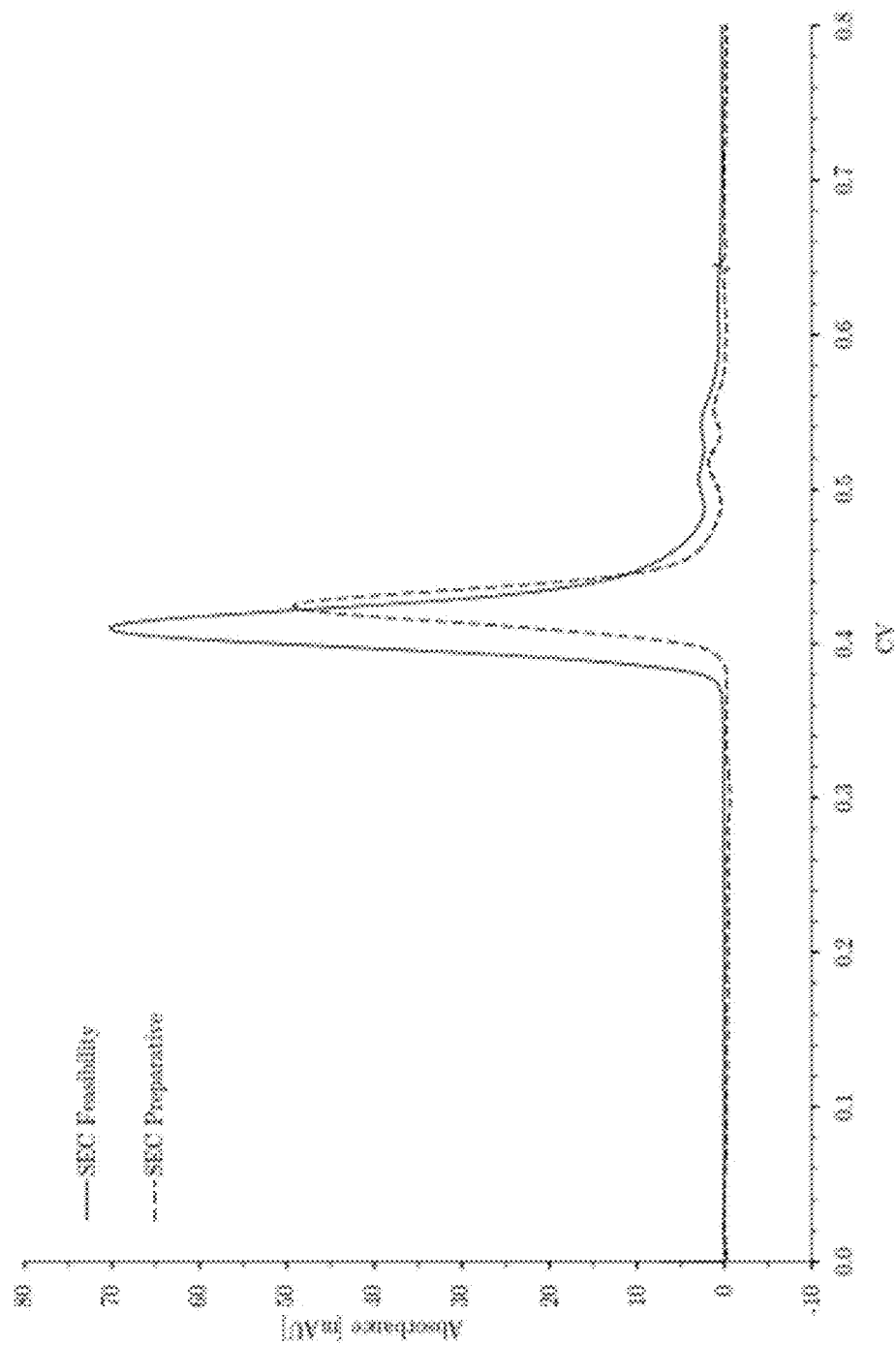

FIG. 32: Performance comparison of (1) small scale SEC column Superdex 200 Increase (solid line) and the preparative scale SEC column Superdex 200 Prep Grade (broken line). Both curves show the respective elution phases of the full length heavy chain with a molecular weight of 180 kDa. Column dimensions: (1) 1.0 cm inner diameter×30.0 cm bed height, 23.56 mL column volume, (2) 5.0 cm inner diameter×94.4 cm bed height, 1853.54 mL column volume.

Figure 33:
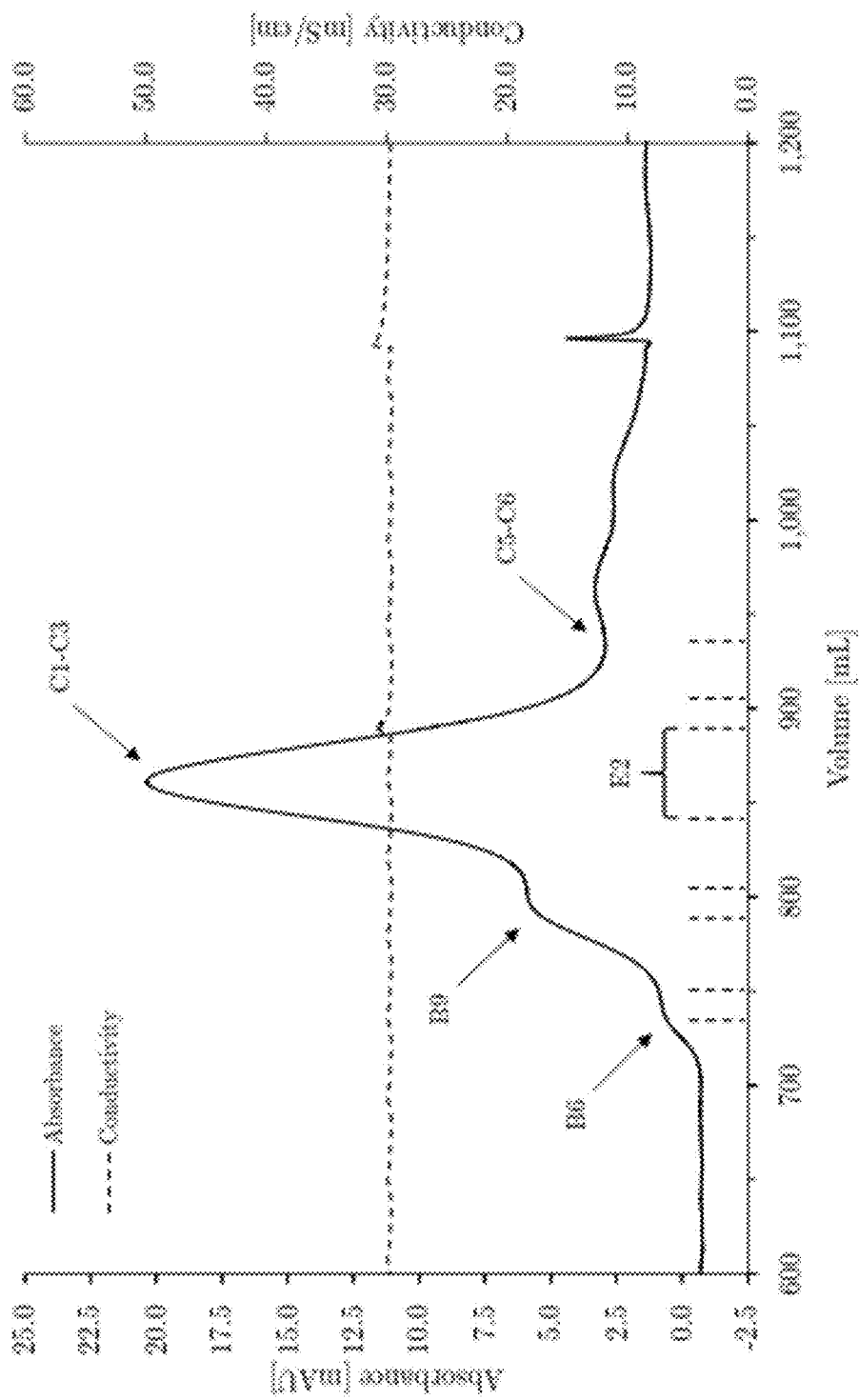

FIG. 33: Chromatogram of the preparative scale size exclusion chromatography for the purification of the 150 kDa truncated heavy chain fragment. Column dimensions: 5.0 cm inner diameter×94.4 cm bed height, 1853.54 mL column volume. Fraction size: C1: 15.80 mL, C2: 15.75 mL, C3: 15.74 mL, E2: 45.69 mL.

Figure 34:
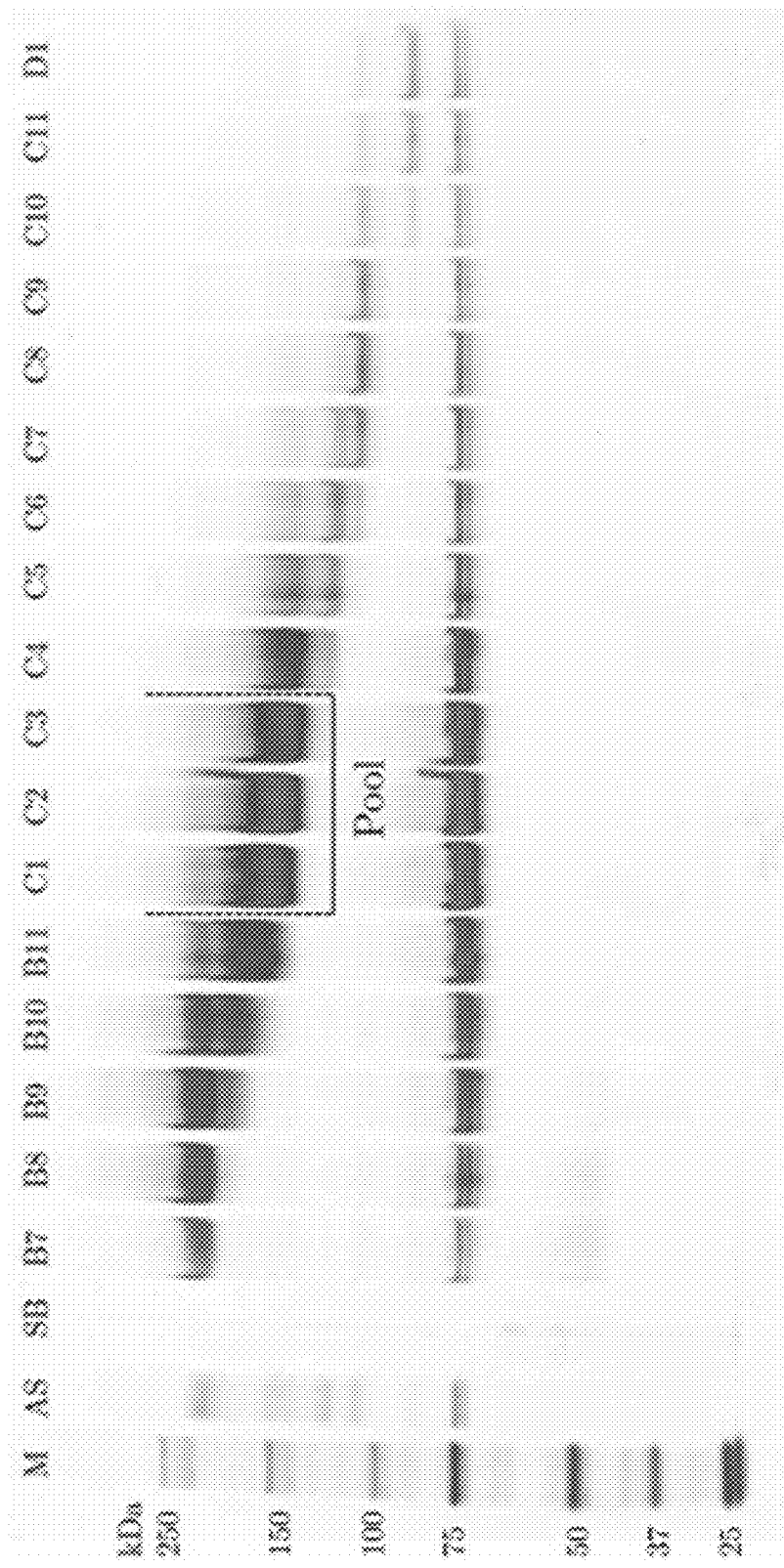

FIG. 34: SDS page gel electrophoresis of the preparative scale size exclusion chromatography step for the purification of the 150 kDa truncated heavy chain fragment derived from preparative MonoQ anion exchange chromatography. M) Molecular weight marker, AS) Standard of the commercially available FVIII drug substance, showing all relevant heavy- and light chain species, SB) Sample buffer, Fractions B7-D1.

Figure 35:
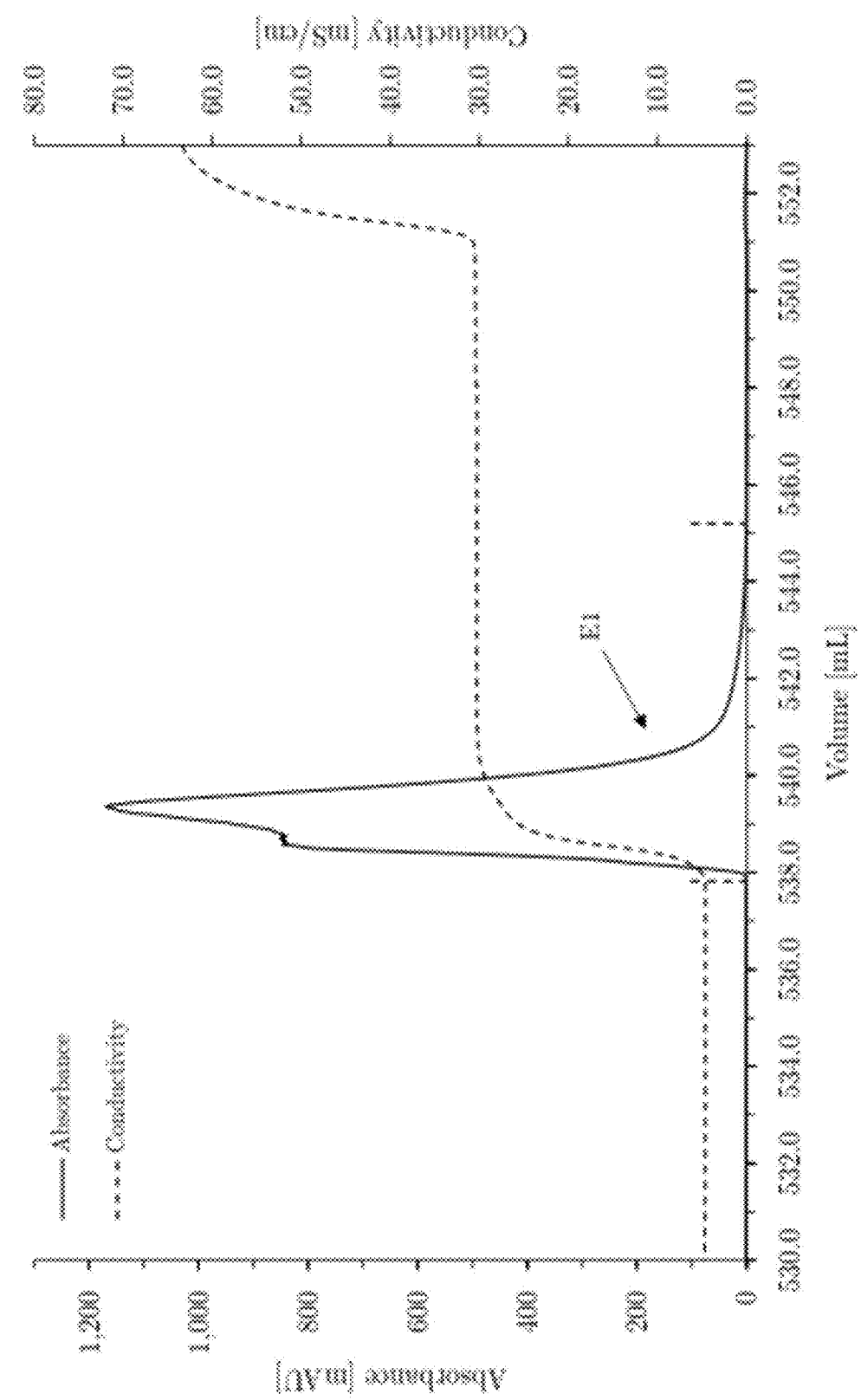

FIG. 35: Chromatogram of the preparative scale anion exchange chromatography elution phase of the 150 kDa full length heavy chain concentrated on SourceQ resin. Step elution: 300 mM sodium chloride. Column dimensions: 1.0 cm inner diameter×3.9 cm bed height, 3.06 mL column volume. Fraction size E2: ~7.5 mL.

Figure 36:
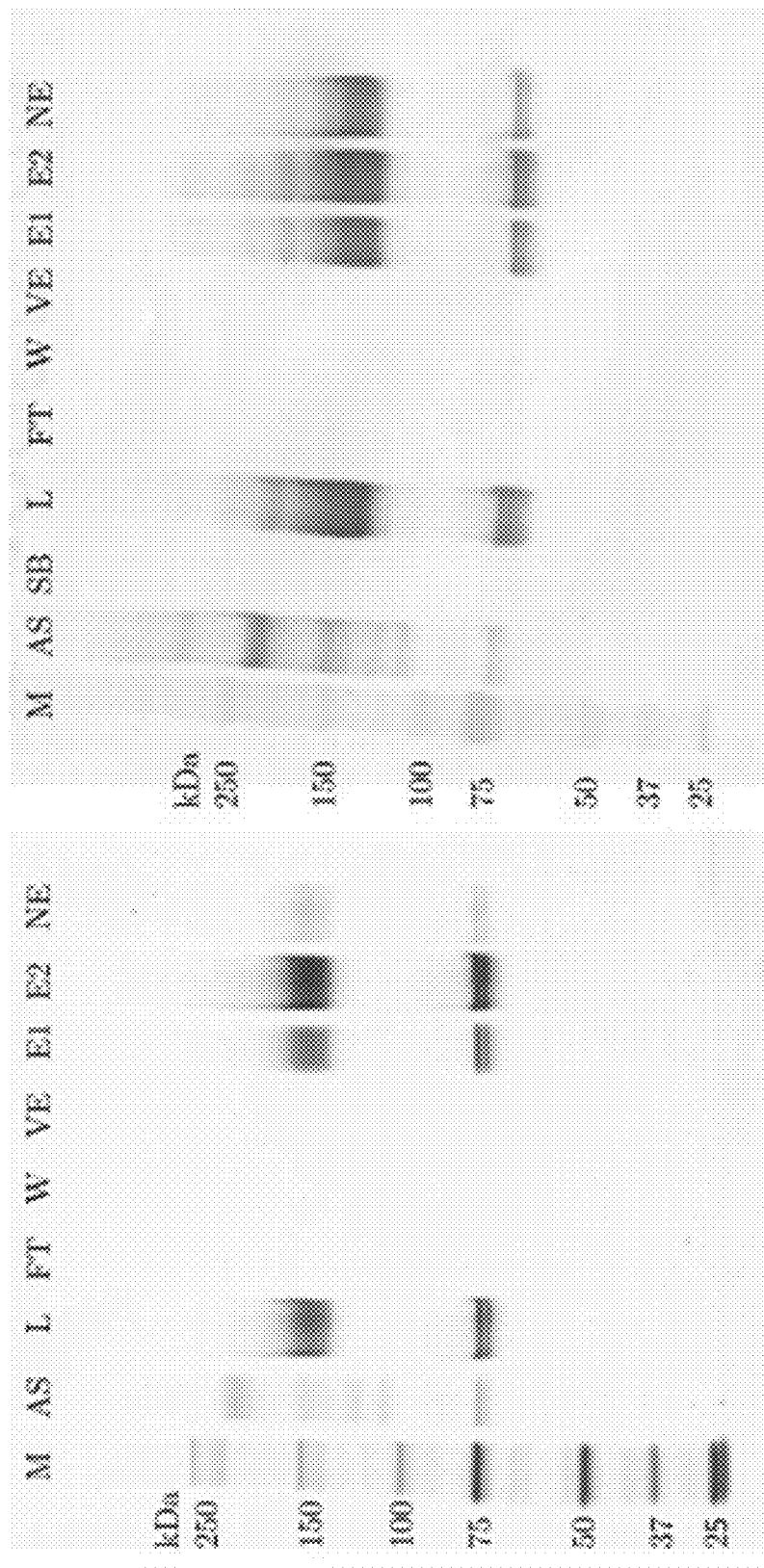

FIG. 36: SDS page gel electrophoresis of the SourceQ AIEX step for concentration of the 150 kDa truncated heavy chain fragment derived from preparative scale size exclusion chromatography, silver stained (left) and FVIII western blot (right). M) Molecular weight marker, AS) Standard of the commercially available FVIII drug substance, showing all relevant heavy- and light chain species, L) Load, SB) Sample buffer, FT) Flow through, W) Washing phase, VE) Pre-eluate, E1) Eluate pool in 1:120 dilution (silver stain) and 1:160 dilution (FVIII western blot), E2) Eluate pool in 1:40 dilution (silver stain) and 1:53 dilution (FVIII western blot), NE) Posteluate.

Figure 37:
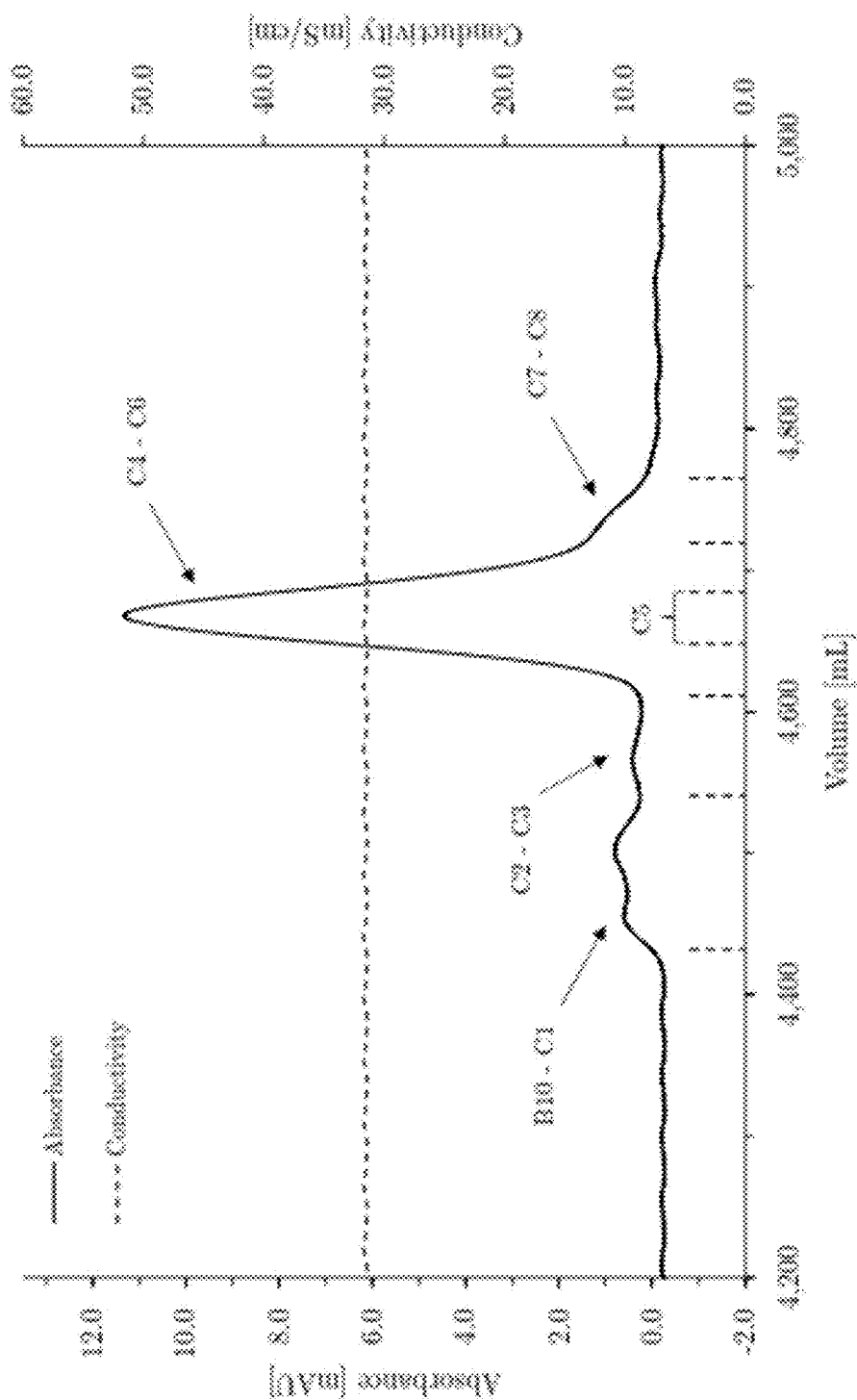

FIG. 37: Chromatogram of the preparative scale size exclusion chromatography for the purification of the 110 kDa truncated heavy chain fragment. Column dimensions: 5.0 cm inner diameter×94.4 cm bed height, 1853.54 mL column volume. Fraction size: B10-C1: 140 mL, C2-C3: 70 mL, C4: 35 mL, C5: 35 mL, C6: 35 mL, C7-C8: 70 mL.

Figure 38:
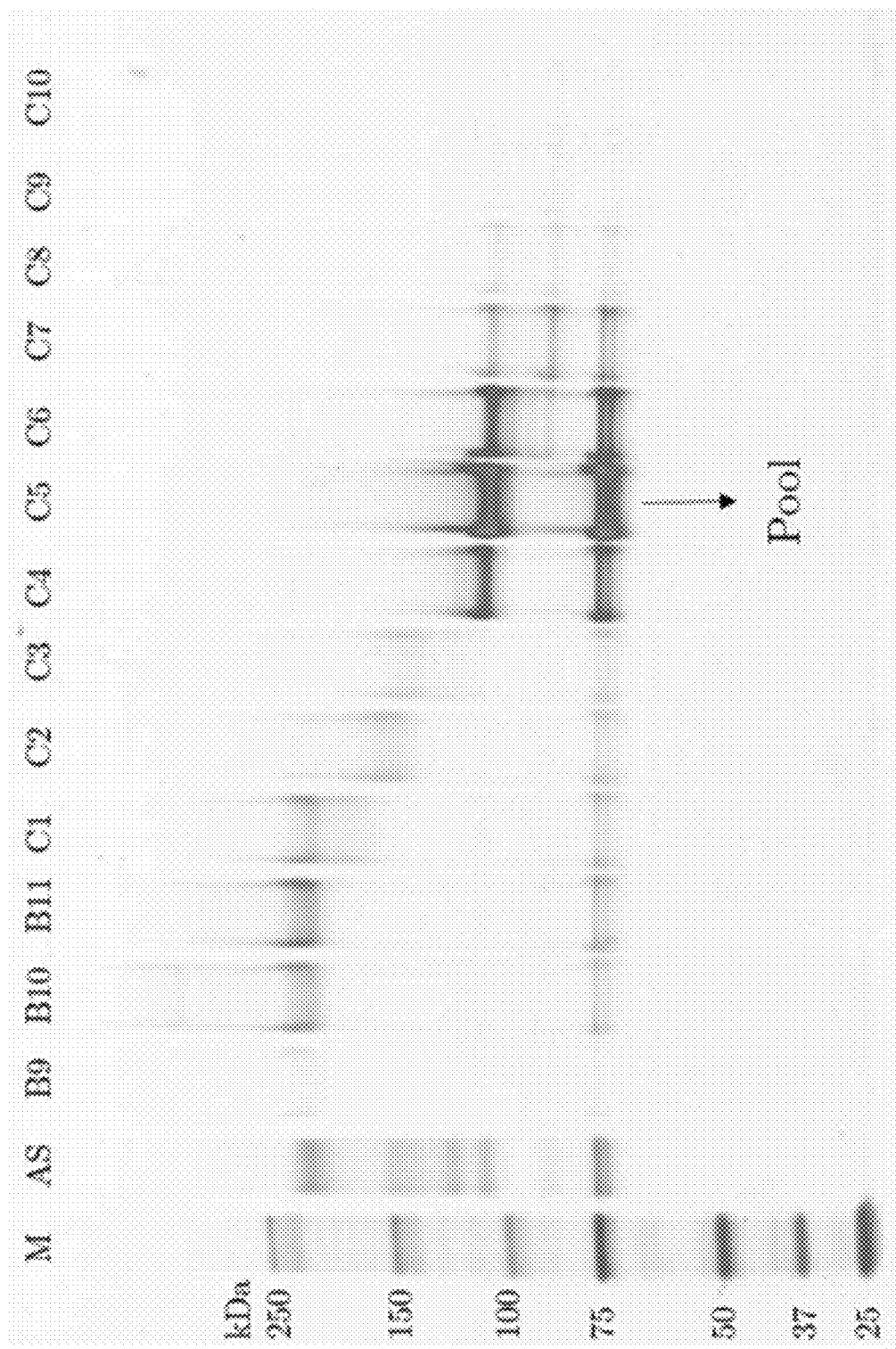

FIG. 38: SDS page gel electrophoresis of the preparative scale size exclusion chromatography step for the purification of the 110 kDa truncated heavy chain fragment derived from preparative MonoQ anion exchange chromatography. M) Molecular weight marker, AS) Standard of the commercially available FVIII drug substance, showing all relevant heavy- and light chain species, Fractions B9-C10.

Figure 39:
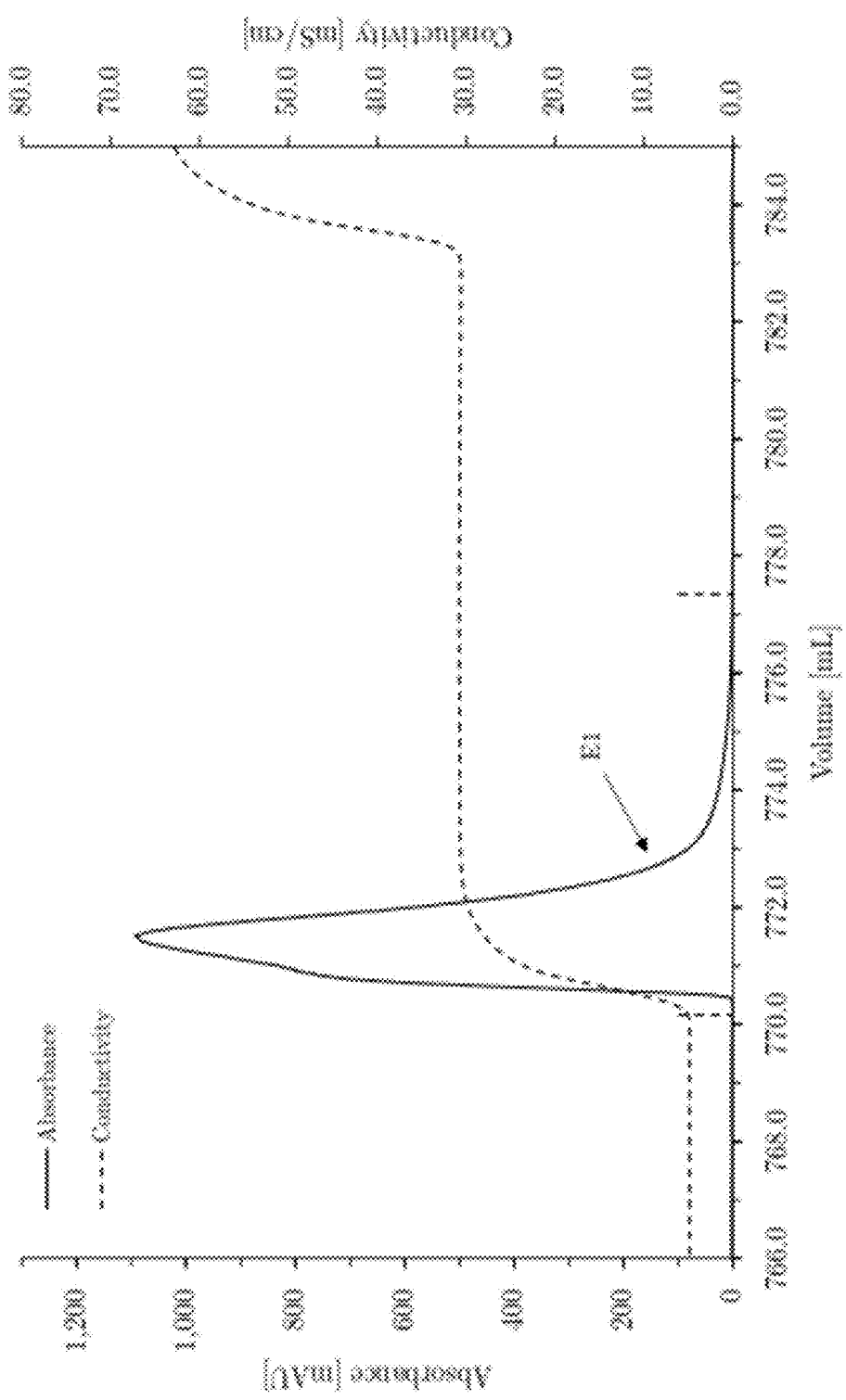

FIG. 39: Chromatogram of the preparative scale anion exchange chromatography elution phase of the 110 kDa full length heavy chain concentrated on SourceQ resin. Step elution: 300 mM sodium chloride. Column dimensions: 1.0 cm inner diameter×3.9 cm bed height, 3.06 mL column volume. Fraction size E1: 7.20 mL.

Figure 40:
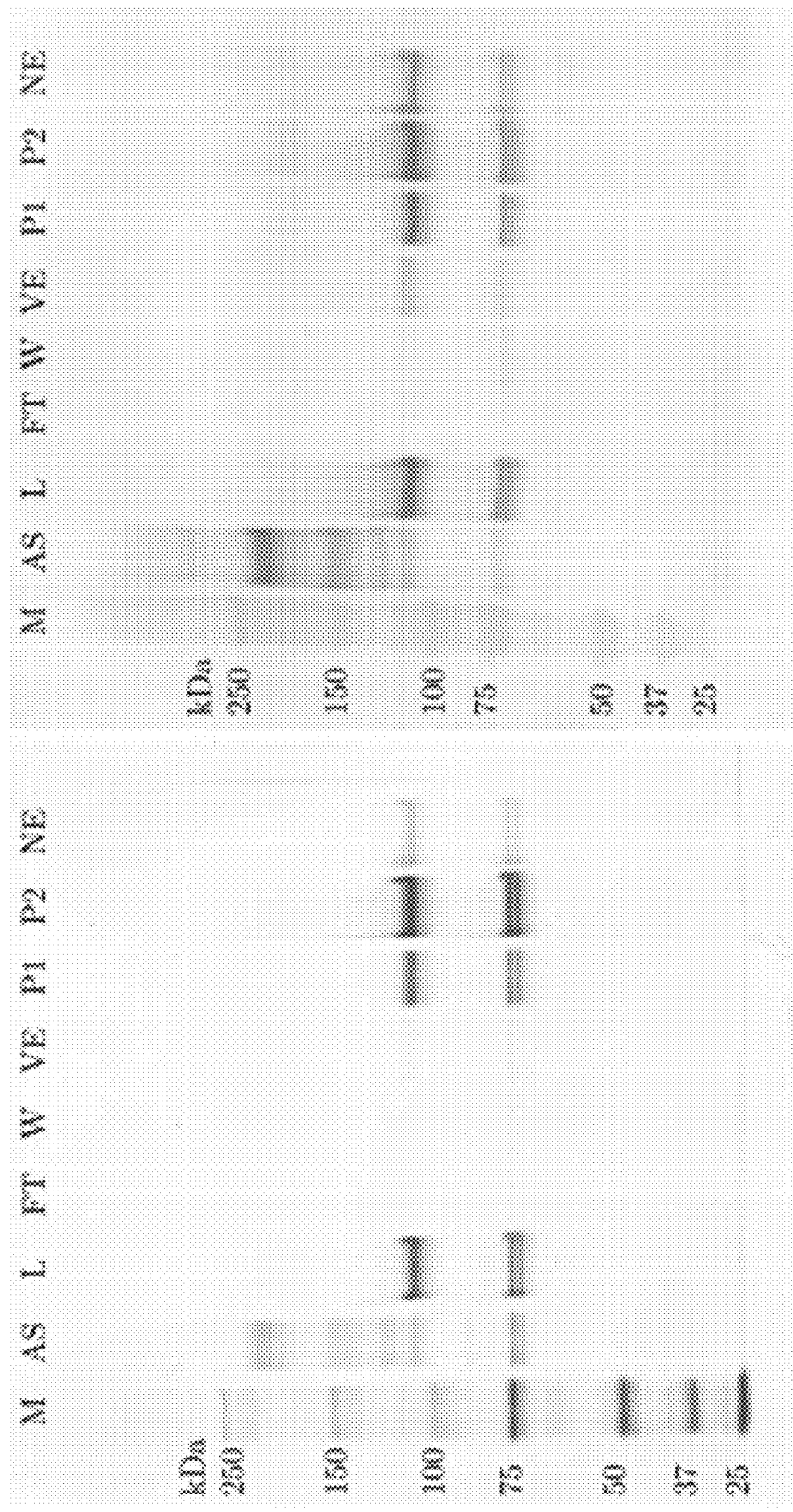

FIG. 40: SDS page gel electrophoresis of the SourceQ AIEX step for concentration of the 110 kDa truncated heavy chain fragment derived from preparative scale size exclusion chromatography, silver stained (left) and FVIII western blot (right). M) Molecular weight marker, AS) Standard of the commercially available FVIII drug substance, showing all relevant heavy- and light chain species, L) Load, FT) Flow through, W) Washing phase, VE) Pre-eluate, E1) Eluate pool in 1:147 dilution (silver stain) and 1:196 dilution (FVIII western blot), E2) Eluate pool in 1:49 dilution (silver stain) and 1:65 dilution (FVIII western blot), NE) Posteluate.

Figure 41:
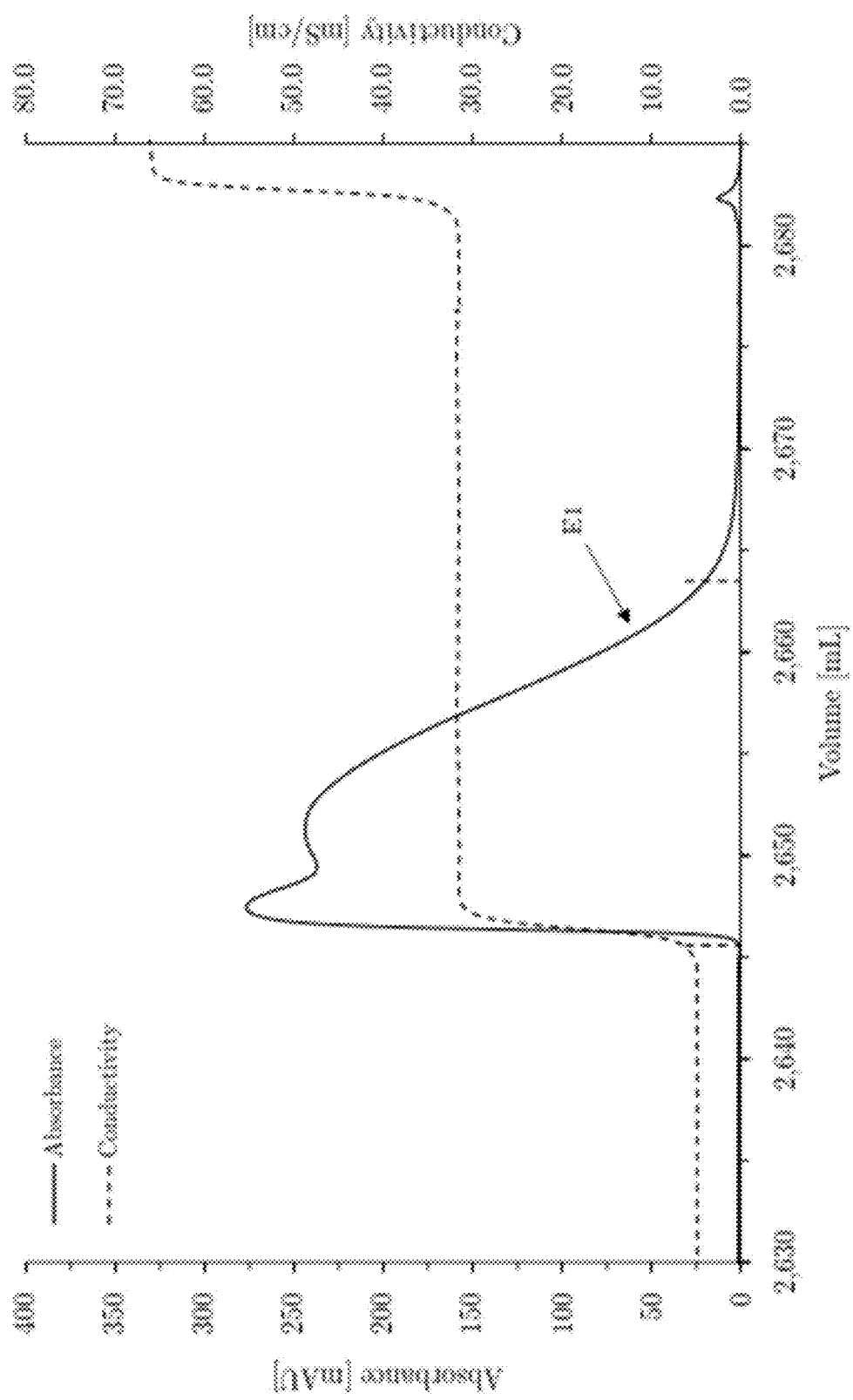

FIG. 41: Chromatogram of the preparative scale anion exchange chromatography elution phase of the 90 kDa full length heavy chain concentrated on SourceQ resin. Step elution: 300 mM sodium chloride. Column dimensions: 1.0 cm inner diameter×8.9 cm bed height, 7.0 mL column volume. Fraction size E1: 18.37 mL.

Figure 42:
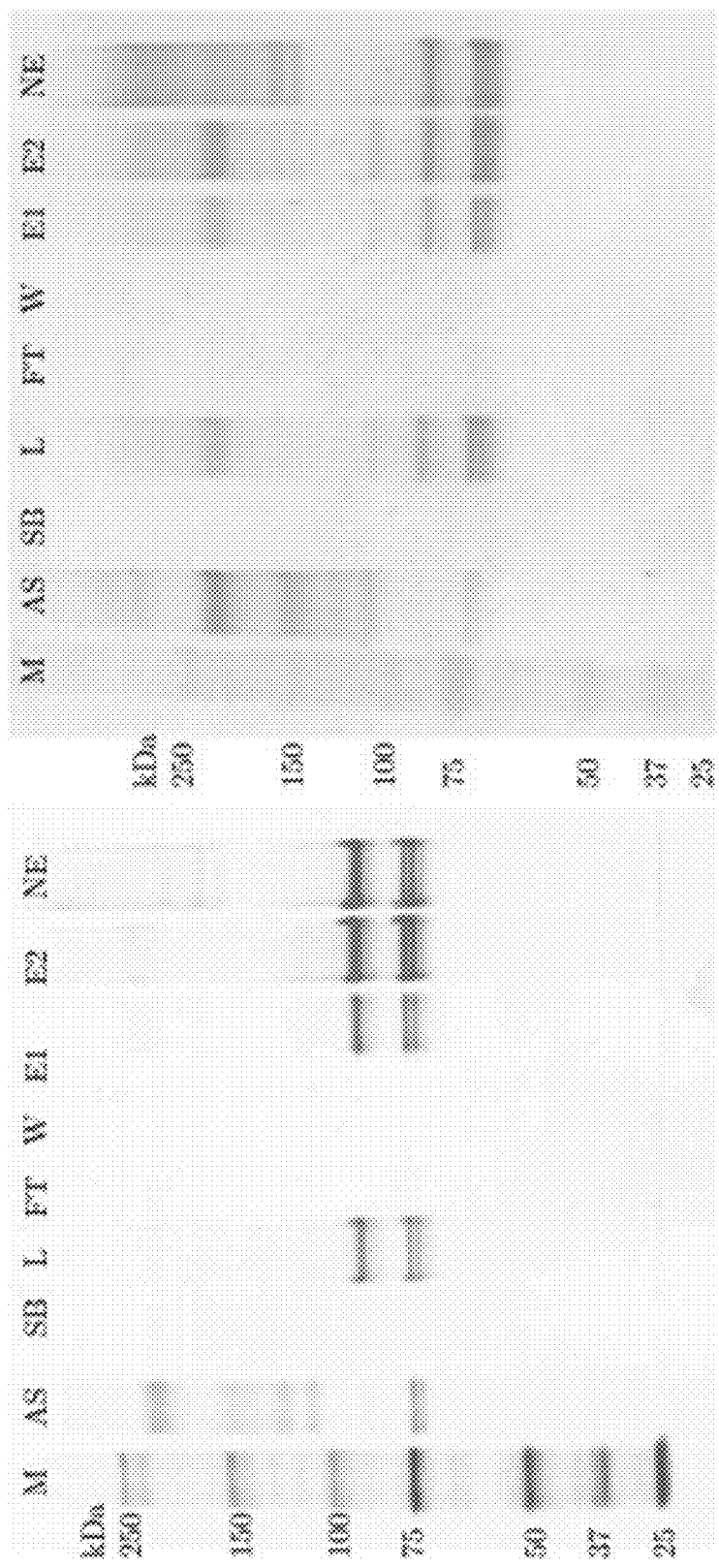

FIG. 42: SDS page gel electrophoresis of the SourceQ AIEX step for concentration of the 90 kDa B-domain depleted heavy chain fragment derived from preparative scale size exclusion chromatography, silver stained (left) and FVIII western blot (right). M) Molecular weight marker, AS) Standard of the commercially available FVIII drug substance, showing all relevant heavy- and light chain species, SB) Sample buffer L) Load, FT) Flow through, W) Washing phase, E1) Eluate pool in 1:99 dilution (silver stain) and 1:132 dilution (FVIII western blot), E2) Eluate pool in 1:33 dilution (silver stain) and 1:44 dilution (FVIII western blot), NE) Posteluate.

Figure 43:
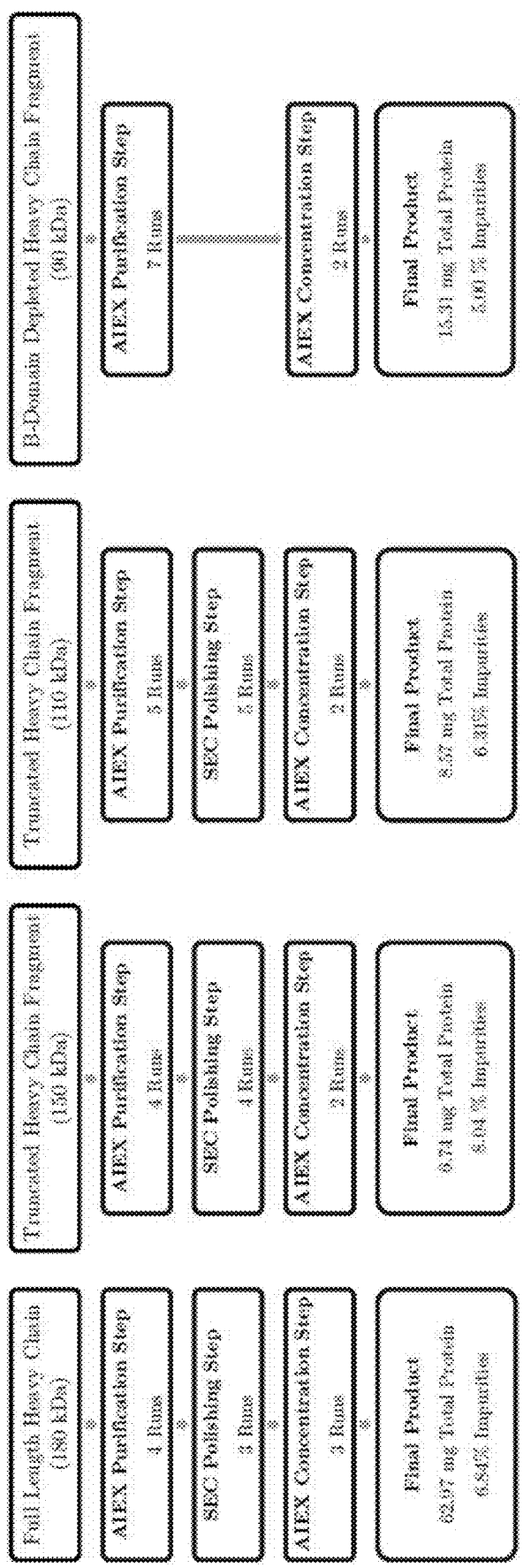

FIG. 43: Summary of the preparative purification process of FVIII molecular subspecies. From left to right: 180 kDa full length heavy chain fragment, 150 kDa truncated heavy chain fragment, 110 kDa truncated heavy chain fragment, 90 kDa B-domain depleted heavy chain fragment.

Figure 44:
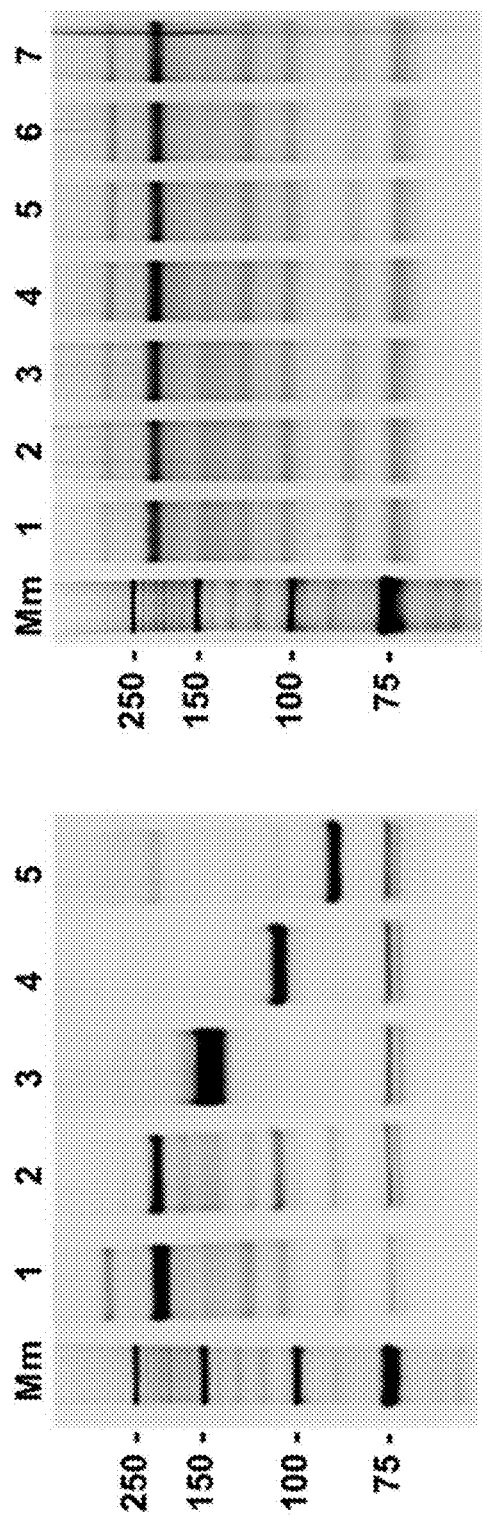

FIG. 44: FVIII heterogeneity and molecular species. (Left) Silver-stained SDS-PAGE gel of FL-rFVIII (1), pdFVIII (2), purified rFVIII species B70-rFVIII (3), B20-rFVIII (4), BDD-rFVIII (5) and of (right) historical lots of FL-rFVIII produced in 2005 (1), 2007 (2), 2008 (3), 2012 (4), 2013 (5), 2014 (6) and 2015 (7); HC, heavy chain; LC, light chain; Mm, precision plus unstained protein standard (Bio-Rad).

Figure 45:
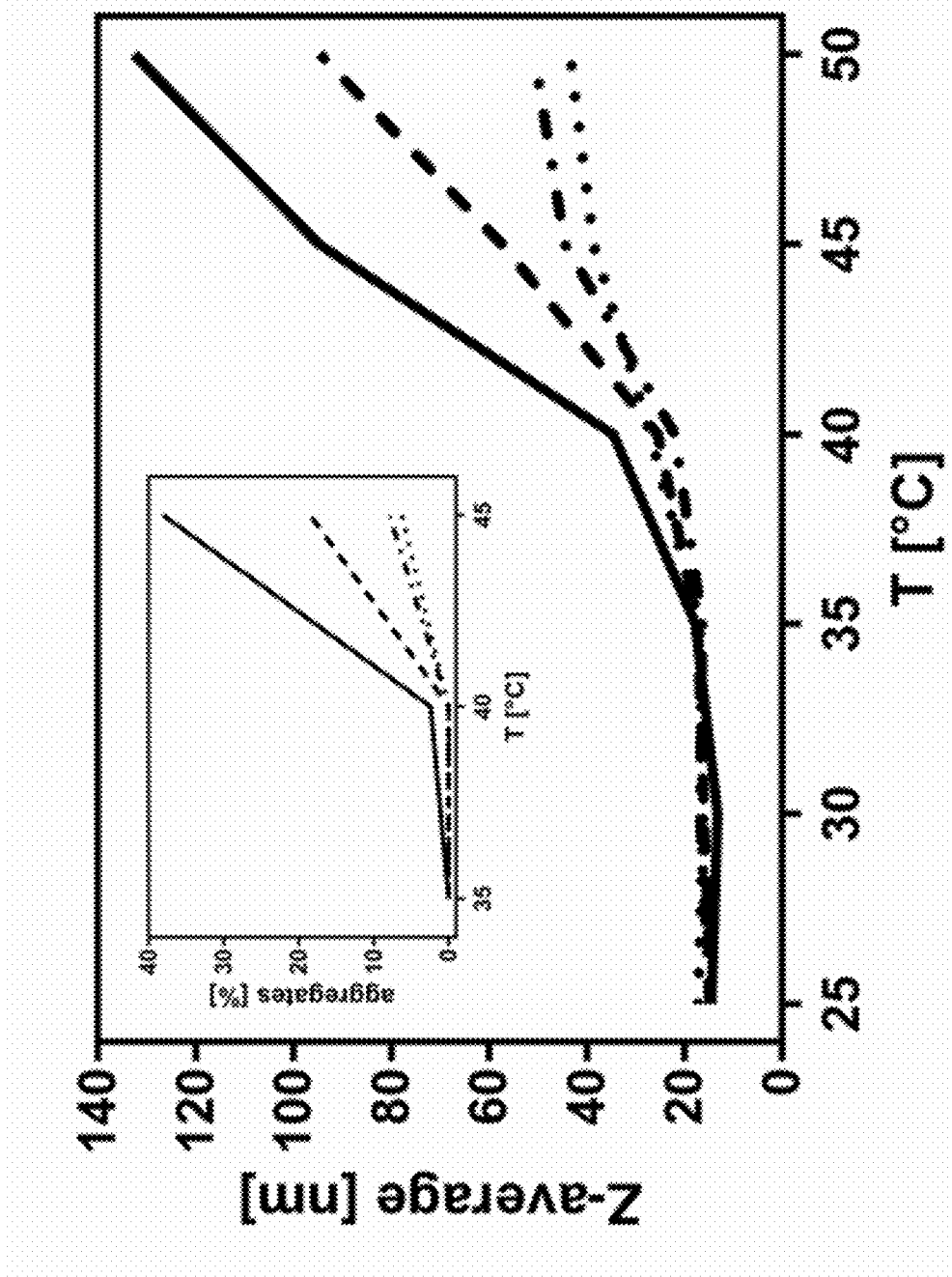

FIG. 45: Aggregation of rFVIII at elevated temperature. Thermally induced aggregates of FL-rFVIII (dotted line), B70-rFVIII (dotted and dashed line), B20-rFVIII (dashed line) and BDD-rFVIII (solid line) were analyzed by DLS. The inset depicts the corresponding samples analyzed by HPLC-SEC.

Figure 46:
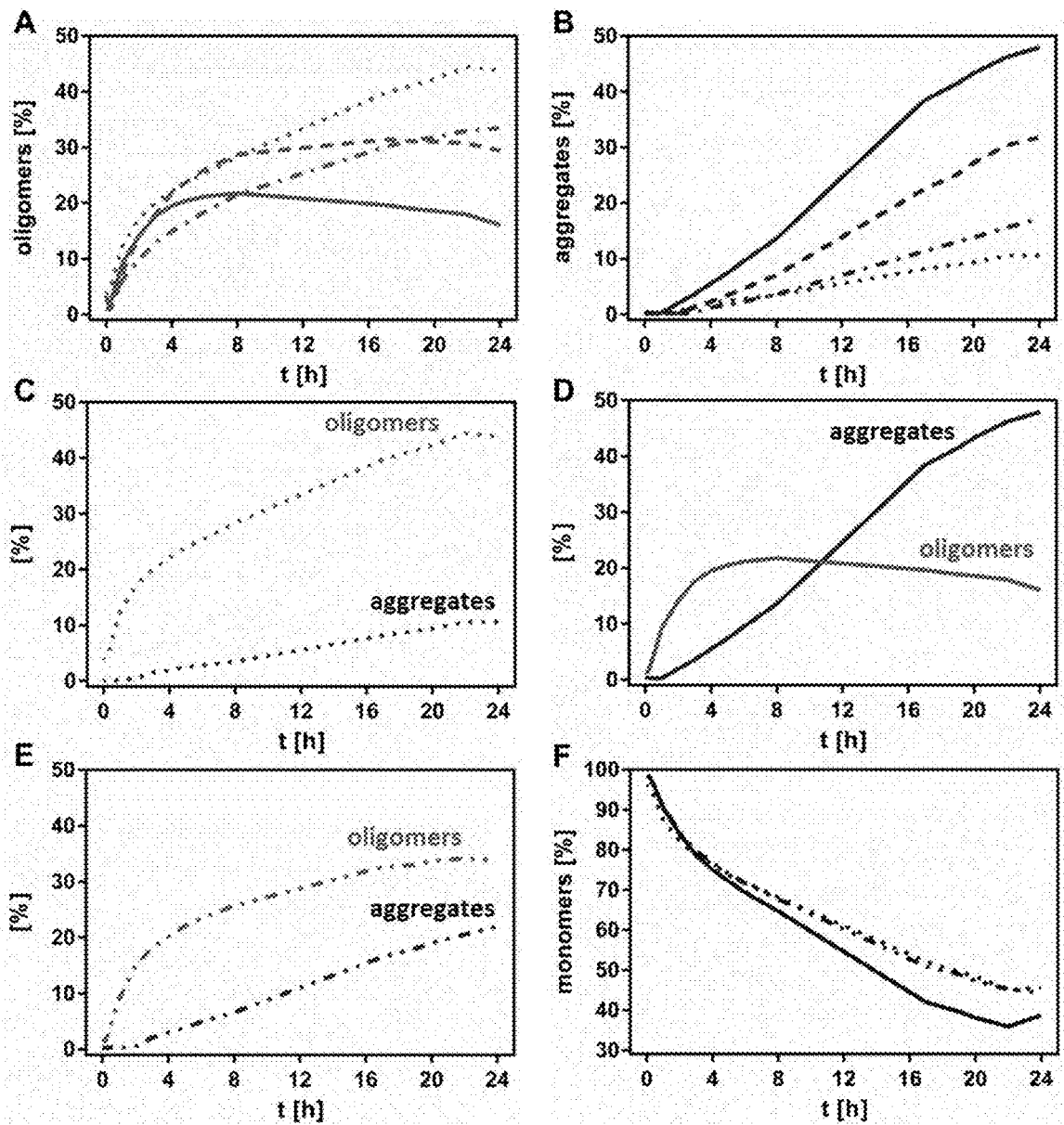

FIG. 46: Pathways of rFVIII oligomer and aggregate formation. FL-rFVIII (dotted line, C), B70-rFVIII (dotted and dashed line), B20-rFVIII (dashed line), BDD-rFVIII (solid line, D) and pdFVIII (double dotted and dashed line, E) were incubated at 45° C. for 24 hours. The amount of oligomers (A), aggregates (B) and monomers (F) was continuously analyzed by HPLC-SEC and plotted against time of incubation.

Figure 47:
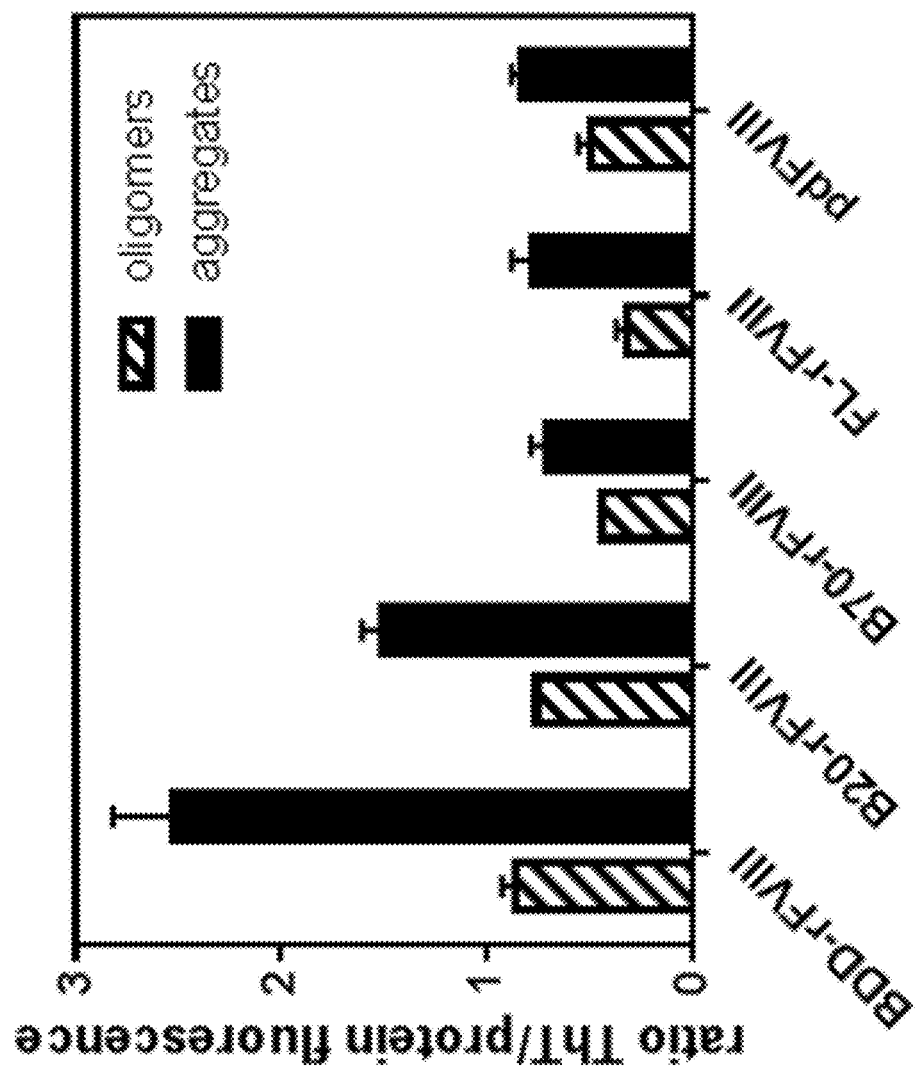

FIG. 47: Binding of the fluorescent dye ThT to oligomers and aggregates of FVIII. The binding capacity of ThT to protein oligomers and aggregates is expressed as the ratio of the fluorescent signals at 440 and 280 nm excitation after 24 h of incubation at 45° C. n=2-4, error bars indicate SD values.

Figure 48:
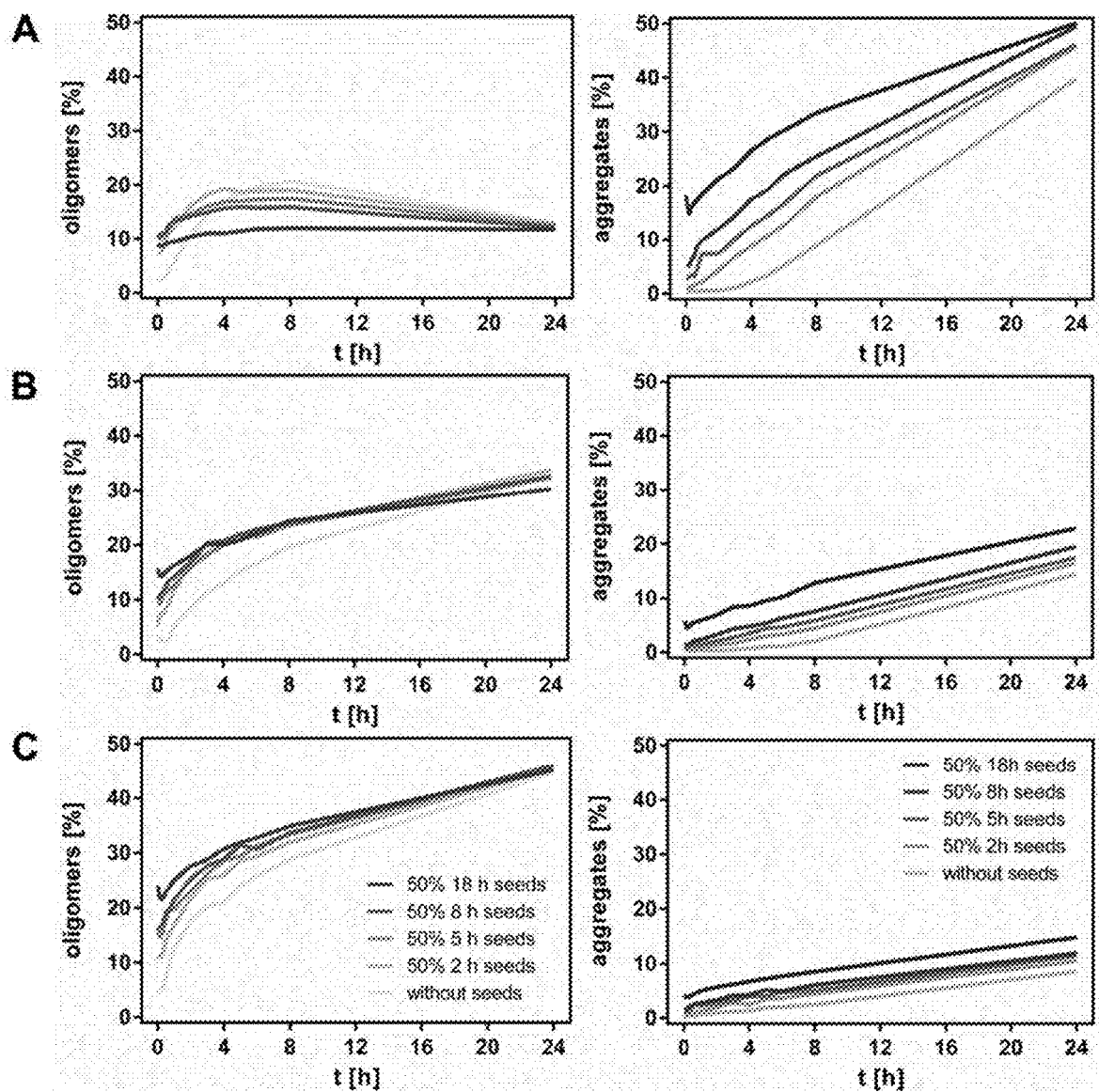

FIG. 48: Homologous seeding of rFVIII aggregation. Seeds were prepared by incubation of BDD-rFVIII, B70-rFVIII and FL-rFVIII for either, 2, 5, 8 or 18 h at 45° C. BDD-rFVII (A), B70-rFVIII (B) and FL-rFVIII (C) samples were mixed 1:1 with respective preformed seeds and incubated at 45° C. for 24 h. The amount of oligomers (left panels) and aggregates (right panels) was continuously analyzed by HPLC-SEC and plotted against time of incubation.

Figure 49:
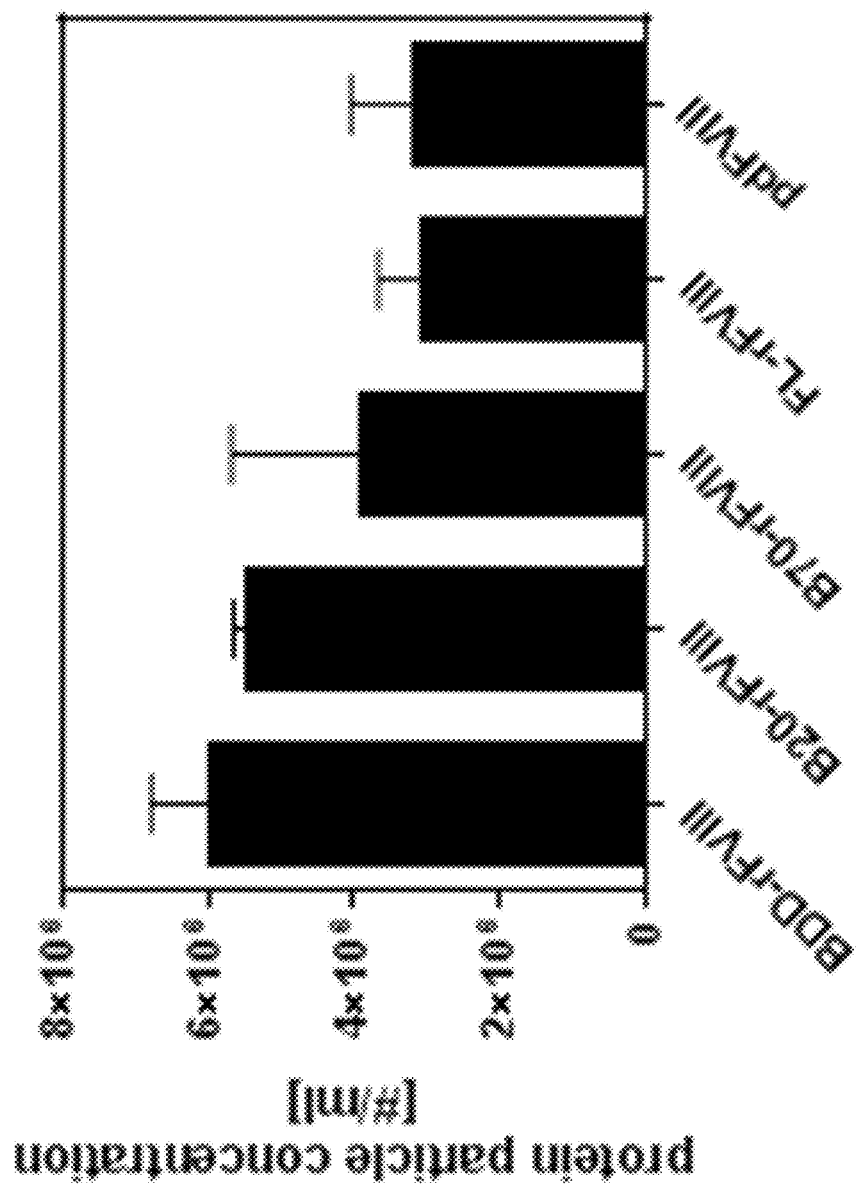

FIG. 49: Formation of protein containing subvisible particles. FVIII samples (0.244 µM) were exposed to agitation and shear stress and subjected to flow cytometry-based particle analysis. The statistical difference was shown by using unpaired t-test. Protein particle concentrations were shown to be significantly different between BDD-rFVIII vs. FL-rFVIII (P=0.0002) and pdFVIII (P=0.0010) as well as between B20-rFVIII vs. FL-rFVIII (P<0.0001) and pdFVIII (P<0.0001); n=4-6, error bars indicate SD values.

Figure 50:
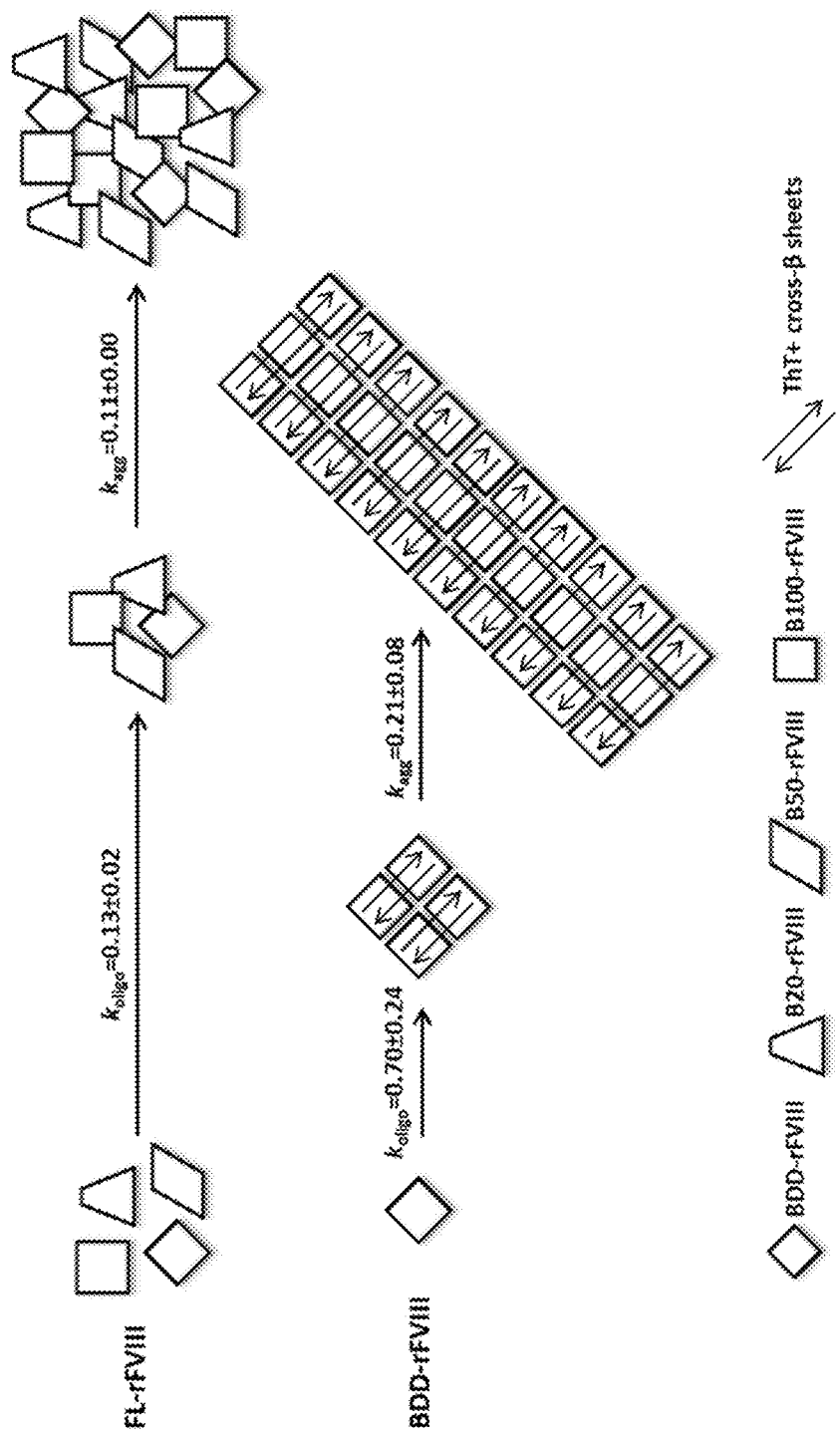

FIG. 50: Schematic model of the formation of oligomers and aggregates after exposure of rFVIII to thermal stress. FL-rFVIII is depicted as heterogeneous mixture of rFVIII species but does not reflect the actual ratio of species. The length of arrows is indicative for the differences in oligomerization and aggregation rates of FL-rFVIII and BDD-rFVIII.

Figure 51:
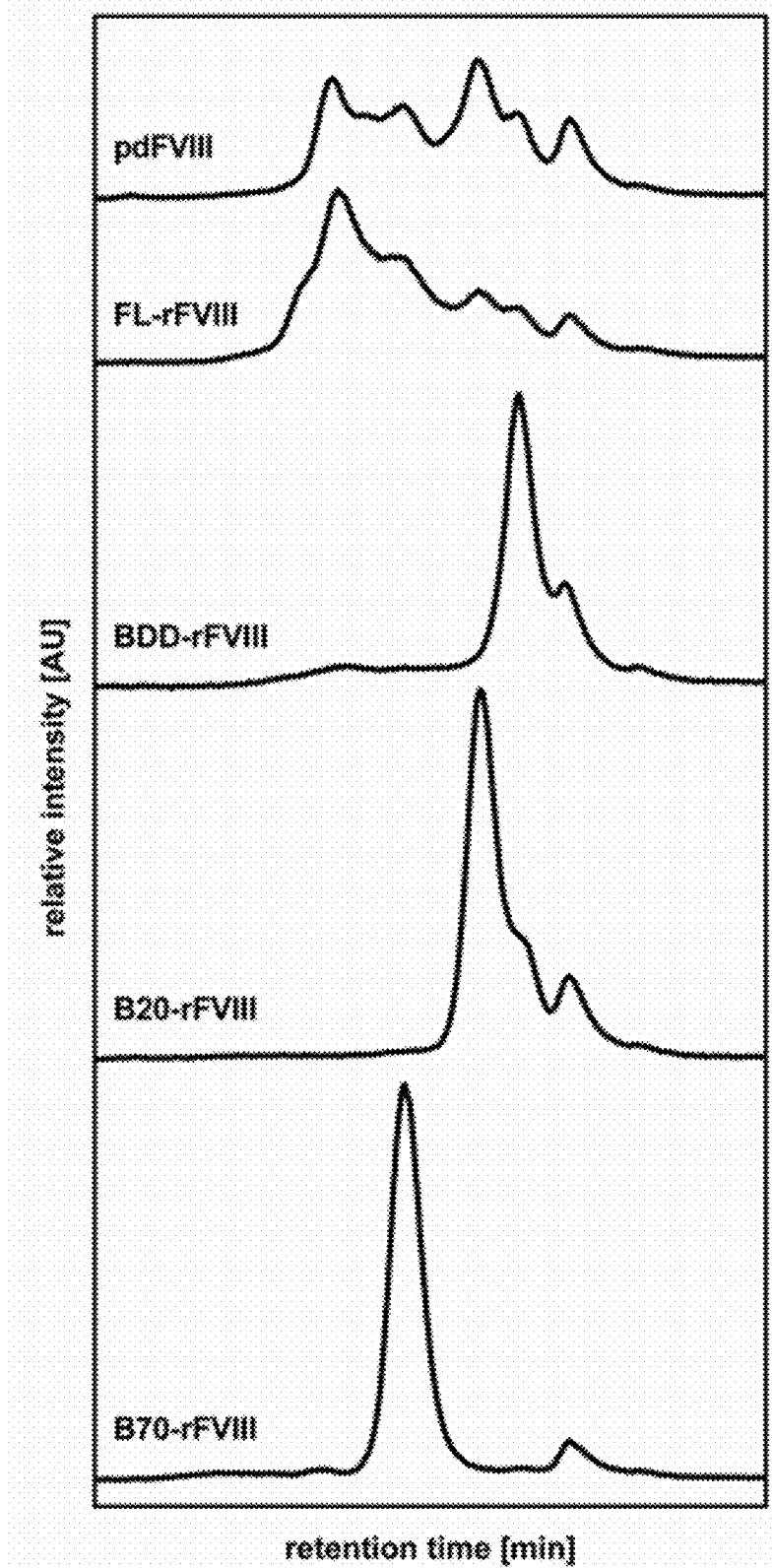

FIG. 51: Size exclusion chromatographic profiles of highly purified pdFVIII, FL-rFVIII and purified rFVIII molecular species at equimolar concentrations (0.122 µM).

FIGS. 52A-52J: HDX-MS heat map of B70-rFVIII. The HDX-MS kinetics of 120 peptides was measured after 3 s, 10 s, 30 s, 2 min, 10 min, 60 min and 3 h of incubation time. Levels of gray indicate the % of deuterium incorporation.

Figure 53:
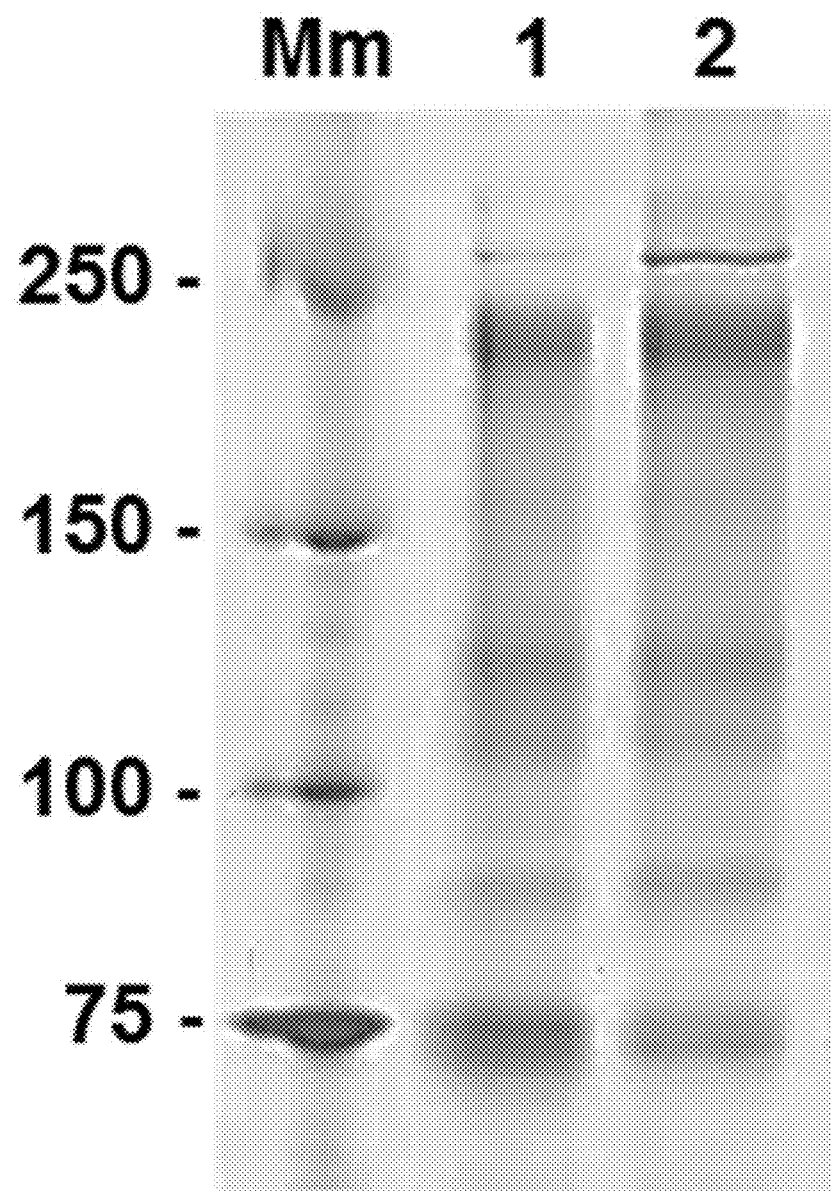

FIG. 53: Composition of FL-rFVIII aggregates. Silver-stained SDS-PAGE gel of native FL-rFVIII (1) and purified aggregates of FL-rFVIII (2); Mm, precision plus unstained protein standard (Bio-Rad).

Figure 54:
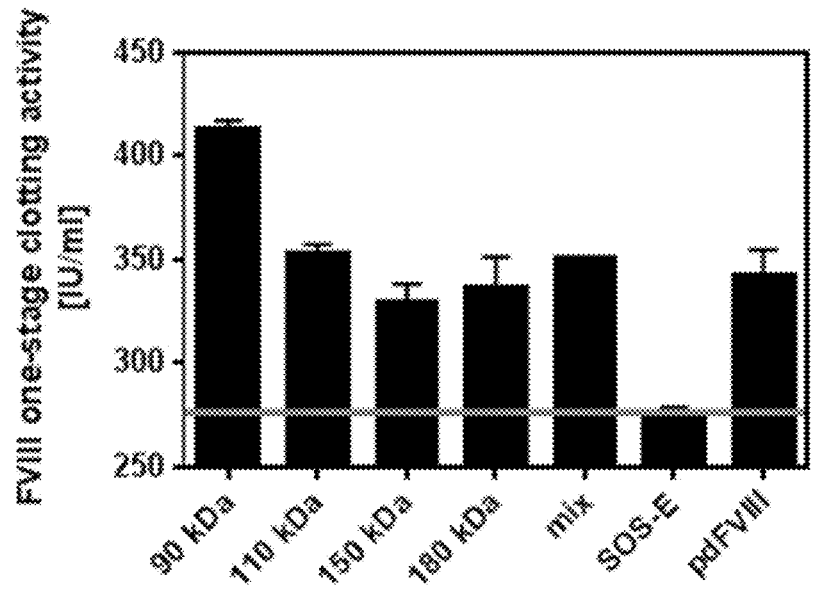
Figure 54:
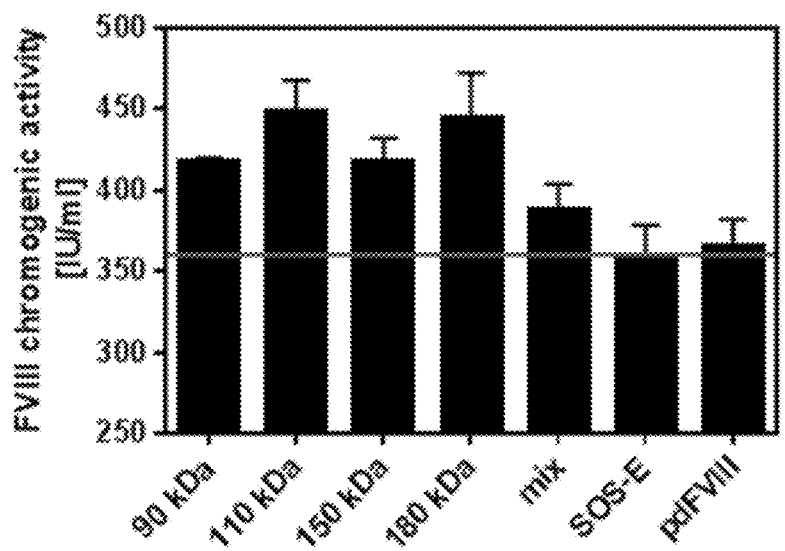

FIG. 54: (A) FVIII one-stage clotting activity. The gray line indicates the level of SOS-E activity, which was the starting material of FVIII species purification. Samples were measured in duplicates. The arrow bar indicates SD values. (B) FVIII chromogenic activity. The gray line indicates the level of SOS-E activity, which was the starting material of FVIII species purification. Samples were measured in duplicates. The arrow bar indicates SD values.

Figure 55:
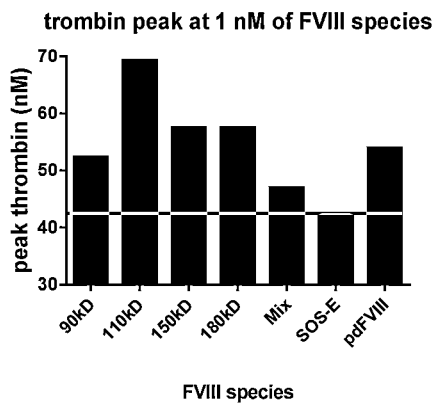
Figure 55:
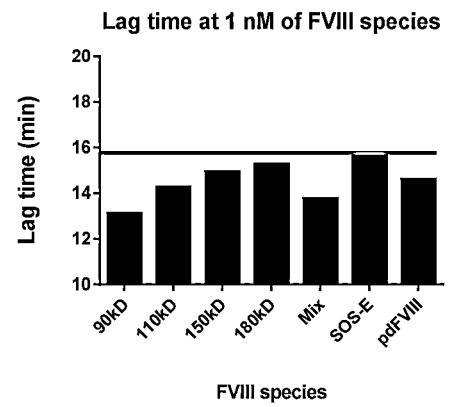
Figure 55:
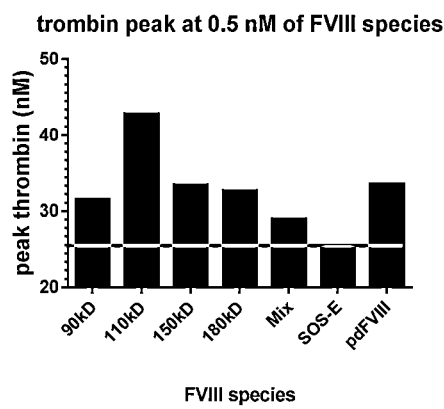
Figure 55:
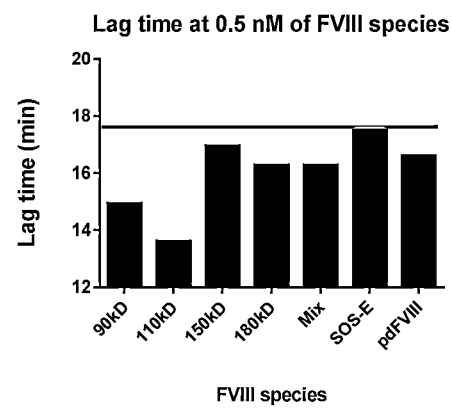
Figure 55:
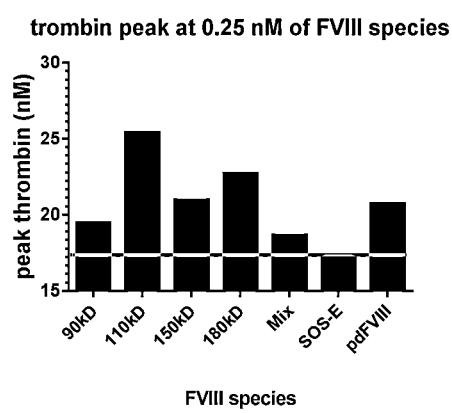
Figure 55:
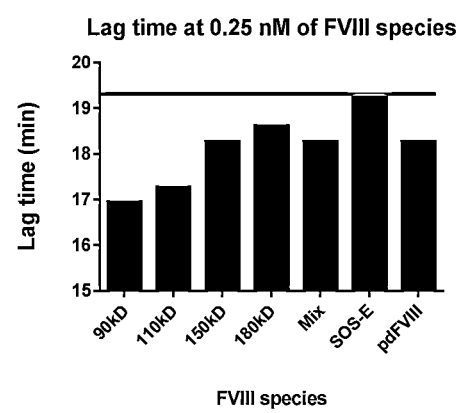

FIG. 55: Thrombin peak and lag time of FVIII species. The gray line indicates the level of SOS-E activity, which was the starting material of FVIII species purification.

Figure 56:
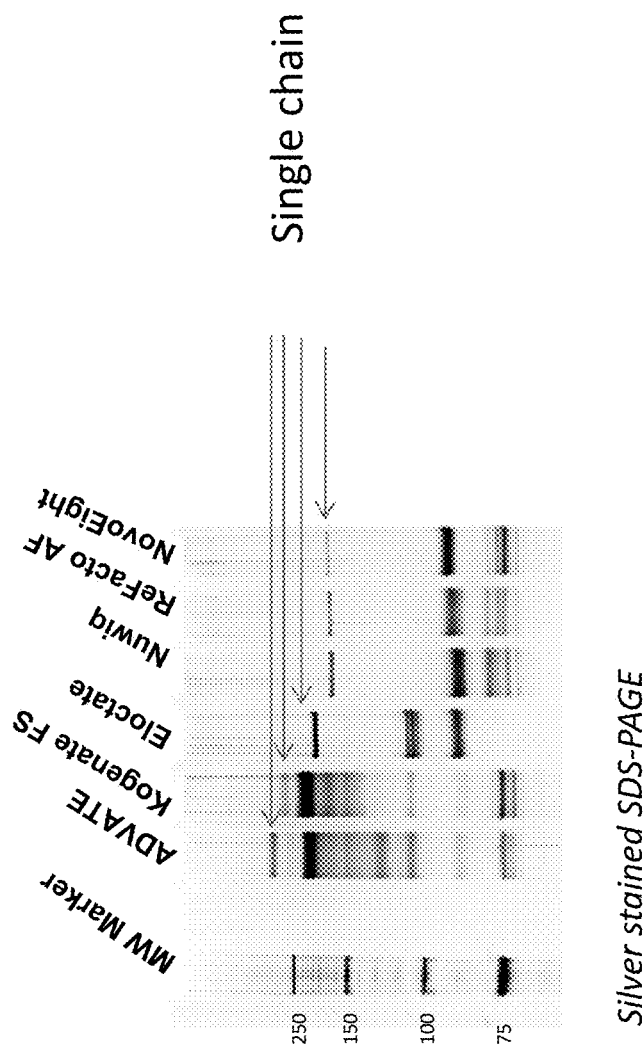

FIG. 56: Silver stained SDS-PAGE of FVIII products.

Figure 57:
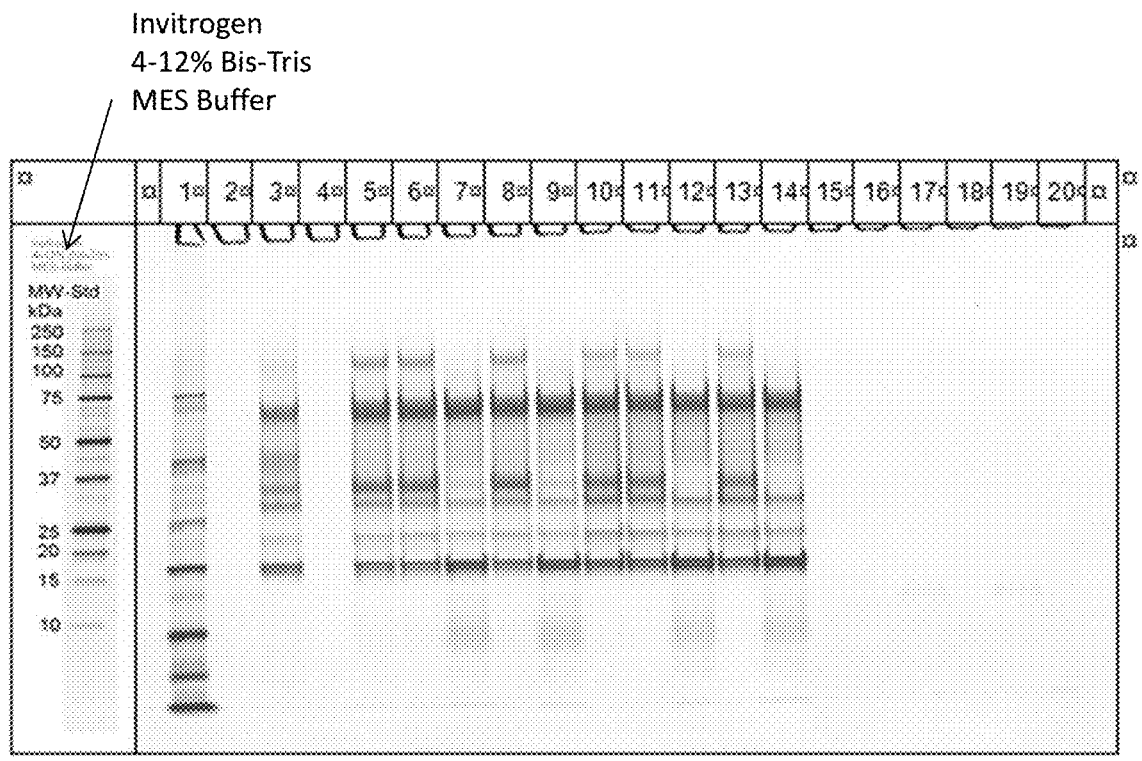

FIG. 57: Silver-stained SDS-PAGE of FL-rFVIII after furin treatment. NuPAGE 3-8% TrisAcetate Midi Gel (1.0 mm; 20 well, Invitrogen Cat. Nr WG1602BOX). Samples were incubated 1:2 with reducing LDS-SB for 1 h at 37° C. 20 µl/100 µl 750 mM Iodacetamid solution was added. Gel was run for 70 min at 150V (constant) and silver-stained.

Figure 58:
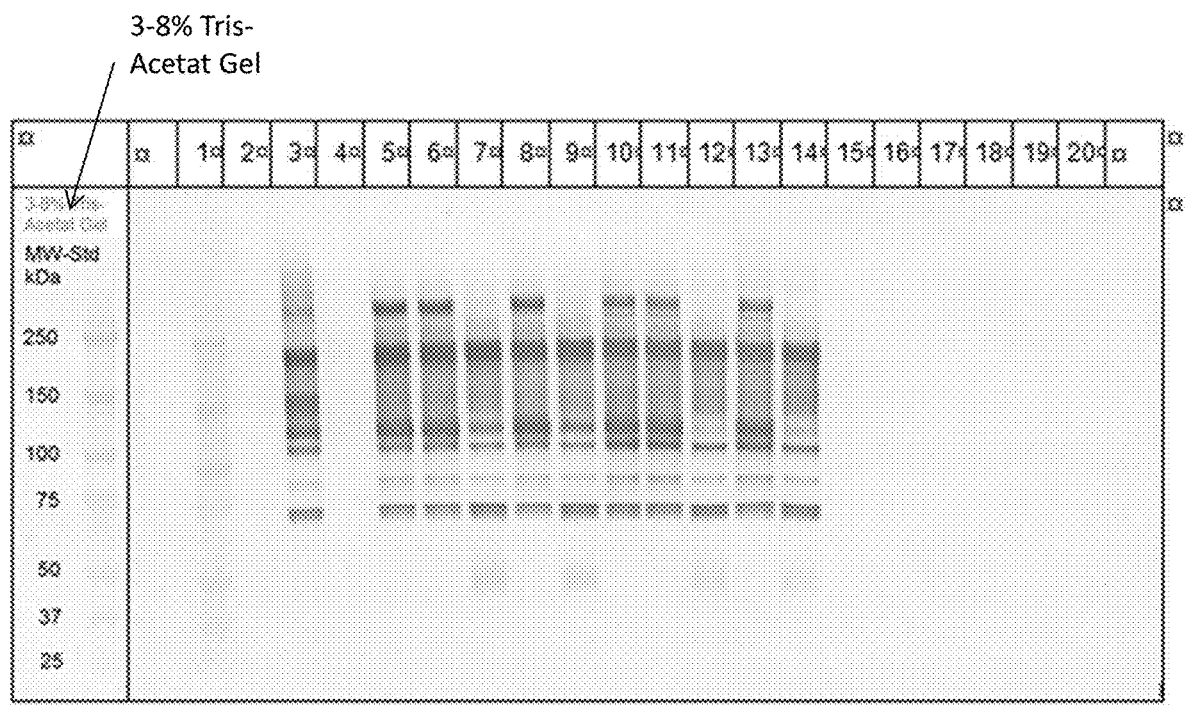

FIG. 58: SDS-PAGE and anti-FVIII-Western Blot of FL-rFVIII after furin treatment. NuPAGE 3-8% TrisAcetate Midi Gel (1.0 mm; 20 well, Invitrogen Cat. Nr WG1602BOX). Samples were incubated 1:2 with reducing LDS-SB for 1 h at 37° C. 20 µl/100 µl 750 mM Iodacetamid solution was added. Gel was run for 70 min at 150V (constant). Western Blot: 1st Antibody: Sheep anti FVIII:C 2nd Antibody Donkey anti sheep IgG ALP.

DETAILED DESCRIPTION OF THE INVENTION

Unless otherwise defined below, the terms used in the present invention shall be understood in accordance with their common meaning known to the person skilled in the art.

All publications, patents and patent applications cited herein are hereby incorporated by reference in their entirety for all purposes.

In accordance with the present invention, each occurrence of the term "comprising" may optionally be substituted with the term "consisting of".

The following abbreviations are used in the present disclosure:

| Abbreviation | Full Context/Description |
| --- | --- |
| AIEX | Anion Exchange Chromatography |
| ALP | Alkaline Phosphatase |
| AS | FVIII Standard |
| B14390000-30 | SourceS derived starting material |

-continued

| Abbreviation | Full Context/Description |
|---|---|
| B20/B70/B100-rFVIII | human recombinant factor VIII containing 20%/70%/100% B domain |
| BDD-rFVIII | human B domain deleted recombinant factor VIII |
| BDS | Bulk Drug Substance |
| C18 | Reversed phase HPLC stationary phase with straight chain alkanes containing 18 carbon atoms (n-Octadecane) |
| C4 | Reversed phase HPLC stationary phase with straight chain alkanes containing four carbon atoms (n-Butane) |
| CHO | Chinese Hamster Ovary |
| CIEX | Cation Exchange Chromatography |
| CL4B | Cross-linked agarose base matrix |
| Crillet 4 HP | Trade name for Polysorbat 80 |
| CV | Column volume |
| Cys2 | Cystine |
| DLS | dynamic light scattering |
| DTT | Dithiothreitol |
| E1 | Eluate pool 1 |
| E2 | Eluate pool 2 |
| EG | Ethylene glycol |
| ELISA | Enzyme-linked Immunosorbent Assay |
| EtOH | Ethanol |
| ExPASy | Swiss Institute of Bioinformatics Bioinformatics Resource Portal |
| F8_AD2_90kDa | 90 kDa subspecies enriched starting material derived from SourceQ and MonoQ runs |
| F8A | Gene locus encoding for Blood Coagulation Factor VIII |
| Fc | Fragment crystallizable |
| FIX | Blood Coagulation Factor IX |
| FIXa | Activated Blood Coagulation Factor IX |
| FL-rFVIII | (preferably human) full-length recombinant factor VIII |
| FPLC | Fast Protein Liquid Chromatography |
| Frac | Fraction collector |
| FT | Flow through |
| FV | Blood Coagulation Factor V |
| FVa | Activated Blood Coagulation Factor V |
| FVII | Blood Coagulation Factor VII |
| FVIIa | Activated Blood Coagulation Factor VII |
| FVIII | Blood Coagulation Factor VIII |
| FVIIIa | Activated Blood Coagulation Factor VIIIa |
| FX | Blood Coagulation Factor X |
| FXa | Activated Blood Coagulation Factor X |
| FXI | Blood Coagulation Factor XI |
| FXIa | Activated Blood Coagulation Factor XI |
| FXII | Blood Coagulation Factor XII |
| FXIII | Blood Coagulation Factor XIII |
| FXIIIa | Activated Blood Coagulation Factor XIII |
| HAc | Acetic acid |
| HDX-MS | hydrogen/deuterium exchange-mass spectrometry |
| HEPES | 4-(2-hydroxyethyl)-1-piperazineethanesulfonic acid |
| HIC | Hydrophobic Interaction Chromatography |
| HPLC | High Performance Liquid Chromatography |
| HPLC-SEC | High performance size exclusion chromatography |
| HRP | Horseradish Peroxidase |
| IgG | Immunoglobulin G |
| IPA | Isopropyl alcohol |
| IU | international unit |
| kDa | kilo Dalton |
| L | Load |
| LDS | Lithium dodecyl sulfate |
| M | Molecular weight marker |
| M | Molar |
| mAB | Monoclonal antibody |
| MES | 2-(N-morpholino)ethanesulfonic acid |
| MilliQ | Ultrapure water type 1 |
| NaCl | Sodium chloride |
| NaOH | Sodium hydroxide |
| NE | Post eluate |
| OC1 | Alkaline equilibration buffer |
| Out 1-7 | Outlet valve 1-7 |
| P1 | Product pool 1 |
| P2 | Product pool 2 |
| pdFVIII | (preferably human) plasma derived factor VIII |
| PE | Post eluate |
| PETG | Polyethylene terephthalate |
| Polysorbate 80 | Nonionic surfactant |
| ProtParam | Tool for the calculation of various physical and chemical parameters of proteins |
| PVDF | Polyvinyldisulfone |
| QA1 | AIEX equilibration buffer |
| QB1 | AIEX elution buffer 1 |
| QB2 | AIEX elution buffer 2 |
| Rel. Abs. | Relative absorbance |
| rFVIII | Recombinant blood coagulation factor VIII |
| RP | Reversed phase |
| S/D | Solvent/Detergent |
| SA3 | CIEX equilibration buffer |
| SDS | Sodium dodecyl sulfate |
| SDS-Page | Sodium dodecyl sulfate polyacrylamide gel electrophoresis |
| SEC | Size Exclusion Chromatography |
| SOP | Standard Operating Procedure |
| SOS-E | SourceS eluate |
| TFA | Trifluoroacetic acid |
| TFPI | Tissue factor pathway inhibitor |
| ThT | Thioflavin T |
| TNBP | Tributyl phosphate |
| Tris | Tris(hydroxymethyl)-aminomethan |
| Triton X100 | 4-(1,1,3,3-Tetramethylbutyl)phenyl-polyethylene glycol |
| Trp | Tryptophan |
| TWA | 1M sodium chloride solution |
| Tween 80 | Trade name for Polysorbat 80 |
| Tyr | Tyrosine |
| UV | Ultraviolet |
| v/v | volume/volume |
| VE | Pre-eluate |
| vWF | Von Willebrand factor |
| W1-3 | Washing phase 1-3 |

Figure 1:
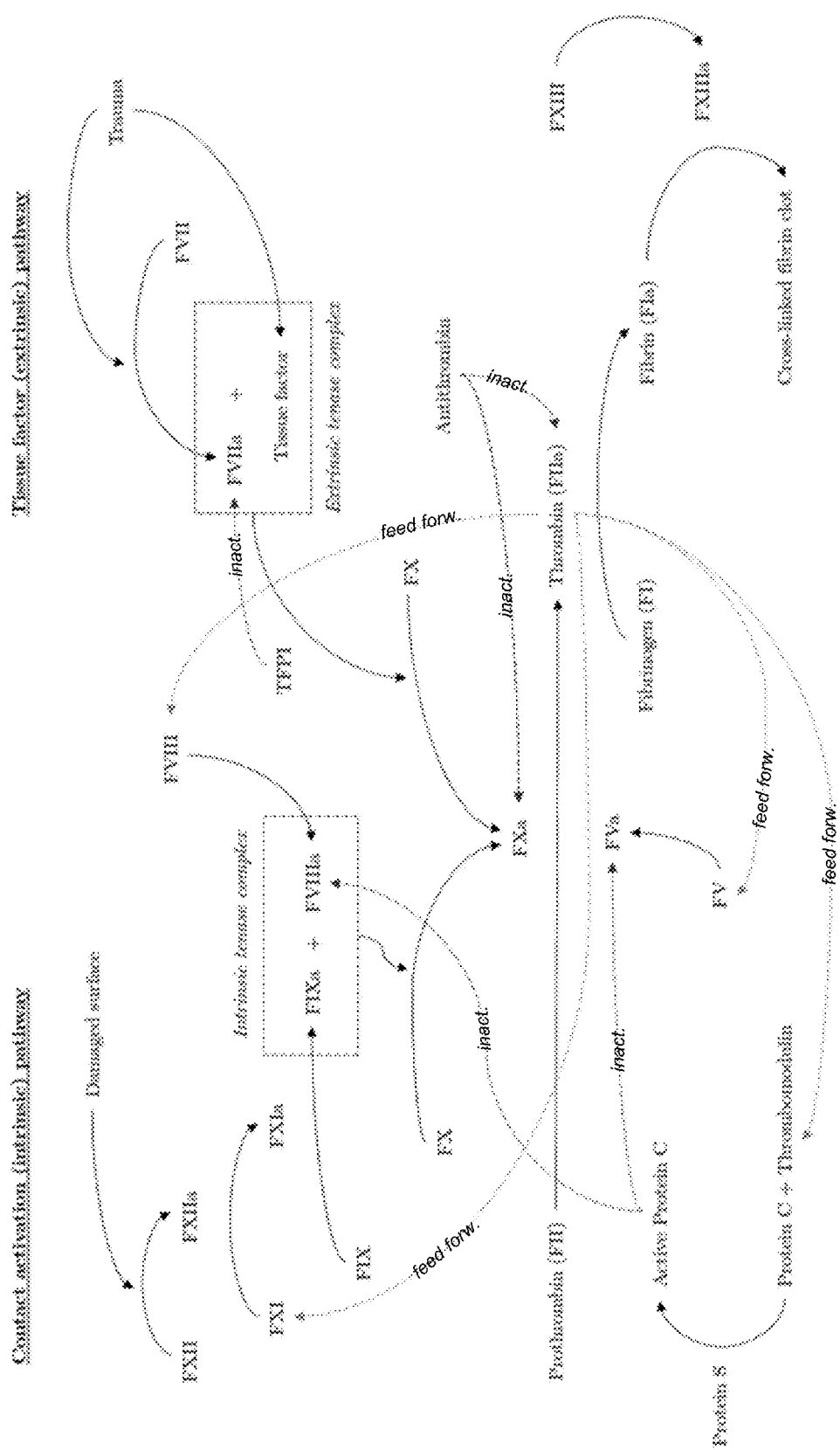
FIG. 1: Blood Coagulation Cascade including the tissue factor dependent or extrinsic pathway on the right-hand side and the contact activation or intrinsic pathway on the left-hand side with black arrows indicating activation of the respective blood coagulation factor and dashed lines labelled "feed forw." and "inact." showing feed forward inactivating effect, respectively. Illustration based on Schaller et al. (2008).
Figure 2:
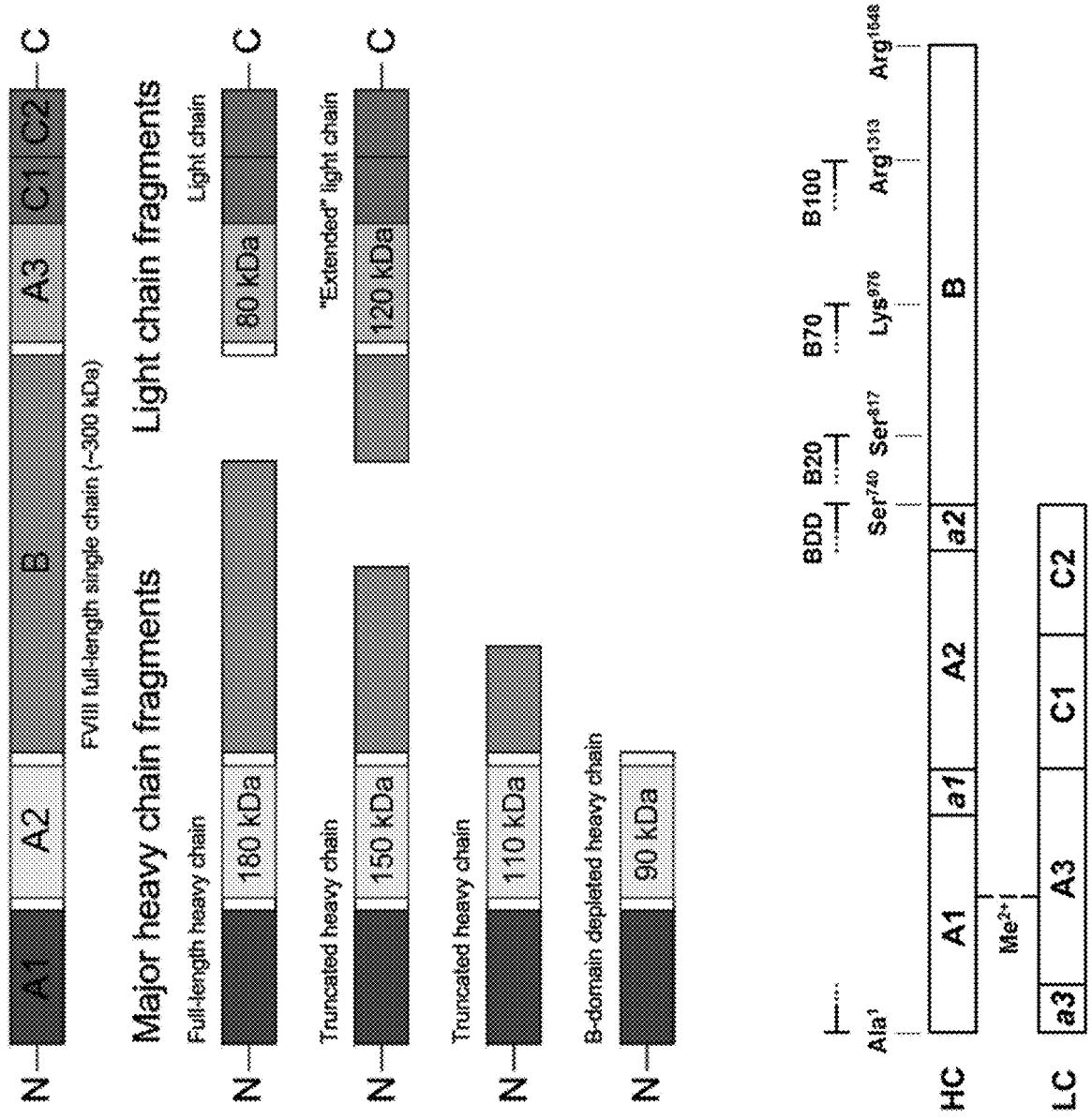
FIG. 2: (A) Schematic presentation of factor VIII single chain molecule on top and the thereof derived heavy chain fragments on the left-hand side and light chain fragments on the right-hand side. Illustration based on (Schaller et al., 2008). The particular protein domains A1, A2, B, A3 and C1 plus C2 are shown in different grey shades. The B-domain is distributed to different extend to heavy- and light chain fragments. White spaces between the coloured domain areas represent highly acid sequences with different functions. (B) FVIII heterogeneity and molecular species. Domain structure of FVIII. Brackets indicate major HC/B domain species with terminating amino acids present in FL-FVIII.

As depicted in FIG. 2A, the full-length single chain Factor VIII (FVIII) comprises six main domains, designated A1, A2, B, A3, C1 and C2. During biosynthesis, the single chain FVIII is cleaved into two chains, one heavy chain and one light chain. The presence of different cleavage positions throughout the single chain FVIII leads to the generation of four heavy chain variants and two light chain variants: the full-length heavy chain variant (180 kDa), the truncated heavy chain variants (150 kDa and 110 kDa) and the B-domain depleted heavy chain variant (90 kDa), the standard light chain (80 kDa) and the extended light chain (120 kDa). Herein, the heavy chain variants will mostly be referred to as FVIII 180 kDa heavy chain or B100-FVIII, FVIII 150 kDa heavy chain or B70-FVIII, FVIII 110 kDa heavy chain or B20-FVIII, and FVIII 90 kDa heavy chain or BDD-FVIII. Association of one of these heavy chain variants with one of the light chains results in a number of heterogeneous FVIII subspecies, each comprising one heavy and one light chain.

The term "a composition comprising FVIII" as used herein refers to a composition wherein all FVIII is defined as follows. Unless indicated otherwise, the term "Factor VIII" or "FVIII" as used herein refers to naturally processed FVIII, comprising several heterogeneous FVIII subspecies. However, even after natural processing, FVIII may comprise residual single chain (i.e., uncleaved) FVIII (see below). If natural processing is inefficient, FVIII may even comprise mostly single chain FVIII. Thus, the term "Factor VIII" or "FVIII" as used herein also refers to naturally processed FVIII comprising residual single chain FVIII or even mostly single chain FVIII.

As will be known to a person skilled in the art, the term "full-length rFVIII" as used herein refers to rFVIII expressed from the full-length FVIII cDNA. As described above, full-length rFVIII is comprised of a heterogeneous mixture of rFVIII subspecies.

As will be known to a person skilled in the art, the molecular weights of the various FVIII heavy chains, i.e. 180 kDa, 150 kDa, 110 kDa and 90 kDa, as well as the molecular weights of the FVIII light chains, i.e. 80 kDa and 120 kDa, are "apparent molecular weights" as seen on SDS page. If necessary, the skilled person will be aware of how the "true molecular weights" can be calculated based on the known amino acid sequences of the individual FVIII heavy and light chains.

As will be understood by a person skilled in the art, "single chain FVIII" as used herein generally refers to uncleaved FVIII. The single chain can comprise all domains of Factor VIII, as depicted in FIG. 2A. However, it is also possible to produce FVIII lacking some domains, one domain, or part of a domain that is/are present in full-length FVIII. In such a case, "single chain FVIII" still refers to the uncleaved FVIII product lacking some domains, one domain, or part of a domain, respectively.

As will be understood by a person skilled in the art, in the method of purifying a FVIII subspecies according to the present invention the composition comprising FVIII is preferably a solution, although the composition may also be a solid that is dissolved before performing the method of the present invention. As described above, intracellular generation of FVIII usually results in the generation of a number of heterogeneous active FVIII subspecies. Therefore, as will be clear to a person skilled in the art, the composition comprising FVIII contains more than one FVIII subspecies.

As used herein, the term "weight ratio" refers to a ratio of weights. For example, the weight ratio of a purified FVIII subspecies in a composition to all other FVIII subspecies in the composition is calculated by dividing the weight of the purified FVIII subspecies in a composition by the weight of all other FVIII subspecies in the composition.

As will be understood by a person skilled in the art, the method of purifying a FVIII subspecies according to the present invention refers to increasing the weight ratio of a FVIII subspecies to all other FVIII subspecies comprised in the composition. The composition comprising FVIII that is used as a starting material for the method of the present invention may contain a different buffer and have a different volume than the composition comprising the purified FVIII subspecies after performing the method of the present invention. Nevertheless, for assessing the increase in the weight ratio (i.e., for assessing the purification) by performing the method of the present invention, the weight of the FVIII subspecies is determined in the composition comprising FVIII that is used as a starting material for the method of the present invention, and in the composition after performing the method of the present invention. Additionally, the weight of all other subspecies is determined in the composition comprising FVIII that is used as a starting material for the method of the present invention, and in the composition after performing the method of the present invention. Then, the weight ratio of a FVIII subspecies to all other FVIII subspecies can be calculated in the composition comprising FVIII that is used as a starting material for the method of the present invention, and in the composition after performing the method of the present invention, and an increase in the weight ratio can be determined.

For determining the weight ratio of a FVIII subspecies to all other FVIII subspecies in a composition, the weight of FVIII subspecies is determined by C4 reversed phase HPLC as described below. As will be clear to a person skilled in the art, using C4 reversed phase HPLC, areas under the curve and thus concentrations of FVIII subspecies in a composition are determined (see below). In a solution with a given volume, the ratio of the concentration of a FVIII subspecies to the concentration of all other FVIII subspecies is equal to the weight ratio of a FVIII subspecies to all other FVIII subspecies. Thus, in the present invention the ratio of the areas under the curve and thus the ratio of the concentrations is used for assessing an increase in the weight ratio of a FVIII subspecies to all other FVIII subspecies comprised in a composition.

As mentioned above, a FVIII subspecies usually comprises one heavy chain and one light chain, which are associated with each other. Thus, in the method for purifying a FVIII subspecies according to the present invention, the composition comprising FVIII that is used as a starting material and the composition comprising the purified FVIII subspecies after performing the method of the present invention preferably comprise FVIII subspecies that are composed of one heavy chain and one light chain. However, it is also possible that the FVIII heavy chain and the FVIII light chain are dissociated, either before or while performing the method of the present invention. Thus, in an alternative embodiment of the method of the present invention, after performing the method of the present invention the purified FVIII subspecies comprises one heavy chain, but no light chain. In such embodiment, the composition comprising FVIII that is used as a starting material for the method of the present invention can comprise one or more FVIII subspecies that is/are composed of one heavy chain, but no light chain, or of one heavy chain that is associated with one light chain. Of course, if the composition comprising FVIII that is used as a starting material for the method of the present invention comprises FVIII subspecies that are composed of one heavy chain, but no light chain, dissociated light chains may still be present in the composition.

Herein, the term "FVIII species" is generally used as an equivalent to "FVIII subspecies". However, it will be clear to a person skilled in the art that occasionally, the term "FVIII species" as used herein can also refer to a single FVIII heavy or light chain.

As will be clear to a person skilled in the art, the individual steps of method of the present invention can be repeated before proceeding to any next step. In such embodiment, the solutions (e.g., the chromatography eluates) resulting from each repetition of the same step can be pooled and then used as the starting material for the next step.

Preferably, the FVIII of the present invention is human FVIII, and the FVIII subspecies to be purified is a human FVIII subspecies.

Preferably, the FVIII of the present invention is recombinant FVIII, and the FVIII subspecies to be purified is a recombinant FVIII subspecies. However, it is also possible that the FVIII of the present invention is plasma-derived (pd) FVIII, and that the FVIII subspecies to be purified is a plasma-derived (pd) FVIII subspecies.

In principle, any composition comprising Factor VIII can be used as a starting material for performing the method for purifying a Factor VIII subspecies according to the present invention.

For example, the recombinant human anti-haemophilic factor VIII ADVATE (a product of Baxalta) or the ADVATE Bulk Drug Substance (BDS) can be used in the method of the present invention. ADVATE is alternatively referred to as Octocog alfa, and further information on ADVATE can be found e.g. in Keating et al. (Keating et al., 2012; incorporated herein in its entirety). During ADVATE production, recombinant FVIII is secreted through vesicular transport and is thus enriched in the fermentation supernatant. After purification, the rFVIII product pool is deep frozen at −80° C. and will herein be referred to as ADVATE Bulk Drug Substance (BDS). Notably, ADVATE/ADVATE BDS comprises a number of heterogeneous FVIII subspecies.

Alternatively, eluates such as SOS-E can be used as a starting material in the method of the present invention. SOS-E is produced as the ADVATE BDS described above, but missing a final purification step.

Alternatively, other compositions comprising human full-length FVIII (FL-FVIII) can be used as a starting material in the method of the present invention. Notably, as described above, during biosynthesis the single chain FVIII is processed into different heavy and light chains. Thus, the FL-FVIII that can be used as a starting material for the method of the present invention generally comprises a number of heterogeneous FVIII subspecies, each comprising one heavy and one light chain.

In the method of the present invention, furin protease treatment of the Factor VIII comprising composition improves the separation of a Factor VIII subspecies during chromatography, yielding a composition comprising said Factor VIII subspecies at even higher purity and concentration. Furin treatment is performed as will be known to a person skilled in the art. For example, furin treatment may be performed by mixing the composition comprising the FVIII with furin, or by applying the composition comprising the FVIII to a column that comprises furin. For example, furin may be immobilized in the column, and the composition comprising FVIII may then be applied to the column. Alternatively, FVIII may be bound in the column, and furin may then be applied to the column. In the present invention, when subjecting the FVIII comprised in the composition to furin protease treatment, the final concentration of furin is preferably more than 100 IU/mL. Final concentration as used herein refers to the furin concentration during incubation of the composition comprising FVIII with furin, i.e. after mixing the composition comprising FVIII with furin.

During furin protease treatment, most of the extended FVIII light chain (120 kDa) that may be comprised in a FVIII-comprising composition is cleaved to yield the standard light chain (80 kDa). Thus, when the method of the present invention involves furin protease treatment, the purified FVIII subspecies preferably contains the FVIII 80 kDa light chain, and almost no FVIII 120 kDa light chain. Almost no FVIII 120 kDa light chain refers to a weight FVIII 120 kDa light chain of less than 5%, preferably less than 1% of the total weight of all FVIII light chain in the purified FVIII subspecies.

In the method of the present invention, several chromatography steps are performed for purifying the FVIII subspecies. Each of these chromatography steps comprises "collecting the eluate comprising said FVIII subspecies". As used herein, "collecting the eluate comprising said FVIII subspecies" usually means that only a fraction of the eluate is collected, i.e. the fraction comprising the FVIII subspecies to be purified. Said fraction comprising the FVIIII subspecies to be purified does not need to comprise all of the FVIII subspecies to be purified that is present in the eluate. Rather, the fraction comprising the FVIII subspecies to be purified is selected to comprise a maximum amount of the FVIII subspecies to be purified while comprising a minimum amount of other FVIII subspecies. The person skilled in the art will be aware of various methods to select the fraction comprising a maximum amount of the FVIII subspecies to be purified while comprising a minimum amount of other FVIII subspecies. For example, the eluate can be collected in a number of separate aliquots of equal volume. Then, the concentration of the FVIII subspecies to be purified and the concentration of all other FVIII subspecies in each aliquot can be determined by known methods such as spectrophotometric determination of protein concentration, polyacrylamide gel electrophoresis plus silver staining and/or western blotting, or chromatography. Finally, the aliquots containing the highest amounts of the FVIII subspecies to be purified while comprising the lowest amounts of other FVIII subspecies can be selected as the fraction comprising the FVIII subspecies to be purified. These aliquots can be pooled and used as the eluate comprising the FVIII subspecies according to the present invention.

As will be clear to a person skilled in the art, the process of selecting the aliquots containing the highest amounts of the FVIII subspecies to be purified while containing the lowest amounts of other FVIII subspecies will influence the purity and concentration of the purified FVIII subspecies obtained by performing the method of the present invention. For example, any omission of aliquots containing FVIII subspecies to be purified from the eluate comprising the FVIII subspecies according to the present invention will reduce the concentration of the purified FVIII subspecies obtained by performing the method of the present invention. Also, including aliquots containing significant amounts of other FVIII subspecies will reduce the purity of the purified FVIII subspecies obtained by performing the method of the present invention. Thus, depending on the desired concentration and purity of the purified FVIII subspecies obtained by performing the method of the present invention, the skilled person will be able to determine which aliquots to select as the fraction comprising the FVIIII subspecies to be purified.

As will be clear to a person skilled in the art, once the eluate comprising the FVIII subspecies to be purified has been determined once or a limited number of times in the method of the present invention, the method can be repeated without determining the eluate comprising the FVIII subspecies to be purified. In such embodiment, the eluate comprising the FVIII subspecies to be purified is selected based on previous determination of the eluate comprising the FVIII subspecies to be purified, and the same eluate is collected. Of course, even when the method of the present invention is performed without determining the eluate comprising the FVIII subspecies to be purified, selection of the fraction comprising a maximum amount of the FVIII subspecies to be purified while comprising a minimum amount of other FVIII subspecies can be monitored, e.g. using chromatograms.

The method for purifying a FVIII subspecies of the present invention comprises several chromatography steps. As will be known to a person skilled in the art, there are different modes of performing chromatography in the methods according to the present invention. For example, the purification of samples containing just one or two products with few impurities and very different behaviour on the corresponding resin can be performed either using an isocratic elution mode or a step gradient elution and results may seem to be sufficient. While isocratic elution is performed with an unchanged eluent mixture throughout the entire elution phase, stepwise elution increases the fraction of one eluent gradually.

Figure 3:
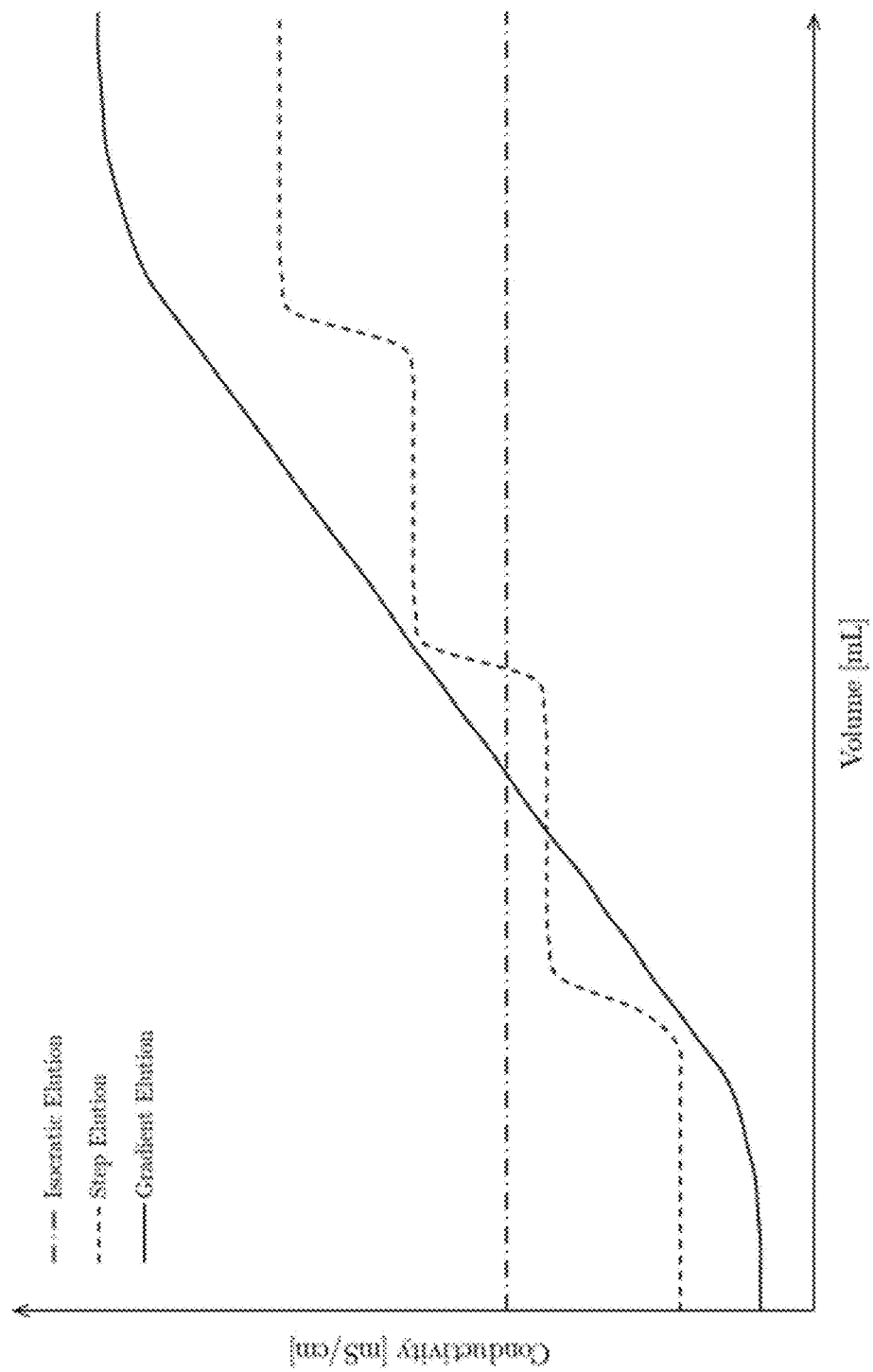
FIG. 3: Schematic presentation of the three most common types of elution modes, which are (1) Isocratic elution shown as dash-dot line, (2) Step elution shown as dashed line and (3) Gradient elution shown as solid line.

As mentioned above, the composition of typical full-length recombinant FVIII is highly heterogeneous, since it contains all possible heavy chain and light chain fragments. Moreover all subspecies exhibit more or less similar behaviour as they are derived from the same single chain molecule. Thus, generally isocratic elution may not lead to satisfying results. Preferably, the method for the purification of FVIII subspecies according to the methods of the present invention is linear gradient elution. Although not limited thereto, a brief description is given in the following, including the general principle of linear gradient elution as well as advantages and disadvantages over other types of elution (see also FIG. 3).

In contrast to isocratic elution mode, the relative amounts of two eluents in a linear gradient elution vary over the course of time. Linear gradient elution is often started with a low percentage of strong eluent. Its amount is then constantly raised, accordingly decreasing the fraction of weak eluent. The elution causing property of the eluent phase, e.g. polarity in ion exchange chromatography, is thereby intensified over time. Gradient length and slope behave inversely proportional to each other. The steeper the slope, the shorter the gradient length and thereby the elution phase. Gradient length is most often expressed as a multiple of the column volume. The gradient slope has great influence on the elution behaviour. Substances with weak affinities will elute at the beginning of a gradient, whereas substances with strong affinities require higher amounts of strong eluent to break their linkage with the stationary phase.

Linear gradient elution is preferably suitable for mixtures of similar molecules. In contrast to other elution types the whole range of conditions is covered in linear elution mode. This ensures that the adequate condition for elution of a certain molecule is given at some point. Even if two molecules exhibit high similarity, their differences cause at least slightly different elution behaviour. Flattening of gradient slopes can help to resolve those two substances at least partly by eluting the weaker binding substance, while that one with high affinity remains attached. In general this makes linear gradient elution a very robust process with many fields of application. But flattening of gradient slopes has its drawbacks. The flatter the gradient the more mobile phase is carried through the column, thereby effecting higher total volumes. It takes longer to elute a certain substance and requires more eluate and thus makes it more diluted in the final eluate fraction. So called peak broadening is observed in the chromatogram. Conversely, linear gradients can also minimise peak broadening in comparison to isocratic elution. Isocratic elution might cause molecules to elute over long ranges in form of broad peaks. If the elution behaviour is known, a steeper linear gradient can be applied to accelerate elution of distinct substances. The resultant peaks are sharper and the eluate fractions are higher concentrated.

The various chromatography steps of the methods of the present invention are performed as will be known to a person skilled in the art. The following describes preferable embodiments of the different chromatography steps performed in the methods according to the present invention. However, the invention is not limited to these embodiments.

As will be clear to a person skilled in the art, the methods of the present invention can be performed in small scale or in large (i.e., preparative) scale. In small scale, the methods can be performed under various different conditions to find the optimal conditions, which can then be used in large scale. Conditions that the inventors found to be particularly suitable are given below. However, the invention is not limited thereto.

Preceding to all chromatography runs of the present invention, the chromatography system can be treated with 1 M sodium hydroxide, 1 M acetic acid and finally MilliQ for sanitisation. Additionally, the system pumps and the sample pump can be purged to remove trapped air from the pump body. Finally, all inlets can be flushed with the corresponding buffers.

First Chromatography Step of the Methods of the Present Invention:

In the method for purifying a Factor VIII subspecies according to the present invention, the first chromatography step is an anion exchange chromatography step. The inventors have surprisingly found that its high resolution offers high separation capacity.

In small scale, several runs can be performed using MonoQ resins under different conditions to evaluate the most suitable combination of parameters. Such runs can, e.g., be performed on ÄKTA Avant 25 or ÄKTA Pure 25 systems at 4° C. using the MonoQ Small Scale column with a column volume of 0.982 mL. A rough separation of FVIII subspecies is achieved.

As will be clear to a person skilled in the art, the standard MonoQ buffer system and standard conditions can be used for the (first) anion exchange chromatography step of the methods of the present invention. Exemplary MonoQ buffers that can be used in the methods of the present invention are listed in Table 9. The starting material can be a composition comprising FL-rFVIII, e.g. a composition called SourceS eluate (SOS-E). SOS-E has been eluted under high ionic strength conditions and is stored at <−60° C. To avoid a loss of activity the starting material is preferably thawed slowly at room temperature. The native sample can subsequently be diluted by a dilution factor of four with a low ionic strength buffer, e.g. QA1 buffer. This reduces conductivity to a sufficient extent and therefore allows binding of the product to the MonoQ resin. The sample solution can finally be sterile filtered with a 0.2 μm membrane filter to avoid potential contamination or blocking of the column bed. The following table shows an exemplary general chromatography scheme including information about buffers, gradient, linear flow rate and residence time as well as column volume and flow direction for each chromatographic step.

TABLE 1

Exemplary chromatography scheme of the small scale MonoQ anion exchange chromatography, giving information about the used buffers and solutions, inlet settings, linear flow rate, residence time, applied column volume, flow direction in the column and outlet setting for each step. The respective sample volume depends on the sample preparation procedure.

| Step | Buffer/Sample | Inlet | Linear Flow Rate [cm/h] | Residence Time [min] | Column Volume | Flow Direction | Outlet |
| --- | --- | --- | --- | --- | --- | --- | --- |
| Equilibration 1 | OC1 | A2 | 35.71 | 8.40 | 6.0 | Downflow | Waste |
| Equilibration 2 | MilliQ | A3 | 35.71 | 8.40 | 2.0 | Downflow | Waste |
| Equilibration 3 | 65% QA1/13% QB1 | A1/B1 | 35.71 | 8.40 | 5.0 | Downflow | Waste |
| Equilibration 4 | QA1 | A1 | 35.71 | 8.40 | 10.0 | Downflow | Waste |
| Sample Application | SourceS eluate | S1 | 35.71 | 8.40 | sample volume | Downflow | Out 1 |
| Wash 1 | QA1 | A1 | 35.71 | 8.40 | 4.0 | Downflow | Frac |

TABLE 1-continued

Exemplary chromatography scheme of the small scale MonoQ anion exchange chromatography, giving information about the used buffers and solutions, inlet settings, linear flow rate, residence time, applied column volume, flow direction in the column and outlet setting for each step. The respective sample volume depends on the sample preparation procedure.

| Step | Buffer/Sample | Inlet | Linear Flow Rate [cm/h] | Residence Time [min] | Column Volume | Flow Direction | Outlet |
|---|---|---|---|---|---|---|---|
| Wash 2 | 87% QA1/13% QB1 | A1/B1 | 35.71 | 8.40 | 10.0 | Downflow | Frac |
| Wash 3 | 82% QA1/18% QB1 | A1/B1 | 35.71 | 8.40 | 10.0 | Downflow | Frac |
| Gradient Elution | 18-100% QB1 | A1/B1 | 20.00 | 15.00 | 8.0 | Downflow | Frac |
| Linear Elution | 100% QB1 | B1 | 19.62 | 15.29 | 5.0 | Downflow | Frac |
| Regeneration 1 | MilliQ | A3 | 60.48 | 4.96 | 5.0 | Upflow | Waste |
| Regeneration 2 | 75% HAc | B4 | 19.05 | 15.75 | 5.0 | Upflow | Waste |
| Regeneration 3 | MilliQ | A3 | 60.48 | 4.96 | 5.0 | Upflow | Waste |
| Regeneration 4 | 1 M NaOH | B3 | 38.10 | 7.88 | 5.0 | Upflow | Waste |
| Regeneration 5 | MilliQ | A3 | 60.48 | 4.96 | 5.0 | Upflow | Waste |
| Regeneration 6 | 75% Hac | B4 | 19.05 | 15.75 | 5.0 | Upflow | Waste |
| Regeneration 7 | MilliQ | A3 | 60.48 | 4.96 | 5.0 | Upflow | Waste |
| Regeneration 8 | 1 m NaOH | B3 | 38.10 | 7.88 | 5.0 | Upflow | Waste |
| Regeneration 9 | MilliQ | A3 | 60.48 | 4.96 | 5.0 | Upflow | Waste |
| Storage | 10 nM NaOH | B2 | 38.10 | 7.88 | 5.0 | Downflow | Waste |

The following describes an exemplary ("standard") embodiment of how small scale chromatography is performed in the first step of the method according to the present invention. As will be clear to a person skilled in the art, all conditions merely represent preferable parameters and conditions, without limiting the invention thereto. Moreover, all listed parameters and conditions can be combined with any other listed parameters and conditions for performing the first chromatography step according to the methods of the present invention. At the beginning the column preferably undergoes an intensive equilibration phase composed of four distinct steps. The column is washed for six column volumes with OC1 buffer, which is a high ionic strength alkaline solution, followed by a washing step with ultrapure water in order to remove the OC1 buffer from the column. The treatment with OC1 buffer ensures that all quaternary ammonium groups of the MonoQ resin are coupled to their corresponding counter ion, which is in this case the monovalent chloride ion. The exchange of ions like hydroxide arising from previous storage or any other remaining molecule for chloride takes preferentially place under alkaline conditions. In order to prepare the column for the final buffer composition the resin can be equilibrated for five column volumes with a mixture of 65% QA1 and 35% QB1. Both are 50 mM Tris buffers only differing in their sodium chloride concentration. Additionally, both buffers contain 5 mM calcium chloride and 0.1% Polysorbate 80 which are necessary for stabilisation of protein structure and prevention of adsorption to negatively charged surfaces, respectively. The already mentioned ratio of QA1 and QB1 buffer gives a sodium chloride molarity of approximately 260 mM. The fourth and actual equilibration step is preferably performed exclusively with QA1 buffer. As this is the last step prior to sample application a total volume of ten column volumes is passed through the column to assure low conductivity and almost neutral pH conditions, which are both required for binding of FVIII molecules to the resin. The sample can be prepared as described above and then applied to the column using sample pump and air sensor. The column load is approximately 18,500 IU/mL MonoQ resin. The resulting flow through can be collected via the outlet valve and used for further analysis of remaining, unbound product. Unbound sample solution can be removed from the column by a washing step using four column volumes of QA1 buffer. Minor impurities can be removed by low salt concentrations. Hence, two washing steps both ten column volumes with 13% and 18% QB1 buffer are preferably implemented. All these steps described so far can be performed with a linear flow rate of 35.71 cm/h, corresponding to a residence time of 8.40 minutes. The flowrate during linear gradient elution is preferably lowered to 20.0 cm/h and the concentration of QB1 buffer increases from 18% to 100% over eight column volumes. This gives a conductivity gradient starting at 20 mS/cm and finally ending at roughly 80 mS/cm. This level can be maintained for another five column volumes at almost similar flow rate to remove eventually remaining FVIII subspecies. All three washing steps as well as gradient and linear step elution can be gathered in the fraction collector in reasonable fraction sizes for afterwards sampling. Once the elution is completed the column has to be regenerated to remove all kinds of remaining substances from the resin, mainly proteins and peptides. A sequence of MilliQ, 75% acetic acid, MilliQ and 1 M sodium hydroxide, each step five column volumes is preferably repeated twice and finally completed with another step of MilliQ rinsing. The flow is directed upwards, because it is assumed that binding occurs in the upper areas of the column due to the huge binding capacity of the MonoQ resin. The capacity limit is almost never reached. A down flow mode in the regeneration phase would however just transport impurities from one binding site to the next until it would finally remove it at the column exit. Upflow mode in contrast removes impurities much more efficiently. In addition, column sanitisation prevents biological contamination by bacteria or algae. The linear flow rate during the regeneration cycle depends on the respective solution. The maximum linear flow rate of 60.48 cm/h is only used for MilliQ due to its low viscosity. 75% acetic acid is much more viscous and would be able to cause pressure problems in the column. To prevent this its flow can be slowed down to 19.05 cm/h, roughly a third of the maximum flow rate. The steps using 1 M sodium hydroxide solution are preferably operated at intermediate flow rates. The final step can be column storage. MonoQ resins are stored in 10 mM sodium hydroxide solution in order to keep them sterile or at least prevent microbiological fouling. The column can be flushed with five column volumes of 10 mM sodium hydroxide solution in down flow mode at an intermediate flow rate of 38.10 cm/h.

In the first chromatography step according to the methods of the present invention, it is preferable to extend the gradient length in the elution phase. The inventors have surprisingly found that this enhances separation of FVIII subspecies. The standard linear gradient length is set to eight column volumes, as described above. The resulting gradient is relatively steep and of short duration since conductivity reaches its target value in just eight column volumes. A doubling of the gradient length to 16 column volumes leads to a two times flatter rise of conductivity. The buffer system itself and the other phases do not need to be further modified.

In a preferred embodiment, furin protease maturation may be performed before the first chromatography step in the method according to the present invention. The furin protease is usually responsible for cleavage of propeptides and immature proteins to their respective active forms. The inventors have surprisingly found that incubation of the sample with a certain amount of active furin leads to reduction of heterogeneity and therefore to a different behaviour during elution. Therefore, it is preferable that a maturation procedure is included into the standard sample preparation. In such embodiment, the native sample can be diluted by a dilution factor of two, e.g. with room tempered QA1 buffer, in order to decrease its ionic strength and to increase the solution temperature. Both are necessary for the enzyme to exhibit its proper function and activity. A certain amount of enzyme solution can then be added so that the concentration at this point is at least 100 IU/mL diluted sample solution. After incubation, e.g. for a minimum duration of four hours at room temperature, another dilution step (1:2) with cold QA1 buffer can be performed to stop the enzymatic reaction and to further decrease sample conductivity. Both dilution steps can correspond to a total dilution factor of four. The sample solution can finally be filtered through a 0.2 μm sterile filter capsule to remove eventually occurring solid particles and prevent column damage. In addition to the furin protease treatment, it is preferably to apply the approach of gradient length prolongation as described above. The gradient length of 16 column volumes for the elution phase can be retained.

A further embodiment of the first chromatography step according to the methods of the present invention achieves the separation of FVIII subspecies through further extended gradient length and ethylene glycol as an additive in the elution phase. The chromatography scheme can be almost identical to the one described in table 1, except for gradient length and buffer composition. The furin protease treated and diluted sample can be applied to the column and afterwards flushed with four column volumes of the original QA1 buffer. The next two washing steps can be performed with ethylene glycol containing QA1 and QB1 buffers. The elution can then be carried out by raising the percentage of ethylene glycol containing QB1 buffer from 18% to 100% over an increased gradient length of 32 column volumes. The extended gradient length should further spread the distribution of FVIII subspecies peaks. Ethylene glycol decreases the conductivity of the buffers during elution. It can be added in order to increase the resolution by addressing the hydrophobic properties of the target proteins.

The following describes an exemplary embodiment of how large scale (preparative) chromatography can be performed in the first step of the method according to the present invention. As will be clear to a person skilled in the art, all conditions merely represent preferable parameters and conditions, without limiting the invention thereto. Moreover, all listed parameters and conditions can be combined with any other listed parameters and conditions for performing the first chromatography step according to the methods of the present invention. Preparative anion exchange chromatography as first step of large scale purification of FVIII subspecies can be performed using the MonoQ Prep Scale column with approximately 20 mL column volume. Further information regarding the MonoQ resin and the corresponding column hardware is provided below. The preparative runs can be performed under similar conditions as described above. Thus, the preferred embodiments described for the small scale runs are also preferred embodiments of the preparative runs. Nevertheless, some parameters evaluated as useful are preferably implemented into the exemplary chromatography scheme for preparative MonoQ runs, which is shown in the following table.

TABLE 2

Exemplary chromatography scheme of the preparative scale MonoQ anion exchange chromatography, giving information about the used buffers and solutions, inlet settings, linear flow rate, residence time, applied column volume, flow direction in the column and outlet setting for each step. The respective sample volume depends on the sample preparation procedure.

| Step | Buffer/Sample | Inlet | Linear Flow Rate [cm/h] | Residence Time [min] | Column Volume | Flow Direction | Outlet |
| --- | --- | --- | --- | --- | --- | --- | --- |
| Equilibration 1 | OC1 | A1 | 71.0 | 8.40 | 6.0 | Downflow | Waste |
| Equilibration 2 | MilliQ | A2 | 71.0 | 8.40 | 2.0 | Downflow | Waste |
| Equilibration 3 | 65% QA1/13% QB1 | A3/B1 | 71.0 | 8.40 | 5.0 | Downflow | Waste |
| Equilibration 4 | QA1 | A3 | 71.0 | 8.40 | 10.0 | Downflow | Waste |
| Sample Application | SourceS eluate | S1 | 71.0 | 8.40 | sample volume | Downflow | Out 1 |
| Wash 1 | QA1 | A3 | 71.0 | 8.40 | 4.0 | Downflow | Out 2 |
| Wash 2 | 87% QA1/13% QB1 | A3/B1 | 71.0 | 8.40 | 10.0 | Downflow | Out 3 |
| Wash 3 | 82% QA1/18% QB1 | A3/B1 | 71.0 | 8.40 | 10.0 | Downflow | Out 4 |
| Gradient Elution | 18-100% QB1 | A3/B1 | 40.0 | 15.00 | 32.0 | Downflow | Out 5/Frac/Out 6 |
| Linear Elution | 100% QB1 | B1 | 39.0 | 15.30 | 5.0 | Downflow | Out 7 |
| Regeneration 1 | MilliQ | A2 | 121.0 | 5.0 | 5.0 | Upflow | Waste |
| Regeneration 2 | 75% HAc | A4 | 38.0 | 15.8 | 5.0 | Upflow | Waste |
| Regeneration 3 | MilliQ | A2 | 38.0/121.0 | 15.8/5.0 | 1.0 + 5.0 | Upflow | Waste |
| Regeneration 4 | 1 M NaOH | A5 | 76.0 | 7.9 | 5.0 | Upflow | Waste |
| Regeneration 5 | MilliQ | A2 | 76.0/121.0 | 7.9/5.0 | 1.0 + 5.0 | Upflow | Waste |
| Regeneration 6 | 75% Hac | A4 | 38.0 | 15.8 | 5.0 | Upflow | Waste |
| Regeneration 7 | MilliQ | A2 | 38.0/121.0 | 15.8/5.0 | 1.0 + 5.0 | Upflow | Waste |
| Regeneration 8 | 1 M NaOH | A5 | 76.0 | 7.9 | 5.0 | Upflow | Waste |
| Regeneration 9 | MilliQ | A2 | 76.0/121.0 | 7.9/5.0 | 1.0 + 5.0 | Upflow | Waste |
| Storage | 10 nM NaOH | A6 | 76.0 | 7.9 | 5.0 | Downflow | Waste |

Similar to the small scale runs, SOS-E can be used as starting material for preparative runs. The column loading can be set to 20,000 IU/mL MonoQ resin. Preferably, the required amount corresponding to the column loading is slowly thawed and subsequently diluted, e.g. with room tempered QA1 buffer, by a dilution factor of two. The furin protease maturation can be performed at an activity level of 100 IU/mL diluted sample solution, e.g. for at least four hours at room temperature. The furin maturated sample solution can then once again be diluted with QA1 buffer by a dilution factor of two, so that the total dilution equals 1:4. This time the used QA1 buffer is preferably cooled down to 4° C. in order to decrease furin activity by lowering the solution temperature. The sample solution can finally be filtered through a 0.2 µm sterile filter module at a flowrate of 50 mL/min, using a peristaltic pump and sterile silicon tubing. There can be a difference in buffer composition of the starting materials, e.g. due to different chromatographic steps from which they are derived. For example, in the present invention the purification of the 90 kDa subspecies pool termed F8_AD2_90 kDa makes it necessary to develop a modified sample preparation procedure. When there is no chromogenic value available for starting material without much protein other than FVIII, the activity can be roughly derived from the protein concentration, using the approximate specific activity of 5000 IU/mg of protein. An example is shown below:

$$\text{column loading} = \frac{\text{specific activity} \times \text{sample amount}}{\text{column volume}}$$

$$\text{column loading} = \frac{5000 \text{ IU/mg} \times 15.7 \text{ mg}}{20.11 \text{ mL}} \approx 4000 \text{ IU/mL}$$

Here, 4000 IU/mL is much less than the upper column loading limit of 20,000 IU/mL, so the entire sample pool can be applied to the column in one single run. The sample can therefore be thawed and afterwards diluted, e.g. with room tempered QA1 buffer and SA3 buffer, until a conductivity of 11 mS/cm and a pH value of 6.5 is reached. The ratio of native sample volume to QA1 buffer to SA3 buffer is approximately 1:4:2.9. This procedure guarantees similar conditions regarding buffer composition, conductivity and pH value as if starting with the SourceS eluate. Furin maturation and sterile filtration are preferably not performed if the material has already passed through an entire purification cycle and should therefore be very pure. The general chromatography steps and buffers can be retained unchanged. The column equilibration can start with six column volumes of the alkaline OC1 buffer at a linear flow rate of 71.0 cm/h. The linear flow rate can be maintained until the gradient elution phase. Two column volumes of ultrapure water can subsequently be applied to the column in order to remove the alkaline OC1 buffer. The actual column equilibration can be performed similar to the standard procedure. First, five column volumes of a mixture containing 65% QA1 buffer and 35% QB1 buffer can be applied to the column and followed by ten column volumes of QA1 buffer in order to achieve proper conditions for sample loading. The sample application can be carried out by direct application onto the column using sample pump and air sensor. Passing through liquid can be collected for further analysis of eventually unbound sample components. Afterwards the unbound sample can be washed out by four column volumes of QA1 buffer. Weak binding sample components can be eluted by two washing steps with step gradients of 13% and 18% QB1 in QA1 buffer, respectively. Both have phase lengths of ten column volumes and can be performed with linear flow rates of 71.0 cm/h. The linear gradient elution itself raises the amount of QB1 elution buffer from 18% to 100% in 32 column volumes. The extended gradient length is preferably used, because of the evaluation in small scale runs. The flow rate during elution phase is preferably reduced to 40.0 cm/h. Another five column volumes of QB1 buffer at a linear flow rate of 39.0 cm/h are supposed to remove protein which is still bound to the column. Column regeneration can be almost identical to the standard regeneration phases described above. In order to prevent high pressure conditions when using a low viscosity solution like ultrapure water upon a high viscosity solution as 75% acetic acid the consequent phase can be operated for one column volume with the lower linear flow rate of the previous phase before increasing the flow. Column regeneration can be driven in up flow mode. The column can finally be stored in 10 mM sodium hydroxide solution. Preparative MonoQ runs can be performed on AKTA Pure 150 systems. All phases, starting with sample application and ending with the linear elution phase, can be collected through different outlets and the fraction collector. The first part and the end of the linear gradient elution phase can be collected into outlet positions whereas the range in which the product is ultimately eluted is preferably collected in small fractions with the fraction collector for subsequent pooling.

Second Chromatography Step of the Methods of the Present Invention:

The following describes an exemplary embodiment of how small scale chromatography can be performed in the second step of the method according to the present invention. As will be clear to a person skilled in the art, all conditions merely represent preferable parameters and conditions, without limiting the invention thereto. Moreover, all listed parameters and conditions can be combined with any other listed parameters and conditions for performing the second chromatography step according to the methods of the present invention. Size exclusion chromatography as a second chromatography step of the methods of the present invention serves as process step for further purification of eluates produced by anion exchange chromatography on MonoQ columns. It can also be referred to as final polishing step for the removal of minor impurities. The development of a general procedure for size exclusion chromatography can be realised on a prepacked Superdex Increaese 200 column with 30 cm bed height and an approximate column volume of 23.5 mL. Size exclusion chromatography is based on the different gel volumes which are accessible for a molecule dependent on its size. Hence, SEC resins do not carry any functional groups that bind or retain the target protein. Consequently, it is not necessary to have a specific equilibration or elution buffer but rather a buffer which serves as running buffer during equilibration, sample application and elution phase. The SEC running buffer is preferably composed of 20% QA1 buffer and 80% QB2 buffer, in order to obtain roughly 300 mM sodium chloride. This is in the same range of salt concentration in which the product is preferably eluted from MonoQ resins. The general chromatography scheme can be found in table 3. The first equilibration phase is used to remove 20% ethanol in which the column is usually stored. Therefore, 1.5 column volumes of MilliQ can be flushed at 20.0 cm/h which corresponds to a residence time of 90 minutes. The column can then be equilibrated in SEC running buffer for two column volumes at a linear flow rate of 45.0 cm/h. This can also be the default flow rate for all steps, except column storage. Higher flow rates have been tested but turned out to be inappropriate, because of high pressure conditions that they sometimes cause. Recommended sample volumes range from 25 µL to 500 µL in order to obtain satisfying separation results. Such small sample volumes can be applied using a capillary loop. The sample can be washed out by 1.5 column volumes of running buffer during elution phase, in which separation takes actually place. This volume is collected in small fractions using the fraction collector. Afterwards the column can undergo a short regeneration phase comprising two column volumes of 0.5 M sodium hydroxide solution and two column volumes of ultrapure water at default flow rate. The column can finally be flushed with two column volumes of 20% ethanol at a reduced linear flow rate of 20.0 cm/h for storage.

TABLE 3

Exemplary chromatography scheme of the small scale size exclusion chromatography on Superdex 200 increase resin, giving information about the used buffers and solutions, inlet settings, linear flow rate, residence time, applied column volume, flow direction in the column and outlet setting for each step.

| Step | Buffer/Sample | Inlet | Linear Flow Rate [cm/h] | Residence Time [min] | Column Volume | Flow Direction | Outlet |
|---|---|---|---|---|---|---|---|
| Equilibration 1 | MilliQ | A2 | 20.0 | 90.0 | 1.5 | Downflow | Waste |
| Equilibration 2 | SEC Buffer | A1 | 45.0 | 40.0 | 2.0 | Downflow | Waste |
| Sample Application | MonoQ eluate | loop | 45.0 | 40.0 | ~600 µL | Downflow | Waste |
| Elution | SEC Buffer | A1 | 45.0 | 40.0 | 1.5 | Downflow | Frac |
| Regeneration 1 | 0.5 M NaOH | B1 | 45.0 | 40.0 | 2.0 | Downflow | Waste |
| Regeneration 2 | MilliQ | A2 | 45.0 | 40.0 | 2.0 | Downflow | Waste |
| Storage | 20% EtOH | B2 | 20.0 | 90.0 | 2.0 | Downflow | Waste |

The following describes an exemplary embodiment of how large scale (preparative) chromatography is performed in the second step of the method according to the present invention. As will be clear to a person skilled in the art, all conditions merely represent preferable parameters and conditions, without limiting the invention thereto. Moreover, all listed parameters and conditions can be combined with any other listed parameters and conditions for performing the second chromatography step according to the methods of the present invention. The procedure for preparative scale size exclusion chromatography is based on the small scale procedure described above and therefore, most parameters are kept constant. Since the preparative scale SEC columns bed height is almost 100 cm it is much more sensitive to gel bed compression. Thus, the flow rate has to be decreased dramatically in order to avoid overpressure conditions and potentially occuring column damage. The first step of equilibration is used to remove the storage solution, which is usually 0.1 M sodium hydroxide but in some cases also 20% ethanol solution is used. One column volume of ultrapure water can be flushed through the column at reduced flowrates prior to the actual equilibration phase for that purpose. This phase can be executed with two column volumes of SEC equilibration/elution buffer at a flow rate of 9.5 cm/h, which corresponds to a residence time of 596.21 minutes. All following steps are preferably performed with a default flow rate of 10.7 cm/h, which is equivalent to 529.35 minutes of residence time. A MonoQ eluate sample of approximately 30-35 mL, containing the desired FVIII subspecies can be slowly thawed at room temperature and directly applied to the column via a 50 mL superloop. The original elution phase preferably used in small scale experiments is 1.5 column volumes is length and has been fractionated entirely. The preparative scale column size makes it necessary to split the original elution phase into three distinct elution phases, in order to be able to collect the interesting range of elution in appropriate fractions. Similar to the other elution phases the first one is preferably performed with SEC equilibration/elution buffer at default flow rate for 0.24 column volumes, which is collected via an outlet valve. The actual elution of product should take place in the second elution phase. The total volume of 0.49 column volumes can be collected in 55 fractions of ~16.5 mL each. The third elution phase can be 0.77 column volumes in length and similar to the first elution phase completely collected via an outlet valve. All three elution phases together can be 1.5 column volumes in total, which is equivalent to the original preferred elution procedure of the small scale experiments. Thereafter, a short column regeneration can take place which contains treatment with 0.5 M sodium hydroxide and ultrapure water. Each of both phases can be two column volumes in length and carried out at the default flow rate of 10.7 cm/h. The column can finally be flushed with 1.5 column volumes of 0.1 M sodium hydroxide solution for storage. Column regeneration and column storage can eventually be skipped if two or more batches of the same FVIII subspecies are purified in sequence. In such cases, reequilibration with SEC equilibration/elution buffer can be placed directly after the third elution phase.

TABLE 4

Exemplary chromatography scheme of the preparative scale size exclusion chromatography on Superdex 200 Prep Grade resin, giving information about the used buffers and solutions, inlet settings, linear flow rate, residence time, applied column volume, flow direction in the column and outlet setting for each step.

| Step | Buffer/Sample | Inlet | Linear Flow Rate [cm/h] | Residence Time [min] | Column Volume | Flow Direction | Outlet |
|---|---|---|---|---|---|---|---|
| Equilibration 1 | MilliQ | A2 | 1.5 | 3,777 | 1.0 | Downflow | Waste |
| Equilibration 2 | SEC Buffer | A1 | 9.5 | 596.21 | 2.0 | Downflow | Waste |
| Sample Application | MonoQ eluate | loop | 10.7 | 529.35 | ~32 mL | Downflow | Waste |
| Elution 1 | SEC Buffer | A1 | 10.7 | 529.35 | 0.24 | Downflow | Out 1 |
| Elution 2 | SEC Buffer | A1 | 10.7 | 529.35 | 0.49 | Downflow | Frac |
| Elution 3 | SEC Buffer | A1 | 10.7 | 529.35 | 0.77 | Downflow | Out 2 |
| Regeneration 1 | 0.5 M NaOH | B1 | 10.7 | 529.35 | 2.0 | Downflow | Waste |
| Regeneration 2 | MilliQ | A2 | 10.7 | 529.35 | 2.0 | Downflow | Waste |
| Storage | 0.1 M NaOH | B2 | 10.7 | 529.35 | 1.5 | Downflow | Waste |

In another embodiment of the second chromatography step in the methods according to the present invention, hydrophobic interaction chromatography is performed as an alternative way of separating the 150 kDa and 180 kDa subspecies from each other. Runs can be performed on a 1.0 mL phenyl sepharose high performance column on an AKTA Avant 25 system at room temperature. Different parameters and conditions can be varied and tested. An exemplary chromatography scheme for a run under standard conditions can been seen in table 5. Since the mechanism of hydrophobic interaction chromatography is opposite to ion exchange chromatography, sample binding occurs under high salt conditions, whereas elution is caused by low conductivities. The standard set up is a two dimensional chromatography using two consecutive linear gradients with elution buffers of different strength. The following describes an exemplary embodiment of how hydrophobic interaction chromatography can be performed in the second step of the method according to the present invention. As will be clear to a person skilled in the art, all conditions merely represent preferable parameters and conditions, without limiting the invention thereto. Moreover, all listed parameters and conditions can be combined with any other listed parameters and conditions for performing the second chromatography step according to the methods of the present invention. The upper column loading limit can be specified with 10,000 IU/mL resin and the actual column loading can be chosen to be even below that limit. A certain amount of e.g. SourceS eluate is preferably slowly thawed at room temperature. Afterwards, furin protease can be added to such an extent that the furin activity is above 100 IU/mL of sample solution. Upon furin maturation at room temperature for four hours the sample can be diluted with HIC buffer A by a dilution factor of two. This is necessary to increase salt concentration and to enable sample binding. Sterile filtration through a 0.2 µm filter disk can be the final step of sample preparation. A 20% ethanol solution is commonly used for column storage. The column can initially be flushed with two column volumes of the HIC equilibration buffer E1 to remove ethanol from the column. This can be carried out with a linear flow rate of 10 cm/h. The column can afterwards be equilibrated with five column volumes of the ethylene glycol containing buffer D and five column volumes of the high salt equilibration buffer E1. A linear flow rate of 20 cm/h can be used as default flow rate for those two steps as well as for all following steps. After the column has been equilibrated in high salt conditions the sample can be applied. Hydrophobic areas on the protein surface tend to bind the hydrophobic phenyl groups on the resin in order to avoid contact to the highly polar surrounding aqueous phase. Sample application can be carried out with sample pump and air sensor until the entire sample volume passed through the column. The flow through fraction can be collected via an outlet position. After washing the column with five column volumes of equilibration buffer E1 the elution phase can start. At first the percentage fraction of elution buffer C can be raised from 0-100% in 20 column volumes. This level is preferably kept for further five column volumes until the second part of the elution starts. The level of ethylene glycol containing buffer D can be increased to 100% in 16 column volumes and maintained for another five column volumes. The entire elution phase comprising both gradients can be collected in small fractions using the fraction collector. The column can be regenerated by a sequence of ultrapure water, isopropyl alcohol, ultrapure water, 1 M sodium hydroxide solution and finally again ultrapure water. The column can thereafter be flushed with five column volumes of 20% ethanol solution for storage.

In another embodiment of hydrophobic interaction chromatography step in the methods according to the present invention, buffers are adjusted and the gradient length is extended. Although the overall procedure is similar to the embodiment described above some parameters are preferably varied in this embodiment. A new equilibration buffer with a sodium chloride molarity of 750 mM is preferably implemented and termed HIC buffer E2—its conductivity is approximately 71 mS/cm. The starting material can be replaced by a 150 kDa enriched MonoQ eluate pool. If such sample has already been treated with furin protease prior to loading it onto the MonoQ column a second furin maturation is not necessary. The sample solutions conductivity is preferably increased to approximately 71 mS/cm with HIC buffer A and 2 M sodium chloride solution in order to adjust it to the same level as the equilibration buffer. Column equilibration, sample application and column regeneration can be equal to the standard procedure. The washing phase following sample application is preferably doubled to ten column volumes using the new equilibration buffer E2. The elution phase itself preferably consists of only one gradient using the elution buffer C, which contains no sodium chloride at all. The amount of buffer C is preferably raised much flatter to 100% in an extended gradient length of 40 column volumes. The level of 100% buffer C can be kept for another five column volumes. Immediately afterwards the column can undergo the usual regeneration procedure. Preferably, the second gradient using the ethylene glycol containing buffer D is not used any more.

In a preferred embodiment of the second chromatography step in the methods according to the present invention, the hydrophobic interaction chromatography is a negative mode chromatography. The negative mode chromatography aims at binding impurities rather than the product. In the present invention, remaining subspecies other than the 150 kDa subspecies are supposed to bind to the column, whereas the 150 kDa subspecies is thought to more or less pass through the column and elute in the flow through fraction. The procedure for negative mode chromatography is quite different from the other HIC approaches and an exemplary procedure is presented in table 5. The following describes an exemplary embodiment of how negative mode chromatography can be performed in the second step of the method according to the present invention. As will be clear to a person skilled in the art, all conditions merely represent preferable parameters and conditions, without limiting the invention thereto. Moreover, all listed parameters and conditions can be combined with any other listed parameters and conditions for performing the second chromatography step according to the methods of the present invention. The sample can be a 150 kDa subspecies enriched MonoQ eluate pool derived from a preparative purification step. The sample solution is preferably thawed and diluted with the same amount of room tempered buffer A (1:2 dilution). The conductivity can then be further raised to 70.0 mS/cm using the high salt buffer G. The equilibration buffer E2 can be similarly adjusted to a conductivity level of 75.0 mS/cm by the addition of buffer G. The column can be equilibrated according to the standard procedure. The diluted and adjusted MonoQ eluate can be directly applied to the column using the sample pump. The maximum column loading can be by far exceeded, in which case at some point a break through is likely to be observed. The washing phase is preferably extended to 30 column volumes, since this is the step in which the product is expected to be washed out of the column. The washing phase can be collected in small fractions to allow detailed analysis of single fractions. In order to elute the column, it can be flushed with ten column volumes of elution buffer C for removal of all bound protein. Column regeneration can be performed according to the standard procedure.

TABLE 5

Exemplary chromatography scheme of the small scale hydrophobic interaction chromatography performed on phenyl sepharose high performance resin, giving information about the used buffers and solutions, inlet settings, linear flow rate, residence time, applied column volume, flow direction in the column and outlet setting for each step. The respective sample volume depends on the sample preparation procedure.

| Step | Buffer/Sample | Inlet | Linear Flow Rate [cm/h] | Residence Time [min] | Column Volume | Flow Direction | Outlet |
|---|---|---|---|---|---|---|---|
| Equilibration 1 | Buffer E1 | A1 | 10.0 | 30.0 | 2.0 | Downflow | Waste |
| Equilibration 2 | Buffer D | A2 | 20.0 | 15.0 | 5.0 | Downflow | Waste |
| Equilibration 3 | Buffer E1 | A1 | 20.0 | 15.0 | 5.0 | Downflow | Waste |
| Sample Application | SourceS eluate | S1 | 20.0 | 15.0 | sample volume | Downflow | Out 1 |
| Wash | Buffer E1 | A1 | 20.0 | 15.0 | 5.0 | Downflow | Frac |
| Gradient Elution 1 | 0-100% Buffer C | A1/B1 | 20.0 | 15.0 | 20.0 | Downflow | Frac |
| Liner Elution 1 | Buffer C | B1 | 20.0 | 15.0 | 5.0 | Downflow | Frac |
| Gradient Elution 2 | 0-100% Buffer D | B1/A2 | 20.0 | 15.0 | 16.0 | Downflow | Frac |
| Liner Elution 2 | Buffer D | A2 | 20.0 | 15.0 | 5.0 | Downflow | Frac |
| Regeneration 1 | MilliQ | A3 | 20.0 | 15.0 | 5.0 | Downflow | Waste |
| Regeneration 2 | IPA | B2 | 20.0 | 15.0 | 10.0 | Downflow | Waste |
| Regeneration 3 | MilliQ | A3 | 20.0 | 15.0 | 5.0 | Downflow | Waste |
| Regeneration 4 | 1 M NaOH | A4 | 20.0 | 15.0 | 10.0 | Downflow | Waste |
| Regeneration 5 | MilliQ | A3 | 20.0 | 15.0 | 5.0 | Downflow | Waste |
| Storage | 20% EtOH | A6 | 20.0 | 15.0 | 5.0 | Downflow | Waste |

Concentration Step of the Methods of the Present Invention (e.g., a Third Chromatography Step)

In the concentration step according to the methods of the present invention, anion exchange chromatography can be performed for concentration. The anion exchange resin SourceQ is similar to the MonoQ resin. The functional groups are identical but SourceQ particles are three times larger than MonoQ particles—the resolution on the SourceQ resin is therefore lower. The SourceQ anion exchanger can—in the present invention—be used as final step of preparative purification of FVIII subspecies. But instead of further purifying eluates arising from size exclusion chromatography, this step can be used for concentration. The MonoQ eluates are greatly diluted during the preparative size exclusion chromatography, which makes a concentration step necessary. The general procedure includes column equilibration, sample application, a sharp step elution phase which aims at the rapid elution of the whole protein content in a small volume and finally the column regeneration and storage. There are two SourceQ columns available for concentration of SEC eluates. Since the binding capacity of SourceQ resins is comparable to MonoQ resins, which have very high binding capacities, it is in most cases sufficient to use the small SourceQ column with approximately 3 mL column volume. The preferable chromatography scheme shown in table 6 refers to the small SourceQ column. But some product pools may make it necessary to use the larger SourceQ column with 7 mL column volume, due to their higher protein concentrations. The chromatography scheme for the larger column is in principle similar to that one shown in table 6. The linear flow rates are scaled up according to the respective column properties in such a way that the residence times are kept constant.

TABLE 6

Exemplary chromatography scheme of the preparative scale SourceQ anion exchange chromatography, giving information about the used buffers and solutions, inlet settings, linear flow rate, residence time, applied column volume, flow direction in the column and outlet setting for each step. The respective sample volume depends on the sample preparation procedure.

| Step | Buffer/Sample | Inlet | Linear Flow Rate [cm/h] | Residence Time [min] | Column Volume | Flow Direction | Outlet |
|---|---|---|---|---|---|---|---|
| Equilibration 1 | OC1 | A3 | 29.80 | 7.85 | 6.8 | Downflow | Waste |
| Equilibration 2 | MilliQ | A2 | 78.80 | 2.97 | 2.0 | Downflow | Waste |
| Equilibration 3 | 30% QA1/70% QB2 | A1/B2 | 78.80 | 2.97 | 5.0 | Downflow | Waste |
| Equilibration 4 | QA1 | A1 | 78.80 | 2.97 | 10.0 | Downflow | Waste |
| Sample Application | SEC eluate | S1 | 78.80 | 2.97 | sample volume | Downflow | Out 1 |
| Wash | QA1 | A1 | 78.80 | 2.97 | 4.0 | Downflow | Out 2 |
| Step Elution 1 | 20% QA1/80% QB2 | A1/B2 | 78.80 | 2.97 | 4.0 | Downflow | Frac |
| Step Elution 2 | 100% QB2 | B1 | 78.80 | 2.97 | 2.0 | Downflow | Frac |
| Regeneration 1 | MilliQ | A2 | 48.90 | 4.79 | 5.5 | Downflow | Waste |
| Regeneration 2 | 50% HAc | A4 | 14.90 | 15.70 | 5.5 | Downflow | Waste |
| Regeneration 3 | MilliQ | A2 | 48.90 | 4.79 | 5.5 | Downflow | Waste |
| Regeneration 4 | 1 M NaOH | A5 | 31.90 | 7.34 | 5.5 | Downflow | Waste |
| Regeneration 5 | MilliQ | A2 | 48.90 | 4.79 | 5.5 | Downflow | Waste |
| Storage | 10 M NaOH | A6 | 38.30 | 6.11 | 5.0 | Downflow | Waste |

The following describes an exemplary embodiment of how chromatography can be performed in the third step of the method according to the present invention. As will be clear to a person skilled in the art, all conditions merely represent preferable parameters and conditions, without limiting the invention thereto. Moreover, all listed parameters and conditions can be combined with any other listed parameters and conditions for performing chromatography in the third chromatography step according to the methods of the present invention. The equilibration can be first started with 6.8 column volumes of the alkaline OC1 buffer at a reduced linear flow rate of 29.8 cm/h in order to associate the functional groups with chloride as counter ion. The OC1 buffer can be subsequently removed by rinsing the column with two column volumes of MilliQ at a flow rate of 78.8 cm/h, which corresponds to a residence time of 2.97 minutes. The column can thereafter be treated with a mixture of 30% QA1 and 70% QB2 buffer for five column volumes. This mixture contains approximately 260 mM sodium chloride and prevents washing out of the chloride counter ions from the functional groups, when changing the buffer system. The fourth equilibration phase can be performed exclusively with QA1 buffer. Ten column volumes can be applied to the column at a flow rate of 2.97 cm/h in order to bring the column to adequate conditions for sample application. Sample application takes only place at low conductivity conditions. The preparative size exclusion chromatography is preferably operated at intermediate sodium chloride concentrations causing conductivity levels of around 30 mS/cm which would prevent sample binding of the SourceQ column. It is thus necessary to lower the conductivity level by the addition of QA1 buffer until 11 mS/cm or less is reached. This can cause roughly a fivefold increase of sample volume. The sample can be applied to the column using sample pump and air sensor with a linear flow rate of 78.8 cm/h. Following that, the column can be washed with four column volumes of QA1 buffer before the elution phase starts. Elution is preferably carried out with a step gradient of 80% QB2 buffer and 20% QA1 buffer for four column volumes. This correlates to a sodium chloride concentration of 300 mM or a conductivity of 30 mS/cm. The target protein is thereby rapidly eluted in a small volume. Fractions can be collected in the fraction collector. The respective fractions can be pooled in such a way that a suitable protein concentration is achieved. The second level of elution is preferably performed with 100% QB2 buffer which corresponds to 375 mM sodium chloride concentration. The column can then be regenerated by a sequence of ultrapure water, 50% acetic acid, ultrapure water, 1 M sodium hydroxide and finally ultrapure water once again, each 5.5 column volumes in length at various flow rates according to their viscosities. Antimicrobial storage conditions can be obtained by flushing the column with five column volumes of 10 mM sodium hydroxide.

As will be clear to a person skilled in the art, any suitable chromatography system can be used to perform the methods of the present invention. For example, small scale and large scale purifications can be performed on AKTA FPLC (Fast Protein Liquid Chromatography) systems. AKTA Pure 25 and AKTA Avant 25 systems are suitable for small scale columns and low flow rates, whereas AKTA Pure 150 systems are used for the purification of higher amounts of proteins and concomitant larger column diameters as well as higher flow rates. All AKTA chromatographs can be operated by the UNICORN software package.

TABLE 7

Information on chromatography resins that can be used for anion exchange-, size exclusion-, and hydrophobic interaction chromatography steps of the present invention.

| Resin | Manufacturer | Type | Functional Group | Matrix | Bead Form | Particle Size |
|---|---|---|---|---|---|---|
| Mono 10Q | GE Healthcare | Strong Anion Exchanger | Quaternary Ammonium | Polystyrene/divinyl benzene | monodisperse | 10 μm |
| Source 30Q | GE Healthcare | Strong Anion Exchange | Quaternary Ammonium | Polystyrene/divinyl benzene | monodisperse | 30 μm |
| Superdex 200 Increase | GE Healthcare | Gel Filtration Media | not specified | Agarose and dextran | crosslinked | 8.6 μm |
| Superdex 200 Prep Grade | GE Healthcare | Gel Filtration Media | not specified | Agarose and dextran | crosslinked | 24 μm to 44 μm |
| Phenyl Sepharose High Performance | GE Healthcare | Hydrophobic Interaction Chromatography Media | Phenyl | 6% cross-linked agarose | crosslinked | 24 μm to 44 μm |

TABLE 8

Information on chromatography column hardware types, packing dimensions and parameters that can be used in the methods of the present invention. The column code is a freely defined label for the different columns that can be used in the methods of the present invention and is used in the following to describe the respective column hardware and resin combination. The manufacturer name refers to the column hardware and is not necessarily identical to the resin manufacturer.

| Column Code | Resin | Column Hardware | Manufacturer | Inner Diameter [cm] | Area [cm$^2$] | Bed Height [cm] | Gel Volume [mL] |
|---|---|---|---|---|---|---|---|
| MonoQ Small Scale | Mono 10Q | Tricorn 5/50 | GE Healthcare | 0.5 | 0.1963 | 5.0 | 0.98 |
| MonoQ Prep Scale | Mono 10Q | HR16/10 | GE Healthcare | 1.6 | 2.011 | 10.0 | 20.11 |
| SEC Small Scale | Superdex 200 Increase | Tricorn 10/300 | GE Healthcare | 1.0 | 0.7854 | 30.0 | 23.56 |
| SEC Prep Scale | Superdex 200 Prep Grade | XK50/100 | GE Healthcare | 5.0 | 19.63 | 94.4 | 1853.54 |
| SOQ Small Scale | Source 30Q | ECO Plus 10/250 | Kroulab/YMC | 1.0 | 0.7854 | 3.9 | 3.06 |
| SOQ Prep Scale | Source 30Q | Tricorn 10/100 | GE Healthcare | 1.0 | 0.7854 | 8.9 | 7.0 |
| HIC Small Scale | Phenyl Sepharose High Performance | Eco Plus 5/125 | Kroulab/YMC | 0.5 | 0.1963 | 5.0 | 0.98 |

TABLE 9

General buffers and solutions as well as buffers that can be especially used for chromatography runs. The latter are listed in sections according to the respective type of chromatography. The given abbreviations are used herein.

| Name | Abbreviation | Description |
|---|---|---|
| General Buffers and Solutions | | |
| Ultrapure Water | MilliQ | Type 1 Ultrapure Water (18.2 MΩ × cm at 25° C.) |
| 1M Sodium Hydroxide | 1M NaOH | 1M sodium hydroxide in MilliQ |
| 0.5M Sodium Hydroxide | 0.5M NaOH | 0.5M sodium hydroxide in MilliQ |
| 10 mM Sodium Hydroxide | 10 mM NaOH | 10 mM sodium hydroxide in MilliQ |
| 2M Sodium Chloride | TWA | 2M sodium chloride in MilliQ |
| 1M Acetic Acid | 1M HAc | 1M acetic acid in MilliQ |
| 75% Acetic Acid | 75% HAc | 75% acetic acid in MilliQ |
| 20% Ethanol Solution | 20% EtOH | 20% ethanol in MilliQ |
| Furin Protease Solution I | Furin Solution | Enriched Furin Protease solution (84.960 U/mL) |
| Furin Protease Solution II | Furin Solution | Enriched Furin Protease solution (66.990 U/mL) |
| Anion Exchange Chromatography | | |
| MonoQ/SourceQ Equilibration Buffer | QA1 | 50 mM Tris, 5 mM $CaCl_2 \times 2H_2O$, 0.1% (v/v) Tween 80, pH 6.7 ± 0.2 at 25° C. |
| MonoQ Elution Buffer/SourceQ Elution Buffer II | QB1 | 50 mM Tris, 5 mM $CaCl_2 \times 2H_2O$, 750 mM NaCl, 0.1% (v/v) Tween 80, pH 6.7 ± 0.2 at 25° C. |
| SourceQ Elution Buffer I | QB2 | 50 mM Tris, 5 mM $CaCl_2 \times 2H_2O$, 375 mM NaCl, 0.1% (v/v) Tween 80, pH 6.7 ± 0.2 at 25° C. |
| MonoQ/SourceQ Alkaline Equilibration Buffer | OC1 | 10 mM NaOH, 1 M NaCl |
| MonoQ Acetate Equilibration Buffer | 30 mM Acetate Buffer | 30 mM acetate, 0.1% (v/v) Polysorbate 80, pH 6.0 ± 0.2 at 25° C. |
| MonoQ Acetate Elution Buffer | 30 mM Acetate/NaCl Buffer | 30 mM acetate, 750 mM NaCl, 0.1% (v/v) Polysorbate 80, pH 6.0 ± 0.2 at 25° C. |
| MonoQ Tris Buffer | 20 mM Tris Buffer | 20 mM Tris, 0.1% (v/v) Polysorbate 80, pH 8.0 ± 0.2 a 4° C. |
| MonoQ Tris Equilibration Buffer | 20 mM Tris Buffer | 20 mM Tris, 0.1% (v/v) Polysorbate 80, pH 7.7 ± 0.2 at 4° C. |
| MonoQ Tris Elution Buffer | 20 mM Tris/NaCl Buffer | 20 mM Tris, 750 mM NaCl 0.1% (v/v) Polysorbate 80, pH 7.7 ± 0.2 at 4° C. |
| MonoQ Phosphate Equilibration Buffer | 20 mM Phosphate Buffer | 20 mM Phosphate, 0.1% (v/v) Polysorbate 80, pH 7.4 ± 0.2 at 25° C. |
| MonoQ Phosphate Elution Buffer | 20 mM Phosphate/NaCl Buffer | 20 mM Phosphate, 750 mM NaCl, 0.1% (v/v) Polysorbate 80, pH 7.4 ± 0.2 at 25° C. |
| MonoQ HEPES Equilibration Buffer | 20 mM HEPES Buffer | 20 mM HEPES, 0.1% (v/v) Polysorbate 80, pH 7.0 ± 0.2 at 25° C. |
| MonoQ HEPES Elution Buffer | 20 mM HEPES/NaCl Buffer | 20 mM HEPES, 750 mM NaCl 0.1% (v/v) Polysorbate 80, pH 7.0 ± 0.2 at 25° C. |
| MonoQ Ethylene Glycol Equilibration Buffer | QA1/EG Buller | 50 mM Tris, 5 mM $CaCl_2 \times 2H_2O$, 0.1% (v/v) Tween 80, 10% (v/v) Ethylene glycol, pH 6.7 ± 0.2 at 25° C. |
| MonoQ Ethylene Glycol Elution Buffer | QB1/EG Buffer | 50 mM Tris, 5 mM $CaCl_2 \times 2H_2O$, 750 mM NaCl, 0.1% (v/v) Tween 80, 10% (v/v) Ethylene glycol, pH 6.7 ± 0.2 at 25° C. |
| Hydrophobic Interaction Chromatography | | |
| HIC Sample Preparation Buffer I | HIC Buffer A | 40 mM Tris, 1 M NaCl, 2 mM $CaCl_2$, pH 7.4 ± 0.2 at 25° C. |
| HIC Sample Preparation Buffer II | HIC Tris Buffer | 1 M Tris, pH 9.0 ± 0.3 at 25° C. |
| HIC Equilibration Buffer I | HIC Buffer B | 20 mM Tris, 500 mM NaCl, 2 mM $CaCl_2$, pH 7.4 ± 0.2 at 25° C. |
| HIC Equilibration Buffer II | HIC Buffer E1 | 20 mM Tris, 680 mM NaCl, 2 mM $CaCl_2$, pH 7.4 ± 0.2 at 25° C. |
| HIC Equilibration Buffer III | HIC Buffer E2 | 20 mM Tris, 750 mM NaCl, 2 mM $CaCl_2$, pH 7.4 ± 0.2 at 25° C. |
| HIC Equilibration Buffer IV | HIC Buffer F | 20 mM Tris, 740 mM NaCl, 2 mM $CaCl_2$, pH 7.4 ± 0.2 at 25° C. |
| HIC Elution Buffer I | HIC Buffer C | 20 mM Tris, 2 mM $CaCl_2$, pH 7.4 ± 0.2 at 25° C. |
| HIC Elution Buffer II | HIC Buffer D | 20 mM Tris, 2 mM $CaCl_2$, 50% (v/v) Ethylene glycol, pH 7.4 ± 0.2 at 25° C. |
| HIC Buffer for Conductivity Adjustment | HIC Buffer G | 20 mM Tris, 2 M NaCl, 2 mM $CaCl_2$, pH 7.4 ± 0.2 at 25° C. |
| HIC Isopropyl alcohol | HIC IPA | 30% (v/v) isopropyl alcohol in MilliQ |
| Size Exclusion Chromatography | | |
| SEC Equilibration/Elution Buffer | 20% QA1/80% QB2 | 50 mM Tris, 5 mM $CaCl_2 \times 2H_2O$, ~ 300 mM NaCl, 0.1% (v/v) Tween 80, pH 6.7 ± 0.2 at 25° C. |

As will be clear to a person skilled in the art, the final concentration step of the methods of the present invention is not necessarily a chromatography step. The person skilled in the art will be aware of numerous suitable alternatives for concentrating the eluate comprising the FVIII subspecies of the preceding (second) chromatography step of the present invention. For example, ultrafiltration could be used for concentration.

As will be obvious to a person skilled in the art, the method for purifying a FVIII subspecies according to the present invention can also be used for purifying other proteins or protein subunits from compositions comprising several proteins or protein subunits with high purity. Of course, the compositions comprising purified proteins or protein subunits can then be used, e.g., as a medicament.

Surprisingly, the inventors have also found that furin treatment of recombinant FVIII increases the activity of FVIII, even without subspecies purification. Such furin treatment of FVIII can be performed as described above for the furin treatment as part of the method for purifying a FVIII subspecies. Preferably, recombinant FVIII which comprises single chain (i.e., uncleaved) FVIII is subjected to the furin treatment without subspecies purification of the present invention. Such furin treatment can be performed using furin at a final concentration of more than 50 IU/mL, more than 100 IU/mL, more than 200 IU/mL or more than 300 IU/mL, but it is preferably performed using furin at a final concentration of more than 100 IU/mL. The furin treatment can be performed for 1 h at room temperature, i.e. at around 21° C. After furin treatment, the furin can be separated from the FVIII. The furin-treated FVIII can be used as a medicament, e.g. for treating patients with bleeding disorders such as hemophilia A.

As will be known to a person skilled in the art, there are different methods available for the determination of protein concentration in aqueous solutions. The spectrophotometric measurement in the ultraviolet range at 280 nm is suitable for highly purified protein solutions and is therefore preferably used in the present invention. According the Lambert Beers Law $$A = \varepsilon \cdot l \cdot c$$

is the measured absorbance A a linear function of protein concentration c (M), the cell path length l (cm) and the extinction coefficient $\varepsilon$ ($M^{-1}$ $cm^{-1}$). The underlying principle for absorbance of protein solutions at 280 nm is the content of the aromatic amino acids tryptophan and tyrosine as well as cystine, i.e. disulphide bonds, which contributes to the total absorbance to a lesser extent. Phenylalanine contributes to the absorbance only at lower wavelengths and is therefore not relevant for UV measurements at 280 nm. To be able to observe protein concentrations from aqueous solutions, the extinction coefiicient for a particular protein, which is mainly dependent on the amino acid composition and the abundance of aromatic amino acids and cystine has to be determined. Due to the heterogeneous composition of recombinant FVIII (see above), specific extinction coefficients for each FVIII subspecies are necessary in order to calculate protein concentrations for the purified subspecies fractions. The calculation of these subspecies specific extinction coefficients at a protein concentration of 1 mg/mL can be found below. Conversion factors based on these subspecies specific extinction coefficients were calculated to further simplify the calculation of the protein concentration. The measurement itself is performed against a blank solution, which contains an identical buffer composition as the sample. The degree of absorption can be converted into the respective protein concentration, using the above equation. The protein concentration as target value of this method is e.g. used as a measure of how effective a chromatographic concentration step works.

As will be known to a person skilled in the art, polyacrylamide gel electrophoresis is a technique used to separate macromolecular biomolecules, e.g. proteins according to their size, conformation and charge. The usage of sodium-dodecyl-sulfate (SDS) or lithium-dodecyl-sulfate (LDS) causes disruption of secondary and tertiary structures by complexation and thereby protein linearisation. Reducing agents such as dithiothreitol (DTT) and iodoacetamide are used to separate disulphide bonds and to prevent reformation. In addition, binding of SDS produces a negative net charge of polypeptide chains, which makes separation only dependent on the proteins molecular weight. The gel itself is composed of acrylamide monomers and crosslinking bis-acrylamide, whereby the density and the pore size of the gel is defined by the concentration of bis-acrylamid. When an electric field is applied to the gel, the proteins migrate towards the positive pole (i.e. anode) at different velocities depending on their actual weight. Subsequent staining makes separated protein fractions visible and accessible for further processing or interpretation. Polyacrylamide gel electrophoresis makes a qualitative statement regarding both purity and concentration of applied samples. The person skilled in the art will know of various ways of performing polyacrylamide gel electrophoresis as well as corresponding staining procedures. For example, polyacrylamide gel electrophoresis as well as corresponding staining procedures can be performed with Tris-acetate buffered equipment under reducing conditions. Exemplary equipment and general conditions are summarised in the following table.

TABLE 10

Exemplary equipment and buffers for polyacrylamide gel electrophoresis. All buffers as well as the polyacrylamide gel itself are ready to use equipment manufactured by Thermo Fisher Scientific, Tradename Invitrogen. The respective catalogue numbers are listed.

| Equipment | Description | Cat. Nr |
|---|---|---|
| Gel | NuPAGE 3-8% TrisAcetate Midi Gel | Invitrogen WG1602BOX |
| Running Buffer | Acetat SDS Running Buffer 2 × | Invitrogen LA0041 |
| Sample Buffer | LDS Sample Buffer | Invitrogen NP0007 |
| | NuPAGE Reducing Agent | Invitrogen NP0009 |

As will be known to a person skilled in the art, silver staining after gel electrophoresis is a rapid and very sensitive method to detect protein bands. Its fundamental principle is the binding of silver ions to the protein surface and subsequent reduction to fine metallic silver, which produces dark coloured protein bands. Excessive silver ions have to be removed after developing to avoid occurrence of unspecific signals. Basic staining protocols may also involve additional preparation steps such as removal of interfering ions, increasing sensitivity and contrast and several washing steps. Silver staining is a unspecific method which stains any protein present in the sample. It can therefore be used for purity assessment in the present invention.

As will be known to a person skilled in the art, western blotting is an even more sensitive method to detect protein bands. In addition, it is also specific for a particular type of protein, which allows distinction between target protein and impurities. After protein separation in gel electrophoresis, proteins are transferred to a membrane. This can be achieved by different mechanisms. The most prominent is electroblotting, where an electric field is used to force protein migration towards the membrane. The development involves two different antibodies. To prevent unspecific binding of the antibodies to the membrane surface, it is essential to block the membrane with bovine serum albumin or non-fat dry milk. The primary antibody is highly specific for the target protein (e.g. blood coagulation FVIII). The secondary antibody is coupled to alkaline phosphatase (ALP) and directed against the primary antibody. Upon binding of both antibodies, an ALP specific substrate is added and subsequently converted to an insoluble, coloured form, which precipitates in close proximity to immobilised FVIII.

As will be known to a person skilled in the art, the FVIII chromogenic assay relies on the generation of a chromogenic product whose appearance can be followed by spectrophotometric measurement at 405 nm. In such assay, the FVIII sample is mixed with a solution of thrombin, phospholipids, FIXa and $Ca^{2+}$. Inactive FVIII is activated to its active form FVIIIa by thrombin and forms a complex containing FVIIIa, FIXa, phospholipids and calcium. This complex is capable of activating FX to active FXa, which in turn degrades a chromogenic substrate. This reaction releases para-nitroanilin, whose formation can be followed by photometric measurement at 405 nm. The increase of extinction is directly proportional to the amount of FXa, which is in turn directly proportional to the amount of FVIII in the sample. In the present invention, chromogenic activity assays can be performed as known in the art. For example, FVIII activity assay can be performed with commercially available reagents (Siemens, Germany) on an automated coagulation analyzer (BCS XP, Siemens). In the first step of the chromogenic assay, a sample containing an unknown amount of functional FVIII, can be added to a reaction mixture consisting of thrombin, activated FIX (FIXa), phospholipid, FX and a buffer containing calcium. FVIII is activated by thrombin. Activated FVIII (FVIIIa) forms a complex with phospholipids, FIXa and calcium resulting in the activation of Factor X (FXa). In the second step of the chromogenic assay FXa can be measured through cleavage of an FXa specific peptide nitroanilide substrate. P-nitroaniline is produced, giving a color that can be measured photometrically by absorbance at 405 nm. The color produced is directly proportional to the amount of functional FVIII present in the sample. The reference standard can be full-length FVIII, calibrated against WHO international standard.

One-stage clotting assays can be performed as known in the art. For example, FVIII activity by one-stage clotting assay can be performed with a commercially available aPTT reagent, Actin FSL (Siemens, Germany) on an automated coagulation analyzer (BCS XP, Siemens, Germany). A sample containing an unknown amount of functional FVIII can be mixed with human FVIII-deficient plasma and the activator. After incubation at +37° C., coagulation can be initiated by addition of calcium chloride and the time to clot formation is recorded. Coagulation time is indirectly proportional to the FVIII concentration in the sample. Results can be given in IU FVIII/mL, read from a reference curve. The reference standard can be full-length rFVIII, traceable to the WHO international standard.

Tissue factor triggered thrombin generation assays can be performed as known in the art. For example, the calibrated automated thrombography (CAT), a type of thrombin generation assay (TGA), is a global hemostatic assay that is increasingly used in clinical studies as ex vivo efficacy parameter and as research tool. The thrombogram describes the concentration of thrombin in clotting plasma and is therefore a function test of the hemostatic system under close to physiological conditions. The assay is based on the measurement of fluorescence that is generated by the cleavage of the fluorogenic substrate Z-G-G-R-AMC by thrombin over time upon initiation of coagulation by Tissue Factor. The assay is performed on a Thrombograph™, a 96-well plate fluorometer, and uses a thrombin calibrator that is needed to correct for inner filter effect, donor-to-donor variability in color of plasma, substrate depletion and instrumental differences.

The following CAT parameters characterize the hemostatic state of a plasma sample:
  Lag time [min]:represents clotting time, the initiation of thrombin generation
  Time to peak [min]:time until maximal amount of thrombin is generated
  Thrombin peak [nM]:maximal thrombin concentration formed
  Endogenous Thrombin Potential (ETP) [nM min]:Area under the thrombin generation curve representing the total amount of thrombin that is generated.

As will be known to a person skilled in the art, enzyme linked immunosorbent assay is an immunological approach that uses antibodies and a coloured reaction—usually mediated by enzymes to detect and quantify an antigen. Antigens can be either immobilised directly on the surface of a 96 deep well plate or are bound by an antibody which has been immobilised on the surface prior to sample application. In each case the antigen is immobilised so that a secondary, antigen specific antibody can attach to the antigen. In many cases the secondary antibody is conjugated with an enzyme that is capable of converting a colourless substrate to a coloured substance, which can be detected by photometric measurement. It is therefore a quantitative method which gives information about the activity of FVIII protein in the respective sample. A standard curve generated under identical conditions is needed for interpretation of the results.

If recombinant protein (e.g. rFVIII) produced in CHO cells is used in the methods of the present invention, the determination of CHO host cell protein content can be used to interpret the starting materials quality. To this end, a 96 deep well plate can be covered with CHO specific polyclonal goat IgG antibody. The addition of different dilutions of sample solution leads to the formation of an immune complex, comprising primary anti CHO antibody and antigen. Exceeding sample proteins can be removed by washing. The secondary HRP-conjugated goat anti CHO polyclonal antibody recognises the immune complex. Upon binding and another additional washing step the substrate solution can be added. It contains ortho-phenylendiamin which is converted to yellow-orange coloured 2,3-diaminophenazine under catalysis of horseradish peroxidase. The degree of colouring is directly proportional to the amount of CHO host cell proteins in the sample and can be detected at 490 nm by photometric measurement.

As will be known to a person skilled in the art, the basic principle of vWF Antigen ELISA is similar to that described above. A rabbit anti human vWF antibody is used to immobilise vWF present in the sample. The secondary HRP-conjugated rabbit anti-human vWF antibody binds the immune complex. After a washing step, ortho-phenylendiamin solution is added and converted to 2,3-diaminophenazine under catalysis of horseradish peroxidase. Detection is similar to the CHO Antigen ELISA described above.

As will be known to a person skilled in the art, high performance liquid chromatography (HPLC) can be used to analytically separate, identify and quantify all components within a sample. While traditional liquid chromatography operates at low pressure, HPLC is performed under high pressure conditions. The term reversed phase refers to the hydrophobic properties of the stationary phase, which is opposite to the historically called normal phase using polar stationary resins such as silica gels. Reversed phase resins are generated by alkylation of silica gel matrices with carbohydrate chains of varying lengths, usually ranging from four to eighteen carbon atoms (C4 to C18). Typical eluents are polar, aqueous solutions of salts or acids on the one hand and unpolar, organic solvents such as acetonitrile or methanol on the other hand. Separation of blood coagulation FVIII subspecies is preferably carried out on a C4 reversed phase column (Jupiter® 5 m C4 300 Å, LC Column 150×2 mm, Phenomenex) with 0.1% trifluoroacetic acid (TFA) in water as eluent A and 0.085% TFA in acetonitrile as eluent B with increasing percentage of eluent B during elution as illustrated in the following table.

TABLE 11

Preferred conditions and parameters for the
C4 reversed phase high performance
liquid chromatography analysis of FVIII
molecular subspecies. Percentage A
and percentage B are referred to the percentage fractions of
the two mobile phases used for separation. (A) 0.1% trifluoroacetic
acid in ultrapure water, (B) 0.085% trifluoroacetic acid in acetonitrile.

| Step | Time [min] | Flow Rate [mL/min] | Percentage A | Percentage B |
|---|---|---|---|---|
| 1 | 0.0 | 0.2 | 68.0 | 32.0 |
| 2 | 12.0 | 0.2 | 56.0 | 44.0 |
| 3 | 24.0 | 0.2 | 48.0 | 52.0 |
| 4 | 30.0 | 0.2 | 0.0 | 100.0 |
| 5 | 35.0 | 0.2 | 0.0 | 100.0 |
| 6 | 36.0 | 0.2 | 68.0 | 32.0 |

The amount of sample injected preferably corresponds to 15 μg or 75 IU protein, respectively. Since hydrophobic interactions are temperature dependent, the column is preferably heated to 60° C. to increase resolution. Eluting proteins are preferably detected with a photodiode array detector at 214 nm, which corresponds to the excitation wavelength of the peptide bond. Reversed phase HPLC by itself is responsible for the separation of proteins due to their different hydrophobicity. The mode of detection is of spectrophotometric nature. Both, separation and detection together allow the measurement of absorbance intensities of the differently eluting proteins and upon integration of the area under the curve the calculation of the respective protein concentration. This is of major significance, because it can be used as a measure for the quality of separation success in the present invention, and it is used for determining the weight ratio of FVIII subspecies as described above.

As will be known to a person skilled in the art, the calculation of molar extinction coefficients for each FVIII subspecies, as well as the full length single chain molecule is an approximation, based on the actual properties of the respective molecule. General information, as given in table 12, can be derived from the ProtParam tool (entry number P00451), provided by the ExPASy bioinformatics resources portal. This includes the number of amino acids, the theoretical isoelectric point, the molecular weight of the amino acid backbone and the approximate extinction coefficients for a 1 g/L solution of FVIII subspecies at a wavelength of 280 nm. Glycosylations and other posttranslational modifications are not included in the amino acid backbone molecular weight data. The theoretical molar absorption coefficient for a molecule can be derived from the following equation.

$$\epsilon = N(Tyr) \cdot \epsilon(Tyr) + N(Trp) \cdot \epsilon(Trp) + N(Cys2) \cdot \epsilon(Cys2)$$

The number of the three amino acids contributing to light absorption at 280 nm—these are Tyrosine, Trytophan and Cysteine—are multiplied with their respective molar extinction coefficients. The sum of all three products equals the total extinction coefficient of the molecule for a concentration of 1 g/L. The calculation does not include posttranslational modifications, such as glycosylation and tyrosine sulphation. In addition, it is assumed that all cysteine residues form cystine, as cystine contributes to light absorption, while cysteine does not. The actual location of tyrosine, tryptophan and cystine residues in the folded protein and therefore eventually occurring influence by the surrounding environment are not taken into account for this estimation. Each FVIII heavy chain is associated either with the 80 kDa light chain or the 120 kDa extended light chain. It is assumed that a solution containing one heavy chain species and one light chain species is made up of 50% of each. Both, heavy and light chain species exhibit their distinct light absorption coefficients, contributing to the total absorption of the solution as a function of their mass fraction. The mass fraction is calculated as quotient of the respective molecular weight of the amino acid backbone of one subspecies and the total molecular weight of both subspecies.

$$\omega_{heavychain} = \frac{M_{heavychain}}{M_{heavychain} + M_{lightchain}}$$

TABLE 12

General information on FVIII molecular subspecies: number of amino acids,
theoretical isoelectric point, molecular weight of the amino acid
backbone (glycosylations not included), percentage with
reference to full length single chain and absorption coefficients at 280 nm.

| Designation | Number of amino acids | Theoretical pI | Molecular weight of amino acid backbone [kDa] | % of single chain [%] | Extinction Coefficient e at 280 nm for 1 g/L |
|---|---|---|---|---|---|
| Single chain | 2332 | 6.97 | 264.72 | 100 | 1.219 |
| 180 kDa subspecies | 1313 | 6.30 | 148.45 | 56 | 1.066 |
| 150 kDa subspecies | 976 | 5.68 | 110.41 | 42 | 1.293 |
| 110 kDa subspecies | 817 | 5.84 | 93.47 | 35 | 1.452 |
| 90 kDa subspecies | 740 | 5.74 | 84.67 | 32 | 1.520 |
| Light chain | 687 | 7.74 | 78.99 | 30 | 1.617 |
| Extended light chain | 1019 | 8.58 | 116.29 | 44 | 1.414 |

A combination of 180 kDa heavy chain and 80 kDa light chain for example gives mass fractions of 0.65 and 0.35, respectively.

$$\omega_{heavychain} = \frac{148.45 \text{ kDa}}{148.45 \text{ kDa} + 78.99 \text{ kDa}} = 0.65$$

$$\omega_{lightchain} = \frac{78.99 \text{ kDa}}{78.99 \text{ kDa} + 148.45 \text{ kDa}} = 0.35$$

This means that the 180 kDa heavy chain with its specific extinction coefficient of 1.066 M$^{-1}$cm$^{-1}$ contributes to 65% to the total absorbance of the solution. The 80 kDa light chain in contrast contributes to a lower extend of only 35% with an extinction coefficient of 1.617 M$^{-1}$cm$^{-1}$. The sum of products of mass fraction and subspecies specific extinction coefficient ε for both, heavy and light chain, gives the total extinction coefficient $\epsilon_{total}$ for a 1 g/L protein solution.

$$\epsilon_{total} = \omega_{heavy\ chain} \cdot \epsilon_{heavy\ chain} + \omega_{light\ chain} \cdot \epsilon_{light\ chain}$$

Accordingly, a protein solution containing 180 kDa heavy chain associated with the 80 kDa light chain has an approximate extinction coefficient given by the following equation.

$$\epsilon_{total} = 0.65 \cdot 1.066~M^{-1}cm^{-1} + 0.35 \cdot 1.617~M^{-1}cm^{-1} = 1.26~M^{-1}cm^{-1}$$

The total extinction coefficient $\epsilon_{total}$ for solutions containing each of the four heavy chain variants (180 kDa, 150 kDa, 110 kDa and 90 kDa) in combination with the 80 kDa light chain can be calculated in an equal way. The results are shown in table 13.

TABLE 13

Calculation of FVIII subspecies specific relative absorbance values derived from the mass fraction of a 50% heavy chain and 50% light chain mixture and the respective extinction coefficients.

| Designation | Molar fraction | Mass fraction | e [M$^{-1}$cm$^{-1}$] | Rel. Abs [M$^{-1}$cm$^{-2}$] |
|---|---|---|---|---|
| 180 kDa heavy chain + 80 kDa light chain | | | | |
| 180 kDa heavy chain | 50% | 0.65 | 1.066 | 0.70 |
| 80 kDa light chain | 50% | 0.35 | 1.617 | 0.56 |
| Sum | 100% | 1.00 | — | 1.26 |
| 150 kDa heavy chain + 80 kDa light chain | | | | |
| 150 kDa heavy chain | 50% | 0.58 | 1.293 | 0.75 |
| 80 kDa light chain | 50% | 0.42 | 1.617 | 0.67 |
| Sum | 100% | 1.00 | — | 1.43 |
| 110 kDa heavy chain + 80 kDa light chain | | | | |
| 110 kDa heavy chain | 50% | 0.54 | 1.452 | 0.79 |
| 80 kDa light chain | 50% | 0.46 | 1.617 | 0.74 |
| Sum | 100% | 1.00 | — | 1.53 |
| 90 kDa heavy chain + 80 kDa light chain | | | | |
| 90 kDa heavy chain | 50% | 0.52 | 1.520 | 0.79 |
| 80 kDa light chain | 50% | 0.48 | 1.617 | 0.78 |
| Sum | 100% | 1.00 | — | 1.57 |

As will be clear to a person skilled in the art, any suitable laboratory equipment can be used to perform the methods of the present invention. However, the following table shows exemplary small laboratory equipment that can be used for the methods of the present invention. The exemplary list includes equipment for buffer preparation, sample preparation, chromatography experiments itself, as well as analysis and storage. Some corresponding information regarding manufacturer, product code, measuring range etc. is provided.

TABLE 14

Exemplary list of general laboratory equipment that can be used in the method of the present invention. Some information regarding manufacturer, product code, measuring range etc. is provided.

| Equipment | Description |
|---|---|
| Deep Freezer (−60° C.) | Thermo Scientific, model no. ULT2186-10-V49 |
| Laminar Flow Workbench | Thermo Scientific HERA Safe |
| Laboratory Balance I | Sartorius LA 230S (10 mg-230 g) |
| Laboratory Balance II | Sartorius lab balance (0.5 g-6200 g) |
| Laboratory Balance III | Sartorius QC64EDE-S0CE (50 g-64.2 kg) |
| Magnetic Stirrer | VWR VS-C10 magnetic stirrer |
| Magnetic Stirring Bars | Magnetic stirring bars in various dimensions |
| Glass Bottles | Schott Duran borosilicate glass bottles (100 mL, 250 mL, 500 mL, 1 L, 2 L, 5 L) |
| Pipette Boy | Brand accn-jet pro |
| Graduated Pipettes | Costan single use sterile pipettes (2 mL, 5 mL, 10 mL, 25 mL) |
| Positive Displacement Pipettors | Eppendorf Reference Pipettors (10-100 μL, 50-200 μL, 100-1000 μL) |
| Pipette Tips | Sterile and non-sterile Eppendorf tips (2-200 μL, 50-1000 μL) |
| Graduated Cylinder | VWR Boro 3.3, Brand or Duran graduated cylinders (5 mL, 10 mL, 25 mL, 50 mL, 100 mL, 250 mL, 500 mL, 1 L, 2 L) |
| Glass Beakers | Schott Duran borosilicate glass beakers (10 mL, 20 mL, 50 mL, 100 mL, 250 mL, 400 mL, 600 mL) |
| Safe Lock Tubes | Eppendorf 1.5 mL safe lock tubes in different colours |
| Cryo Vials | Thermo Scientific nunc CryoTube vials (1.8 mL) |
| Spectrophotometer | Thermo Scientific Nano Drop 2000 c |
| Cuvettes | Semi-micro disposable UV-Cuvettes, Brand |
| Storage Bottle | Nalgene PETG square media bottle (30 mL, 60 mL, 125 mL, 250 mL, 500 mL, 1 L, 2 L) |
| Peristaltic Pump | Watson Marlow 520 S |
| Sterile Filter Units | Sartorius Sartopore 2, 150 0.22 μm sterile filter capsule, Millipak 20 Gamma Gold 0.22 μm sterile filter unit |
| Silicone Tubing | Flexible silicone tubing (30-70 cm) |
| Deep Well Plates | GE Healthcare, Uniplate (96 wells, 2 mL), Polypropylen, Round Bottom |
| Graduated Centrifuge Tubes | VWR disposable centrifuge tubes (50 mL, 15 mL) |
| Dual Channel Conductivity/pH-Meter | Mettler-Toledo Seven Multi dual channel |

In the following, the present invention will be illustrated by examples, without being limited thereto.

EXAMPLES

Unless indicated otherwise, all method steps in the following Examples 1-16 have been performed in accordance with the respective (preferred) embodiments that are described in detail in the above section "Detailed Description of the Invention".

Example 1

Starting Material for Purifying FVIII Subspecies

Almost all of the following purification experiments are performed with a SourceS eluate (SOS-E) containing FL-rFVIII, designated B14390000-30. SOS-E is produced as the ADVATE BDS, but missing a final purification step.

The second starting material only used in one large scale purification is a pool of various MonoQ and SourceQ post eluates, containing enriched 90 kDa FVIII subspecies in low concentration. The single post eluates were pooled to receive one large product pool. This pool is termed F8__AD2_90 kDa.

Example 2

Small Scale Purification of FVIII Subspecies—First Chromatography Step

Regardless of the general type of chromatography—anion exchange chromatography using MonoQ resins or size exclusion chromatography on Superdex 200 resins—the results produced during the following small scale experiments are used for the large scale process of the preparative purification steps. The results are important for configuration of the respective chromatography procedure.

Since the anion exchange chromatography is the first purification step of FVIII subspecies, it is of great interest for refinement of operating conditions. MonoQ as an analytical AIEX resin with monodisperse particles of 10 µm in size and almost uniform shape exhibits by far the best resolution and the most promising separation properties. Hence, this step has undergone a lot of parameter testing and variations including sample preparation.

Figure 4:
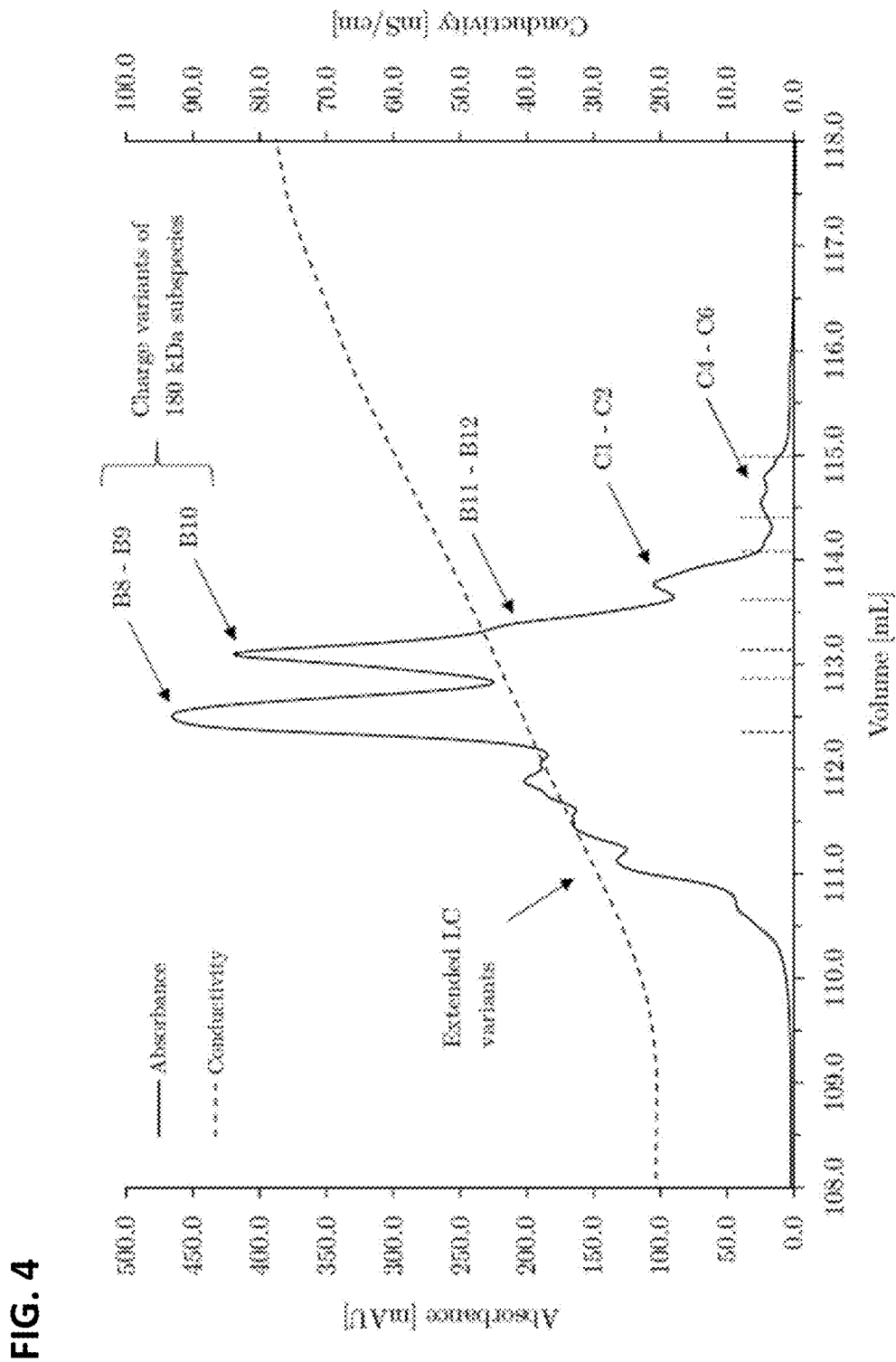
FIG. 4: Chromatogram of the elution phase of FVIII molecular subspecies on AIEX Mono 10Q resin separated with standard buffers QA1 and QB1 at pH 6.7. Gradient: 135.0-750.0 mM sodium chloride in eight column volumes. Column dimensions: 0.5 cm inner diameter×5.0 cm bed height, 0.98 mL column volume.
Figure 5:
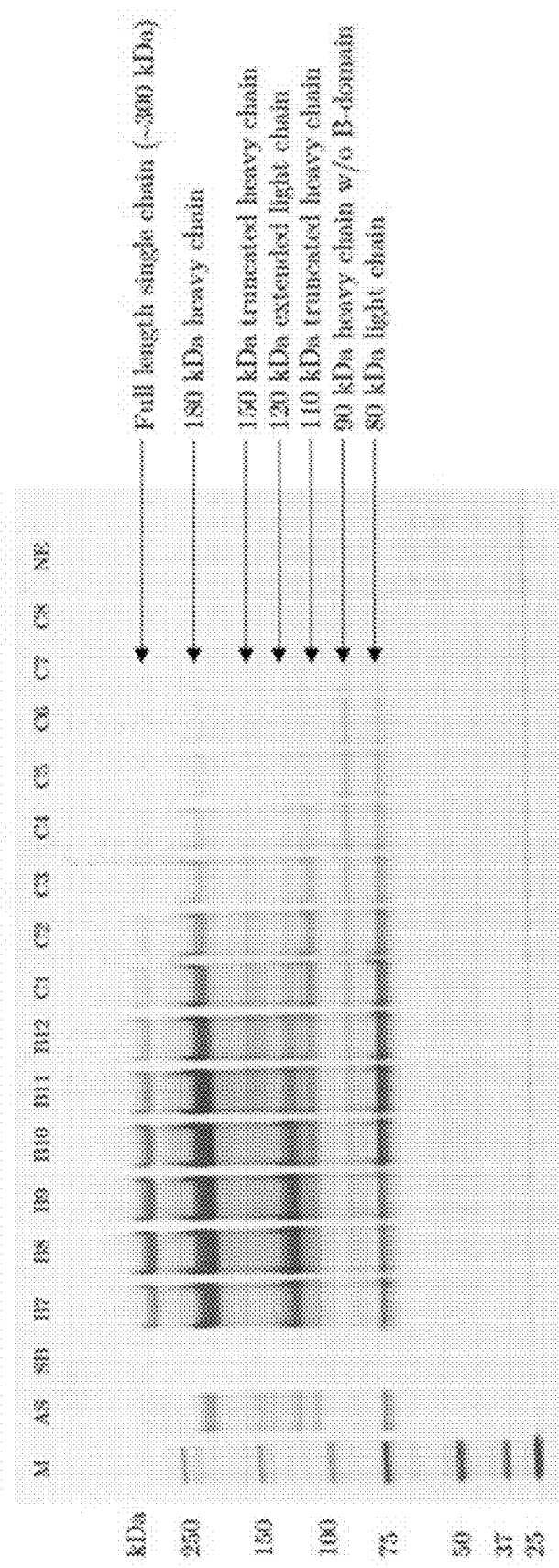
FIG. 5: SDS page gel electrophoresis of the separation of FVIII molecular subspecies on Mono 10Q resin separated with standard buffers QA1 and QB1 at pH 6.7. Gradient: 135.0-750.0 mM sodium chloride in eight column volumes. M) Molecular weight marker, AS) Standard of the commercially available FVIII drug substance, showing all relevant heavy- and light chain species, SB) Sample buffer, Fractions B7-C8, NE) Posteluate. From top to bottom: Full length single chain (300 kDa), 180 kDa heavy chain, 150 kDa truncated heavy chain, 120 kDa extended light chain, 110 kDa truncated heavy chain, 90 kDa heavy chain without B-domain, 80 kDa light chain.

FIG. 4 shows a chromatogram of the non-furin treated SourceS eluate B14390000-30, separated under standard conditions. The elution phase is eight column volumes in length and operated with the standard buffers QA1 and QB1. The elution starts relatively early with the first increase of conductivity. There are a few diffuse peaks as well as a very prominent peak recognisable as soon as the UV signal increases in its intensity. These are known to be differently charged variants of the full length heavy chain (180 kDa) most likely caused by different glycosylation in the B-domain area as well as combinations of the extended light chain with the other heavy chain subspecies. The underlying mechanism is yet not fully understood but hydrophobic interactions might also be a reason for this specific elution behaviour. The most prominent peak eluted in fraction numbers B8 and B9 can be seen in the corresponding SDS page picture (FIG. 5). It is mainly composed of 180 kDa full length heavy chain fragment. But there is also a certain amount of full length single chain, which can be seen above the 250 kDa marker position on top of the gel. In the lower parts of the gel is an intense signal slightly above 100 kDa caused by the 120 kDa extended light chain. Directly below are traces of the 110 kDa truncated heavy chain subspecies. Another strong band can be seen around 75 kDa. It represents the 80 kDa light chain fragment.

There is another intense peak collected in the fraction B10. Its composition on the SDS page gel is quite similar to that one described above. It seems to arise mainly from a mixture of 180 kDa full length heavy chain, as well as 120 kDa extended light chain and 80 kDa light chain with smaller amounts of 110 kDa heavy chain fragment and full length single chain. But in addition, fractions B11 and B12 also contain a weak signal in the area of 150 kDa. It is the 150 kDa truncated heavy chain subspecies, which is identifiable as small shoulder on the descending side of the peak in the chromatogram.

The next interesting point in the chromatogram is a small peak with an approximate intensity of 100 mAU, which is not base line separated from its left neighbouring peak. The fractions C1 and C2 show that there is a maximum amount of 110 kDa heavy chain subspecies, compared to other fractions. There is also a certain amount of the 180 kDa subspecies in these fractions, which is because the resins resolution is not sufficient of separating both peaks. Nevertheless, is this small peak caused be the 110 kDa truncated heavy chain fragment. Finally, there is a small double peak with an intensity of roughly 40 mAU in fractions C4 to C6. This peak represents the B-domain depleted 90 kDa heavy chain, as indicated by the SDS page. The general sequence of elution with rising conductivity is therefore:

1. Differently charged variants of heavy chain subspecies, mainly 180 kDa full length fragment, single chain FVIII and different combinations of extended light chain together with other subspecies
2. Full length heavy chain (180 kDa)
3. Heavy chain with partial B-domain truncation (150 kDa)
4. Heavy chain with partial B-domain truncation (110 kDa)
5. B-domain depleted heavy chain (90 kDa)

Example 3

Small Scale Purification of FVIII Subspecies—Optimizing the Gradient Length in the First Chromatography Step A flatter gradient is equivalent to better separation due to a slower percentage increase of strong eluent. FIG. 6 shows an overlay of two different feasibility experiments, the one is operated with an eight column volume gradient indicated as solid line for the UV signal and as broken line for the conductivity, whereas the other one is performed with a 16 column volume gradient elution, shown as dotted line for the UV signal and as dashed line for the corresponding conductivity signal. It is clearly visible that the conductivity increases much slower during the 16 column volume elution in comparison to the eight column volume elution. The respective UV signals share high similarity in terms of their overall pattern but the elution behaviour is obviously different. The dotted curve, representing the 16 column volume elution UV signal is broadened and the small shoulder representing the 150 kDa subspecies is better visible compared to the eight column volume UV curve. Since the volume in which the elution phase is collected is twice as much for the 16 column volume elution as for the eight column volume elution, it is also likely that some of these structures may be collected in separate fractions. The most prominent difference can be seen in the area where usually the 150 kDa B-domain truncated subspecies tends to elute from the column. This area is rather short in the eight column volume elution phase. It seems as if the 180 kDa full heavy chain signal decreases rapidly its intensity and then raises again because the 110 kDa subspecies elution takes place. The 16 column volume elution phase in contrast resolves the elution of the 150 kDa subspecies. The separation success may not be satisfying at all but at the descending side of the 180 kDa full length heavy chain peak a small shoulder is recognisable. This is because under steadily increasing conductivity conditions some point under which the 180 kDa full heavy chain elutes while the 150 kDa B-domain truncated chain still binds is retained for a longer period of time.

FIG. 7 shows an overlay of two UV curves derived from a 16 column volume elution phase shown as solid line and a 32 column volume elution phase with 10% ethylene glycol as additive shown as broken line. Both samples have been treated with furin protease prior to sample application. The peak broadening effect of an elution phase twice as long as the original is clearly visible. The shoulder arising from the elution of the 150 kDa B-domain truncated heavy chain during the 32 column volume elution phase more prominent as it is in the 16 column volume elution phase. In addition, its volume is twice as much as for the 16 column volume elution and therefore given that fractionation occurs in adequate fraction sizes, it should be possible to generate an enriched 150 kDa product pool suitable for further purification.

Example 4

Small Scale Purification of FVIII Subspecies—Furin Protease Treatment Before the First Chromatography Step Furin protease is a proteolytic enzyme responsible for the intracellular processing of FVIII. There are various positions throughout the entire FVIII sequence where furin can attach and cleave its substrate. Since FVIII, even if it is derived from recombinant source is not completely processed, there is a high degree of heterogeneity. It is not only the B-domain, which contributes to heterogeneity. It may also be that different types of glycosylation influence the way in which a certain FVIII molecule behaves during elution. This is especially valid for the 180 kDa full length heavy chain. This subspecies still contains the entire B-domain, which is highly glycosylated (Pipe et al. (1998)). Different kinds of glycosylation and therefore differently charged areas on the protein surface seem to be the reason why the full length heavy chain does not only elute as a single peak, but as two distinct peaks.

FIG. 8 shows an overlay of the UV curves of an furin treated sample (solid line) and a sample which has not been treated with furin protease prior to sample application (broken line). Both runs are performed with 16 column volume elution phases as indicated by the high similarity of conductivity curves. The only difference is the type of sample preparation, either including furin maturation or not. The first thing that is obvious is that there is a significant decrease of peak intensity of the furin treated sample in the first half of the elution phase. This area mainly represents differently charged heavy chain variants in combination with the extended light chain. In addition, the most prominent peak of non-furin treated sample almost completely disappeared on the solid curve. In turn, the typical full length heavy chain peak is significantly intensified. Furin maturation seems to increase the intensity of other subspecies as well. Even the intensity of B-domain depleted 90 kDa subspecies and 110 kDa subspecies are higher compared to the non furin treated sample.

The elution of the furin treated sample is shown is FIG. 9. Almost every fraction is applied to SDS page analysis (FIGS. 10 and 11) in order to elucidate their respective compositions. The fraction numbers B5 to C7 appear virtually uniform in terms of their composition. Although this area contains individual peaks in the chromatogram, all of them are obviously consisting of full length heavy chain variants with different glycosylation, which make no difference on the SDS page. Having a view on the ascending side of the following, most intense peak, there are already some fractions (C8-C10) of full length heavy chain fragment (180 kDa), which seem sufficiently pure for further purification. The descending part of the peak is as usual mixed up with the truncated 150 kDa heavy chain fragment, but both species show up more apart from each other compared to the standard, not furin maturated separation. Regarding the truncated 110 kDa subspecies, especially the fractions D4 and D5 are well separated containing only minor amounts of other subspecies. The B-domain free 90 kDa heavy chain is entirely separated and may even be ready for concentration. One of the most noticeable differences concern the distribution of light chain variants. As it can be seen throughout the entire gel, there is no trace of the 120 kDa extended light chain left. It has obviously been processed by furin protease resulting in nearly exclusively 80 kDa light chain fragments, which greatly reduces the starting materials heterogeneity.

Some modifications are implemented for the following large scale (preparative) purification:
1. In order to reduce heterogeneity and to improve the overall separation success of FVIII subspecies, the sample is treated with >100 IU/mL furin protease prior to sample application.
2. The length of linear gradient elution is increased fourfold to 32 column volumes. The increased spreading of subspecies specific peaks in the second half of elution seem to overcome the effects of fraction dilution.

Example 5

Small Scale Purification of FVIII Subspecies—Second Chromatography Step

Size exclusion chromatography is used as a polishing step for removal of minor impurities from a pool which already contains the desired product in high purity. It is also suitable as second purification step for FVIII molecular subspecies, following the MonoQ anion exchange chromatography step. Therefore, each sample which is going to be purified by means of size exclusion, is originally derived from anion exchange chromatography and obtained by subsequent pooling of fractions that contain the desired subspecies. Assuming that the 120 kDa extended light chain has been completely removed during the course of furin maturation, each heavy chain variant present in the respective sample should be bound exclusively to the 80 kDa light chain. Therefore, the average difference in molecular weight between all subspecies is approximately 50 kDa, which should be sufficient to obtain satisfying results.

Example 6

Small Scale Purification of FVIII Subspecies—Purification of the Truncated Heavy Chain Fragment in the Second Chromatography Step The right-hand side of FIG. 13 shows a section of a SDS page gel electrophoresis of an earlier MonoQ anion exchange chromatography run. Since the fractions G4, G5 and G6 show the 110 kDa heavy chain in sufficient purity, they have been pooled and used for further purification by size exclusion chromatography. The corresponding chromatogram as well as the silver stained gel electrophoresis of most fractions can be seen in FIG. 12 and on the left-hand side of FIG. 13, respectively. All four heavy chain subspecies are obviously present in the sample, but they elute from the column at distinct points of time due to their different molecular weight and size. The full length heavy chain (180 kDa) is the largest of all FVIII variants. It can thus access the fewest volume of all subspecies and elutes first of all, which can be seen in fractions C4 to C7 on the gel. A second peak is visible in fractions C9 to C11, which is caused by the 150 kDa truncated heavy chain species. The most prominent peak is, as expected, the 110 kDa truncated heavy chain fragment, which starts to elute in fraction D1 and proceeds until fraction D9. The fragments with 150 kDa and 110 kDa are clearly separated from each other, but it is also visible that traces of the B-domain depleted 90 kDa heavy chain contaminates the fractions D5 and the following. Both, 110 kDa and 90 kDa subspecies seem to be capable of penetrating similar pore volumes, which is not surprising since their molecular weight difference is only 20 kDa. However, the intensity of the B-domain depleted 90 kDa subspecies is very low in comparison to the 110 kDa target protein and fractions D2, D3 and D4 appear absolutely pure.

Example 7

Small Scale Purification of FVIII Subspecies—Purification of the Full Length Heavy Chain in the Second Chromatography Step An anion exchange chromatography eluate serves as starting material for further purification and polishing of the full length heavy chain fragment. The fractions F4, F5 and F6, shown in FIG. 15 are mainly composed of the 180 kDa subspecies. Minor impurities arise from truncated heavy chain species (110 kDa) and B-domain depleted heavy chain fragment (90 kDa), but also to a lower extend from 150 kDa truncated heavy chain variant. These factions have been pooled and applied to size exclusion chromatography. The respective chromatogram can be seen in FIG. 14, as well as the corresponding SDS page gel electrophoresis on the left-hand side of FIG. 15. The protein concentration in this experiment is generally higher compared to the purification results of 110 kDa truncated heavy chain fragment. Therefore, absorbance is higher and signals on the SDS page gel electrophoresis are more intense. As already mentioned above is the 180 kDa full length fragment the first subspecies eluting from the column. It shows up as a large peak of approximately 70 mAU absorbance in the chromatogram in fractions C4 to D1. The appropriate silver stained SDS page shows clearly that this peak exclusively originates from 180 kDa full length heavy chain, but there is also contamination by 150 kDa truncated heavy chain in fractions O10 to D1. Nevertheless, the first half of the peak (fractions C4 to C9) appear definitely pure. The 150 kDa truncated heavy chain is only visible on the electrophoresis gel but not in the chromatogram, which might be because of its low amount is eluted at a point at which the 180 kDa full length fragment is still eluting. The 110 kDa truncated heavy chain fragment, as well as the B-domain depleted heavy chain fragment can be made out as particular peaks of quite low intensity. Both are also apparent on the SDS page in fractions D3-D8 and D6-D9, respectively. As already seen in Example 6 is there a sufficient separation between the 150 kDa species and the 110 kDa species. Full length heavy chain and 150 kDa heavy chain are not that well separated, which makes carefully considered pooling of fractions necessary to obtain pure product pools. The same is true for the 110 kDa species and the 90 kDa B-domain free heavy chain. Those are by far not completely separated at all and carefully considered pooling will be required here as well.

Example 8

Small Scale Purification of FVIII Subspecies—Hydrophobic Interaction Chromatography in theI Second Chromatography Step The hydrophobic interaction chromatography approach has been tested in the small scale phase as a possible alternative method for the partitioning of full length heavy chain (180 kDa) and truncated heavy chain fragment (150 kDa), whose behaviour in anion exchange chromatography is similar which makes separation quite difficult.

The chromatogram of the two-dimensional elution phase of a furin treated SourceS eluate can be seen in FIG. 16. The general procedure of two-dimensional hydrophobic interaction chromatography is in accordance with the respective (preferred) embodiments that are described in detail in the above section "Detailed Description of the Invention". Upon sample application is complete, a short washing phase with equilibration buffer takes place. The difference in conductivity is approximately just 2 mS/cm but it seems already sufficient of causing an increase of the UV signal. This first shoulder, which is only around 4 mAU of UV absorbance can be seen in the corresponding SDS page (FIGS. 17 and 18) as fraction numbers A5 to B4. It mainly arises from the 150 kDa truncated heavy chain subspecies, indicating that it binds weakest and elutes already at low conductivity reduction.

The elution phase itself contains two linear gradients directly adjacent to each other. The first elution buffer does not contain sodium chloride, which leads to the initial, rapid decrease in conductivity. After reaching a certain level of conductivity of around 3 mS/cm the second elution buffer is applied to the column. It contains ethylene glycol and therefore lowers the conductivity even more down to less than 1 mS/cm. The eluting peaks are not so definite as on the MonoQ resin. It is rather a transition of broadly eluting proteins, not sharply separated from each other. The actual composition of fractions over the course of elution is only visible on the SDS page gel electrophoresis. The UV signal steeply rises with the beginning of the first gradient resulting in a very broadened peak with a shoulder on its descending side, that lasts until the beginning of the second gradient. The SDS page shows that this area of elution is mainly caused by full length heavy chain fragment (180 kDa), as well as 110 kDa truncated heavy chain fragment and B-domain depleted 90 kDa fragment, which all start to unbind more or less at the same point. The shoulder collected in fractions C12-D6 may come from the 110 kDa truncated fragment, which seems to elute a second time at that point. The second gradient with ethylene glycol containing elution buffer generates an unstructured pattern of tendentially decreasing UV signals. As known from earlier experiments, this area is caused by the elution of small amounts of subspecies with 180 kDa, 110 kDa and 90 kDa. The corresponding 80 kDa light chain is distributed all over the entire elution phase. Its intensity varies with respect to the general intensity of the UV signal. Finally, it is conspicuous that the truncated 150 kDa heavy chain fragment is shifted forth as is elutes earlier than the others—already during the washing phase. The elution itself does not really separate the other subspecies, as they eluate more or less in the same fashion as they have been applied to the column.

Relying on the results of the two-dimensional HIC experiment the main purpose in the following is the separation of the 150 kDa truncated heavy chain species from the others, especially the full length fragment.

The following one-dimensional elution procedure is therefore derived from the two-dimensional hydrophobic interaction chromatography described above. The second linear gradient phase using ethylene glycol buffer is skipped, since it does not really contribute to separation of FVIII subspecies. Instead of this, the washing phase following sample application is doubled to ten column volumes and the actual elution phase is extended to 40 column volumes in order to enhance separation. In addition, the column loading is reduced significantly. As consequence thereof, the general intensities of UV signals are decreased (FIG. 19). As it can be seen in FIG. 20 is the separation of the 150 kDa truncated heavy chain fragment from the adjacent 180 kDa full heavy chain fragment not significantly improved. Moreover, the collected fractions are highly diluted and the yield seems to be so low that a preparative process would be very inefficient.

Example 9

Small Scale Purification of FVIII Subspecies—Negative Mode Hydrophobic Interaction Chromatography in the Second Chromatography Step The negative mode chromatography approach aims at the washout of the 150 kDa truncated heavy chain fragment during breakthrough and washing phase, while other subspecies are thought to remain bound to the column. It is assumed that this subspecies binds so weak that it is capable of spontaneously unbinding just by the movement of the passing through mobile phase. A 150 kDa subspecies enriched MonoQ eluate pool serves as load, whose conductivity is increased for binding to the column. The original washing phase is greatly prolonged for that reason. FIG. 21 shows that the columns capacity is exceeded somewhere around fraction A9. The break though occurs at this point and leads to an increase of the UV signal.

The SDS page electrophoresis (FIG. 22) shows that even the break through (fractions A10-A12) contains highly purified 150 kDa truncated heavy chain fragment. The UV signal decreases with the beginning of the washing phase in fraction B1 and proceeds until the end of the phase. The corresponding fractions on the SDS page (B1-C2) show mainly 150 kDa truncated heavy chain fragment, although there are also traces of the 110 kDa and 90 kDa subspecies and even the 120 kDa extended light chain, which may arise from an uncompleted furin maturation prior to the MonoQ purification step. The elution itself is executed as a sharp step of 100% elution buffer. This leads to the rapid elution of all remaining FVIII proteins from the column. It is remarkable that almost the entire amount of 180 kDa full length heavy chain fragment is eluted at this point but not earlier. It seems to bind much stronger that the others as there is no 180 kDa subspecies found during break through and washing phase. Both subspecies can be separated in negative mode easily and to a satisfying degree.

Example 10

Large Scale (Preparative) Purification of FVIII Subspecies

The preparative scale purification of FVIII subspecies involves the initial MonoQ anion exchange chromatography step for enrichment of the desired heavy chain fragment, followed by the polishing step on the large scale size exclusion chromatography column, whose separation capacity is sufficient of separating other subspecies which are considered as impurities. The B-domain depleted heavy chain fragment (90 kDa) is an exception, since the size exclusion step is skipped for this subspecies. It is already purified to a satisfying degree by the MonoQ AIEX step and does not require further polishing. The final step for all of the four different subspecies is concentration because of the high dilution during size exclusion chromatography. This is performed by another AIEX step on a SourceQ anion exchange resin.

FIG. 23 provides an overview of the whole process for the respective FVIII subspecies.

Example 11

Large Scale (Preparative) Purification of FVIII Subspecies—First Chromatography Step The anion exchange chromatography is the primary step of purification of FVIII molecular subspecies and achieves the rough separation of all four desired heavy chain fragments in such a way, that adequate fractions can be pooled for further purification. FIG. 24 shows the first chromatogram of an elution phase of the AIEX step on the large scale MonoQ column. The starting material B14390000-30 is separated according to the modified standard procedure described above and gives a characteristic elution pattern, which is already known from the small scale experiments. The elution phase is pooled in eight product pools, each of them containing a certain heavy chain fragment in purified and enriched form. The first half of the elution is known to be dominated by differently glycosylated full length heavy chain variants, which elute as more or less separated peaks. Those peaks which can be clearly distinguished from the neighbouring ones are used for individual product pools but will not be further evaluated.

Table 15 gives an impression of how the fraction pooling occurs and shows that the first four product pools E1-E4 are dedicated to those differently glycosylated full length heavy chain variants. The most abundant full length heavy chain is collected in the product pool E5, which contains the fractions 2.C2 to 2.D3 and gives an approximate protein concentration of 0.689 mg/mL. The SDS page gel electrophoresis shown in FIG. 25 also confirms the purity of the E5 product pool and additionally shows that this full length heavy chain variant is the most prominent, since its concentration is the highest. Besides that, all other full length heavy chain variants (E1-E4) show almost the same pattern on the SDS page—there is only little difference in position of the respective bands supporting the assumption of different glycosylation of the B-domain. The fraction numbers 2.D7 to 2.E6 contain the truncated heavy chain fragment with a molecular weight of 150 kDa, but it is well known from earlier experiments that this fraction is usually contaminated with the full length heavy chain, which can also be made out on the SDS page image. The product pool E6 shows two bands at ~180 kDa and ~150 kDa of relatively similar intensity, indicating comparable amounts of both. The fractions 2.D4, 2.D5 and 2.D6 are not used for any of both adjacent product pools, as those fractions contain a mixture of the 180 kDa and 150 kDa subspecies, which would contaminate either of them. The product pool E7 is composed of the fractions 2.E7-3.A7 and contains the 110 kDa truncated heavy chain fragment. The respective peak in the chromatogram is much better separated from the previous ones and also the SDS page shows mainly the truncated heavy chain fragment at approximately 110 kDa, although there are traces of full length heavy chain here as well. The eighth product pool contains the B-domain depleted heavy chain fragment with 90 kDa molecular weight, collected in fractions 3.B8 to 3.E1.

It is already visible in the chromatogram that the 90 kDa subspecies peaks are rather low and it is thus not surprising that the protein concentration of this product pool is with 0.025 mg/mL by far too low. On the other hand, those peaks are base line separated from everything else that has already been eluted and therefore the purity of this fraction is satisfying. This in fact allows to skip the polishing step by means of size exclusion chromatography and directly proceed with concentration. At the same moment this makes obvious that very different amounts of the four subspecies are present in the starting material and simple separation of those is not the only challenge. Just as there is plenty of full length heavy chain contained in the starting material, it seems rather hard to collect sufficient amounts of the less existing subspecies. The product pool E6 of this run, containing a sufficient amount of 150 kDa truncated heavy chain fragment is selected for subsequent purification on the preparative scale size exclusion chromatography column. In contrast, the product pool E8 which contains the 90 kDa B-domain depleted heavy chain fragment will be directly concentrated by the AIEX step on SourceQ, skipping any other kind of purification or polishing. The appropriate results will be discussed in the following.

TABLE 15

Pooling scheme for the AIEX purification step of Sources eluate B14390000-30 on the preparative scale MonoQ column shown in FIG. 24.

| Pool Designation | Fraction | Heavy Chain Subspecies | Molecular Weight [kDa] | Absorbance at 280 nm (Pool) | Protein Concentration [mg/mL] |
|---|---|---|---|---|---|
| E1 | 1.B4-1.C3 | Full length heavy chain variant | 180 | 0.085 | 0.067 |
| E2 | 1.C4-1.D6 | Full length heavy chain variant | 180 | 0.249 | 0.198 |
| E3 | 1.D7-1.A2 | Full length heavy chain variant | 180 | 0.350 | 0.278 |
| E4 | 2.A3-2.C1 | Full length heavy chain variant | 160 | 0.310 | 0.246 |
| E5 | 2.C2-2.D3 | Full length heavy chain variant | 190 | 0.868 | 0.689 |
| E6 | 2.D7-2.E6 | Truncated heavy chain fragment | 150 | 0.442 | 0.309 |
| E7 | 2.E7-3.A7 | Truncated heavy chain fragment | 110 | 0.250 | 0.163 |
| E8 | 3.B8-3.E1 | B-domain depleted heavy chain fragment | 90 | 0.040 | 0.025 |

TABLE 16

Pooling scheme for the AIEX purification step of Sources eluate B14390000-30 on the preparative scale MonoQ column shown in FIG. 26.

| Pool Designation | Fraction | Heavy Chain Subspecies | Molecular Weight [kDa] | Absorbance at 280 nm (Pool) | Protein Concentration [mg/mL] |
|---|---|---|---|---|---|
| E1 | 1.A1-1.E7 | Full length heavy chain variant | 180 | not specified | not specified |
| E2 | 1.E8-1.A8 | Full length heavy chain variant | 180 | 0.633 | 0.502 |
| E3 | 1.C4-1.D3 | Truncated heavy chain fragment | 110 | 0.182 | 0.119 |
| E4 | 2.D4-2.B5 | B-domain depleted heavy chain fragment | 90 | not specified | not specified |

A second example of an elution phase of the preparative scale AIEX is shown in FIG. 26 and FIG. 27 for the corresponding SDS page gel image. The general procedure of pooling is not very different from that one previously discussed. A summary of the pooled fractions and the associated protein concentrations can be found in table 16.

The product pools designated as E2 and E3 contain the full length heavy chain and the 110 kDa truncated heavy chain fragment and are interesting fractions for further purification and polishing on the preparative scale size exclusion chromatography step. Not all fractions can be seen on the SDS page electrophoresis and the fractions which are used for pooling are therefore partly determined by optical means. Instead, there is data available from the C4 reversed phase HPLC analysis (table 17) giving evidence of how the product pools E2 and E3 are composed. This data reveals that the full length heavy chain product pool E2 already contains approximately 91% target protein, which includes all 180 kDa full length heavy chain variants as well as both light chain variants. The product pool E3 does not show an equal purity after the first AIEX step but 82.5% of target protein at a protein concentration of 0.119 mg/mL seems to be a good basis for further processing.

TABLE 17

Composition of the product pools E2 (full length heavy chain) and E3 (truncated heavy chain fragment with a molecular weight of 110 kDa) determined by C4 reversed phase HPLC analysis. The product pool E2 contains approximately 91% target protein including all full length heavy chain fragments as well as both light chain variants. The product pool E3 contains approximately 82.5% target protein with respect to the 110 kDa truncated heavy chain fragment and both light chain variants.

| Variable | Product Pool E2 [%] | Product Pool E3 [%] |
|---|---|---|
| Extended light chain | 1.22 | 1.71 |
| Light chain | 34.16 | 42.10 |
| Single heavy, light chain 1 | 2.11 | 1.97 |
| Single heavy, light chain 2 | 17.69 | 2.03 |
| 180 kDa heavy chain | 35.80 | 4.39 |
| 150 kDa heavy chain | 4.05 | 2.59 |
| 110 kDa heavy chain | 3.77 | 38.69 |
| 90 kDa heavy chain varant 1 | 0.76 | 2.90 |
| 90 kDa heavy chain varant 2 | 0.44 | 3.61 |
| Sum target protein | 90.98 | 82.50 |
| Sum impurities | 9.02 | 17.49 |
| Sum (respective peaks) | 100.00 | 99.99 |

Example 12

Large Scale (Preparative) Purification of FVIII Subspecies—Purification and Concentration of Full Length Heavy Chain (180 kDa) in Second and Third Chromatography Step As indicated in the process flow diagram in FIG. 23 is the purification of the full length heavy chain composed of the three steps AIEX and SEC as true purification steps and another AIEX step for concentration. Based on the evaluation of the SDS page gel electrophoresis of the first AIEX purification the most promising fractions, which exhibit both high protein content as well as low fractions of impurities, are chosen, pooled and applied to the preparative SEC column. The collected output from the size exclusion chromatography is further applied to a SourceQ column and finally concentrated by step elution. The according results will be discussed in the following.

FIG. 28 shows the subsequent purification of the AIEX product pool E2 containing enriched 180 kDa full length heavy chain on the large scale size exclusion chromatography column. The general procedure of preparative scale SEC can be found in the respective embodiment of the "Detailed Description of the Invention" section above. It is considered that minor impurities come from the 150 kDa truncated heavy chain fragment which could not be entirely separated by means of AIEX. The most prominent peak of the chromatogram shows approximately 50 mAU of absorbance intensity and starts to elute in fraction 1.B5. The image of the silver stained SDS page gel electrophoresis (FIG. 29) shows that fractions 1.B5 to 1.B11 are mainly composed of the desired full length heavy chain (180 kDa) in association with the 80 kDa light chain. The 150 kDa truncated heavy chain fragment elutes in fractions 1.C1 to 1.C4, which cannot be detected in the chromatogram. It appears more like the tailing of the 180 kDa subspecies peak but it is actually the 150 kDa subspecies. It is also visible on the SDS page image that the subspecies with 180 kDa and 150 kDa molecular weight tend to overlap in the rear fractions of the target peak, which makes them unsuitable for pooling. Two peaks of rather low intensities appear in fractions 1.C6-1.C9 and 1.C10-1.D3, respectively. Those peaks arise from the 110 kDa truncated heavy chain fragment and the B-domain depleted heavy chain fragment and both of them are clearly separated from the desired full length heavy chain peak.

Since size exclusion chromatography is the final true purification step it has to be carefully considered which fractions should find their way into the ultimate product pool. On the one hand, skipping fractions at the beginning and the end of the target peak might decrease the chance of bringing other subspecies into the product pool, but on the other hand this decreases the yield dramatically since each fraction which is not used for pooling equals a protein loss of approximately 1 mg of total protein or even more. A product pool encompassing fractions 1.B7-1.B10 is likely to be the best compromise between generating reasonable purities and still maintaining an efficient process. This product peak is referred to as E1 and its most significant parameters are listed in tables 18 and 19.

The final sample volume is approximately 70 mL with a protein concentration of 0.134 mg/mL, giving nearly 10 mg of full length heavy chain FVIII protein. The purity is only slightly increased to 92% of target protein, where the 150 kDa truncated heavy chain species is still the biggest source of contamination (5.71%).

TABLE 18

Pooling scheme for the SEC purification step of AIEX eluate pool E2 (180 kDa full length heavy chain) on the preparative scale size exclusion chromatography column.

| Fraction | Absorbance at 280 nm | Protein Concentration [mg/mL] | Fraction Volume [mL] | Total Protein [mg] |
|---|---|---|---|---|
| 1.B7 | 0.135 | 0.107 | 16.6 | 1.78 |
| 1.B8 | 0.231 | 0.183 | 16.6 | 3.04 |
| 1.B9 | 0.234 | 0.186 | 16.6 | 3.08 |
| 1.B10 | 0.121 | 0.104 | 16.6 | 1.73 |
| Sum (E1) | 0.169 | 0.134 | ~70.0 | 9.39 |

TABLE 19

Composition of the product pool E1 (full length heavy chain) derived from preparative scale size exclusion chromatography determined by C4 reversed phase HPLC analysis.

| Variable | Product Pool E1 [%] |
|---|---|
| Extended light chain | 1.29 |
| Light chain | 33.97 |
| Single heavy, light chain 1 | 2.82 |
| Single heavy, light chain 2 | 16.67 |
| 180 kDa heavy chain | 36.89 |
| 150 kDa heavy chain | 5.71 |
| 110 kDa heavy chain | 1.96 |
| 90 kDa heavy chain varant 1 | 0.31 |
| 90 kDa heavy chain varant 2 | 0.37 |
| Sum target protein | 91.64 |
| Sum impurities | 8.35 |
| Sum (respective peaks) | 99.99 |

Due to the dilution on the SEC column, it is necessary to implement a step for concentration of those diluted eluates in order to achieve the desired end concentration of >0.3 mg/mL. The diluted fractions are applied to another anion exchange chromatography step performed on Source30Q resin. A step gradient, in its composition equivalent to the desired final buffer composition, leads to the immediate elution of all product bound to the column. The product pool E1 containing SEC fractions 1.B7-1.B10 is applied to the second AIEX step for concentration and eluted in a step gradient as shown in FIG. 30. There is no separation effect at all, instead the entire protein content is eluted starting in fraction 1.A6 and showing a peak tailing appearance reaching up to fraction 1.B7. Accordingly, all fractions between 1.A6 and 1.B8 are pooled to the ultimate product pool, resulting in approximately 7 mL of product volume. The subsequent UV measurement for determination of protein concentration gives a value of about 0.982 mg/mL which corresponds to 6.85 mg of total protein. FIG. 31 shows two images of a SDS gel electrophoresis with silver stain development on the left-hand side and a FVIII western blot on the right-hand side. Both of them show exclusively full length heavy chain fragment in combination with the 80 kDa light chain variant, but no other signals in between. The C4 reversed phase HPLC data gives satisfying results as well, as shown in table 20. The final product solution of the 180 kDa full length heavy chain contains 94.52% target protein, including all full length heavy chain variants and both light chain variants. In comparison, only less than 6% of the entire protein amount are impurities which mainly arise from the truncated heavy chain species with 3.28% and 1.76% of 150 kDa and 110 kDa species, respectively.

TABLE 20

Composition of the product pool E1 (full length heavy chain) derived from preparative scale AIEX on SourceQ determined by C4 reversed phase HPLC analysis.

| Variable | Product Pool E1 [%] |
|---|---|
| Extended light chain | 1.16 |
| Light chain | 33.61 |
| Single heavy, light chain 1 | 2.32 |
| Single heavy, light chain 2 | 18.51 |
| 180 kDa heavy chain | 38.92 |
| 150 kDa heavy chain | 3.28 |
| 110 kDa heavy chain | 1.76 |
| 90 kDa heavy chain varant 1 | 0.18 |
| 90 kDa heavy chain varant 2 | 0.26 |
| Sum target protein | 94.52 |
| Sum impurities | 5.48 |
| Sum (respective peaks) | 100.00 |

This procedure of purification of the full length heavy chain was repeated several times to yield the desired amount of protein. The according data is not further shown.

Since the chromatography resins used during the small scale experiments and the preparative purification process are slightly different, it is interesting to evaluate the difference regarding performance and resolution. FIG. 32 shows an overlay of a feasibility run and a preparative purification of the 180 kDa full length heavy chain, which have been conducted under comparable conditions. The running buffers, the applied sample, the residence times and the length of the elution phase is similar for both runs.

The methods have 1.5 column volume elution phases, which makes it easy to compare them—given that the x-axis is converted to column volumes. The curves have been shifted so that both have the same starting point which is in this case the end of the injection step. The elution of the feasibility run—shown as solid line—starts around 0.36 CV whereas the preparative run—shown as dashed line—is slightly delayed by 0.02 CV. The difference is marginal and under consideration of the very different column sizes and buffer volumes passed through it seems not meaningful to make statements based on values. Nevertheless, both curves seem to be identical in respect of the overall shape and the number of column volumes needed for eluting the first fragment—the 180 kDa full length heavy chain. In this case, the Superdex 200 Increase is roughly only one third of the length of the Superdex 200 Prep Grade column, meaning that the separation efficiency of the Superdex 200 Increase is approximately three times better compared to the Superdex 200 Prep Grade. However, upscale has not been performed according to any constant quantity but was instead subject to the availability of columns this size and dimension. It is therefore even more beneficial that both resins with their respective geometry perform more or less similar as it makes the SEC feasibility experiments comparable with the preparative Size exclusion purifications.

Example 13

Large Scale (Preparative) Purification of FVIII Subspecie—Purification and Concentration of Truncated Heavy Chain Fragment (150 kDa) in Second and Third Chromatography Step The procedure for the purification of the 150 kDa truncated heavy chain fragment is in principle similar to the one used for purification of the full length heavy chain, described in the previous sections. Since the typical shoulder as which the 150 kDa subspecies usually appears gives much less fractions with sufficient purity, it is rather difficult to purify adequate total amounts of this type of FVIII subspecies. As indicated by the number of runs necessary and the total amount of each subspecies an the end, FIG. 43 shows that the same number of runs yields only about one tenth of the truncated heavy chain fragment (6.74 mg) compared to the full length heavy chain (62.97 mg).

The purification of the truncated heavy chain subspecies with a molecular weight of 150 kDa (MonoQ AIEX product pool E6) by size exclusion chromatography is shown in FIG. 33. The general pattern of elution is different from the purification of the full length heavy chain fragment. Since its molecular weight is 30 kDa below the one of the full length heavy chain, it can access more pores and therefore a higher volume of the resin. Its elution is considered to be somewhere in between the 180 kDa subspecies and the 110 kDa truncated heavy chain fragment, but since there has not been any feasibility experiments for this fragment, the exact elution behaviour is unknown. There are different peaks of varying intensities appearing throughout the elution phase. The UV signal starts to rise in fraction 1.B4 and gives a double peak like structure with maximum intensities observed in fractions 1.B6 and 1.B9. As the SDS page gel electrophoresis elucidates do both peaks come from full length heavy chain (180 kDa) remains (see FIG. 34). Although the fact that there are different kinds of full length heavy chain fragments due to varying glycosylation of the B-domain, it is not known why they elute as more or less particular peaks in size exclusion chromatography. In addition, the elution of the enriched 180 kDa subspecies did no show distinct full length heavy chain peaks. Fractions 1.B10-1.C5 contain the highest intensity peak which clearly comes from the desired 150 kDa truncated heavy chain fragment. But the number of fractions which exclusively contain the desired fragment and have satisfying protein concentrations at the same time is highly limited. The fraction 1.B11 is still contaminated with the 180 kDa full length heavy chain, but the following fractions appear almost pure, although fraction 1.C5 is only low in protein concentration and there is a certain amount of 120 kDa extended light chain detectable. The 110 kDa truncated heavy chain fragment elution starts in fraction 1.C6 and is then mixed up with the B-domain depleted heavy chain which does not appear as a separated peak. Due to their high protein concentrations and likewise low contaminations with other subspecies, the fractions 1.C1, 1.C2 and 1.C3 are chosen to be used for the product pool termed E2. Depending on the protein concentration measurements for the single fractions, the entire pool is calculated to have a total protein amount of 2.67 mg at rather low protein concentration.

TABLE 21

Pooling scheme for the SEC purification step of AIEX eluate pool E6 on the preparative scale size exclusion chromatography column. The values for volume and total protein are not determined by means of separate measurement, but rather represent the sum of the values of the particular fractions which are used for pooling.

| Fraction | Absorbance at 280 nm | Protein Concentration [mg/mL] | Fraction Volume [mL] | Total Protein [mg] |
| --- | --- | --- | --- | --- |
| 1.C1 | 0.068 | 0.051 | 16.90 | 0.86 |
| 1.C2 | 0.085 | 0.064 | 16.85 | 1.08 |
| 1.C3 | 0.058 | 0.044 | 16.84 | 0.73 |
| Sum (E2) | not specified | not specified | ~50.59 | ~2.67 |

In order to concentrate the previously polished preparative SEC fraction E2 and another similar SEC eluate pool of the 150 kDa truncated heavy chain fragment, both are pooled and applied to the SourceQ AIEX step. Apart from that, all parameters are kept constant so that the elution starts as usual in fraction 1.A6 and lasts until fraction 1.B7 in a peak tailing fashion, as shown in the chromatogram in FIG. 35. The peaks height is approximately 1200 mAU, which comes from the higher amount of protein loaded as a result of concentrating two SEC eluate pools in one AIEX step instead of just one. Since the main priority is to lose as few product as possible all fractions with UV absorbance (1.A6-1.B8) are used for product pooling.

The associated SDS gel electrophoresis is shown in FIG. 36 with a silver stain development on the left-hand side and the FVIII western blot on the right-hand site, where the designations E1 and E2 correspond to two dilutions (1:40 and 1:120 for silver stain development and 1:53 and 1:160 for FVIII western blot) of the final product pool. The silver stain development does not show any additional bands, indicating a composition of exclusively 150 kDa truncated heavy chain species in combination with the 80 kDa light chain variant. The FVIII western blot in contrast is much more sensitive and has low colouring in the 180 kDa area, suggesting that at least minor impurities of the full length heavy chain are still left. As already mentioned during the discussion of the size exclusion step of the 150 kDa truncated heavy chain species the yield of one purification sequence for this subspecies is rather low. An amount of only 2.5 mg could be purified in the SEC stage after one passage. It is therefore necessary to repeat the respective purification sequence several times in order to purifiy the required amount of 10 mg of pure FVIII 150 kDa truncated heavy chain. Those runs are performed according to the same procedure and will not be further discussed, since the results are equal. A total number of four SEC eluate pools are concentrated in two subsequent Source30Q AIEX steps and afterwards pooled to one single, ultimate product pool, which is analysed by C4 reversed phase HPLC.

The appropriate data is represented in table 22, whereby extended light chain, light chain and 150 kDa heavy chain are regarded as target protein species while all other subspecies are considered as impurities. The percentage of target protein is nearly 92%, which means that the goal of less than 10% other subspecies could be fulfilled for the final product pool of the truncated heavy chain fragment with a molecular weight of 150 kDa.

TABLE 22

Composition of the final product pool E1 for the 150 kDa truncated heavy chain fragment derived from two preparative scale AIEX runs on SourceQ determined by C4 reversed phase HPLC analysis.

| Variable | Product Pool E1 [%] |
| --- | --- |
| Extended light chain | 1.28 |
| Light chain | 40.27 |
| Single heavy, light chain 1 | 1.58 |
| Single heavy, light chain 2 | 0.99 |
| 180 kDa heavy chain | 1.80 |
| 150 kDa heavy chain | 50.43 |
| 110 kDa heavy chain | 3.05 |
| 90 kDa heavy chain variant 1 | 0.29 |
| 90 kDa heavy chain variant 2 | 0.33 |
| Sum target protein | 91.98 |
| Sum impurities | 8.04 |
| Sum (respective peaks) | 100.02 |

Example 14

Large Scale (Preparative) Purification of FVIII Subspecies—Purification and Concentration of Truncated Heavy Chain Fragment (110 kDa) in Second and Third Chromatography Step The truncated heavy chain subspecies with a molecular weight of 110 kDa is purified according to the standard procedure already used for the FVIII subspecies with 180 kDa and 150 kDa. Since the peak with the desired fragment is much better separated from neighbouring peaks both in the first AIEX step and in the size exclusion chromatography it seems to be much easier to select and pool convenient fractions. The results are presented in the following two sections.

Further polishing of the MonoQ AIEX product pool E3 containing the 110 kDa truncated heavy chain subspecies is considered to be unproblematic. The B-domain depleted 90 kDa heavy chain has already been separated sufficiently on MonoQ AIEX purification step and only low amounts are expected to be still left. The chromatogram in FIG. 37 shows three peaks of low intensity at the beginning. The two of them in fractions 1.B10-1.C1 are both arising from full length heavy chain variants as indicated in the gel electrophoresis (FIG. 38). The following peak in fractions 1.C2 and 1.C3 comes from minor amounts of 150 kDa truncated heavy chain fragment. The most intense peak with absorbance values of approximately 10-11 mAU is caused by the 110 kDa truncated heavy chain fragment. The SDS gel electrophoresis shows three fractions containing the desired subspecies, namely 1.C4, 1.C5 and 1.C6. Fraction 1.C4 represents the ascending part of the peak, which seems already relatively pure. The peak maximum falls in fraction 1.C5, which shows high protein concentration and satisfying purity at the same time. The descending part of the peak is collected in fraction 1.C6, which already contains trace amounts of the B-domain depleted heavy chain fragment (90 kDa).

It can also be seen in the chromatogram that this subspecies appears as a shoulder of the main peak and therefore seems to contaminate the descending part of the product peak. Table 23 shows protein concentrations and the total protein amount of fraction numbers 1.C4, 1.C5 and 1.C6 which encompass the product peak. Since the fractions 1.C4 and 1.C6 contain negligible amounts of protein it seems not worth it to use those fractions for pooling because of the potential risk of contamination. As consequence only fraction 1.C5 will be used for the AIEX concentration step on the SourceQ column. The data from the C4 reversed phase HPLC analysis is given in table 24 and clearly confirms the decision to discard fraction 1.C4 and 1.C6 as already fraction 1.C5 by itself contains 8.82% of impurities.

TABLE 23

Pooling scheme for the SEC purification step of AIEX eluate pool E3 on the preparative scale size exclusion chromatography column. Only fraction 1.C5 is used for the subsequent concentration step on SourceQ AIEX step, while fractions 1.C4 and 1.C6 are discarded.

| Fraction | Absorbance at 280 nm | Protein Concentration [mg/mL] | Fraction Volume [mL] | Total Protein [mg] |
|---|---|---|---|---|
| 1.C4 | 0.013 | 0.010 | 35.0 | 0.34 |
| 1.C5 | 0.054 | 0.041 | 35.0 | 1.42 |
| 1.C6 | 0.020 | 0.015 | 35.0 | 0.53 |

TABLE 24

Composition of the fraction 1.C5 derived from preparative scale size exclusion chromatography determined by C4 reversed phase HPLC analysis.

| Variable | SEC Fraction 1.C5 [%] |
|---|---|
| Extended light chain | 1.79 |
| Light chain | 44.14 |
| Single heavy, light chain 1 | 1.97 |
| Single heavy, light chain 2 | 1.00 |
| 180 kDa heavy chain | 0.91 |
| 150 kDa heavy chain | 0.23 |
| 110 kDa heavy chain | 45.25 |
| 90 kDa heavy chain varant 1 | 2.18 |
| 90 kDa heavy chain varant 2 | 2.53 |
| Sum target protein | 91.18 |
| Sum impurities | 8.82 |
| Sum (respective peaks) | 100.00 |

The chromatogram of the AIEX concentration step for the 110 kDa truncated heavy chain fragment can be seen in FIG. 39. The eluate pools of three particular size exclusion chromatography runs are pooled and concentrated simultaneously. The conductivity is first on a stable level of about 5 mS/cm until it is steeply raised to ~30 mS/cm in order to elute all bound sample in a rapid manner. As indicated by the UV curve starts the sample to elute in fraction 1.A7 and reaches its maximum absorbance of approximately 1100 mAU in fraction 1.A9. The absorbance drops rapidly down in fractions 1.A10-1.A12 and then passes into a long tailing phase which finally reaches baseline level in fraction 1.B6. The fractions 1.A7-1.B8 are used for the final product pool.

Since the sample has already passed through two different purification steps, it should only contain the 110 kDa truncated heavy chain fragment. This is also confirmed by FIG. 40, which shows a silver stained image of the SDS page gel electrophoresis on the left-hand side and a FVIII western blot development on the right-hand side.

Both show exclusively 110 kDa truncated heavy chain fragment in combination with the 80 kDa light chain variant in the load, which has been probed prior to column loading. The other fractions, namely flow through, washing phase and the first fractions of the elution phase which are not used for the product pool (designated as VE) do not show relevant amounts of product. This means that the columns capacity was high enough to bind the entire sample amount. A second concentration step is performed in the same way and both eluates are pooled to one final product pool, exclusively composed of the 110 kDa truncated heavy chain fragment. Two different dilutions—1:147 (P1) and 1:49 (P2) for silver stain and 1:196 (P1) and 1:65 (P2) for FVIII western blot—of that product pool can be seen as almost pure 110 kDa truncated heavy chain fragment. The silver stained image does not show any other subspecies, while there is a low signal for the full length heavy chain visible for the P2 dilution in the FVIII western blot image. Table 25 provides the corresponding analytical data regarding composition of the final product pool including all concentrated SEC eluate pools. The fraction of target protein in the final pool is 93.7%7 which includes both the 120 kDa extended light chain and the 80 kDa light chain variant as well as the 110 kDa truncated heavy chain variant. The fraction of impurities is 6.3% which is less than 10%.

TABLE 25

Composition of the product pool E1 containing 110 kDa truncated heavy chain fragment derived from preparative scale AIEX on SourceQ determined by C4 reversed phase HPLC analysis. The final product pool is composed of eluates from two SourceQ AIEX runs, which have been used for concentration of five size exclusion chromatography eluate pools.

| Variable | Product Pool E1 [%] |
|---|---|
| Extended light chain | 1.46 |
| Light chain | 42.39 |
| Single heavy, light chain 1 | 1.53 |
| Single heavy, light chain 2 | 0.47 |
| 180 kDa heavy chain | 1.07 |
| 150 kDa heavy chain | 0.52 |
| 110 kDa heavy chain | 49.85 |
| 90 kDa heavy chain varant 1 | 1.44 |
| 90 kDa heavy chain varant 2 | 1.28 |
| Sum target protein | 93.70 |
| Sum impurities | 6.31 |
| Sum (respective peaks) | 100.01 |

Example 15: Large scale (preparative) purification of FVIII subspecies—concentration of B-domain depleted heavy chain (90 kDa) fragment in third chromatography step The B-domain depleted heavy chain fragment is the least present FVIII subspecies in the starting material B1439000-30. In order to obtain a satisfying amount of this subspecies it would be necessary to run an enormous number of AIEX purifications, which would require a large volume of this starting material whose availability is rather limited. As a consequence of that a second starting material named F8_AD2_90 kDa with an approximate content of ~38% of 90 kDa subspecies is used for this purpose. Independent of its source, the polishing step by size exclusion chromatography is skipped and the solutions will be directly concentrated on a SourceQ column. There are two of them available in two different sizes—since the volume and the total protein content of both starting materials exceed the capacity of the small scale SourceQ column, a larger one with 7.0 mL column volume will be used instead. The following will be limited to the results of the purification of B14390000-30 derived B-domain depleted heavy chain species.

As already mentioned earlier the 90 kDa B-domain depleted heavy chain fragment is almost completely separated from other subspecies in the MonoQ AIEX step and does therefore not require any further purification or polishing by means of size exclusion chromatography. As it is already highly diluted this would also lead to insufficient results on the size exclusion chromatography and furthermore would cause high losses of this particular fragment. A typical MonoQ AIEX product pool of the 90 kDa B-domain depleted species such as product pool E8 described in Example 11 contains only 0.025 mg/mL protein and makes it thus necessary to concentrate a higher number of such product pools in order to achieve the desired amount of 10 mg of target protein. FIG. 41 shows the elution phase of an AIEX SourceQ run for the concentration of six MonoQ eluate pools simultaneously. The small SourceQ column with ~3 mL column volume is no longer suitable because the significantly increased product volumes would cause too long sample holding times at room temperature. It was therefore inevitable to roughly double the column volume to ~7 mL to maintain holding times in an acceptable range. The elution itself is similar to the ones discussed before, although the peak seems to be broadened. As already seen in the elution phases of MonoQ anion exchange chromatography does the B-domain depleted heavy chain fragment elute last as it requires the highest conductivity of all subspecies for unbinding. The step gradient of the SourceQ AIEX step may not provide conductivities high enough to elute the B-domain depleted fragment in a fast and sharp order. Instead it takes higher volumes of elution buffer to remove all protein from the resin and thereby causes peak broadening. However, the fractions 1.A11 to 1.D12 are used for the final product pool, which shows a protein concentration of 0.493 mg/mL and a total protein amount of 9.06 mg. The respective SDS gel electrophoresis can be seen in FIG. 42, as usual providing a silver stained gel image on the left-hand side and a FVIII western blot development on the right-hand side. Although the silver stained image appears quite pure, it can be seen on the much more sensitive FVIII western blot image that there is still a significant amount of full length heavy chain visible in the load and the eluate pool dilutions. The C4 reversed phase HPLC analysis confirms an amount of 3.84% of full length heavy chain still present in the final product pool, but 94.49% of target protein complies with the purity goal of <10% other subspecies. This procedure of purification of the full length heavy chain was repeated several times to yield the desired amount of protein.

TABLE 26

Composition of the product pool E1 (90 kDa B-domain depleted heavy chain fragment) derived from preparative scale AIEX concentration step of six AIEX runs determined by C4 reversed phase HPLC analysis.

| Variable | Product Pool E1 [%] |
|---|---|
| Extended light chain | 1.51 |
| Light chain | 46.75 |
| Single heavy, light chain 1 | 2.40 |
| Single heavy, light chain 2 | 0.45 |
| 180 kDa heavy chain | 0.99 |
| 150 kDa heavy chain | 0.48 |
| 110 kDa heavy chain | 1.19 |
| 90 kDa heavy chain varant 1 | 18.36 |
| 90 kDa heavy chain varant 2 | 27.87 |
| Sum target protein | 94.49 |
| Sum impurities | 5.51 |
| Sum (respective peaks) | 100.0 |

Example 16

Summary of Large-Scale (Preparative) Purification

The preparative purification process of FVIII subspecies encompasses the AIEX step on MonoQ for initial separation, the SEC step on a Superdex 200 resin for polishing and finally a concentration step on the anion exchange resin Source30Q. The full length chain as well as the two truncated fragments have to pass through these three steps for proper purification success. The B-domain depleted fragment is an easy to purify exception, which skips the polishing step and is simply applied to the anion exchange steps. FIG. 43 gives an overview of the complete purification program driven during the present invention. The full length heavy chain with a molecular weight of 180 kDa including all differently glycosylated variants required a total number of four AIEX purification runs, three SEC runs and three AIEX runs for concentration. This produced 62.97 mg of target protein, including all full length heavy chain variants, as well as both light chain variants. The percentage of impurity is 6.84% or in other words, the final product pool shows 93.16% purity which fulfils the goal concerning protein amount and purity. The impurities arise mainly from the two truncated heavy chain species. The 150 kDa truncated heavy chain fragment is one of the most challenging ones to purify. A total number of four AIEX runs on MonoQ, four SEC polishing runs and two AIEX runs for concentration were necessary to produce the rather low amount of 6.74 mg target protein, including the truncated heavy chain species (150 kDa) and both light chain variants. The percentage of impurities could be kept below 10% (8.04%) almost exclusively arising from the full length heavy chain, which complies with the goal. The 110 kDa truncated heavy chain species was purified by five AIEX purification runs followed by five SEC polishing runs and finally two AIEX concentration runs. The final 8.57 mg of 110 kDa truncated heavy chain fragment exhibit 6.31% of impurities, which are caused by all of the other subspecies. The B-domain depleted heavy chain fragment demanded seven AIEX runs and two AIEX concentrations runs on the large scale Source30Q column. This purification process gave a total amount of protein of 15.31 mg, including both 90 kDa subspecies variants in combination with the two light chain variants. The percentage of impurities is exactly 5.00% which is the lowest percentage number of impurities of all subspecies, although the intermediate polishing step has not been performed. Both goals are therefore fulfilled for the B-domain depleted heavy chain fragment. In conclusion, the goal regarding the limit of <10% impurities could be accomplished for all subspecies. The total amount of protein is very satisfying for the full length heavy chain fragment because of its high abundance in the starting material, but also the results for the B-domain depleted heavy chain fragment are in the correct range.

The protein concentration for all four final product pools is 0.974 mg/mL for the full length heavy chain, 0.568 mg/mL for the 150 kDa truncated heavy chain fragment, 0.640 mg/mL for the 110 kDa truncated heavy chain fragment and 0.537 mg/mL for the B-domain depleted heavy chain fragment. The goal of all product pools to be above the limit of 0.3 mg/mL is therefore clearly accomplished. Furthermore, all product species are provided in the desired buffer matrix.

In conclusion, the small-scale experiments where different conditions and parameters have been tested on four different resins was very important for the upscale and the final purification process. This final strategy led to satisfying results. Especially the truncated heavy chain fragment with 150 kDa molecular weight is quite challenging to purify. Furthermore, it is also consuming a lot of starting material because of its rather low content. Nevertheless, almost 7.0 mg of it could be produced which is a good result. The final purification strategy offers a straightforward procedure for the purification of all four subspecies. Table 27 summarises the outcomes of the present invention and gives an assessment in respect of the prerequisites.

TABLE 27

Summary of the final experimental outcomes and assessment in respect of the goals. Total protein amount, purity and concentration are shown for all target fractions, as well as the corresponding evaluation, which states whether the projects goals could be achieved or partly achieved.

| FVIII Variant | Protein Amount [mg] | Purity [%] | Conentration [mg/mL] | Assessment |
|---|---|---|---|---|
| 180 kDa Heavy Chain | 62.97 | 93.16 | 0.974 | Achieved |
| 150 kDa Heavy Chain | 6.74 | 91.96 | 0.568 | Partly achieved |
| 110 kDa Heavy Chain | 8.57 | 93.69 | 0.640 | Partly achieved |
| 90 kDa Heavy Chain | 15.31 | 95.00 | 0.537 | Achieved |

Initially, the hydrophobic interaction chromatography was thought to be an alternative to the MonoQ AIEX step, as it might elute the 150 kDa truncated heavy chain species more separated from the full length heavy chain. First experiments showed that it actually does but the content of the 150 kDa subspecies appeared relatively low for purification. A possible solution to it was to incorporate a negative mode HIC as an alternative to the size exclusion chromatography. One experiment has been performed, and it was successful and showed that a 150 kDa subspecies enriched pool could be purified to a satisfying degree. Further experiments can reveal the proper conditions regarding conductivity level which is assumed to have the greatest influence on the binding behaviour.

Finally the goals have been met and provided a novel and efficiently working procedure for the purification of FVIII subspecies, as well as a novel approach for the replacement of the size exclusion chromatography step. In addition, providing pure protein solutions of all four subspecies is a corner stone that enables further investigations of the nature of FVIII molecular subspecies. Moreover, the purified FVIII subspecies or a mixture thereof may be useful for treating bleeding disorders.

Example 17

Functional Characterization of Purified FVIII Subspecies—Materials and Methods

In the following, experimental details are given for all Examples relating to the "Functional characterization of purified FVIII subspecies".

FVIII Samples and Chemicals

FL-rFVIII (a process intermediate material of a commercially available FL-rFVIII product, 0.23 mg/ml) produced in Chinese Hamster Ovary (CHO), historical lots of FL-rFVIII and commercially available lyophilized plasma FVIII product were provided by Shire, Vienna, Austria. Chemicals were purchased from Sigma Aldrich, MO, USA. Unless indicated otherwise, FL-rFVIII refers to human FL-rFVIII, and pdFVIII refers to human pdFVIII.

Purification of pdFVIII and rFVIII Molecular Species vWF-free, pdFVIII was purified from a commercially available lyophilized plasma FVIII product. Reconstitution of multiple vials was performed in a buffer solution followed by pooling to achieve a homogeneous starting material. Separation of vWF and FVIII was induced by chemical means. Capture of FVIII was performed on an anti-FVIII affinity column. Further depletion of vWF was achieved by a strong cation exchange chromatography. Finally an additional polishing step on a strong anion exchange resin has been performed for buffer exchange and concentration.

rFVIII molecular species with a different extent of B domain truncation have been isolated from FL-rFVIII. A high-resolution anion exchange chromatography step with a flat gradient has been used to pre-separate the entities. Pools with enriched subspecies have then been generated and further purified by preparative size exclusion chromatography followed by concentration and buffer exchange on a strong anion exchange resin.

SDS-PAGE

SDS-PAGE was carried out using the Novex NuPAGE SDS-PAGE system (ThermoFisher Scientific, MA, USA). Samples (each 50 µl) were mixed with 20 µl 0.5 M iodoacetamide and incubated for 30 min at 37° C. Afterwards, 15 µl deionized water, 25 µl NuPAGE LDS sample buffer and 10 µl NuPAGE reducing agent were added to the reaction mixture and incubation was continued for 30 min at 37° C. Ten µl (30 ng) of each sample and 2 µl precision plus unstained protein standard (Bio-Rad, CA, USA) were loaded onto a NuPAGE 7% Tris-acetate mini gel. Electrophoresis was run for 90 min at 150 V. Protein bands were visualized with SilverQuest silver staining kit (ThermoFisher Scientific).

In Silico Protein Analysis

For calculation of the average hydropathicity of the B domain the BioAnnotator tool from Vector NTI Advance 11 was used.

Hydrogen/Deuterium Exchange-Mass Spectrometry

In order to characterize the structural motifs of rFVIII hydrogen/deuterium exchange-mass spectrometry (HDX-MS) was performed. Local amide HDX kinetics of the protein construct was followed after 3 s, 10 s, 30 s, 2 min 10 min, 60 min, 3 h and 3 days of incubation time. All HDX reactions were performed at room temperature (22° C.), except for the 3 s incubation reaction which was carried out at 6° C. HDX labeling reaction was initiated by mixing rFVIII molecular species B70-rFVII with deuterated buffer (50 mM Tris buffer, pH 6.7, containing 5 mM $CaCl_2$ and 260 mM NaCl). The reaction was stopped by adding ice-cold 100 mM phosphate buffer, pH 2.3, containing 100 mM Tris(2-carboxyethyl)phosphine and 3.3 M urea, and subsequent snap freezing in liquid nitrogen. Deuterated samples were digested using an HPLC column (2.1×30 mm) (ACE, Aberdeen, UK) packed with pepsin-agarose from porcine gastric mucosa (Sigma-Aldrich) and desalted on a 2×10 mm C18 pre-column (ACE). Peptic peptides were subjected to liquid chromatography coupled to MS (LC-MS) using a 2×50 mm HALO C18/1.8 µm column (AMT, DE, USA). Peptides were eluted by an acetonitrile gradient and analyzed on an Orbitrap XL mass spectrometer (60,000 resolution at m/z 400) (ThermoFisher Scientific). Peptic peptide identification was performed by 3 independent LC-MS/MS analysis of a non-deuterated protein sample using the same procedure as for the deuterated samples.

FVIII Chromogenic Activity

FVIII activity measurement was performed according to a commercially available FVIII chromogenic activity assay kit (Siemens Healthcare, Erlangen, Germany) on an automated coagulation analyzer (BCS XP) (Siemens Healthcare). Briefly, the samples containing unknown amount of functional FVIII, were added to the reaction mixture consisting of thrombin, activated coagulation factor IX (FIXa), phospholipid, coagulation factor X (FX) and a buffer containing calcium. After thrombin cleavage FVIIIa formed a complex with phospholipids, FIXa and calcium resulting in the activation of FX. Activated FX (FXa) was measured photometrically through cleavage of the FXa specific chromogenic p-nitroaniline substrate and was directly proportional to the amount of functional FVIII present in the sample. The reference standard was commercially available FL-rFVIII (Shire), calibrated against WHO international standard.

Preparation of FVIII Aggregates

All FVIII samples were dialyzed against PBS containing 0.9 mM $CaCl_2$ and 0.5 mM $MgCl_2$ (PBS++) and diluted to a protein concentration of either 0.122 µM, 0.244 µM or 0.61 µM. To ensure reproducibility all experiments were performed at least twice.

Temperature-Dependent Aggregation

All FVIII samples with protein concentrations of either 0.122 µM for high performance size exclusion chromatography (HPLC-SEC) analysis or 0.61 µM for dynamic light scattering (DLS) analysis, were incubated at either 25° C., 30° C., 35° C., 40° C., 45° C. or 50° C. for 20 h in polystyrene 96-well microplates (Corning, NY, USA) covered with plate sealers in Synergy H4 Hybrid Reader (BioTek, VT, USA) with 20 sec medium shaking every 10 min. Samples were subsequently frozen at −80° C. until DLS and HPLC-SEC analysis.

Time-Dependent Aggregation at 45° C.

All FVIII samples (0.122 µM) were incubated at 45° C. for 24 h in polystyrene 96-well microplates (Corning) covered with plate sealers in PST-60H L plus thermo shaker (Biosan, MI, USA). Samples were withdrawn after various time intervals and immediately frozen at −80° C. until examination by HPLC-SEC.

Homologous Aeeding of FVIII Aggregation

For preparation of seeds FVIII samples (0.122 µM) were incubated for either 2, 5, 8 or 18 h at 45° C. in polystyrene 96-well microplates (Corning) covered with plate sealers in PST-60HL plus thermo shaker (Biosan). Native FVIII samples (0.122 µM) were mixed 1:1 with their corresponding seeds and time dependent aggregation at 45° C. was performed. Samples were stored at −80° C. until H PLC-SEC analysis.

Agitation and Shear Stress Induced Aggregation

FVIII solutions with 0.244 µM protein concentration were agitated by hand for 10 min in a disposable Omnifix syringe (Braun, Melsungen, Germany). The shear stress was induced by injecting the solution through "Winged infusion sets with needle protection" (23G×¾"; L=35 cm, V=0.25 mL) from Terumo Europe, Belgium. This well controlled stress conditions intend to represent potential mishandling of the rFVIII products during reconstitution and application. All samples, after exposure to the stress conditions, were stored at −80° C. until flow cytometry-based particle analysis.

Dynamic Light Scattering

DLS was performed using a Malvern Nanoletasizer ZSP (Malvern Instruments, Malvern, UK). All samples (0.244 µM) were centrifuged (Centrifuge 5415C) (Eppendorf, Vienna, Austria) at 10,000 rpm for 5 min and 60 µL of sample were filled into a ZEN0040 disposable micro cuvette. Operation temperature was set at 25° C. with an equilibration time of 2 min. The angle was set to 173° backscatter to determine the hydrodynamic diameter of a protein. This parameter was used for analyzing the effective size of proteins by DLS. A minimum of three runs per sample were measured to obtain an average result.

High Performance Size Exclusion Chromatography

HPLC-SEC was performed at room temperature using a TSKgel G4000SWx1 column (7.8×300 mm) (Tosoh Bioscience, Tokio, Japan) and a TSK guard column (6×40 mm) (Tosoh Bioscience) coupled to an HPLC 1260 infinity system (Agilent Technologies, Santa Clara, CA, USA). SEC was carried out under isocratic conditions at a flow rate of 0.3 ml/min using an aqueous buffer consisting of 50 mM Tris-HCl, 5 mM $CaCl_2$, 400 mM NaCl and 0.05% $NaN_3$, pH 7.0. A sample volume of 100 μl (0.122 μM protein concentration) was mixed with 3 μl 1 mM Thioflavin T (ThT) and subsequently loaded onto the column. To monitor the elution of the protein with fluorescence detection the excitation and emission wavelengths were set to 280 nm and zero order, respectively. ThT fluorescence was monitored with 440 nm excitation and zero order emission. Peaks eluting with the void volume (retention times 18.0-21.2 min), with retention times 21.2-27.0 min and 27.0-43.0 min were designated as soluble protein aggregates, oligomers and monomers, respectively. The amount of aggregates, oligomers and monomers was calculated as a percentage of the total area of all peaks in the chromatogram. ThT binding was calculated as ratio between ThT and intrinsic protein fluorescence signals. The protein-based gel filtration standard (Bio-Rad) was analyzed in between samples to monitor optimal column performance. All samples were analyzed in random order.

Curve Fitting and Statistical Analysis

Curve fitting was computed by GraphPad Prism 6. Kinetic rate constants for oligomer formation ($k_{oligo}$ [$h^{-1}$]) were derived by fitting data to the one-phase association model following the equation: $y=y_0+(plateau-y_0)*[1-exp(-k_{oligo}*x)]$; y=oligomer amount [%]; x=time [h]; $y_0$=y value when x is zero; plateau=y value at infinite times. Aggregate formation rates ($k_{agg}$ [$h^{-1}$]) were derived by fitting data to the Boltzmann sigmoidal model following the equation: $y=y_{min}+(y_{max}-y_{min})/(1+exp[(x_{1/2}-x)/(1/k_{agg})])$; y=aggregate amount [%]; $y_{min}$=y during lag phase; $y_{max}$=y after aggregation has ended; x=time [h]; $x_{1/2}$=time at half-maximum y (Uversky et al., 2001).

The statistical differences were computed by GraphPad Prism 6 using unpaired t-test.

Flow Cytometry-Based Particle Analysis

A flow cytometry-based particle analysis method for the detection and characterization of subvisible particles was used. The flow cytometry-based method is using a combination of size calibration beads (Fluoresbrite® YG Carboxylate Size Range beads) (Polyscience Inc., PA, USA), counting beads (CountBright™ Absolute Counting Beads) (Invitrogen Corp., CA, USA) and fluorescent probes for characterization of the subvisible particles. To distinguish protein and protein-containing particles from non-protein subvisible particles, samples were stained with the fluorescent dye 4,4'-Dianilino-1,1'-binaphthyl-5,5'-disulfonic acid dipotassium salt (Bis-ANS). The method is described in detail in the publication (Lubich et al., 2015).

Example 18

Functional Characterization of Purified FVIII Subspecies—Similar Heterogeneity of pdFVIII and FL-rFVIII In the following experiments the aim was to investigate the influence of the B domain and the natural heterogeneity originating from the preence of the B domain in FL-rFVIII and plasma derived (pd)FVIII on protein stability and aggregation. Structural characteristics of the B domain were studied and compared the ability of FL-rFVIII, pdFVIII and purified rFVIII molecular species with variable B domain content to withstand physical stress, and their aggregation behavior was explored. Based on the observations, a schematic model of FL-rFVIII and BDD-rFVIII aggregation was built and a new role of the B domain and molecular heterogeneity in ensuring stability of the FVIII molecule was suggested.

A schematic overview of the multi-domain structure of FVIII is shown in FIG. 2B. Brackets indicate molecular species resulting from complex posttranslational processing within the B domain of FL-FVIII. rFVIII molecular species containing 100% (B100-), 70% (B70-), 20% (B20-) or 0% (BDD-rFVIII) B domain present the main FVIII species found in FL-rFVIII (Jankowski et al., 2007, internal analytical data not shown). Percentages of B domain content were calculated based on the apparent molecular masses of the respective rFVIII HC. The B domain part reaching from amino acids $Arg^{1313}$ to $Arg^{1648}$ is, most likely, completely removed after the cleavage process since it wasn't found in any secreted FVIII HC species (Jankowski et al., 2007).

pdFVIII was isolated from pooled human plasma to highest purity by a combination of affinity chromatography and ion exchange chromatography. The amount of vWF was depleted to 7.5 μg vWF/mg FVIII. Nearly identical heterogenic protein profiles were identified for pdFVIII and CHO-derived FL-rFVIII on the silver-stained SDS-PAGE gel (left-hand image in FIG. 44, lanes 1-2). Both displayed the most intense band at approximately 200 kDa, indicating glycosylated B100-HC species, and several truncated HC/B domain species with lower molecular weight migrating at comparable levels in FL-rFVIII and pdFVIII in the gel.

Presence of main molecular FVIII species in both, FL-rFVIII and pdFVIII, was further observed on SEC profiles (FIG. 51). In addition, the heterogeneity in FL-rFVIII showed consistency over historical lots produced from 2005 till 2015 (right-hand image in FIG. 44).

Example 19

Functional Characterization of Purified FVIII Subspecies—Purification and Characterization of rFVIII Molecular Species Single FVIII molecular species were purified from CHO-derived FL-rFVIII by applying size exclusion and ion exchange chromatographic methods. BDD-rFVIII, B20-rFVIII and B70-rFVIII were isolated to 95%, 94% and 92% purity based on C4 HPLC analysis, respectively (data not shown). Whereas a constant apparent molecular weight band of 75 kDa was observed for the LC of each species, the HC of B70-rFVIII, B20-rFVIII and BDD-rFVIII showed, due to varying amounts of B domain, apparent molecular weights of 150, 110 and 90 kDa on the SDS-PAGE gel, respectively, (left-hand image in FIG. 44, lanes 3-5). Integrity of purified rFVIII species was further demonstrated by HPLC-SEC (FIG. 51). B100-FVIII is not used in the following.

Example 20

Functional Characterization of Purified FVIII Subspecies—B Domain Structural Characteristics The B domain possesses an amino acid sequence with low overall hydrophobicity. The average of hydropathicity according to Kyte and Doolittle (Kyte et al., 1982) was calculated as 0.751 for the total B domain amino acid sequence. Clusters of low hydrophobicity are evenly distributed among the B domain sequence. B domain sequences in B100-, B70- and B20-rFVIII exhibit similar average hydropathicity values of −0.779, −0.741 and −0.896, respectively. Low hydrophobicity typically characterizes natively unfolded proteins as reviewed in detail by Uversky (Uversky et al., 2002).

Figure 52:
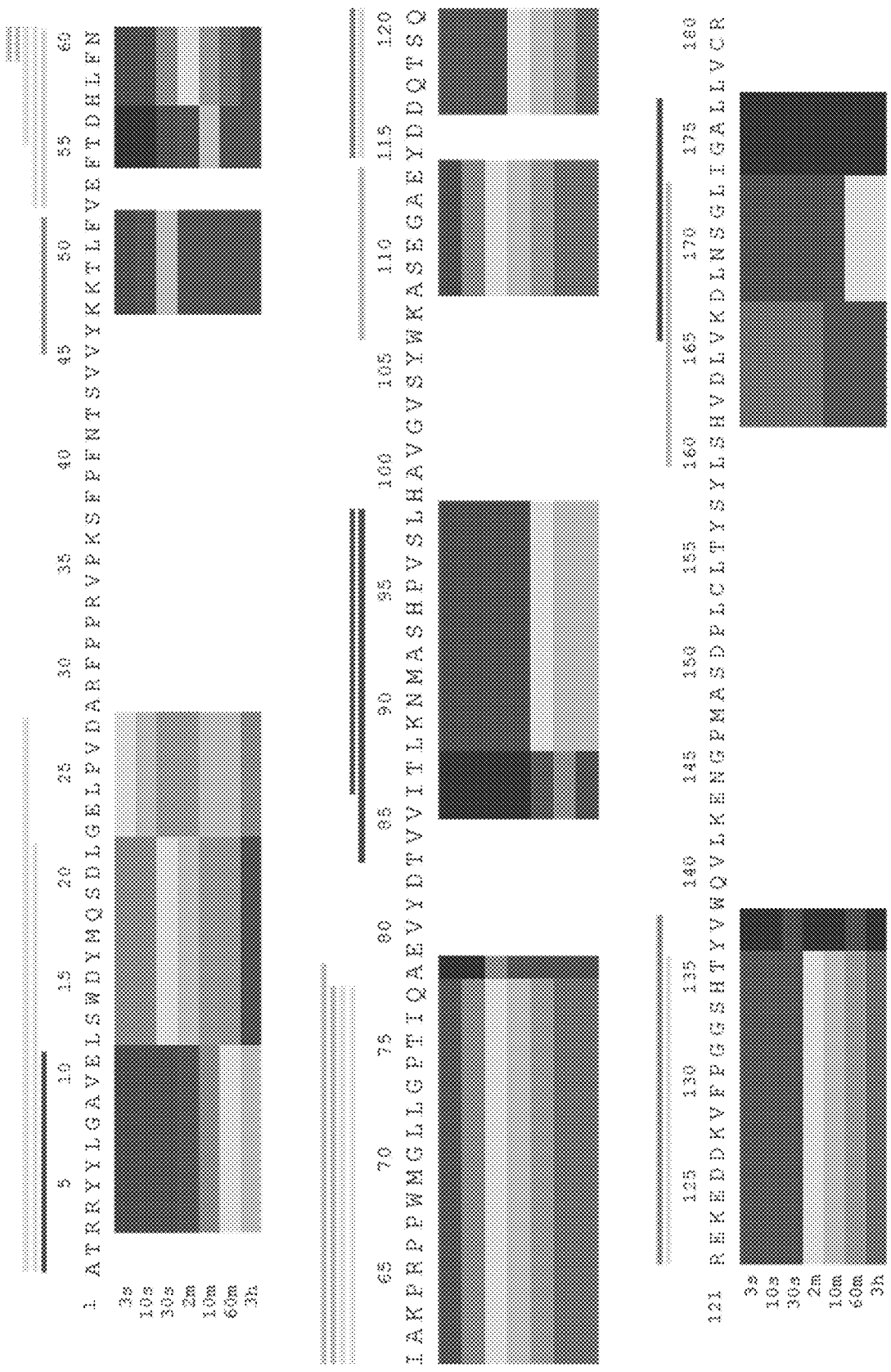
Figure 52:
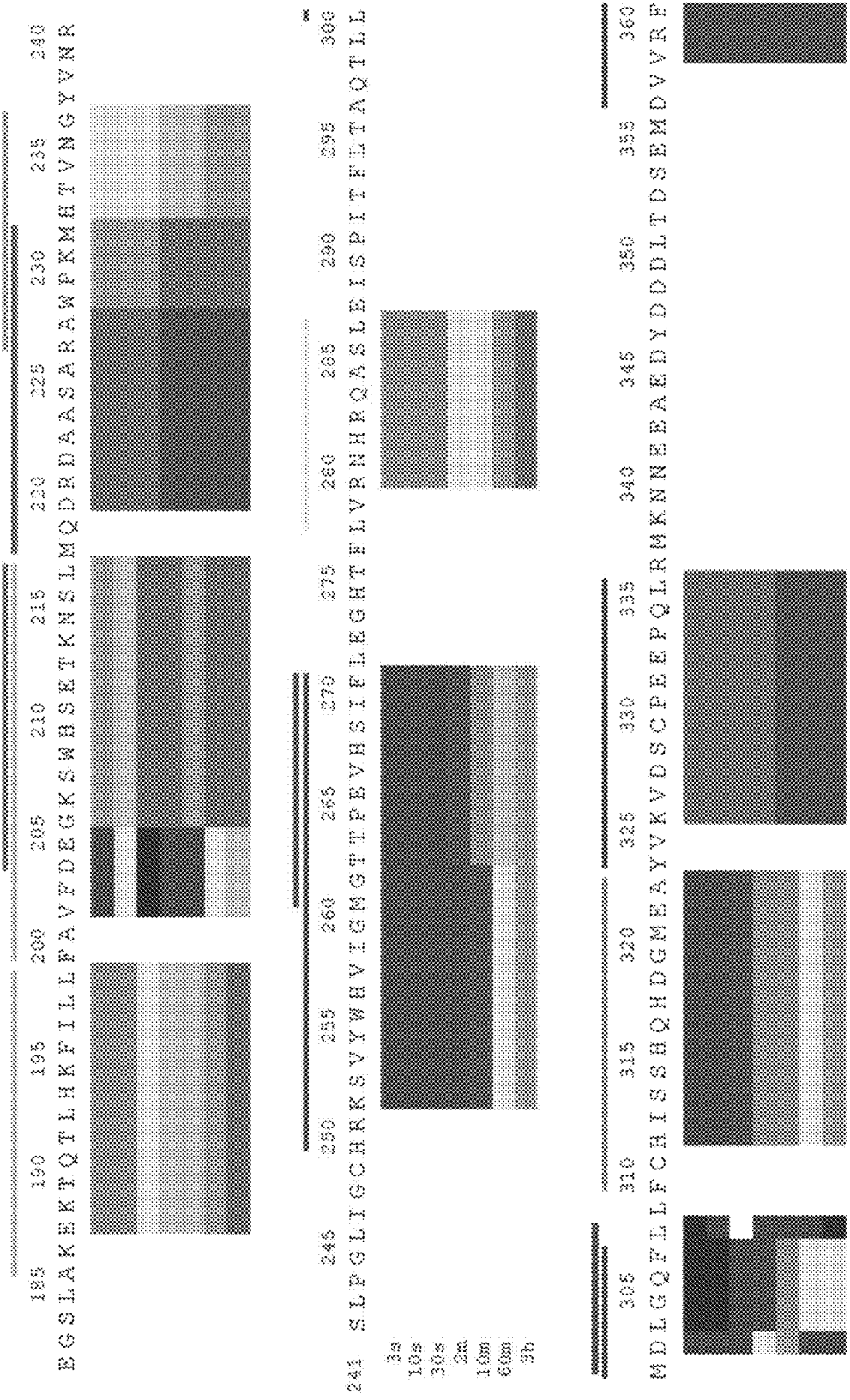
Figure 52:
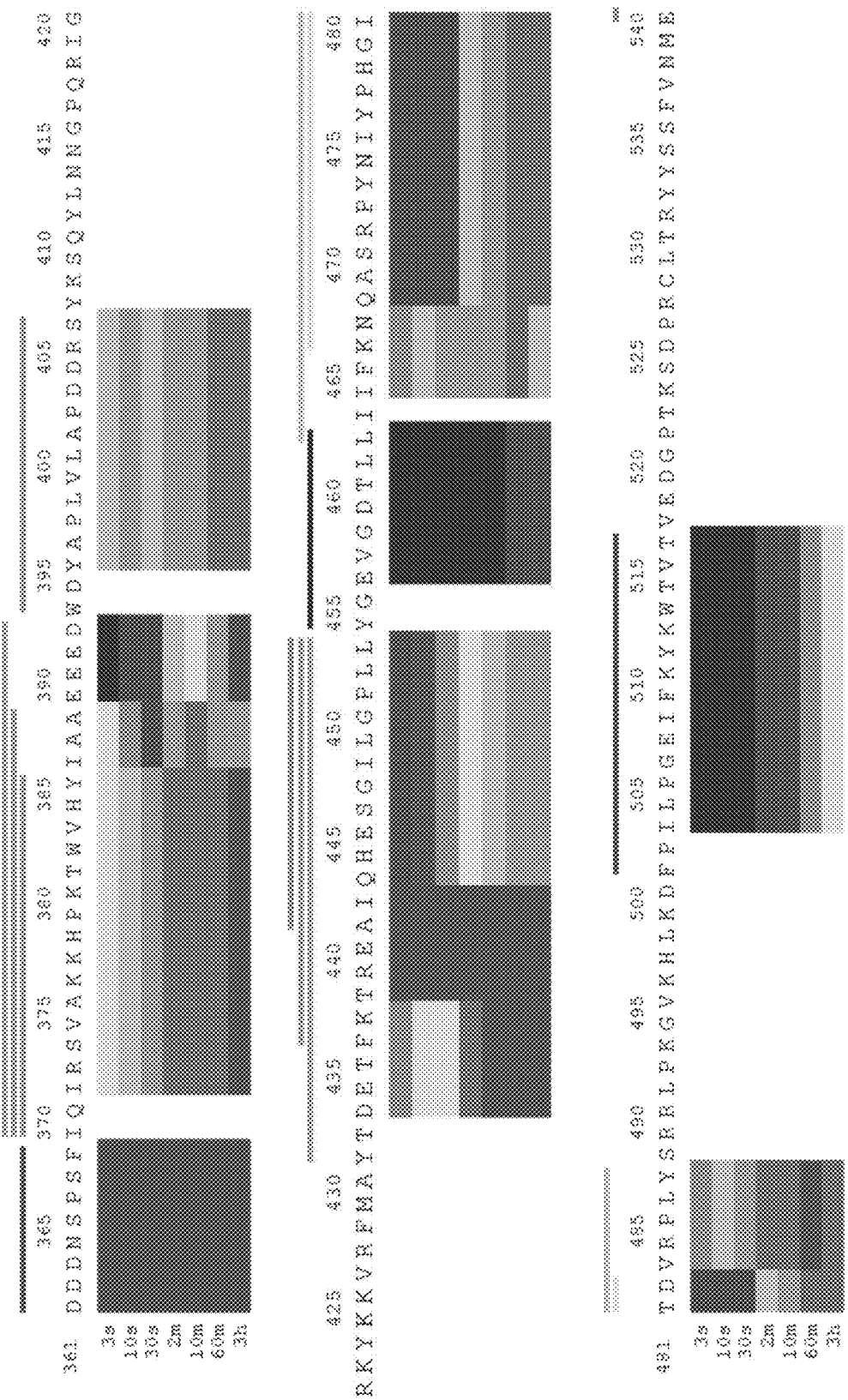
Figure 52:
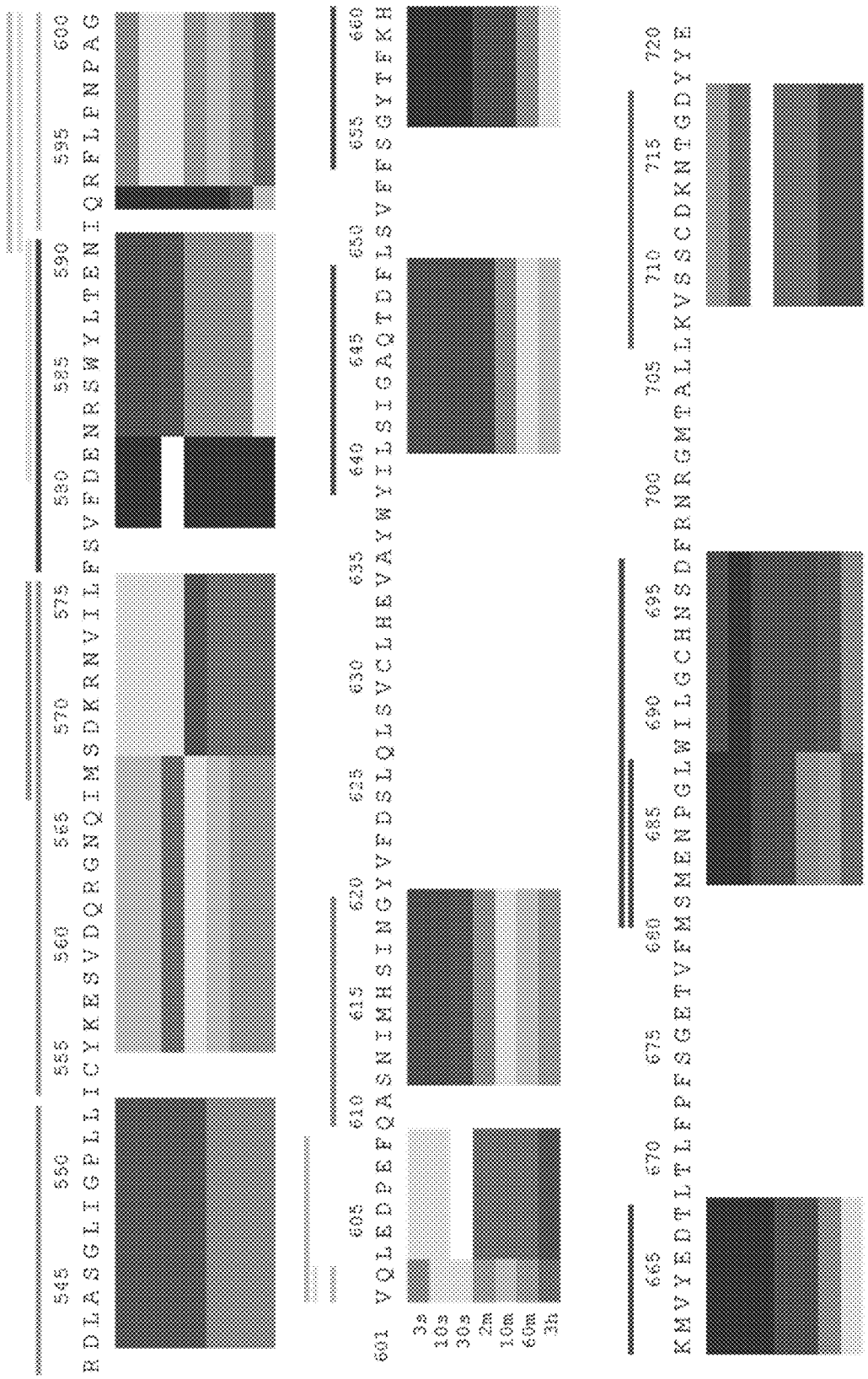
Figure 52:
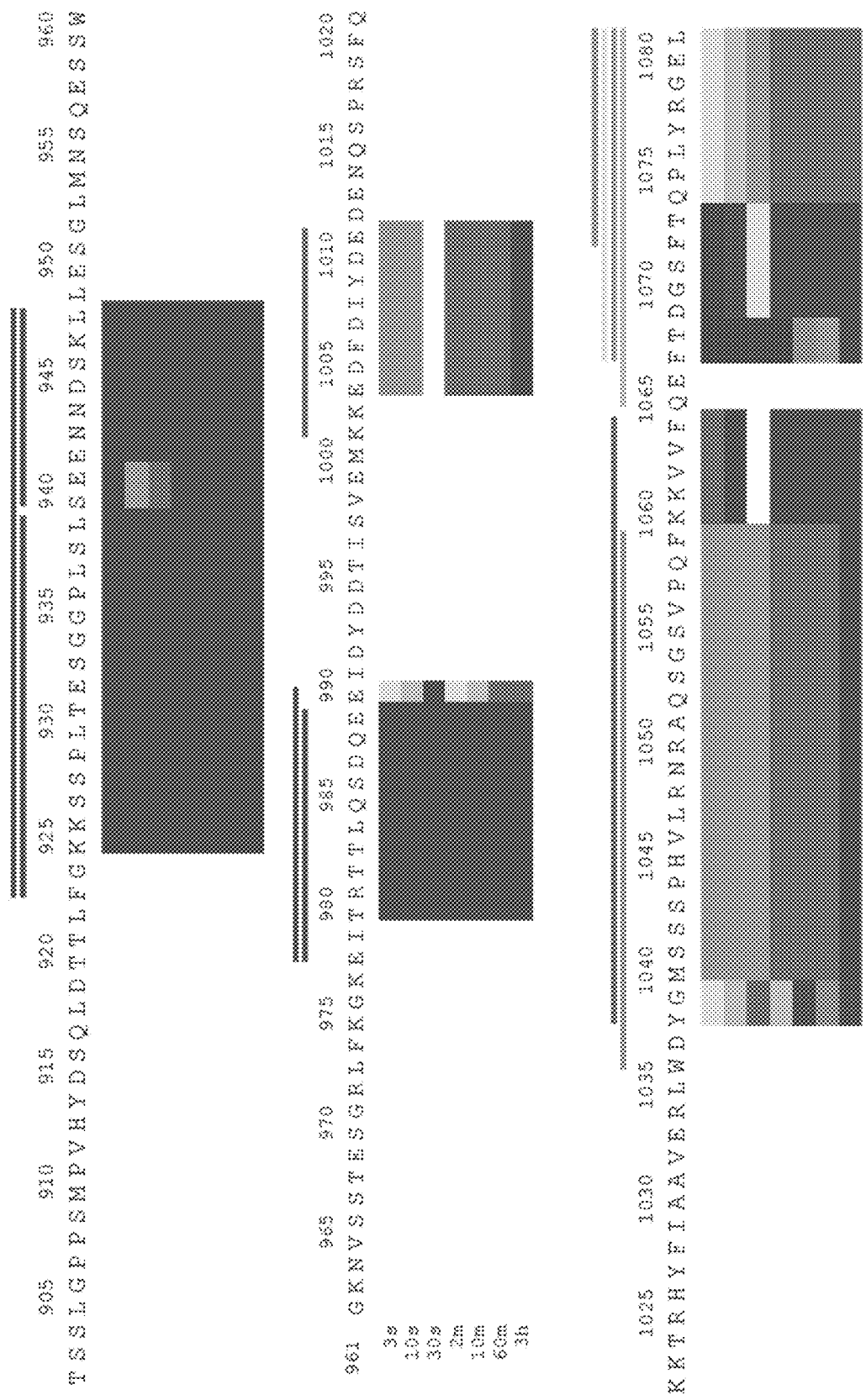
Figure 52:
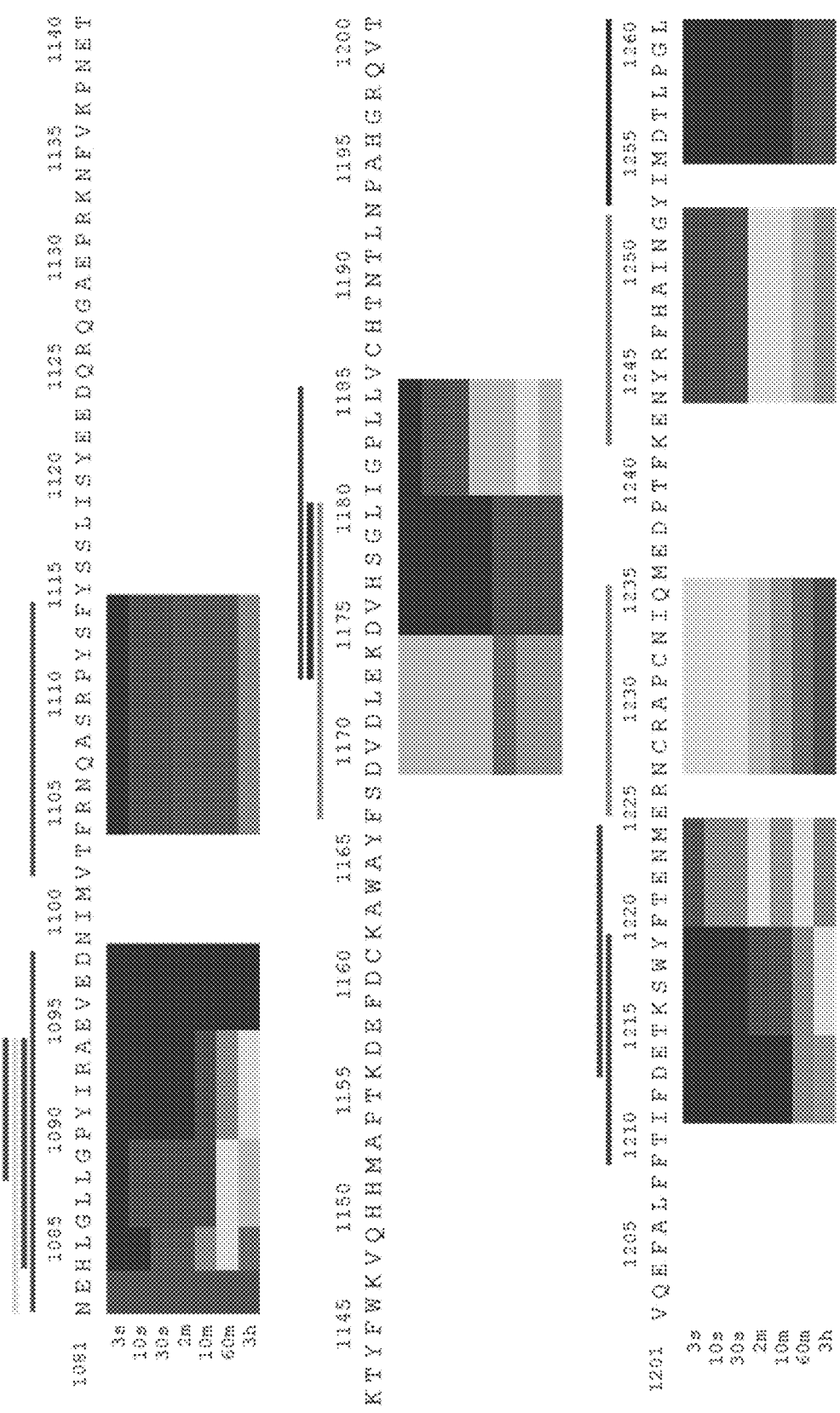
Figure 52:
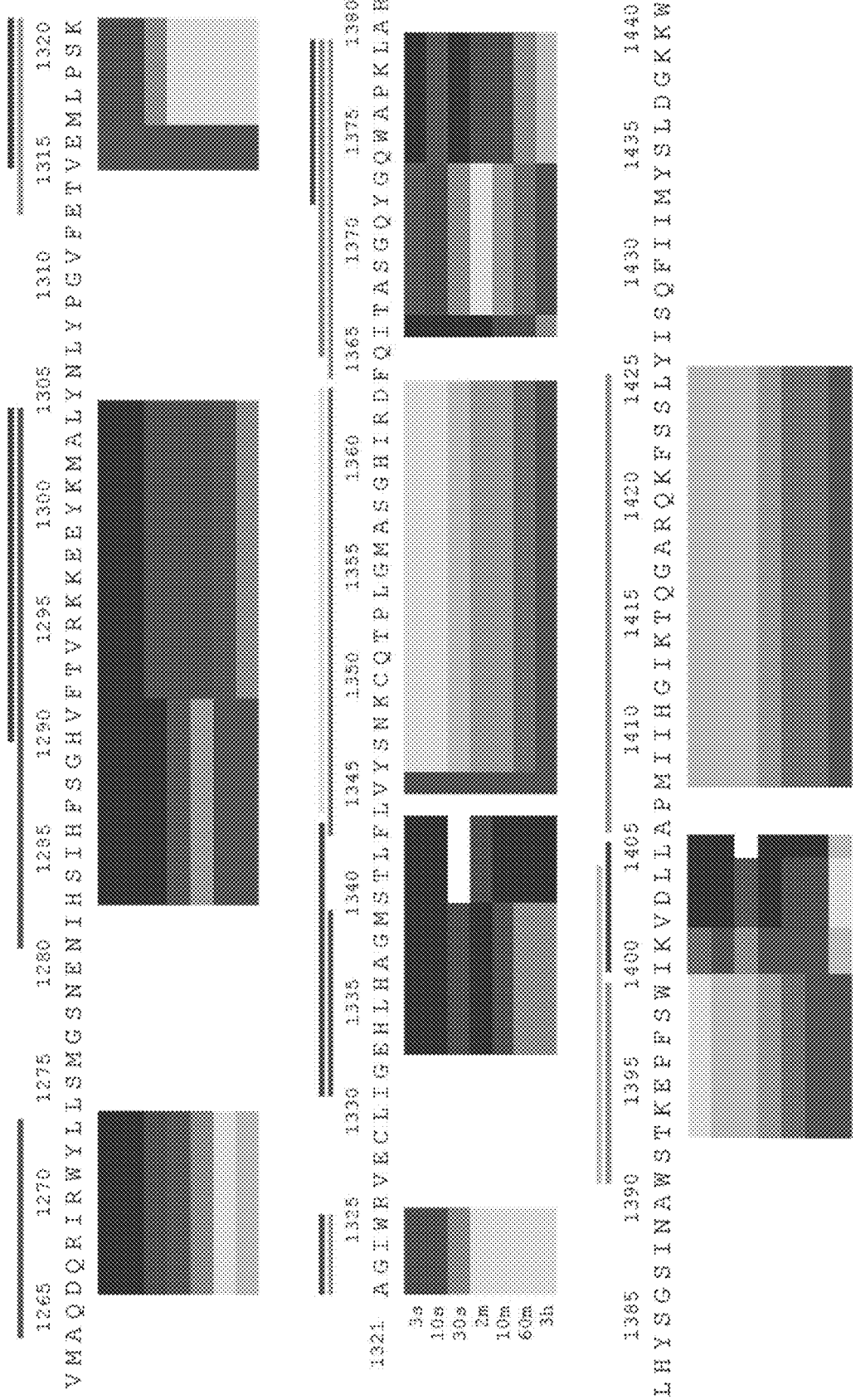
Figure 52:
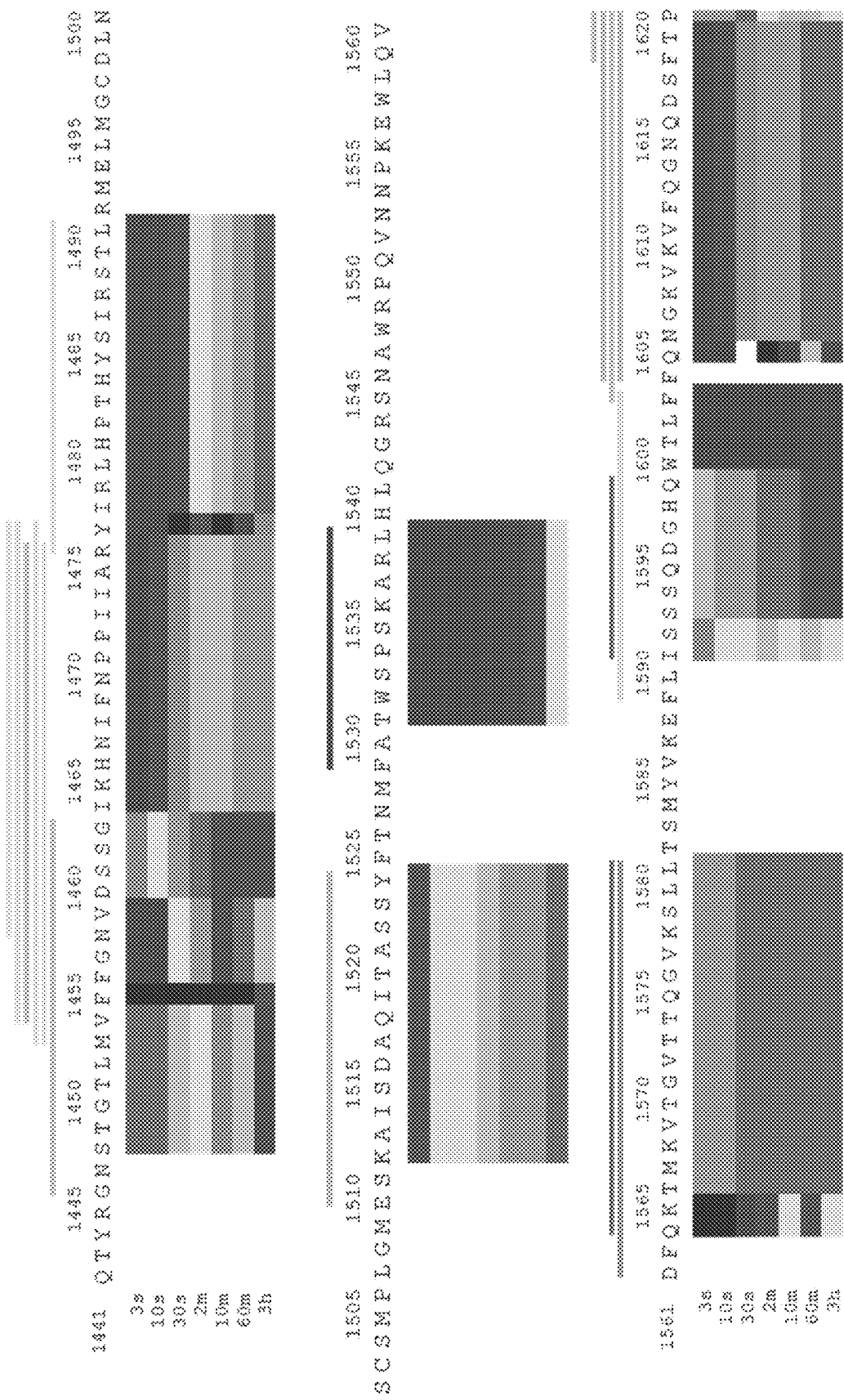
Figure 52:
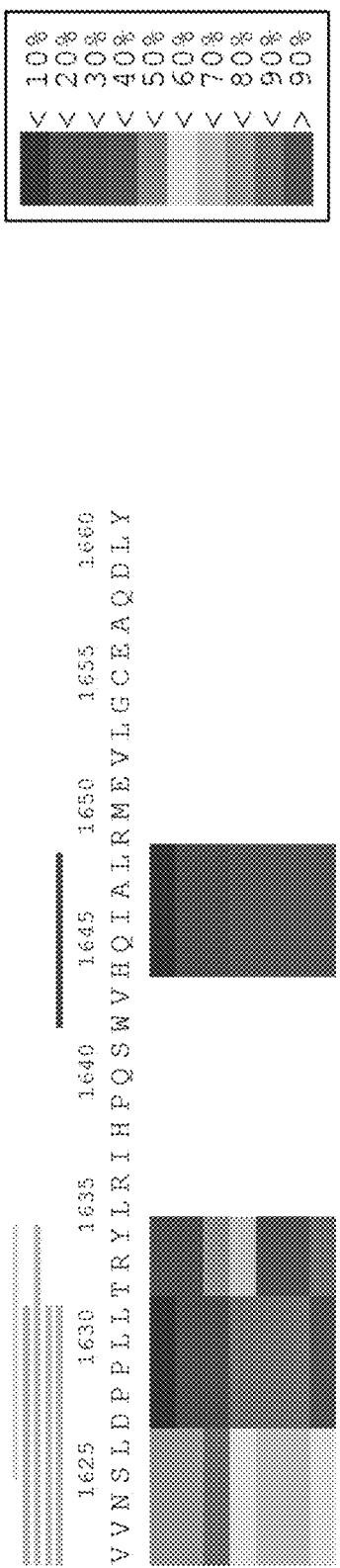

The FVIII molecular species B70-rFVIII was subjected to hydrogen/deuterium exchange-mass spectrometry (HDX-MS). This approach exploits the fact that exposure of the protein to $D_2O$ induces rapid amide HDX in disordered regions, whereas tightly folded elements are much more protected from deuterium incorporation, resulting in slow isotope exchange (Konermann et al., 2011). The HDX-MS kinetics of 120 peptides from B70-rFVIII was measured covering 63% of the total protein sequence and 37% of the B70-rFVIII B domain sequence (FIG. 52). All peptides obtained from sequences belonging to the B domain demonstrated very fast kinetics of deuterium incorporation. Even at the shortest incubation time of 3 seconds all peptides incorporated the same amount of deuterium than their corresponding fully deuterated sample after 3 days of labelling.

The HDX-MS data together with the amino acid sequence characteristics indicate that the B domain of B70-rFVIII lacks secondary structure but rather appears intrinsically disordered and flexible. Based on in silico analysis described above similar solvent exposure and flexibility can be expected for the total B domain and several B domain truncations present in FVIII molecular species.

HDX kinetics results of the HC sequence deleted of any B domain (FIG. 52) are in good agreement with published FVIII crystal structure showing ordered structural elements disrupted by a disordered surface loop in the A1 domain and a flexible linker region between the A1 and A2 domains (Shen et al., 2008).

Example 21

Functional Characterization of Purified FVIII Subspecies—Aggregation Behavior of FL-rFVIII and rFVIII Molecular Secies at Eevated Tmperatures Temperature-dependent aggregation behavior of FL-rFVIII, B70-rFVIII, B20-rFVIII and BDD-rFVIII was investigated. Samples were exposed to elevated temperatures (25-50° C.) and analyzed by DLS and HPLC-SEC (FIG. 45). The Z-average, describing the intensity weighted mean hydrodynamic diameter of protein aggregates, was not changing from 25-35° C. for FL-rFVIII and rFVIII species. Starting at 40° C. an increase in Z-average was observed for all tested items, however, with clear differences between rFVIII samples. Whereas, the fold increase of the aggregate average size observed from 25-50° C. was 9.2 for BDD-rFVIII and 6.4 for B20-rFVIII it merely reached 3.4 for B70-rFVIII and 2.5 for FL-rFVIII. BDD-rFVIII aggregates detected after incubation for 20 hours at 45° C. and 50° C. were 2.5 and 3.1 fold larger in size, respectively, compared to FL-rFVIII aggregates.

The same trend in aggregation behavior as detected by DLS was shown after rFVIII aggregate analysis by HPLC-SEC (FIG. 45 inset).

FL-rFVIII aggregates, separated from FL-rFVIII monomers by HPLC-SEC, were shown to contain each rFVIII molecular species in a similar ratio to native FL-rFVIII as analyzed by SDS-PAGE (FIG. 53).

Summing up, upon exposure to elevated temperatures the mean aggregate size increased as the B domain content decreased (aggregation propensity order BDD-rFVIII>B20-rFVIII>B70-rFVIII>FL-rFVIII). FL-rFVIII, being a heterogenic mixture of rFVIII molecular species, showed lowest propensity of aggregate formation of all tested rFVIII samples.

Example 22

Functional Characterization of Purified FVIII Subspecies—FVIII Aggregation Pathways are Dependent on Molecular Heterogeneity and B Domain Content Detailed time-dependent aggregation analysis was performed at 45° C., the temperature at which the initiation of conformational changes in the FVIII molecule was reported (Grillo et al., 2001, Ramani et al., 2005a). Aggregation kinetics at 45° C. followed by HPLC-SEC revealed clear differences in the pathways of aggregate and oligomer formation between rFVIII molecular species and FL-rFVIII (FIG. 46). Based on the exclusion limit of the column used, aggregates were defined as soluble protein aggregates in the size range of 50-100 nm which were eluting with the void volume. Oligomers (retention times: 21.2-27.0 min) were defined as proteinaceous structures in the size range of 10-50 nm which were retarded by the size exclusion column but eluting prior to protein monomers (retention times: 27.0-43.0). Oligomer formation of all FVIII samples followed a one-phase association curve, however, the less B domain the analyzed molecule contained the more rapidly oligomers were formed (FIG. 46A). The rate constants for oligomer formation ($k_{oligo}$) of FL-rFVIII, B70-rFVIII, B20-rFVIII and BDD-rFVIII were calculated as 0.13±0.02, 0.12±0.05, 0.35±0.24 and 0.70±0.24 $h^{-1}$, respectively. Aggregation curves showed sigmoidal shapes with varying aggregate formation rates ($k_{agg}$), again, clearly depending on the B domain content (FIG. 46B). In the absence of the B domain aggregates formed more rapidly and excessively; $k_{agg}$(FL-rFVIII)=0.11±0.00 $h^{-1}$, $k_{agg}$ (B70-rFVIII)=0.18±0.02 $h^{-1}$, $k_{agg}$ (B20-rFVIII)=0.21±0.07 $h^{-1}$ $k_{agg}$ (BDD-rFVIII)= 0.21±0.08 $h^{-1}$. While amount of oligomers of BDD-rFVIII increased to a maximum of 22% after 8 h and decreased continuously afterwards, quantity of aggregates of BDD-rFVIII increased upon a 1 h lag phase excessively up to 48% after 24 h of incubation (FIG. 46D). The highest value of B20-rFVIII oligomers content (31%) was observed after 17 h, B20-rFVIII aggregate concentration (31%) was the same after 24 h. While 33% B70-rFVIII and 44% FL-rFVIII oligomers were formed at plateau levels after 22-24 h, only low aggregate contents of 17% and 11% for B70-rFVIII and FL-rFVIII, respectively, were observed at the end of incubation time. Aggregation pathways of FL-rFVIII and BDD-rFVIII were most contrarious as depicted in FIGS. 46C and D, respectively. Aggregation of pdFVIII (FIG. 46E) followed a very similar pathway as FL-rFVIII with the rate constants $k_{ahga}$(pdFVIII)=0.24±0.04 and $k_{agg}$(pdFVIII)= 0.15±0.03 $h^{-1}$. Consistent with oligomer and aggregate formation rates the loss of monomers of BDD-rFVIII was faster compared to FL-rFVIII and pdFVIII (FIG. 46F). FVIII activity of each tested sample was reduced according to the decrease in monomer concentration (data not shown).

In summary, the propensity for oligomer formation increased with increasing B domain content, whereas the propensity for aggregate formation was vice versa and both, heterogeneous FL-rFVIII and pdFVIII, showed a very similar but much lower tendency for aggregate formation than any purified monogenic molecular species of rFVIII.

Example 23

Functional Characterization of Purified FVIII Subspecies—Diverging Aggregation Pathways Triggered by Structural Difference of Aggregates To investigate the cause of the detected differences in aggregation behavior ThT fluorescence upon binding to oligomers and aggregates of rFVIII molecular species, FL-rFVIII and pdFVIII after incubation at 45° C. for 24 h was analyzed by HPLC-SEC. ThT is a commonly used fluorescent dye which displays enhanced fluorescence upon binding to cross-β sheet rich structures (Biancalana et al., 2010). Binding capability of ThT to aggregated FVIII protein structures was expressed as ratio of ThT and intrinsic protein fluorescence (FIG. 47). An increased ThT binding to oligomers of BDD-rFVIII compared to oligomers of B domain containing species (B20-rFVIII and B70rFVIII) as well as to FL-rFVIII and pdFVIII was observed. Aggregates of BDD-rFVIII showed a more than 3 fold enhanced ThT binding ability as those of FL-rFVIII and pdFVIII. Further, ThT fluorescence of B20-rFVIII aggregates was greater than that observed for B70-rFVIII aggregates. Measured fluorescence upon ThT binding to oligomers and aggregates of FL-rFVIII and pdFVIII was very similar (FIG. 47). Ratios of ThT fluorescence and protein absorption signals at 280 nm showed the same ThT binding differences between tested FVIII samples compared to ratios ThT/intrinsic protein fluorescence. ThT binding to monomers of any analyzed FVIII sample was not detected.

Example 24

Functional Characterization of Purified FVIII Subspecies—Homologous Seeding of FVIII Aggregation Cross-β sheet containing aggregates are known to serve as seeds which nucleate further protein aggregation upon stress conditions (Gsponer et al., 2006, Jarrett et al, 1993). The ability of aggregated BDD-rFVIII, B70-rFVIII and FL-rFVIII (45° C. for either 2, 5, 8 or 18 h) to seed the aggregation process of the respective sample was explored. FIG. 48 shows time-dependent formation of oligomers and aggregates of FVIII samples containing 50% preformed seeds in comparison to non-seeded FVIII samples. Homologous seeding of B70-rFVIII and heterogeneous FL-rFVIII (FIGS. 48B and C, respectively) did not alter oligomerization and aggregation behavior. rFVIII molecular species lacking B-domain shows a different mechanism. After initial rapid oligomer formation of BDD-rFVIII curves were flattened with addition of homologous seeds and finally an oligomer saturation concentration of 10% was reached. The lag phase of BDD-rFVIII aggregate formation was decreased depending on the type of seeds added. After the addition of seeds which were generated by incubation for 8 or 18 h at 45° C. the lag phase of BDD-rFVIII aggregation curves completely vanished (FIG. 48A). Reduction of the lag phase is a typical characteristic of nucleation-dependent polymerization described previously for a number of proteins including the biotherapeutic insulin (Arosio et al., 2015, Surmacz-Chwedoruk et al., 2014).

Cross-β sheet rich aggregates of BDD-rFVIII were effective in homologous seeding of further protein aggregation. A phenomenon, neither observed for B70-rFVIII nor for FL-rFVIII, which both don't form cross-β sheet positive aggregates. Interestingly, FL-rFVIII, even though due to its natural heterogeneity containing also a small portion of BDD-rFVIII, is least prone to aggregation and seeding when compared to mono-componential rFVIII molecular species.

Example 25

Functional Characterization of Purified FVIII Subspecie—Formation of Subvisible FVIII Particles Under Agitation and Shear Stress Clinically-relevant stress conditions were simulated by applying agitation and shear stress to FL-rFVIII, pdFVIII and rFVIII molecular species. Induced subvisible protein containing particles in the size of 0.75-70 µm are beyond the analytical range of HPLC-SEC and were detected by a flow cytometry-based method (Lubich et al., 2015, Nishi et al., 2014). Detected concentrations of subvisible protein containing particles reached similar levels in FL-rFVIII and pdFVIII in the range of $2.4\text{-}4.2\times10^6$ counts/ml (mean values $3.1\times10^6$ counts/ml and $3.2 \therefore 10^6$ counts/ml, respectively) after exposure to agitation and shear stress. A significantly higher concentration was detected in BDD-rFVIII (mean value $6.0\times10^6$ counts/ml; range $4.9\text{-}6.9\times10^6$ counts/ml). The subvisible protein containing particle concentration of B domain truncated molecular species was depending on the B domain content of the respective species and was higher for B20-rFVIII (mean value $5.5\times10^6$ counts/ml) than for B70-rFVIII (mean value $3.9\times10^6$ counts/ml) (FIG. 49). Non-stressed samples showed subvisible protein particle concentrations in the range of $0.4\text{-}4.6\times10^4$ counts/ml.

Example 26

Functional Characterization of Purified FVIII Subspecies—Discussion of Results In the foregoing Examples, the heterogeneity, stability and aggregation behavior of human FL-rFVIII expressed in CHO cells have been investigated and compared with highly purified human pdFVIII, with purified rFVIII molecular species containing variable amount of B domain. Structural characteristics of the B domain are explored and their potential role in stabilizing the FVIII molecule is addressed.

The data indicate that FL-rFVIII produced in CHO cell line displays natural heterogeneity similar to pdFVIII and possessing all molecular B domain species also present in pdFVIII. Although not yet completely understood, the processing of the B domain during FL-rFVIII secretion is consistent as indicated by identical heterogenic protein profiles of historically CHO cell line produced lots of FL-rFVIII presented in these experiments and identical to pdFVIII. Interestingly, FL-rFVIII produced in baby hamster kidney cell line exhibits a slightly distinct protein profile to CHO cell line derived FL-rFVIII and to pdFVIII (Jankowski et al., 2007). In general, heterogeneity of FVIII, even though with minor differences in the exact length of HC/B domain truncations, is a species independent characteristic. It was observed for human pdFVIII and FL-rFVIII in these experiments and previous work (Jankowski et al., 2007) and also for porcine pdFVIII (Lollar et al., 1988). In contrast, BDD-rFVIII analyzed in these experiments as well as marketed BDD-rFVIII products exhibit a monogenic, nearly artificially appearing protein pattern and, thus, show high differences when compared to heterogenic pdFVIII (D'Amici et al., 2010; Thim et al., 2010; Peters et al., 2013).

The role of heterogeneity and the impact of the B domain on FVIII aggregation were explored. FL-rFVIII was previously shown to be susceptible to aggregation due to minor structural alterations in tertiary structures starting at 45° C. (Grillo et al., 2001) and to initiate aggregation as a result of conformational changes in the lipid binding region in the C2 domain (Ramani et al., 2005a). In the present invention, it was shown that at increasing temperatures heterogeneous FL-rFVIII demonstrated the lowest propensity for aggregation, whereas, monogenic BDD-rFVIII aggregated extensively and also formed much larger aggregates. A tendency of elevated aggregation was observed as the B domain content of rFVIII molecular species decreased. Detailed time-dependent analysis of oligomer and aggregate formation under thermal stress (45° C.) revealed diverging pathways of different FVIII samples. Slow oligomer formation of thermally stressed FL-rFVIII and pdFVIII nearly inhibited aggregation. Much faster oligomer formation and also faster aggregation was observed for BDD-rFVIII. Molecular species of rFVIII were prone to oligomerization or aggregation dependent on the amount of remaining B domain. ThT positive cross-β sheet rich structures were detected in thermally induced BDD-rFVIII oligomers and aggregates, but were to a lower extent or even not present in B domain containing FVIII. Most likely, cross-β sheets in BDD-rFVIII oligomers trigger rapid and extensive aggregation and explain the diverging aggregation behavior between BDD-rFVIII and FL-rFVIII. Further, efficient homologous seeding of BDD-rFVIII aggregation, not observed in any other analyzed FVIII sample, most probably occurred due to this structural difference.

Based on the results observed from thermally induced aggregation in the present invention, a schematic model describing diverging pathways of BDD-rFVIII and FL-rFVIII oligomer and aggregate formation was built (FIG. 50). While the initial starting material in FL-rFVIII represents a heterogenic mixture of all rFVIII species, BDD-rFVIII solely exists of one single species. Arrow lengths in the model indicate rates of oligomer and aggregate formation, which are both much faster for BDD-rFVIII compared to FL-rFVIII. While BDD-rFVIII forms ordered large cross-β sheet rich aggregates, FL-rFVIII aggregates lack repetitive nature being composed of various species and smaller in size. The assembly of soluble proteins into ordered cross-β containing structures is an essential event of many human neurodegenerative diseases, such as Alzheimer's diseases, Parkinson's diseases or spongiform encephalopathies (Chiti et al., 2006). The rapid development of such disorders once clinical symptoms are detected has been associated with the seeding ability of respective accumulated protein aggregates (Jarrett et al., 1993).

In the present invention, it was elucidated that the B domain is solvent exposed, disordered and flexible, further, it displays low hydrophobicity. These observations allow to propose an aggregation-protective function of the B domain for FVIII similar as it was observed in other proteins with significant disordered segments such as α-synuclein. The natively unfolded, highly charged C-terminal region of α-synuclein was shown to be essential in stabilizing and preventing aggregation of the protein. C-terminally truncated fragments of α-synuclein aggregated faster than the full-length protein. Aggregation of truncated fragments was clearly dependent on the length of the C-terminal region and was less the higher the content of the disordered region was (Murray et al., 2003; Serpell et al., 2000; Hoyer et al., 2004).

Interestingly, the lowest propensity of aggregation of all tested FVIII samples in the present invention was observed for heterogenic FL-rFVIII, consisting of a mixture of B domain containing, truncated and B domain deleted rFVIII species. Heterogeneity causes a reduced sequence similarity between individual rFVIII species. In fact, such sequence diversity in proteins has already been demonstrated essential in reducing aggregation susceptibility and seeding processes in previous studies. Wright and coworkers findings on the aggregation behavior of the multidomain protein titin showed that the efficiency of coaggregation between different domains decreases markedly with decreasing sequence identity and, further, they claimed that maintaining a low sequence identity between proteins is an important evolutionary characteristic that strongly inhibits aggregation in the crowded environment of a living system (Wright et al., 2005). Similar, the efficiency of seeding fibril formation of lysozymes was shown to strongly depend on the similarity of their sequences, the lower the sequence identity the lower the seeding efficiency (Krebs et al., 2004). These observations correlate well with the results of the present invention clearly showing lower aggregation propensity and seeding efficiency of heterogenic FL-rFVIII compared to monogenic rFVIII species.

Also the influence of agitation and shear stress on FVIII aggregation was explored in this invention. These clinically-relevant stress conditions mimic potential mishandling of FVIII therapeutic products by patients and can facilitate the interaction of proteins with silicon oil, which is often present in the interior surfaces of syringes to allow smooth plunger movement (Lubich et al., 2015, Thirumangalathu et al., 2009, Gerhardt et al., 2014). This leads to the formation of subvisible protein containing particles which are typically in the size range of 0.1-50 µm (den Engelsman et al., 2011). In the present invention, subvisible protein containing particle formation upon agitation and shear stress was, similar as observed for thermally induced aggregation, clearly dependent on the B domain content. Particle concentrations in FL-rFVIII and pdFVIII reached similar levels, whereas significantly more particles were detected in BDD-rFVIII.

The present invention demonstrates, that FVIII aggregation depends on two major parameters which in turn may influence each other, such as (i) the content of the B domain which has a stabilizing effect on the FVIII molecule by preventing the formation of cross-β sheet rich and seeding prone aggregates and (ii) heterogeneity which suppresses aggregation due to emerging sequence diversity. Previously published, glycosylation was significantly influencing the stability of FL-rFVIII, shown by reduced aggregation resistance of deglycosylated FL-rFVIII (Kosloski et al., 2009). Given that ~80% of the N-glycosylation sites are distributed within the B domain (Fay et al., 2006), it seems likely that deletion of this domain renders the protein more susceptible to aggregation. Manufacturing and formulation are further critical factors influencing aggregation of FVIII and protein therapeutics in general (Eon-Duval et al, 2012). Healthcare professionals should be well aware of these quality differences and the resulting potential safety concerns for patients.

Protein aggregates do not only impact stability and shelf-life of protein drugs, but also enhance their immunogenicity (Eon-Duval et al, 2012). The repetitive nature of protein aggregates can be recognized by pattern recognition receptors or cross-link antigen receptors on immune cell. Formed antidrug antibodies may have a neutralizing effect on the protein, which in turn affect its potency or pharmacokinetics and, especially in case of therapeutics related to an endogenous protein, risk patient safety (Moussa et al., 2016). Inhibitory antibodies are formed in approximately one-fifth of hemophilia A patients treated with FVIII (Gouw et al., 2013; Hay et al., 1998). The influence of FVIII aggregates in inducing inhibitory antibodies in a hemophilia A mouse model was previously investigated. It was shown that protein aggregates modulate FVIII immunogenicity in in vivo models differently depending on the nature of aggregates and how they were formed (Ramani et al., 2005b; Pisal et al., 2012). However, up to date there is no data how protein aggregates in FVIII products modulate immunogenicity of the biotherapeutic in humans and what immunogenic properties may have oligomers and aggregates of FVIII characterized in this study.

In summary, the present invention demonstrates similar protein heterogeneity of FL-rFVIII and pdFVIII, and suggests a beneficial effect of heterogeneity by reducing the protein aggregation susceptibility upon exposure to physical stress. Additionally, a new role of the B domain in ensuring stability of the FVIII molecule by modulating the protein aggregation pathway and protecting FVIII from excessive aggregation was identified.

The above findings can be used in future design of novel FVIII therapeutics for improving their stability, shelf-life and, most important, their safety.

Example 27

Determination of Protein Concentrations of FVIII Species

The following gives an example of how protein concentrations of FVIII species can be determined.
Calculation of FVIII Absorption Coefficients at 280 nm:

Based on the amino acid sequences the absorption coefficients at 280 nm were calculated assuming that all cysteines are in di-sulfide bonds. Tyrosine sulfation was not included in the calculation.

The absorption coefficients are the theoretical absorption of a 1 mg/ml solution of the indicated protein.

The absorption coefficient of SOS-E was calculated based on the ratio of species present in Advate as known from C4 chromatography analytical data. Absorption coefficients of pdFVIII, and a mix of FVIII subspecies were assumed the same as for SOS-E.

TABLE 28

Absorption coefficients at 280 nm of FVIII samples

| FVIII species | Assumed Composition | Absorption coefficient at 280 nm |
| --- | --- | --- |
| 180 kDa | 50 % full length heavy chain 180 kDa 50 % light chain | 1.26 |
| 150 kDa | 50 % truncated heavy chain 150 kDa 50 % light chain | 1.43 |
| 110 kDa | 50 % truncated heavy chain 110 kDa 50 % light chain | 1.53 |
| 90 kDa | 50 % B-domain depleted heavy chain 50 % light chain | 1.57 |
| SOS-E, pdFVIII, mix (see Example 28) | % of 180, 150,110 and 90 kDa heavy chain based on C4 chromatography analytical data 50 % light chain | 1.33 |

Determination of FVIII Protein Concentrations:

The absorption of FVIII samples at 280 nm was spectrophotometrically determined. The concentration was calculated according to:

Concentration (mg/ml)=measured absorption/absorption coefficient at 280 nm

Example 28

Activity of Purified Recombinant FVIII Species and Mixtures Thereof

The activities of purified recombinant FVIII (rFVIII) species and mixtures thereof were measured and compared to the activities of FL-rFVIII (SOS-E) and plasma derived (pd)FVIII.
The Activity of FVIII Samples was Measured by:
  chromogenic activity assay
  one-stage clotting assay
  tissue factor triggered thrombin generation assay by calibrated automated thrombography
FVIII Samples:
  purified rFVIII species (90 kDa, 110 kDa, 150 kDa, 180 kDa)
  mix: mixture of species 90 kDa, 110 kDa, 150 kDa and 180 kDa in molar ratios as present in Advate (based on C4 chromatography analytic data)
  SOS-E: FL-rFVIII, starting material for species purification
  pdFVIII All samples were diluted to 0.244 µM in a buffer at defined pH containing buffer components including salts as well as a surfactant. Due to differences in size and molecular weight of FVIII species concentrations (µg/ml) of species at the molarity of 0.244 µM were as follows:

| FVIII sample | concentration (µg/ml) |
| --- | --- |
| 90 kDa | 40 |
| 110 kDa | 42 |
| 150 kDa | 46 |
| 180 kDa | 55 |
| Mix | 52 |
| SOS-E | 52 |
| pdFVIII | 52 |

Description of Methods:
One-Stage Clotting Assay

FVIII activity by one-stage clotting assay was performed with a commercially available aPTT reagent, Actin FSL (Siemens, Germany) on an automated coagulation analyzer (BCS XP, Siemens, Germany). A sample containing an unknown amount of functional FVIII is mixed with human FVIII-deficient plasma and the activator. After incubation at +37° C., coagulation is initiated by addition of calcium chloride and the time to clot formation is recorded. Coagulation time is indirectly proportional to the FVIII concentration in the sample. Results are given in IU FVIII/mL, read from a reference curve. The reference standard was full-length rFVIII, traceable to the WHO international standard.
Chromogenic Activity Assay FVIII activity assay was performed with commercially available reagents (Siemens, Germany) on an automated coagulation analyzer (BCS XP, Siemens). In the first step of the chromogenic assay, a sample containing an unknown amount of functional FVIII, is added to a reaction mixture consisting of thrombin, activated FIX (FIXa), phospholipid, FX and a buffer containing calcium. FVIII is activated by thrombin. Activated FVIII (FVIIIa) forms a complex with phospholipids, FIXa and calcium resulting in the activation of Factor X (FXa). In the second step of the chromogenic assay FXa is measured through cleavage of an FXa specific peptide nitroanilide substrate. P-nitroaniline is produced, giving a color that can be measured photometrically by absorbance at 405 nm. The color produced is directly proportional to the amount of functional FVIII present in the sample. The reference standard was full-length FVIII, calibrated against WHO international standard.

Tissue Factor Triggered Thrombin Generation Assay

The calibrated automated thrombography (CAT), a type of thrombin generation assay (TGA), is a global hemostatic assay that is increasingly used in clinical studies as ex vivo efficacy parameter and as research tool. The thrombogram describes the concentration of thrombin in clotting plasma and is therefore a function test of the hemostatic system under close to physiological conditions. The assay is based on the measurement of fluorescence that is generated by the cleavage of the fluorogenic substrate Z-G-G-R-AMC by thrombin over time upon initiation of coagulation by Tissue Factor. The assay is performed on a Thrombograph™, a 96-well plate fluorometer, and uses a thrombin calibrator that is needed to correct for inner filter effect, donor-to-donor variability in color of plasma, substrate depletion and instrumental differences.

The following CAT parameters characterize the hemostatic state of a plasma sample:

Lag time [min]:represents clotting time, the initiation of thrombin generation

Time to peak [min]:time until maximal amount of thrombin is generated

Thrombin peak [nM]:maximal thrombin concentration formed

Endogenous Thrombin Potential (ETP) [nM min]:Area under the thrombin generation curve representing the total amount of thrombin that is generated.

Thrombin generation of different rFVIII species and mixtures thereof was measured in hemophilia A patient plasma by calibrated automated thrombography (CAT). Sample dilutions of the rFVIII species and mixtures were prepared in sample buffer (25 mM HEPES, 175 mM NaCl, pH 7.4, 5 mg/mL BSA). The samples were diluted to result in plasma concentrations of 0.0625-1 nM rFVIII in the assay. In a 96-well microtiter plate (Immulon 2HB, Thermo Labsystems, Waltham, MA USA) the following components were combined: 10 µL of the rFVIII sample dilutions, 10 µL of a mixture of tissue factor (TF) and phospholipids (PL) with final concentrations of 1 µM TF and 4 µM PL (PPP-Reagent Low Thrombinoscope, Maastricht, Netherlands), and 80 µL of platelet poor plasma (PPP) pool from hemophilia A patients (FVIII<1% George King Biomedical). The PPP was prior treated with corn trypsin inhibitor (Haematologic Technologies Inc) at 62 µg/mL to avoid pre-activation of plasma. The reaction was started by adding 20 µL fluorogenic substrate Z-G-G-R-AMC and calcium chloride (FluCa Kit, Thrombinoscope). Fluorescence was detected using a Fluoroskan Ascent (Thermo Lab Systems). Thrombin Generation was calculated using the Thrombinoscope software (Thrombinoscope). Analysis by Thrombinoscope software results in thrombin generation curves with time (min) on the x-axis and thrombin (nM) on the y-axis. The software determines the following parameters: lag time (min; time till onset of initial thrombin generation); endogenous thrombin potential (ETP; nM; area under the thrombin generation curve—reflecting the total amount of thrombin generated over the course of the assay); peak thrombin (nM; highest amount of thrombin generated at any one point of the assay), time to peak (min; time till highest amount of thrombin generated at any one point of the assay). The thrombin peak was selected as main parameter to compare the thrombin generation activity of the different rFVIII samples at the different concentrations.

Results:

One-stage clotting activity of FVIII samples at 0.244 mM concentration are displayed and compared in FIG. 54A. Chromogenic activity of FVIII samples at 0.244 mM concentration are displayed and compared in FIG. 54B. Thrombin peaks and lag time of FVIII samples at 0.25 mM, 0.5 mM and 1 mM concentration are displayed and compared in FIG. 55. These results show that all purified rFVIII species and mixtures thereof showed increased activity compared to SOS-E in chromogenic and one-stage clotting FVIII activity assays. pdFVIII showed similar activity to SOS-E in chromogenic activity assay, but increased activity in one-stage clotting assay. All purified rFVIII species, mixtures thereof and pdFVIII showed increased thrombin peaks compared to SOS-E in TF triggered thrombin generation assay. All tested samples showed reduced lag times compared to SOS-E.

Example 29

Furin Maturation of ADVATE BDS and Intermediates

Surprisingly, FIG. 56 shows that single chain FVIII is present in various commercially available FVIII products. Hence, it was tested whether furin maturation would lead to increased activity of FL-rFVIII. The following describes the samples and their preparation:

Samples:

SOS-E: Advate process intermediate without final polishing step

Advate BDS

Buffer: negative control

Sample Preparation:

A: Native Sample

B: Native Sample+100 µl Furin Stock+22.4 µl Milli-Q

C: Native Sample+100 µl Furin Buffer+22.4 µl Milli-Q

D: Native Sample+100 µl Furin Stock+22.4 µl Inhibitor Stock

E: Native Sample+100 µl Furin Buffer+22.4 µl Inhibitor Stock

The total volume for B-E was equal, thus, direct comparisons are possible. rFurin BDS was used. Furin Buffer was equal to Furin Stock only without Furin. Inhibitor Stock: 100 mM Benzamidinehydrochloride.

The following table shows the results of chromogenic activity assays that were performed using the samples described above.

TABLE 29

Results of chromogenic activity assays.

| Samplecode | Sample/Buffer | Furin | Furin Buffer | Inhibitor Stock Solution | Incubation | Final Conc [U/mL] | Activity Increase [%] |
|---|---|---|---|---|---|---|---|
| SOS_240517_DV_1 | SOS-E | | | | | 973.2 | |
| SOS_240517_DV_2 | SOS-E | | add equal volume | | 1 h @ RT | 978.38 | |
| SOS_240517_DV_3 | SOS-E | add to 300 IU/ml | | | 1 h @ RT | 1148.64 | 17.4 |
| SOS_240517_DV_4 | SOS-E | | add equal volume | add to 2 mM | 1 h @ RT | 908.49 | |
| SOS_240517_DV_5 | SOS-E | add to 300 IU/ml | | add to 2 mM | 1 h @RT | 887.82 | |
| ADV_240517_DV_1 | ADVATE BDS | | | | | 1914.675 | |
| ADV_240517_DV_2 | ADVATE BDS | | add equal volume | | 1 h @ RT | 1906.225 | |
| ADV_240517_DV_3 | ADVATE BDS | add to 300 IU/ml | | | 1 h @ RT | 2263.5 | 18.7 |
| ADV_240517_DV_4 | ADVATE BDS | | add equal volume | add to 2 mM | 1 h @ RT | 2038.725 | |
| ADV_240517_DV_5 | ADVATE BDS | add to 300 IU/ml | | add to 2 mM | 1 h @ RT | 2322.975 | |
| BUF_240517_DV_1 | Buffer | | | | | <0.01 | |
| BUF_240517_DV_2 | Buffer | | add equal volume | | 1 h @ RT | <0.01 | |
| BUF_240517_DV_3 | Buffer | add to 300 IU/ml | | | 1 h @ RT | <0.01 | |
| BUF_240517_DV_4 | Buffer | | add equal volume | add to 2 mM | 1 h @ RT | <0.01 | |
| BUF240517_DV_5 | Buffer | add to 300 IU/ml | | add to 2 mM | 1 h @ RT | <0.01 | |

FIG. 57 shows a silver-stained SDS-PAGE gel of the samples prepared as described above. FIG. 58 shows a Western Blot analysis of an SDS-PAGE gel of the samples prepared as described above.

The above results show that full length FVIII as well as extended light chain can be further matured by the addition of furin at an activity of 200-300 The chromogenic activity is thereby increased by about 17-19% SDS-PAGE clearly shows maturation for full length FVIII as well as extended light chain.

INDUSTRIAL APPLICABILITY

The methods of the present invention are useful, e.g., for industrial manufacturing processes. The products of the present invention are useful, e.g., for the manufacturing of medicaments. Thus, the invention is industrially applicable.

REFERENCES

Ahmadi M, Bryson C J, Cloake E A, Welch K, Filipe V, Romeijn S, et al. Small amounts of sub-visible aggregates enhance the immunogenic potential of monoclonal antibody therapeutics. Pharm Res. 2015; 32(4):1383-94.

Arosio P, Knowles T P, Linse S. On the lag phase in amyloid fibril formation. Phys Chem Chem Phys. 2015; 17(12): 7606-18.

Barnard J G, Babcock K, Carpenter J F. Characterization and quantitation of aggregates and particles in interferon-beta products: potential links between product quality attributes and immunogenicity. J Pharm Sci. 2013; 102(3): 915-28.

Biancalana M, Koide S. Molecular mechanism of thioflavin-T binding to amyloid fibrils. Biochim Biophys Acta. 2010; 1804(7):1405-12.

Bonazza K, Rottensteiner H, Schrenk G, Fiedler C, Scheiflinger F, Allmaier G, et al. Ca2+ concentration-dependent conformational change of FVIII B-domain observed by atomic force microscopy. Anal Bioanal Chem. 2015; 407(20):6051-6.

Chiti F, Dobson C M. Protein misfolding, functional amyloid, and human disease. Annu Rev Biochem. 2006; 76:333-66.

Clemetson, K. J. (2012). Platelets and primary haemostasis. Thrombosis Research, 129(3):220-224.

D'Amici G M, Timperio A M, Gevi F, Grazzini G, Zolla L. Recombinant clotting factor VIII concentrates: Heterogeneity and high-purity evaluation. Electrophoresis. 2010; 31(16):2730-9.

den Engelsman J, Garidel P, Smulders R, Koll H, Smith B, Bassarab S, et al. Strategies for the assessment of protein aggregates in pharmaceutical biotech product development. Pharm Res. 2011; 28(4):920-33.

Do H, Healey J F, Waller E K, Lollar P. Expression of factor VIII by murine liver sinusoidal endothelial cells. J Biol Chem. 1999; 274(28):19587-92.

Eon-Duval A, Broly H, Gleixner R. Quality attributes of recombinant therapeutic proteins: an assessment of impact on safety and efficacy as part of a quality by design development approach. Biotechnol Prog. 2012; 28(3): 608-22.

ExPASy (2016). ProtParam Entry number P00451. http://web.expasy.org/cgi-bin/protparam/protparam. [Online; accessed 12 Sep. 2016]

FDA Approval (2003). Food and Drug Administration—Summary of Basis for Approval, pages 18-20. http://www.fda.gov/downloads/BiologicsBloodVaccines/BloodBloodProducts/ApprovedProducts/LicensedProducts-BLAs/FractionatedPlasmaProducts/ucm093516.pdf. [Online; accessed 12 Sep. 2016].

Fay P J. Factor VIII structure and function. Int J Hematol. 2006; 83(2):103-8.

Gerhardt A, McGraw N R, Schwartz D K, Bee J S, Carpenter J F, Randolph T W. Protein aggregation and particle formation in prefilled glass syringes. J Pharm Sci. 2014; 103(6):1601-12.

Gouw S C, van der Bom J G, Ljung R, Escuriola C, Cid A R, Claeyssens-Donadel S, et al. Factor VIII products and inhibitor development in severe hemophilia A. N Engl J Med. 2013; 368(3):231-9.

Grillo A O, Edwards K-LT, Kashi R S, Shipley K M, Hu L, Besman M J, et al. Conformational Origin of the Aggregation of Recombinant Human Factor VIII. Biochemistry. 2001; 40(2):586-95.

Grushin K, Miller J, Dalm D, Parker E T, Healey J F, Lollar P, et al. Lack of recombinant factor VIII B-domain induces phospholipid vesicle aggregation: implications for the immunogenicity of factor VIII. Haemophilia. 2014; 20(5):723-31.

Gsponer J, Vendruscolo M. Theoretical approaches to protein aggregation. Protein Pept Lett. 2006; 13:287-93.

Hay C R. Factor VIII inhibitors in mild and moderate-severity haemophilia A. Haemophilia. 1998; 4(4):558-63.

Hermeling S, Schellekens H, Crommelin D J, Jiskoot W. Micelle-associated protein in epoetin formulations: A risk factor for immunogenicity? Pharm Res. 2003; 20(12): 1903-7.

Hoyer W, Cherny D, Subramaniam V, Jovin T M. Impact of the acidic C-terminal region comprising amino acids 109-140 on alpha-synuclein aggregation in vitro. Biochemistry. 2004; 43(51):16233-42.

Jankowski M A, Patel H, Rouse J C, Marzilli L A, Weston S B, Sharpe P J. Defining 'full-length' recombinant factor VIII: a comparative structural analysis. Haemophilia. 2007; 13(1):30-7.

Jarrett J T, Lansbury Jr. P T. Seeding "one-dimensional crystallization" of amyloid: A pathogenic mechanism in Alzheimer's disease and scrapie? Cell. 1993; 73(6):1055-8.

Joubert M K, Hokom M, Eakin C, Zhou L, Deshpande M, Baker M P, et al. Highly aggregated antibody therapeutics can enhance the in vitro innate and late-stage T-cell immune responses. J Biol Chem. 2012; 287(30):25266-79.

Joubert M K, Luo Q, Nashed-Samuel Y, Wypych J, Narhi L O. Classification and characterization of therapeutic antibody aggregates. J Biol Chem. 2011; 286(28):25118-33.

Kannicht C, Ramstrom M, Kohla G, Tiemeyer M, Casademunt E, Walter O, et al. Characterisation of the post-translational modifications of a novel, human cell line-derived recombinant human factor VIII. Thromb Res. 2013; 131(1):78-88.

Kaufman R J, Wasley L C, Dorner A J. Synthesis, processing, and secretion of recombinant human factor VIII expressed in mammalian cells. J Biol Chem. 1988; 5(263):6352-62.

Keating G M, Dhillon S. Octocog alfa (Advate®): a guide to its use in hemophilia A. BioDrugs 2012; 26(4): 269-273.

Khrenov A V, Ananyeva N M, Saenko E L. Role of the B domain in proteolytic inactivation of activated coagulation factor VIII by activated protein C and activated factor X. Blood Coagul Fibrinolysis. 2006; 17(5):379-88.

Konermann L, Pan J, Liu Y H. Hydrogen exchange mass spectrometry for studying protein structure and dynamics. Chem Soc Rev. 2011; 40(3):1224-34.

Kosloski M P, Miclea R D, Balu-Iyer S V. Role of glycosylation in conformational stability, activity, macromolecular interaction and immunogenicity of recombinant human factor VIII. AAPS J. 2009; 11(3):424-31.

Krebs M R, Morozova-Roche L A, Daniel K, Robinson C V, Dobson C M. Observation of sequence specificity in the seeding of protein amyloid fibrils. Protein Sci. 2004; 13(7):1933-8.

Krishnaswamy S. FVIII-VWF dos-a-dos. Blood. 2015; 126 (8):923-4.

Kyte J, Doolittle R F. A simple method for displaying the hydropathic character of a protein. J Mol Biol. 1982; 157(1):105-32.

Lenting P J, van Mourik J A, Mertens K. The life cycle of coagulation factor VIII in view of its structure and function. Blood. 1998; 92(11):3983-96.

Li X, Gabriel D A. The physical exchange of factor VIII (FVIII) between von Willebrand factor and activated platelets and the effect of the FVIII B-domain on platelet binding. Biochemistry. 1997; 36(35):10760-7.

Liu, M., Shen, B., Nakaya, S., Pratt, K., Fujikawa, K., Davie, E., Stoddard, B., and Thompson, A. (2000). Hemophilic factor VIII C1- and C2-domain missense mutations and their modeling to the 1.5-angstrom human C2-domain crystal structure. Blood Journal, 96(3):979-987.

Lollar P, Hill-Eubanks D C, Parker C G. Association of the factor VIII light chain with von Willebrand factor. J Biol Chem. 1988; 263(21):10451-5.

Lubich C, Malisauskas M, Prenninger T, Wurz T, Matthiessen P, Turecek P L, et al. A Flow-Cytometry-Based Approach to Facilitate Quantification, Size Estimation and Characterization of Sub-visible Particles in Protein Solutions. Pharm Res. 2015; 32(9):2863-76.

Maislos M, Mead P M, Gaynor D H, Robbins D C. The source of the circulating aggregate of insulin in type I diabetic patients is therapeutic insulin. J Clin Invest. 1986; 77(7):717-23.

Mannucci P M, Duga S, Peyvandi F. Recessively inherited coagulation disorders. Blood. 2004; 104(5):1243-52.

Mazurkiewicz-Pisarek, A., Pucienniczak, G., Ciach, T., and Pucienniczak, A. (2016). The factor VIII protein and its function. Acta Biochimica Polonica, 63(1):11-16.

Moussa E M, Panchal J P, Moorthy B S, Blum J S, Joubert M K, Narhi L O, et al. Immunogenicity of therapeutic protein aggregates. J Pharm Sci. 2016; 105(2):417-30.

Murray I V J, Giasson B I, Quinn S M, Koppaka V, Axelsen P H, Ischiropoulos H, et al. Role of alpha-synuclein carboxy-terminus on fibril formation in vitro. Biochemistry. 2003; 42(28):8530-40.

Myles T, Yun T H, Leung L L. Structural requirements for the activation of human factor VIII by thrombin. Blood. 2002; 100(8):2820-6.

Ngo J C, Huang M, Roth D A, Furie B C, Furie B. Crystal structure of human factor VIII: implications for the formation of the factor IXa-factor VIIIa complex. Structure. 2008; 16(4):597-606.

Nishi H, Mathas R, Furst R, Winter G. Label-free flow cytometry analysis of subvisible aggregates in liquid IgG1 antibody formulations. J Pharm Sci. 2014; 103(1):90-9.

OBrien, D. and Tuddenham, E. (1997). The structure and function of factor VIII. Journal of Haemostasis and Thrombosis, pages 333-348.

Peters R T, Toby G, Lu Q, Liu T, Kulman J D, Low S C, et al. Biochemical and functional characterization of a recombinant monomeric factor VIII-Fc fusion protein. J Thromb Haemost. 2013; 11(1):132-41.

Peyvandi, F., Garagiola, I., and Young, G. (2016). The past and future of haemophilia: diagnosis, treatments, and its complications. The Lancet, pages 1-11.

Pipe, S., Morris, J., Shah, J., and Kaufman, R. (1998). Differential interaction of coagulation factor VIII and factor V with protein chaperones calnexin and calreticulin. The Journal of Biological Chemistry, 273(14):8537-8544.

Pipe S W, Miao H Z, Kucab P F, McVey J H, Kaufman R J. The secretion efficiency of factor VIII can be regulated by the size and oligosaccharide content of the B domain. Blood. 2005; 106:Abstract 687.

Pipe S W. Functional roles of the factor VIII B domain. Haemophilia. 2009; 15(6):1187-96.

Pipe S W, Montgomery R R, Pratt K P, Lenting P J, Lillicrap D. Life in the shadow of a dominant partner: the FVIII-VWF association and its clinical implications for hemophilia A. Blood. 2016; 128(16):2007-16.

Pisal D S, Kosloski M P, Middaugh C R, Bankert R B, Balu-lyer S V. Native-like aggregates of factor VIII are immunogenic in von Willebrand factor deficient and hemophilia a mice. J Pharm Sci. 2012; 101(6):2055-65.

Ramani K, Purohit V S, Miclea R D, Middaugh C R, Balasubramanian S V. Lipid binding region (2303-2332) is involved in aggregation of recombinant human FVIII (rFVIII). J Pharm Sci. 2005a; 94(6):1288-99.

Ramani K, Purohit V, Middaugh C R, Balasubramanian S V. Aggregation kinetics of recombinant human FVIII (rFVIII). J Pharm Sci. 2005b; 94(9):2023-9.

Robbins D C, Cooper S M, Fineberg S E, Mead P M. Antibodies to covalent aggregates of insulin in blood of insulin-using diabetic patients. Diabetes. 1987a; 36(7): 838-41.

Robbins D C, Mead P M. Free covalent aggregates of therapeutic insulin in blood of insulin-dependent diabetes. Diabetes. 1987b; 36:147-51.

Roberts C J. Therapeutic protein aggregation: mechanisms, design, and control. Trends Biotechnol. 2014; 32(7):372-80.

Schaller, J., Gerber, S., Kaempfer, U., Lejon, S., and Trachsel, C. (2008). Human Blood Plasma Proteins—Structure and Function. John Wiley and Sons Ltd., pages 96-106.

Serpell L C, Berriman J, Jakes R, Goedert M, Crowther R A. Fiber diffraction of synthetic alpha-synuclein filaments shows amyloid-like cross-beta conformation. Proc Natl Acad Sci USA. 2000; 97(9):4897-902.

Shen B W, Spiegel P C, Chang C H, Huh J W, Lee J S, Kim J, et al. The tertiary structure and domain organization of coagulation factor VIII. Blood. 2008; 111(3):1240-7.

Surmacz-Chwedoruk W, Malka I, Bozycki L, Nieznanska H, Dzwolak W. On the heat stability of amyloid-based biological activity: insights from thermal degradation of insulin fibrils. PLoS One. 2014; 9(1):e86320.

Thim L, Vandahl B, Karlsson J, Klausen N K, Pedersen J, Krogh T N, et al. Purification and characterization of a new recombinant factor VIII (N8). Haemophilia. 2010; 16(2):349-59.

Thirumangalathu R, Krishnan S, Ricci M S, Brems D N, Randolph T W, Carpenter J F. Silicone oil- and agitation-induced aggregation of a monoclonal antibody in aqueous solution. J Pharm Sci. 2009; 98(9):3167-81.

Toole J J, Knopf J L, Wozney J M, Sultzman L A, Buecker J L, Pittman D D, et al. Molecular cloning of a cDNA encoding human antihaemophilic factor. Nature. 1984; 312(5992):342-7.

Toole J J, Pittman D D, Orr E C, Murtha P, Wesley L C, Kaufman R J. A large region (approximately equal to 95 kDa) of human factor VIII is dispensable for in vitro procoagulant activity. Proc Natl Acad Sci USA. 1986; 83(16):5939-42.

Unicorn 6.4 (2016). Unicorn 6.4 software package, GE Healthcare Life Sciences. http://www.fda.gov/downloads/BiologicsBloodVaccines/Blood BloodProducts/Approved Products/Licensed Prod uctsBLAs/FractionatedPlasma-Products/ucm093516.pdf. [Accessed 17 Mar. 2016, Baxalta Innovations GmbH].

Uversky V N. What does it mean to be natively unfolded? Eur J Biochem. 2002; 269(1):2-12.

Uversky V N, Li J, Fink A L. Evidence for a partially folded intermediate in alpha-synuclein fibril formation. J Biol Chem. 2001; 276(14):10737-44.

van Beers M M, Jiskoot W, Schellekens H. On the role of aggregates in the immunogenicity of recombinant human interferon beta in patients with multiple sclerosis. J Interferon Cytokine Res. 2010; 30(10):767-75

Valentino, L. (2010). Blood-induced joint disease: the pathophysiology of hemophilic arthropathy. Journal of Thrombosis and Haemostasis, 8(9):1895-1902.

Vehar G A, Keyt B, Eaton D, Rodriguez H, O'Brien D P, Rotblat F, et al. Structure of human factor VIII. Nature. 1984; 312(5992):337-42.

Wright C F, Teichmann S A, Clarke J, Dobson C M. The importance of sequence diversity in the aggregation and evolution of proteins. Nature. 2005; 438(7069):878-81.

Zhang B, Kaufman R J, Ginsburg D. LMAN1 and MCFD2 form a cargo receptor complex and interact with coagulation factor VIII in the early secretory pathway. J Biol Chem. 2005; 280(27):25881-6.

The invention claimed is:

1. A method for treating a bleeding disorder in a patient, the method comprising the step of administering to the patient in need of such treatment a therapeutically effective amount of a composition comprising:
   a Factor VIII (FVIII) subspecies produced by anion exchange chromatography of a composition comprising FVIII, wherein said FVIII subspecies is a FVIII heavy chain that is associated with a FVIII light chain, and wherein the weight ratio of said FVIII subspecies in the composition is increased as compared to all other FVIII subspecies comprising a FVIII heavy chain that is associated with a FVIII light chain.

2. The method of claim 1, wherein the Factor VIII (FVIII) subspecies is produced by anion exchange chromatography of the composition comprising FVIII followed by size exclusion chromatography.

3. The method of claim 2, wherein the bleeding disorder is hemophilia A.

4. The method of claim 2, wherein the composition comprising said FVIII subspecies was concentrated by anion exchange chromatography following size exclusion chromatography.

5. The method of claim 2, wherein the FVIII is recombinant FVIII (rFVIII) and said FVIII subspecies is a recombinant FVIII (rFVIII) subspecies.

6. The method of claim 2, wherein the anion exchange chromatography comprised a high resolution Q-resin with a bead size of less than 82 μm.

7. The method of claim 2, wherein the size exclusion chromatography comprised a resin with a resolution range of 10000 Da to 60000 Da.

8. The method of claim 2, wherein the composition comprising the FVIII was pretreated with a furin protease.

9. The method of claim 1, wherein said FVIII subspecies was eluted from the anion exchange chromatography resin by linear gradient elution, and wherein the gradient of the linear gradient elution had a length of at least about 16 column volumes, at least about 24 column volumes, or at least about 32 column volumes.

10. The method of claim 1, wherein the Factor VIII (FVIII) subspecies is produced by anion exchange chromatography of the composition comprising FVIII followed by negative mode hydrophobic interaction chromatography.

11. The method of claim 10, wherein the bleeding disorder is hemophilia A.

12. The method of claim 10, wherein the composition comprising said FVIII subspecies was concentrated by anion exchange chromatography following negative mode hydrophobic interaction chromatography.

13. The method of claim 10, wherein the anion exchange chromatography comprised a high resolution Q-resin with a bead size of less than 20 µm.

14. The method of claim 10, wherein the composition comprising the FVIII was pretreated with a furin protease.

15. The method of claim 10, wherein said FVIII subspecies was eluted from the anion exchange chromatography resin by linear gradient elution, and wherein the gradient of the linear gradient elution had a length of at least about 16 column volumes, at least about 24 column volumes, or at least about 32 column volumes.

16. The method of claim 1, wherein said FVIII subspecies is a FVIII 90 kDa heavy chain associated with a FVIII light chain and wherein the weight ratio of said FVIII subspecies in the composition is increased as compared to all other FVIII subspecies comprising a FVIII heavy chain that is associated with a FVIII light chain.

\* \* \* \* \*